(12) United States Patent
Askem et al.

(10) Patent No.: US 9,427,505 B2
(45) Date of Patent: Aug. 30, 2016

(54) NEGATIVE PRESSURE WOUND THERAPY APPARATUS

(71) Applicant: Smith & Nephew PLC, London (GB)

(72) Inventors: Ben Alan Askem, Brough (GB); Trevor John Beckett, Cambridge (GB); Iacopo Claudio Ferrari, Milan (IT); Matthew James Herd, Cambridge (GB); Keith Marshall, Bedfordshire (GB); Tom Moy, Norwich (GB); Alex David Norman, Cambridge (GB); Christian Riva, Milan (IT); Gary Stacey, Cambridge (GB); Philip Walsh, Bristol (GB)

(73) Assignee: SMITH & NEPHEW PLC, London (GB)

( * ) Notice: Subject to any disclaimer, the term of this patent is extended or adjusted under 35 U.S.C. 154(b) by 443 days.

(21) Appl. No.: 13/894,323

(22) Filed: May 14, 2013

(65) Prior Publication Data

US 2013/0331823 A1 Dec. 12, 2013

Related U.S. Application Data

(60) Provisional application No. 61/647,397, filed on May 15, 2012, provisional application No. 61/678,563, filed on Aug. 1, 2012, provisional application No. 61/729,288, filed on Nov. 21, 2012, provisional application No. 61/791,984, filed on Mar. 15, 2013.

(51) Int. Cl.
*A61M 1/00* (2006.01)
*F04B 49/06* (2006.01)
(Continued)

(52) U.S. Cl.
CPC ........... *A61M 1/0072* (2014.02); *A61M 1/009* (2014.02); *A61M 1/0088* (2013.01); *A61M 27/00* (2013.01);
(Continued)

(58) Field of Classification Search
CPC ................. A61F 13/00068; A61M 1/0072; F04B 43/04; F04B 43/0054
See application file for complete search history.

(56) References Cited

U.S. PATENT DOCUMENTS 3,787,882 A 1/1974 Fillmore et al.
3,972,328 A 8/1976 Chen
(Continued)

FOREIGN PATENT DOCUMENTS

CN 101676563 A 3/2010
DE 34 43 101 5/1986
(Continued)

OTHER PUBLICATIONS

Morcos, Anthony C., Voice Coil Actuators & Their Use in Advanced Motion Control Systems, Motion, Jul./Aug. 1995, pp. 25-27.
(Continued)

*Primary Examiner* — Leslie Deak
*Assistant Examiner* — Kai Weng
(74) *Attorney, Agent, or Firm* — Knobbe, Martens, Olson & Bear, LLP

(57) ABSTRACT

Some embodiments disclosed herein are directed to a pump assembly comprising a voice coil, a magnet and a diaphragm, wherein the voice coil is configured to move the diaphragm to pump a fluid through the pump assembly in response to a drive signal applied to the voice coil. Some embodiments disclosed herein are directed to an apparatus for applying negative pressure to a wound comprising a source of negative pressure configured to be coupled to a dressing, the source of negative comprising a voice coil actuator and a diaphragm, and a controller configured to produce a drive signal for the voice coil actuator.

30 Claims, 104 Drawing Sheets

(51) Int. Cl.
*A61M 27/00* (2006.01)
*F04B 43/00* (2006.01)
*F04B 43/04* (2006.01)
*A61F 13/00* (2006.01)

(52) U.S. Cl.
CPC ........... *F04B 43/0054* (2013.01); *F04B 43/04* (2013.01); *F04B 49/06* (2013.01); *A61F 13/00068* (2013.01); *A61F 2013/00174* (2013.01); *A61M 2209/088* (2013.01)

(56) References Cited

U.S. PATENT DOCUMENTS

| | | |
|---|---|---|
| 4,015,912 A | 4/1977 | Kofink |
| 4,293,609 A | 10/1981 | Erickson |
| 4,321,020 A | 3/1982 | Mittal |
| 4,460,642 A | 7/1984 | Errede et al. |
| 4,578,060 A | 3/1986 | Huck et al. |
| 4,585,397 A | 4/1986 | Crawford et al. |
| 4,599,052 A | 7/1986 | Langen et al. |
| 4,604,313 A | 8/1986 | McFarland et al. |
| 4,643,641 A | 2/1987 | Clausen et al. |
| 6,886,116 B1 | 1/1988 | Harvey |
| 4,846,164 A | 7/1989 | Martz |
| 4,969,880 A | 11/1990 | Zamierowski |
| 4,979,944 A | 12/1990 | Luzsicza |
| 4,988,345 A | 1/1991 | Reising |
| 5,115,801 A | 5/1992 | Cartmell et al. |
| 5,160,328 A | 11/1992 | Cartmell et al. |
| 5,197,945 A | 3/1993 | Cole et al. |
| 5,222,714 A | 6/1993 | Morinigo et al. |
| 5,238,732 A | 8/1993 | Krishnan |
| 5,246,353 A | 9/1993 | Sohn |
| 5,291,822 A | 3/1994 | Alsobrooks et al. |
| 5,336,219 A | 8/1994 | Krantz |
| 5,349,896 A | 9/1994 | Connelly et al. |
| 5,354,261 A | 10/1994 | Clark et al. |
| 5,358,494 A | 10/1994 | Svedman |
| 5,360,445 A | 11/1994 | Goldowsky |
| 5,364,381 A | 11/1994 | Soga et al. |
| 5,380,294 A | 1/1995 | Persson |
| 5,391,179 A | 2/1995 | Mezzoli |
| 5,417,743 A | 5/1995 | Dauber |
| 5,447,492 A | 9/1995 | Cartmell et al. |
| 5,449,003 A | 9/1995 | Sugimura |
| 5,449,347 A | 9/1995 | Preen et al. |
| 5,456,660 A | 10/1995 | Reich et al. |
| 5,466,229 A | 11/1995 | Elson |
| 5,470,585 A | 11/1995 | Gilchrist |
| 5,480,377 A | 1/1996 | Cartmell et al. |
| 5,492,313 A | 2/1996 | Pan et al. |
| 5,497,788 A | 3/1996 | Inman et al. |
| 5,538,500 A | 7/1996 | Peterson |
| 5,545,151 A | 8/1996 | O'Connor et al. |
| 5,549,584 A | 8/1996 | Gross |
| 5,562,107 A | 10/1996 | Lavender et al. |
| 5,579,765 A | 12/1996 | Cox et al. |
| 5,591,297 A | 1/1997 | Ahr |
| 5,603,946 A | 2/1997 | Constantine |
| 5,630,855 A | 5/1997 | Lundback |
| 5,634,391 A | 6/1997 | Eady |
| 5,636,643 A | 6/1997 | Argenta et al. |
| 5,637,080 A | 6/1997 | Geng |
| 5,645,081 A | 7/1997 | Argenta et al. |
| 5,662,599 A | 9/1997 | Reich et al. |
| 5,676,525 A | 10/1997 | Berner et al. |
| 5,685,214 A | 11/1997 | Neff et al. |
| 5,687,633 A | 11/1997 | Eady |
| 5,688,516 A | 11/1997 | Raad et al. |
| 5,693,013 A | 12/1997 | Geuder |
| 5,702,356 A | 12/1997 | Hathman |
| 5,704,905 A | 1/1998 | Jensen et al. |
| 5,707,173 A | 1/1998 | Cottone et al. |
| 5,713,384 A | 2/1998 | Roach et al. |
| 5,730,587 A | 3/1998 | Snyder et al. |
| 5,743,170 A | 4/1998 | Pascual et al. |
| 5,759,570 A | 6/1998 | Arnold |
| 5,762,638 A | 6/1998 | Shikani et al. |
| 5,769,608 A | 6/1998 | Seale |
| 5,785,508 A | 7/1998 | Bolt |
| 5,827,213 A | 10/1998 | Jensen |
| 5,840,052 A | 11/1998 | Johns |
| 5,843,025 A | 12/1998 | Shaari |
| 5,863,184 A | 1/1999 | Juterbock et al. |
| 5,882,743 A | 3/1999 | McConnell |
| 5,897,296 A | 4/1999 | Yamamoto et al. |
| 5,897,541 A | 4/1999 | Uitenbroek et al. |
| 5,950,523 A | 9/1999 | Reynolds |
| 6,040,493 A | 3/2000 | Cooke et al. |
| 6,056,519 A | 5/2000 | Morita et al. |
| 6,068,588 A | 5/2000 | Goldowsky |
| 6,071,267 A | 6/2000 | Zamierowski |
| 6,075,177 A | 6/2000 | Bahia et al. |
| 6,080,685 A | 6/2000 | Eady |
| 6,102,205 A | 8/2000 | Greff et al. |
| 6,102,680 A | 8/2000 | Fraser et al. |
| 6,124,520 A | 9/2000 | Roberts |
| 6,124,521 A | 9/2000 | Roberts |
| 6,138,550 A | 10/2000 | Fingar, Jr. |
| 6,142,982 A | 11/2000 | Hunt et al. |
| 6,145,430 A | 11/2000 | Able et al. |
| 6,158,327 A | 12/2000 | Huss |
| 6,162,194 A | 12/2000 | Shipp |
| 6,174,136 B1 | 1/2001 | Kilayko et al. |
| 6,174,306 B1 | 1/2001 | Fleischmann |
| 6,227,825 B1 | 5/2001 | Vay |
| 6,230,609 B1 | 5/2001 | Fingar |
| 6,231,310 B1 | 5/2001 | Tojo et al. |
| 6,249,198 B1 | 6/2001 | Clark et al. |
| 6,297,423 B1 | 10/2001 | Schoenfeldt et al. |
| 6,323,568 B1 | 11/2001 | Zabar |
| 6,327,960 B1 | 12/2001 | Heimueller et al. |
| 6,343,539 B1 | 2/2002 | Du |
| 6,362,390 B1 | 3/2002 | Carlucci et al. |
| 6,388,417 B1 * | 5/2002 | Keith .................... H02P 25/085 318/638 |
| 6,413,057 B1 | 7/2002 | Hong et al. |
| 6,506,175 B1 | 1/2003 | Goldstein |
| 6,514,047 B2 | 2/2003 | Burr et al. |
| 6,528,696 B1 | 3/2003 | Ireland |
| 6,540,490 B1 | 4/2003 | Lilie |
| 6,589,028 B1 | 7/2003 | Eckerbom et al. |
| 6,604,908 B1 | 8/2003 | Bryant et al. |
| 6,613,953 B1 | 9/2003 | Altura |
| 6,618,221 B2 | 9/2003 | Gillis et al. |
| 6,623,255 B2 | 9/2003 | Joong et al. |
| 6,626,891 B2 | 9/2003 | Ohmstede |
| 6,638,035 B1 | 10/2003 | Puff |
| 6,652,252 B2 | 11/2003 | Zabar |
| 6,655,257 B1 | 12/2003 | Meyer |
| 6,673,036 B1 | 1/2004 | Britto |
| 6,685,681 B2 | 2/2004 | Lockwood et al. |
| 6,719,742 B1 | 4/2004 | McCormack et al. |
| 6,752,794 B2 | 6/2004 | Lockwood et al. |
| 6,764,459 B1 | 7/2004 | Donaldson |
| 6,776,769 B2 | 8/2004 | Smith |
| 6,800,074 B2 | 10/2004 | Henley et al. |
| 6,815,846 B2 | 11/2004 | Godkin |
| 6,823,905 B1 | 11/2004 | Smith et al. |
| 6,824,533 B2 | 11/2004 | Risk, Jr. et al. |
| 6,877,419 B2 | 4/2005 | Ohrle et al. |
| 6,885,116 B2 | 4/2005 | Knirck |
| 6,936,037 B2 | 8/2005 | Bubb |
| 6,951,553 B2 | 10/2005 | Bubb et al. |
| 6,979,324 B2 | 12/2005 | Bybordi et al. |
| 7,041,057 B1 | 5/2006 | Faupel et al. |
| 7,049,478 B1 | 5/2006 | Smith et al. |
| 7,108,683 B2 | 9/2006 | Zamierowski |
| 7,128,735 B2 | 10/2006 | Weston |
| 7,151,348 B1 | 12/2006 | Ueda et al. |
| 7,294,752 B1 | 11/2007 | Propp |
| 7,361,184 B2 | 4/2008 | Joshi |
| 7,363,850 B2 | 4/2008 | Becker |
| 7,374,409 B2 | 5/2008 | Kawamura |

(56) References Cited

U.S. PATENT DOCUMENTS

| | | |
|---|---|---|
| 7,381,859 B2 | 6/2008 | Hunt et al. |
| 7,401,703 B2 | 7/2008 | McMichael et al. |
| 7,447,327 B2 | 11/2008 | Kitamura et al. |
| 7,524,315 B2 | 4/2009 | Blott et al. |
| 7,550,034 B2 | 6/2009 | Janse Van Rensburg et al. |
| 7,553,306 B1 | 6/2009 | Hunt et al. |
| 7,569,742 B2 | 8/2009 | Haggstrom et al. |
| 7,615,036 B2 | 11/2009 | Joshi et al. |
| 7,625,362 B2 | 12/2009 | Boehringer et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,722,582 B2 | 5/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,779,625 B2 | 8/2010 | Joshi et al. |
| 7,785,247 B2 | 8/2010 | Tatum et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,909,805 B2 | 3/2011 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,105,295 B2 | 1/2012 | Blott et al. |
| 8,118,794 B2 | 2/2012 | Weston |
| 8,152,785 B2 | 4/2012 | Vitaris |
| 8,162,907 B2 | 4/2012 | Heagle |
| 8,167,869 B2 | 5/2012 | Wudyka |
| 8,186,978 B2 | 5/2012 | Tinholt et al. |
| 8,188,331 B2 | 5/2012 | Barta et al. |
| 8,192,409 B2 | 6/2012 | Hardman et al. |
| 8,207,392 B2 | 6/2012 | Haggstrom et al. |
| 8,215,929 B2 | 7/2012 | Shen et al. |
| 8,241,015 B2 | 8/2012 | Lillie |
| 8,241,261 B2 | 8/2012 | Randolph et al. |
| 8,257,327 B2 | 9/2012 | Blott et al. |
| 8,257,328 B2 | 9/2012 | Augustine et al. |
| 8,282,611 B2 | 10/2012 | Weston |
| 8,294,586 B2 | 10/2012 | Pidgeon et al. |
| 8,303,552 B2 | 11/2012 | Weston |
| 8,323,264 B2 | 12/2012 | Weston et al. |
| 8,350,116 B2 | 1/2013 | Lockwood et al. |
| 8,363,881 B2 | 1/2013 | Godkin |
| 8,372,049 B2 | 2/2013 | Jaeb et al. |
| 8,372,050 B2 | 2/2013 | Jaeb et al. |
| 8,398,614 B2 | 3/2013 | Blott et al. |
| 8,404,921 B2 | 3/2013 | Lee et al. |
| 8,409,157 B2 | 4/2013 | Haggstrom et al. |
| 8,409,160 B2 | 4/2013 | Locke et al. |
| 8,414,519 B2 | 4/2013 | Hudspeth et al. |
| 8,425,478 B2 | 4/2013 | Olson |
| 8,429,778 B2 | 4/2013 | Receveur et al. |
| 8,444,612 B2 | 5/2013 | Patel et al. |
| 8,449,267 B2 | 5/2013 | Debrito et al. |
| 8,460,255 B2 | 6/2013 | Joshi et al. |
| 8,535,296 B2 | 9/2013 | Blott et al. |
| 8,545,464 B2 | 10/2013 | Weston |
| 8,569,566 B2 | 10/2013 | Blott et al. |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink |
| 8,646,479 B2 | 2/2014 | Jaeb et al. |
| 8,663,198 B2 | 3/2014 | Buan et al. |
| 8,715,256 B2 | 5/2014 | Greener |
| 8,734,131 B2 | 5/2014 | McCrone et al. |
| 8,764,732 B2 | 7/2014 | Hartwell |
| 8,791,316 B2 | 7/2014 | Greener |
| 8,795,243 B2 | 8/2014 | Weston |
| 8,808,274 B2 | 8/2014 | Hartwell |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,843,327 B2 | 9/2014 | Vernon-Harcourt et al. |
| 8,905,985 B2 | 12/2014 | Allen et al. |
| 8,945,074 B2 | 2/2015 | Buan et al. |
| 8,956,336 B2 | 2/2015 | Haggstrom et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,127,665 B2 | 9/2015 | Locke et al. |
| 2001/0001278 A1 | 5/2001 | Drevet |
| 2001/0033795 A1 | 10/2001 | Humpheries |
| 2001/0043870 A1 | 11/2001 | Song |
| 2002/0026946 A1 | 3/2002 | McKay |
| 2002/0122732 A1 | 9/2002 | Oh et al. |
| 2002/0161317 A1 | 10/2002 | Risk et al. |
| 2002/0164255 A1 | 11/2002 | Burr et al. |
| 2003/0035743 A1 | 2/2003 | Lee et al. |
| 2003/0040687 A1 | 2/2003 | Boynton et al. |
| 2003/0065292 A1 | 4/2003 | Darouiche et al. |
| 2003/0095879 A1 | 5/2003 | Oh et al. |
| 2003/0097100 A1 | 5/2003 | Watson |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0133812 A1 | 7/2003 | Puff et al. |
| 2003/0161735 A1 | 8/2003 | Kim et al. |
| 2003/0162071 A1 | 8/2003 | Yasuda |
| 2003/0175125 A1 | 9/2003 | Kwon et al. |
| 2003/0175135 A1 | 9/2003 | Heo et al. |
| 2003/0230191 A1 | 12/2003 | Ohrle et al. |
| 2004/0005222 A1 | 1/2004 | Yoshida et al. |
| 2004/0021123 A1 | 2/2004 | Howell et al. |
| 2004/0030304 A1 | 2/2004 | Hunt et al. |
| 2004/0054338 A1 | 3/2004 | Bybordi et al. |
| 2004/0066097 A1 | 4/2004 | Kobayashi et al. |
| 2004/0071568 A1 | 4/2004 | Hyeon |
| 2004/0071572 A1 | 4/2004 | Greter et al. |
| 2004/0115076 A1 | 6/2004 | Lilie et al. |
| 2004/0116551 A1 | 6/2004 | Terry |
| 2004/0118460 A1 | 6/2004 | Stinson |
| 2004/0126250 A1 | 7/2004 | Tsuchiya et al. |
| 2004/0155741 A1 | 8/2004 | Godin |
| 2004/0156527 A1* | 8/2004 | Stiles ............... H04R 9/063 381/412 |
| 2004/0156730 A1 | 8/2004 | Lilie et al. |
| 2004/0163713 A1 | 8/2004 | Schulze et al. |
| 2004/0182237 A1 | 9/2004 | Headley et al. |
| 2004/0189103 A1 | 9/2004 | Duncan et al. |
| 2005/0031470 A1 | 2/2005 | Lee |
| 2005/0098031 A1 | 5/2005 | Yoon et al. |
| 2005/0100450 A1 | 5/2005 | Bryant et al. |
| 2005/0110190 A1 | 5/2005 | Giardini |
| 2005/0111987 A1 | 5/2005 | Yoo et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0135946 A1 | 6/2005 | Kang et al. |
| 2005/0142007 A1 | 6/2005 | Lee et al. |
| 2005/0142008 A1 | 6/2005 | Jung et al. |
| 2005/0155657 A1 | 7/2005 | Kach et al. |
| 2005/0163635 A1 | 7/2005 | Berwanger et al. |
| 2005/0209560 A1 | 9/2005 | Boukhny et al. |
| 2005/0251117 A1 | 11/2005 | Anderson et al. |
| 2005/0261642 A1 | 11/2005 | Weston |
| 2005/0271526 A1 | 12/2005 | Chang et al. |
| 2005/0272142 A1 | 12/2005 | Horita |
| 2005/0276706 A1 | 12/2005 | Radue |
| 2006/0009744 A1 | 1/2006 | Erdman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029675 A1 | 2/2006 | Ginther |
| 2006/0039806 A1 | 2/2006 | Becker |
| 2006/0056979 A1 | 3/2006 | Yoo et al. |

(56) References Cited

U.S. PATENT DOCUMENTS

| | | |
|---|---|---|
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0073036 A1 | 4/2006 | Debrito et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0271020 A1 | 11/2006 | Huang et al. |
| 2006/0282174 A1 | 12/2006 | Haines |
| 2006/0287632 A1 | 12/2006 | Sarangapani |
| 2007/0016152 A1 | 1/2007 | Karpowicz et al. |
| 2007/0032741 A1 | 2/2007 | Hibner et al. |
| 2007/0040454 A1 | 2/2007 | Freudenberger et al. |
| 2007/0041856 A1 | 2/2007 | Hansen et al. |
| 2007/0052144 A1 | 3/2007 | Knirck et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0167927 A1 | 7/2007 | Hunt et al. |
| 2007/0179460 A1 | 8/2007 | Adahan |
| 2007/0196214 A1 | 8/2007 | Bocchiola |
| 2007/0218101 A1 | 9/2007 | Johnson et al. |
| 2007/0219532 A1 | 9/2007 | Karpowicz et al. |
| 2007/0225663 A1 | 9/2007 | Watt et al. |
| 2007/0256428 A1 | 11/2007 | Unger et al. |
| 2007/0260226 A1 | 11/2007 | Jaeb et al. |
| 2007/0282283 A1 | 12/2007 | Kaern et al. |
| 2007/0292286 A1 | 12/2007 | Hell et al. |
| 2007/0295201 A1 | 12/2007 | Dadd |
| 2008/0008607 A1 | 1/2008 | Schade et al. |
| 2008/0015526 A1 | 1/2008 | Reiner et al. |
| 2008/0020178 A1 | 1/2008 | Oehrle et al. |
| 2008/0051708 A1 | 2/2008 | Kumar et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0082059 A1 | 4/2008 | Fink et al. |
| 2008/0089796 A1 | 4/2008 | Schade et al. |
| 2008/0094753 A1 | 4/2008 | Brodkin et al. |
| 2008/0110336 A1 | 5/2008 | Bovill et al. |
| 2008/0125697 A1 | 5/2008 | Gao |
| 2008/0125698 A1 | 5/2008 | Gerg et al. |
| 2008/0132821 A1 | 6/2008 | Propp et al. |
| 2008/0191399 A1 | 8/2008 | Chang |
| 2008/0211435 A1 | 9/2008 | Imagawa |
| 2008/0234641 A1 | 9/2008 | Locke et al. |
| 2008/0240942 A1 | 10/2008 | Heinrich et al. |
| 2008/0260551 A1 | 10/2008 | Simmons |
| 2008/0267797 A1 | 10/2008 | Hell et al. |
| 2008/0281281 A1 | 11/2008 | Meyer et al. |
| 2008/0306456 A1 | 12/2008 | Riesinger |
| 2008/0310980 A1 | 12/2008 | Ramsdorf et al. |
| 2009/0012441 A1 | 1/2009 | Mulligan |
| 2009/0028733 A1* | 1/2009 | Duwel ............... F04B 39/1066 417/546 |
| 2009/0053081 A1 | 2/2009 | Griffiths |
| 2009/0054855 A1 | 2/2009 | Blott et al. |
| 2009/0060750 A1 | 3/2009 | Chen et al. |
| 2009/0071551 A1 | 3/2009 | Chalich |
| 2009/0081049 A1 | 3/2009 | Tian et al. |
| 2009/0087323 A1 | 4/2009 | Blakey et al. |
| 2009/0114293 A1 | 5/2009 | Kanai et al. |
| 2009/0125004 A1 | 5/2009 | Shen et al. |
| 2009/0129955 A1 | 5/2009 | Schubert |
| 2009/0129986 A1 | 5/2009 | Wimberger-Friedl et al. |
| 2009/0148320 A1 | 6/2009 | Lucas |
| 2009/0149821 A1 | 6/2009 | Scherson et al. |
| 2009/0166411 A1 | 7/2009 | Kramer et al. |
| 2009/0169402 A1 | 7/2009 | Stenberg |
| 2009/0206778 A1 | 8/2009 | Roh et al. |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0280015 A1 | 11/2009 | Lillie et al. |
| 2009/0292263 A1 | 11/2009 | Hudspeth et al. |
| 2009/0292264 A1 | 11/2009 | Hudspeth et al. |
| 2009/0299251 A1 | 12/2009 | Buan |
| 2009/0299306 A1 | 12/2009 | Buan |
| 2009/0304534 A1 | 12/2009 | Richter |
| 2009/0312725 A1 | 12/2009 | Braga |
| 2010/0042059 A1 | 2/2010 | Pratt et al. |
| 2010/0068820 A1 | 3/2010 | Meathrel et al. |
| 2010/0098566 A1 | 4/2010 | Kang |
| 2010/0125258 A1 | 5/2010 | Coulthard et al. |
| 2010/0145289 A1 | 6/2010 | Line et al. |
| 2010/0160876 A1 | 6/2010 | Robinson et al. |
| 2010/0160881 A1 | 6/2010 | Lin et al. |
| 2010/0191178 A1 | 7/2010 | Ross et al. |
| 2010/0204663 A1 | 8/2010 | Wudyka |
| 2010/0211030 A1 | 8/2010 | Turner et al. |
| 2010/0244780 A1 | 9/2010 | Turner et al. |
| 2010/0265649 A1 | 10/2010 | Singh et al. |
| 2010/0268179 A1 | 10/2010 | Kelch et al. |
| 2010/0280435 A1 | 11/2010 | Raney et al. |
| 2010/0298792 A1 | 11/2010 | Weston et al. |
| 2010/0305526 A1 | 12/2010 | Robinson et al. |
| 2010/0318052 A1 | 12/2010 | Ha et al. |
| 2010/0318071 A1 | 12/2010 | Wudyka |
| 2010/0320659 A1 | 12/2010 | Chen et al. |
| 2010/0324510 A1 | 12/2010 | Andresen et al. |
| 2011/0000069 A1 | 1/2011 | Ramsdorf et al. |
| 2011/0004172 A1 | 1/2011 | Eckstein et al. |
| 2011/0015587 A1 | 1/2011 | Tumey et al. |
| 2011/0020588 A1 | 1/2011 | Shimizu et al. |
| 2011/0028918 A1 | 2/2011 | Hartwell |
| 2011/0038741 A1 | 2/2011 | Lissner et al. |
| 2011/0043055 A1 | 2/2011 | Chiang |
| 2011/0054421 A1 | 3/2011 | Hartwell |
| 2011/0071415 A1 | 3/2011 | Karwoski et al. |
| 2011/0081267 A1 | 4/2011 | McCrone et al. |
| 2011/0087178 A2 | 4/2011 | Weston |
| 2011/0098600 A1 | 4/2011 | Matsumura et al. |
| 2011/0103984 A1 | 5/2011 | Santa |
| 2011/0118683 A1 | 5/2011 | Weston |
| 2011/0169348 A1 | 7/2011 | Park |
| 2011/0171044 A1 | 7/2011 | Flanigan |
| 2011/0172615 A2 | 7/2011 | Greener |
| 2011/0176945 A1 | 7/2011 | Drevet |
| 2011/0176946 A1 | 7/2011 | Drevet |
| 2011/0184341 A1 | 7/2011 | Baker et al. |
| 2011/0186765 A1 | 8/2011 | Jaeb et al. |
| 2011/0205646 A1 | 8/2011 | Sato et al. |
| 2011/0205647 A1 | 8/2011 | Osaka et al. |
| 2011/0224631 A1 | 9/2011 | Simmons et al. |
| 2011/0229352 A1 | 9/2011 | Timmer |
| 2011/0236265 A1 | 9/2011 | Hasui et al. |
| 2011/0236277 A1 | 9/2011 | Lee et al. |
| 2011/0237863 A1 | 9/2011 | Ricci et al. |
| 2011/0251569 A1 | 10/2011 | Turner et al. |
| 2011/0257572 A1 | 10/2011 | Locke et al. |
| 2011/0282309 A1 | 11/2011 | Adie et al. |
| 2011/0311379 A1 | 12/2011 | Hale et al. |
| 2012/0000208 A1 | 1/2012 | Hon et al. |
| 2012/0008817 A1 | 1/2012 | Grinker et al. |
| 2012/0016323 A1* | 1/2012 | Robinson ............... A61F 13/02 604/319 |
| 2012/0034109 A1 | 2/2012 | Tout et al. |
| 2012/0041399 A1 | 2/2012 | Blott et al. |
| 2012/0046625 A1 | 2/2012 | Johannison |
| 2012/0053543 A1 | 3/2012 | Miau et al. |
| 2012/0095380 A1 | 4/2012 | Gergeley et al. |
| 2012/0109083 A1 | 5/2012 | Coulthard et al. |
| 2012/0109084 A1 | 5/2012 | Blott et al. |
| 2012/0136325 A1 | 5/2012 | Allen et al. |
| 2012/0157942 A1 | 6/2012 | Weston |

(56) References Cited

U.S. PATENT DOCUMENTS

| | | |
|---|---|---|
| 2012/0160091 A1 | 6/2012 | Dadd et al. |
| 2012/0177513 A1 | 7/2012 | Lilie et al. |
| 2012/0184930 A1 | 7/2012 | Johannison |
| 2012/0220960 A1 | 8/2012 | Ruland |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2012/0301341 A1 | 11/2012 | Ota et al. |
| 2013/0017110 A1 | 1/2013 | Villagomez et al. |
| 2013/0042753 A1 | 2/2013 | Becker et al. |
| 2013/0085462 A1 | 4/2013 | Nip et al. |
| 2013/0090613 A1 | 4/2013 | Kelch et al. |
| 2013/0116635 A1 | 5/2013 | Fleischmann |
| 2013/0118622 A1 | 5/2013 | Patzold et al. |
| 2013/0123755 A1 | 5/2013 | Locke et al. |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0209277 A1 | 8/2013 | Locke et al. |
| 2013/0209278 A1 | 8/2013 | Locke et al. |
| 2013/0209279 A1 | 8/2013 | Locke et al. |
| 2013/0209281 A1 | 8/2013 | Locke et al. |
| 2013/0213506 A1 | 8/2013 | Chen et al. |
| 2013/0223979 A1 | 8/2013 | Locke et al. |
| 2013/0236338 A1 | 9/2013 | Locke et al. |
| 2013/0267917 A1 | 10/2013 | Pan et al. |
| 2013/0274688 A1 | 10/2013 | Weston |
| 2013/0276906 A1 | 10/2013 | Locke et al. |
| 2013/0280113 A1 | 10/2013 | Miranda et al. |
| 2013/0331822 A1 | 12/2013 | Patel et al. |
| 2013/0340870 A1 | 12/2013 | Ito et al. |
| 2014/0010673 A1 | 1/2014 | Locke et al. |
| 2014/0017093 A1 | 1/2014 | Locke et al. |
| 2014/0018753 A1 | 1/2014 | Joshi et al. |
| 2014/0072149 A1 | 3/2014 | Yan et al. |
| 2014/0100516 A1 | 4/2014 | Hunt et al. |
| 2014/0107599 A1 | 4/2014 | Fink et al. |
| 2014/0114236 A1 | 4/2014 | Gordon |
| 2014/0114237 A1 | 4/2014 | Gordon |
| 2014/0114268 A1 | 4/2014 | Auguste et al. |
| 2014/0163490 A1 | 6/2014 | Locke et al. |
| 2014/0194835 A1 | 7/2014 | Ehlert |
| 2014/0228791 A1 | 8/2014 | Hartwell |
| 2014/0236106 A1 | 8/2014 | Locke et al. |
| 2014/0249493 A1 | 9/2014 | Hartwell |
| 2014/0276487 A1 | 9/2014 | Locke et al. |
| 2014/0303551 A1 | 10/2014 | Germain et al. |
| 2014/0316359 A1 | 10/2014 | Collinson et al. |
| 2014/0323906 A1 | 10/2014 | Peatfield et al. |
| 2015/0025482 A1 | 1/2015 | Begin et al. |
| 2015/0032035 A1 | 1/2015 | Banwell et al. |
| 2015/0051560 A1 | 2/2015 | Askem |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0100045 A1 | 4/2015 | Allen et al. |
| 2015/0159066 A1 | 6/2015 | Hartwell et al. |

FOREIGN PATENT DOCUMENTS

| | | |
|---|---|---|
| DE | 39 16 648 | 9/1990 |
| DE | 90 17 289 | 6/1992 |
| DE | 198 44 355 | 4/2000 |
| DE | 10 2005 007016 | 8/2006 |
| EP | 0 208 395 | 1/1987 |
| EP | 0 411 564 | 7/1990 |
| EP | 0 541 251 | 5/1993 |
| EP | 0 578 999 | 6/1993 |
| EP | 0 604 953 | 7/1994 |
| EP | 0 578 999 | 5/1996 |
| EP | 0 759 521 | 2/1997 |
| EP | 0775825 | 5/1997 |
| EP | 0 759 521 | 7/1997 |
| EP | 0 793 019 A2 | 9/1997 |
| EP | 0793019 | 9/1997 |
| EP | 0809028 | 11/1997 |
| EP | 0 909 895 | 10/1998 |
| EP | 0898076 | 2/1999 |
| EP | 0 941 726 | 9/1999 |
| EP | 0 688 189 | 9/2000 |
| EP | 1 114 933 | 1/2001 |
| EP | 1 153 218 | 11/2001 |
| EP | 0 909 895 | 12/2002 |
| EP | 0 708 620 | 5/2003 |
| EP | 0 993 317 | 9/2003 |
| EP | 1 406 020 | 9/2003 |
| EP | 1 554 737 A1 | 5/2004 |
| EP | 1 556 942 A1 | 5/2004 |
| EP | 1 449 971 | 8/2004 |
| EP | 1 452 156 | 9/2004 |
| EP | 1 476 217 | 11/2004 |
| EP | 1 469 580 | 12/2005 |
| EP | 1 757 809 | 8/2006 |
| EP | 1 850 005 | 10/2007 |
| EP | 1 897 569 | 3/2008 |
| EP | 1 430 588 B1 | 6/2008 |
| EP | 1 460 270 | 6/2008 |
| EP | 1 791 579 | 7/2009 |
| EP | 1 513 478 | 12/2009 |
| EP | 2 129 915 | 12/2009 |
| EP | 2 145 636 | 1/2010 |
| EP | 2 161 011 | 3/2010 |
| EP | 2 161 448 | 3/2010 |
| EP | 1 932 481 | 6/2010 |
| EP | 2 216 573 | 8/2010 |
| EP | 2 253 353 | 11/2010 |
| EP | 2 302 127 | 3/2011 |
| EP | 1 956 242 | 4/2011 |
| EP | 2 366 721 | 9/2011 |
| EP | 2 577 062 | 12/2011 |
| EP | 1 169 071 | 2/2012 |
| EP | 2 462 908 | 6/2012 |
| EP | 2 531 160 | 12/2012 |
| EP | 2 531 761 | 12/2012 |
| EP | 1 875 081 | 12/2013 |
| EP | 2 616 116 | 12/2014 |
| EP | 2 544 642 | 1/2015 |
| EP | 2 648 668 | 1/2015 |
| EP | 2 830 555 | 2/2015 |
| EP | 2 836 711 | 2/2015 |
| FR | 1163907 | 10/1958 |
| FR | 2939320 | 6/2010 |
| GB | 1 039 145 | 8/1966 |
| GB | 1220857 | 1/1971 |
| GB | 2099306 | 12/1982 |
| GB | 2 235 877 A | 3/1991 |
| GB | 2 273 133 A | 6/1994 |
| GB | 2 306 580 A | 5/1997 |
| GB | 2433298 | 3/2007 |
| GB | 2435422 | 8/2007 |
| JP | 52-040804 | 3/1977 |
| JP | 2000220570 A | 8/2000 |
| JP | 2006/233925 | 9/2006 |
| JP | 2006233925 A | 9/2006 |
| WO | WO 87/07683 | 12/1987 |
| WO | WO 94/21312 | 9/1994 |
| WO | WO 94/23677 | 10/1994 |
| WO | WO 95/04511 | 2/1995 |
| WO | WO 95/14451 | 6/1995 |
| WO | WO 96/21410 | 7/1996 |
| WO | WO 97/11658 | 4/1997 |
| WO | WO 99/39671 | 8/1999 |
| WO | WO 00/00743 | 1/2000 |
| WO | WO 00/07653 | 2/2000 |
| WO | WO 00/22298 | 4/2000 |
| WO | WO 00/42957 | 7/2000 |
| WO | WO 00/49968 | 8/2000 |
| WO | WO 00/56378 | 9/2000 |
| WO | WO 00/79154 | 12/2000 |
| WO | WO 01/16488 | 3/2001 |

(56) References Cited

FOREIGN PATENT DOCUMENTS

| | | |
|---|---|---|
| WO | WO 01/79693 | 10/2001 |
| WO | WO 02/17840 | 3/2002 |
| WO | WO 02/26180 | 4/2002 |
| WO | WO 02/38096 | 5/2002 |
| WO | WO 02/076379 | 10/2002 |
| WO | WO 02/087058 | 10/2002 |
| WO | WO 02/090772 | 11/2002 |
| WO | WO 03/018098 | 3/2003 |
| WO | WO 03/057071 | 7/2003 |
| WO | WO 03/057307 A1 | 7/2003 |
| WO | WO 03/085810 A1 | 10/2003 |
| WO | WO 03/101508 | 12/2003 |
| WO | WO 2004/007960 | 1/2004 |
| WO | WO 2004/060225 | 7/2004 |
| WO | WO 2004/073566 | 9/2004 |
| WO | WO 2004/081421 A2 | 9/2004 |
| WO | WO 2005/001286 | 1/2005 |
| WO | WO 2005/001287 | 1/2005 |
| WO | WO 2005/009488 | 2/2005 |
| WO | WO 2005/046761 | 5/2005 |
| WO | WO 2005/123170 | 12/2005 |
| WO | WO 2006/046060 A2 | 5/2006 |
| WO | WO 2006/052839 | 5/2006 |
| WO | WO 2006/058801 | 6/2006 |
| WO | WO 2006/059098 A1 | 6/2006 |
| WO | WO 2006/062276 A1 | 6/2006 |
| WO | WO 2006/069875 | 7/2006 |
| WO | WO 2006/069884 | 7/2006 |
| WO | WO 2006/069885 | 7/2006 |
| WO | WO 2006/092333 | 9/2006 |
| WO | WO 2006/111775 | 10/2006 |
| WO | WO 2006/117207 | 11/2006 |
| WO | WO 2006/122268 | 11/2006 |
| WO | WO 2007/030601 | 3/2007 |
| WO | WO 2007/049876 | 5/2007 |
| WO | WO 2007/055642 | 5/2007 |
| WO | WO 2007/067359 | 6/2007 |
| WO | WO 2007/087810 A2 | 8/2007 |
| WO | WO 2007/087811 A1 | 8/2007 |
| WO | WO 2008/013896 | 1/2008 |
| WO | WO 2008/027449 | 3/2008 |
| WO | WO 2008/031418 | 3/2008 |
| WO | WO 2008/048527 | 4/2008 |
| WO | WO 2008/049277 | 5/2008 |
| WO | WO 2008/100440 A1 | 8/2008 |
| WO | WO 2008/110022 | 8/2008 |
| WO | WO 2008/131895 | 11/2008 |
| WO | WO 2008/135997 A2 | 11/2008 |
| WO | WO 2009/019415 A2 | 2/2009 |
| WO | WO 2009/047524 A2 | 4/2009 |
| WO | WO 2009/066104 A1 | 5/2009 |
| WO | WO 2009/071935 | 6/2009 |
| WO | WO 2009/089390 A2 | 7/2009 |
| WO | WO 2009/095170 A2 | 8/2009 |
| WO | WO 2009/124100 | 10/2009 |
| WO | WO 2009/126103 A1 | 10/2009 |
| WO | WO 2009/146441 | 12/2009 |
| WO | WO 2009/158128 | 12/2009 |
| WO | WO 2010/039481 A1 | 4/2010 |
| WO | WO 2010/051068 | 5/2010 |
| WO | WO 2010/056977 | 5/2010 |
| WO | WO 2010/079359 A1 | 7/2010 |
| WO | WO 2010/082872 | 7/2010 |
| WO | WO 2010/089448 | 8/2010 |
| WO | WO 2010/093753 A1 | 8/2010 |
| WO | WO 2010/126444 A1 | 11/2010 |
| WO | WO 2010/139926 | 12/2010 |
| WO | WO 2010/142959 | 12/2010 |
| WO | WO 2011/003163 | 1/2011 |
| WO | WO 2011/023650 | 3/2011 |
| WO | WO 2011/068310 | 6/2011 |
| WO | WO 2011/082461 | 7/2011 |
| WO | WO 2011/082461 A1 | 7/2011 |
| WO | WO 2011/087871 A2 | 7/2011 |
| WO | WO 2011/097361 | 8/2011 |
| WO | WO 2011/097362 | 8/2011 |
| WO | WO 2011/103890 | 9/2011 |
| WO | WO 2011/130542 | 10/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/146535 A1 | 11/2011 |
| WO | WO 2011/148188 A1 | 12/2011 |
| WO | WO 2011/150529 | 12/2011 |
| WO | WO 2012/009370 | 1/2012 |
| WO | WO 2012/034238 | 3/2012 |
| WO | WO 2012/048179 A2 | 4/2012 |
| WO | WO 2012/074512 | 6/2012 |
| WO | WO 2012/088572 A1 | 7/2012 |
| WO | WO 2012/095245 A2 | 7/2012 |
| WO | WO 2012/131237 | 10/2012 |
| WO | WO 2012/140180 | 10/2012 |
| WO | WO 2012/140378 | 10/2012 |
| WO | WO 2012/142002 | 10/2012 |
| WO | WO 2012/143665 | 10/2012 |
| WO | WO 2012/146656 | 11/2012 |
| WO | WO 2012/150235 | 11/2012 |
| WO | WO 2013/006932 | 1/2013 |
| WO | WO 2013/007973 A2 | 1/2013 |
| WO | WO 2013/010907 | 1/2013 |
| WO | WO 2013/019017 | 2/2013 |
| WO | WO 2013/064852 | 5/2013 |
| WO | WO 2013/065423 | 5/2013 |
| WO | WO 2013/083800 | 6/2013 |
| WO | WO 2013/090810 | 6/2013 |
| WO | WO 2013/117945 | 8/2013 |
| WO | WO 2013/118447 | 8/2013 |
| WO | WO 2013/119854 | 8/2013 |
| WO | WO 2013/133652 | 9/2013 |
| WO | WO 2013/149078 | 10/2013 |
| WO | WO 2013/158897 | 10/2013 |
| WO | WO 2013/136181 | 11/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/022440 | 2/2014 |
| WO | WO 2014/108476 | 7/2014 |
| WO | WO 2014/113253 | 7/2014 |
| WO | WO 2015/022334 | 2/2015 |
| WO | WO 2015/022340 | 2/2015 |
| WO | WO 2015/023515 | 2/2015 |
| WO | WO 2015/031216 | 3/2015 |

OTHER PUBLICATIONS

Park, Se-Myung, Design and Analysis of VCA for fuel pump in Automobile, World Academy of Science, Engineering and Technology 80, 2011.

International Partial Search Report (and Invitation to Pay) re PCT/IB2013/001513, mailed Sep. 30, 2013.

International Search Report in International Application No. PCT/IB2013/001513, mailed Nov. 2, 2014 in 5 pages.

Protz, Kerstin: "Modern Wundauflagen unterstutzen Heilungsprozess", Wundversorgung: Indikation und Anwendung, Geriatrie Journal, Apr. 2005, pp. 3333-3339, with translation.

* cited by examiner

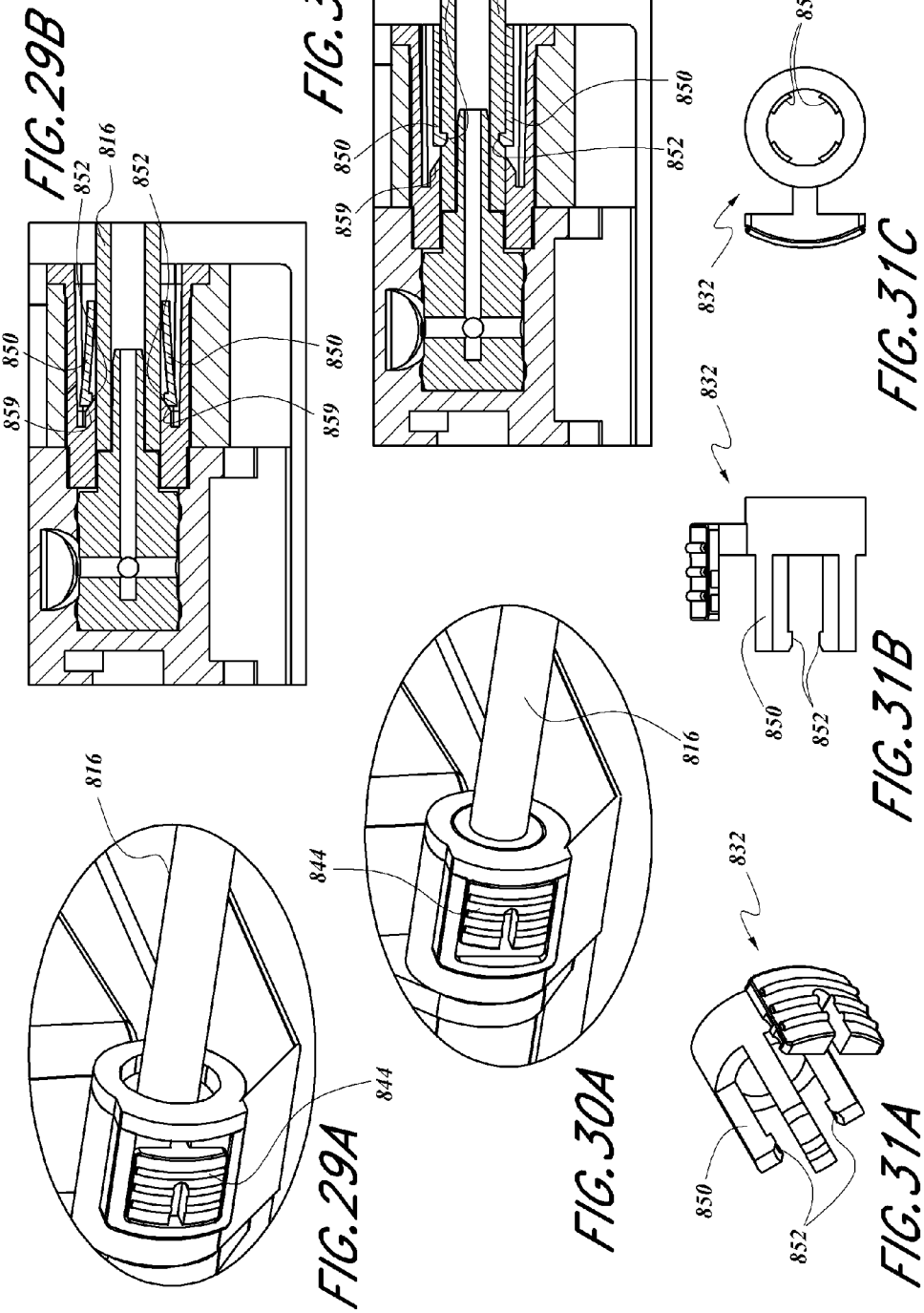

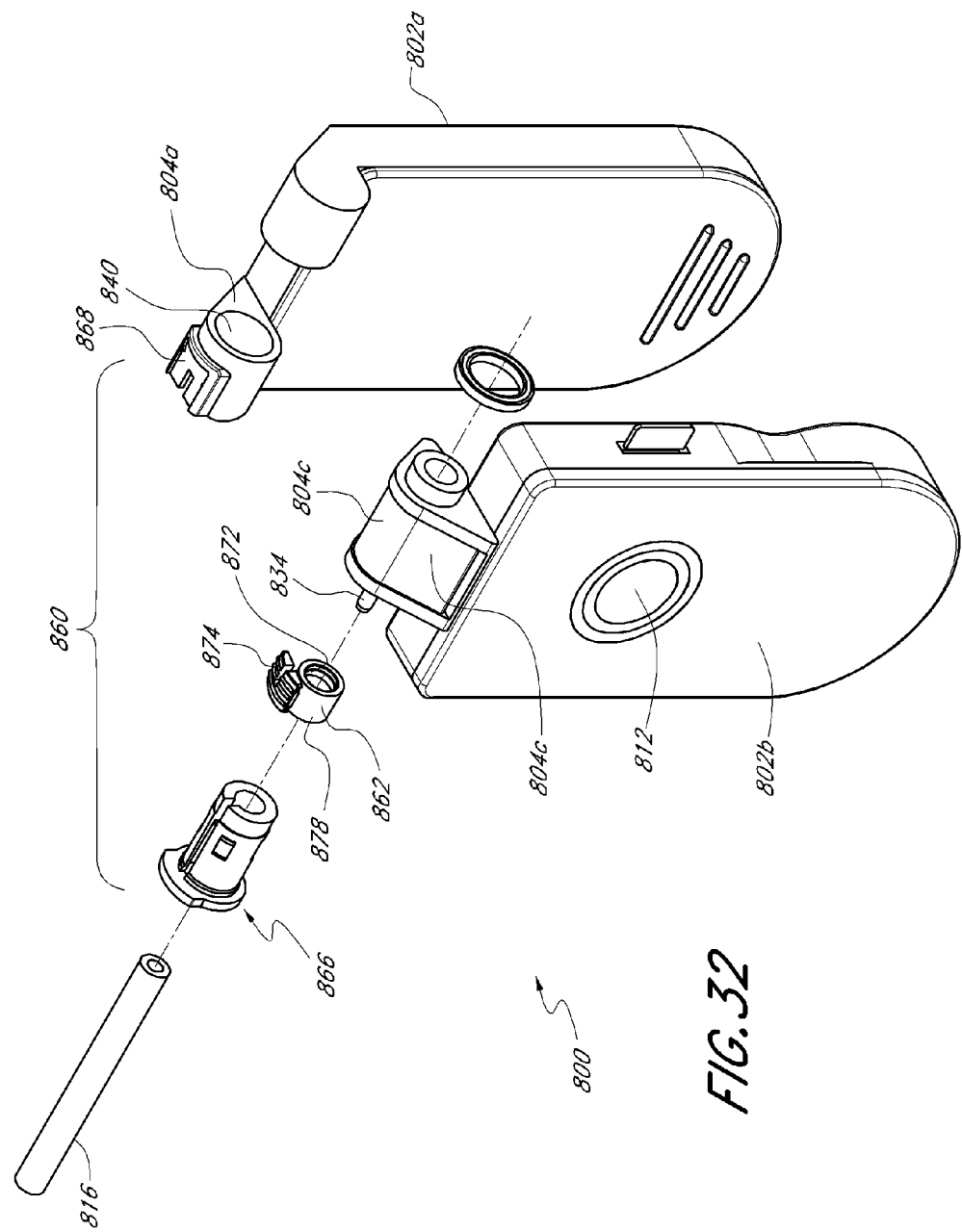

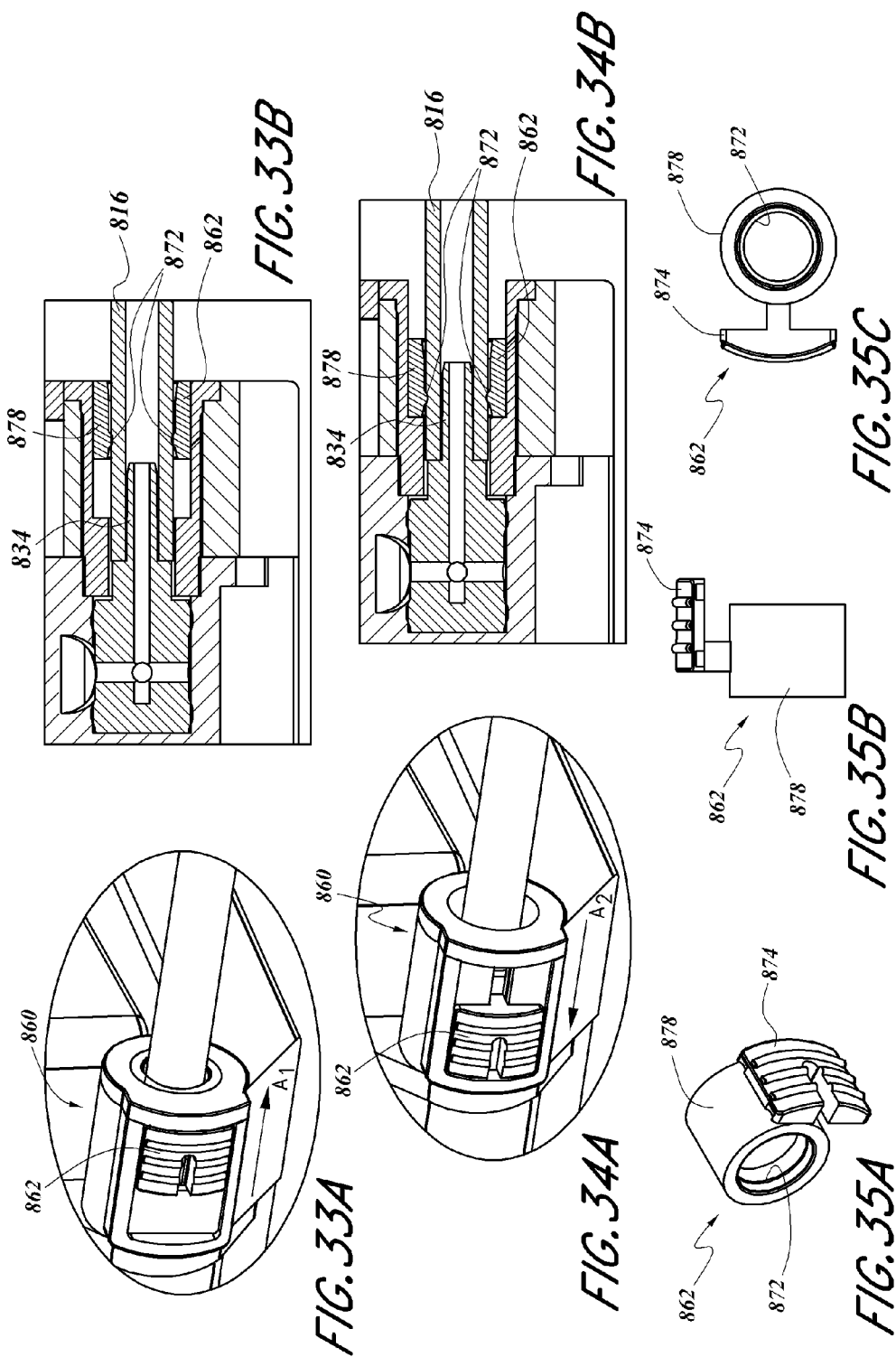

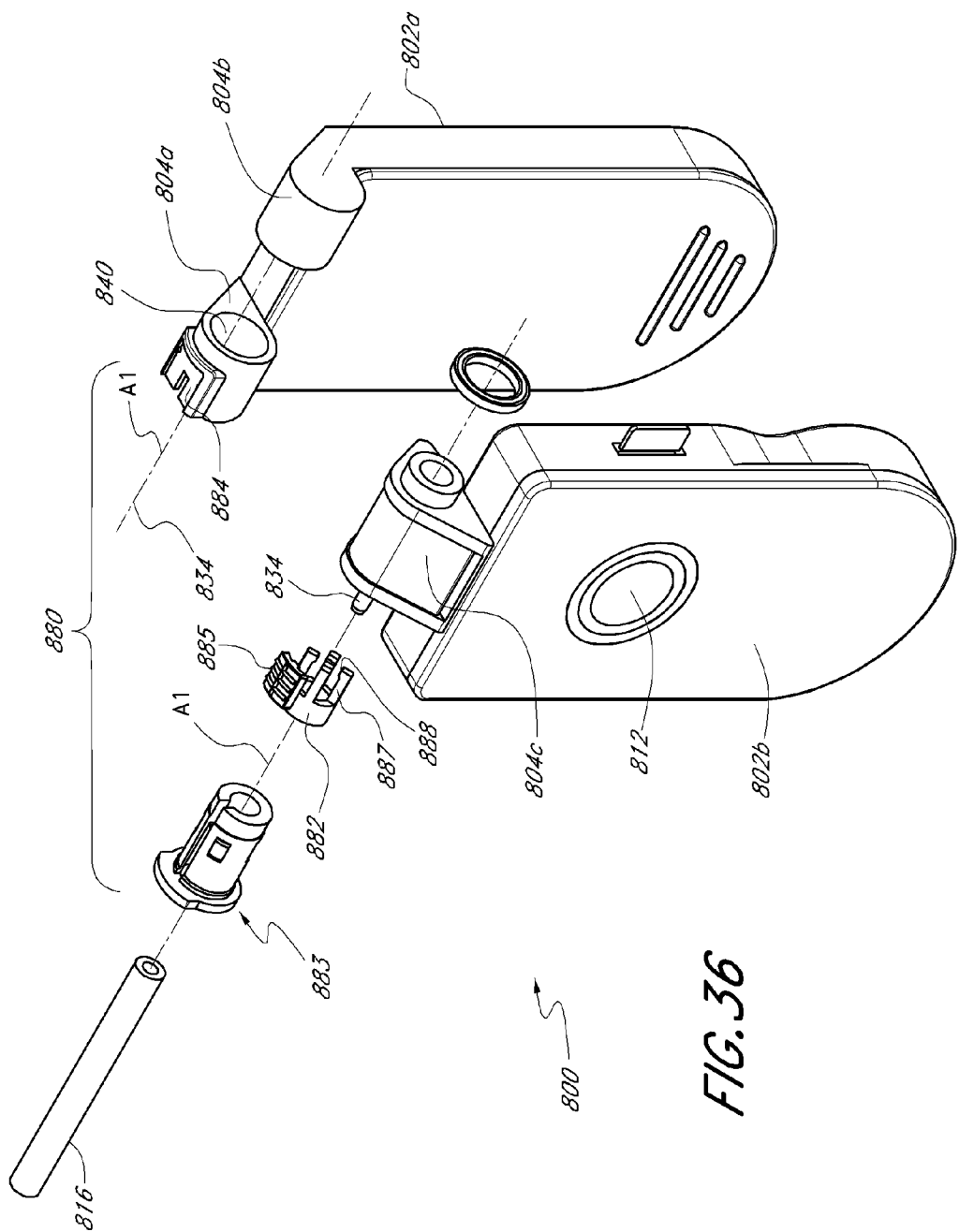

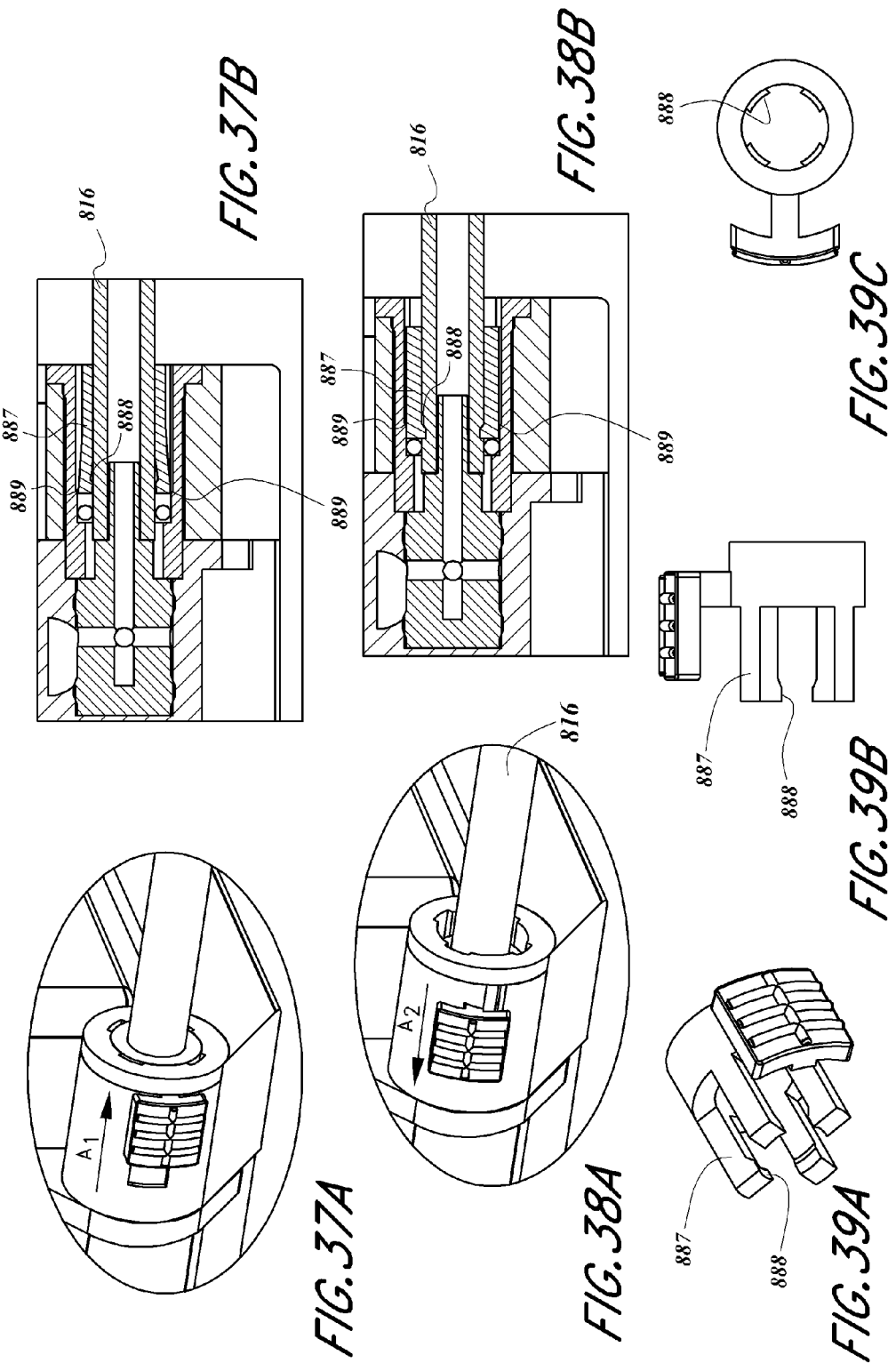

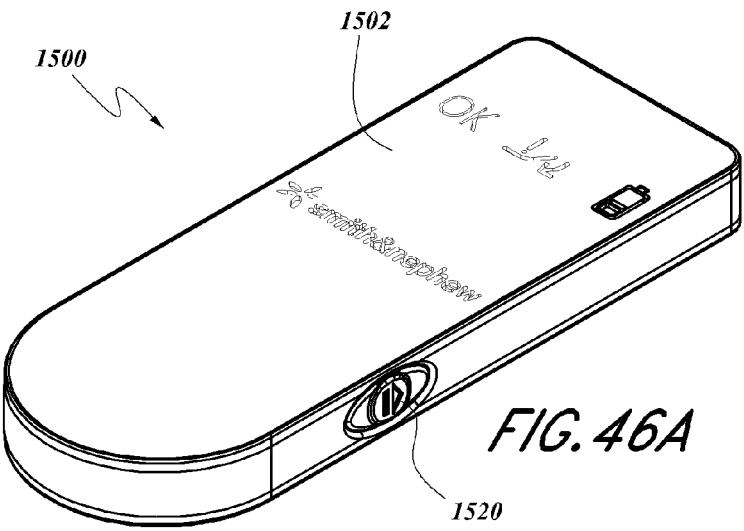
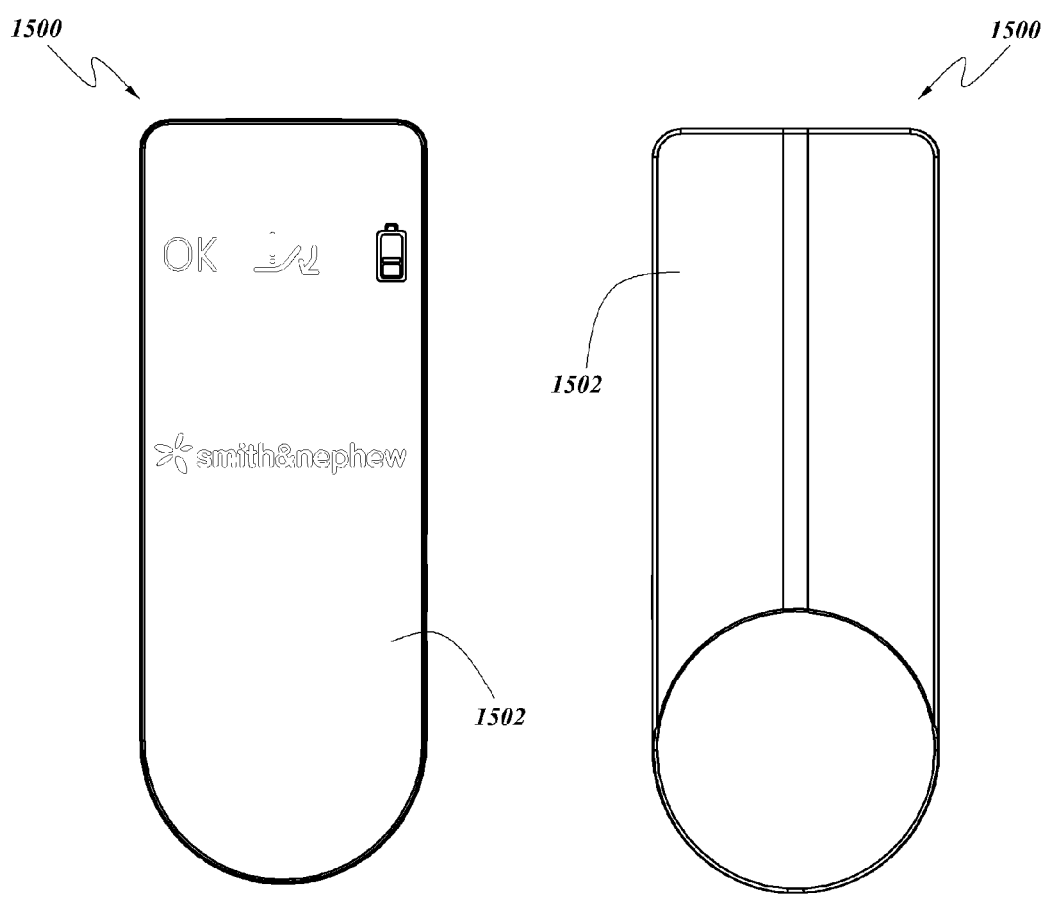
FIG. 46A
FIG. 46B
FIG. 46C

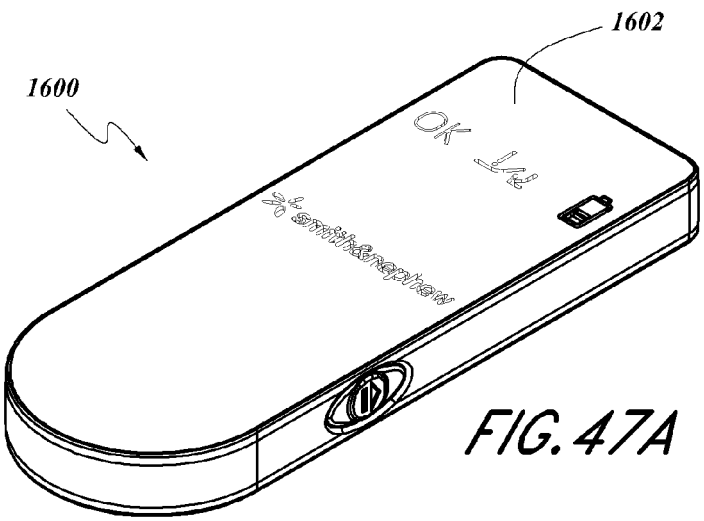
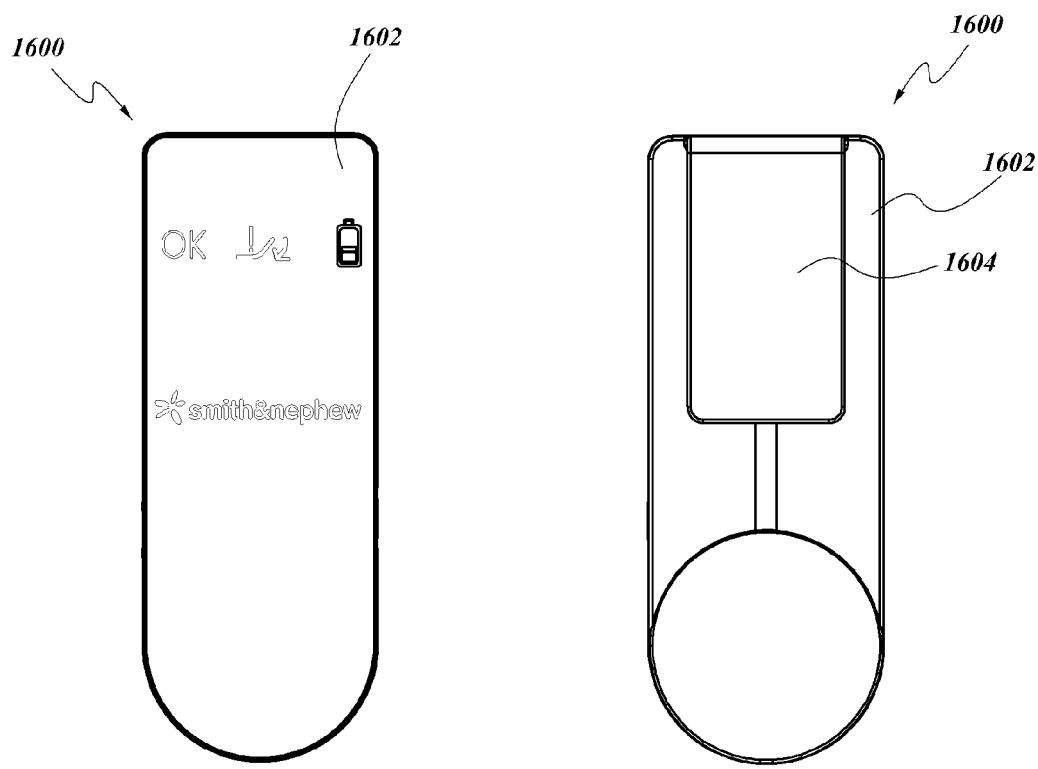
FIG. 47A
FIG. 47B    FIG. 47C

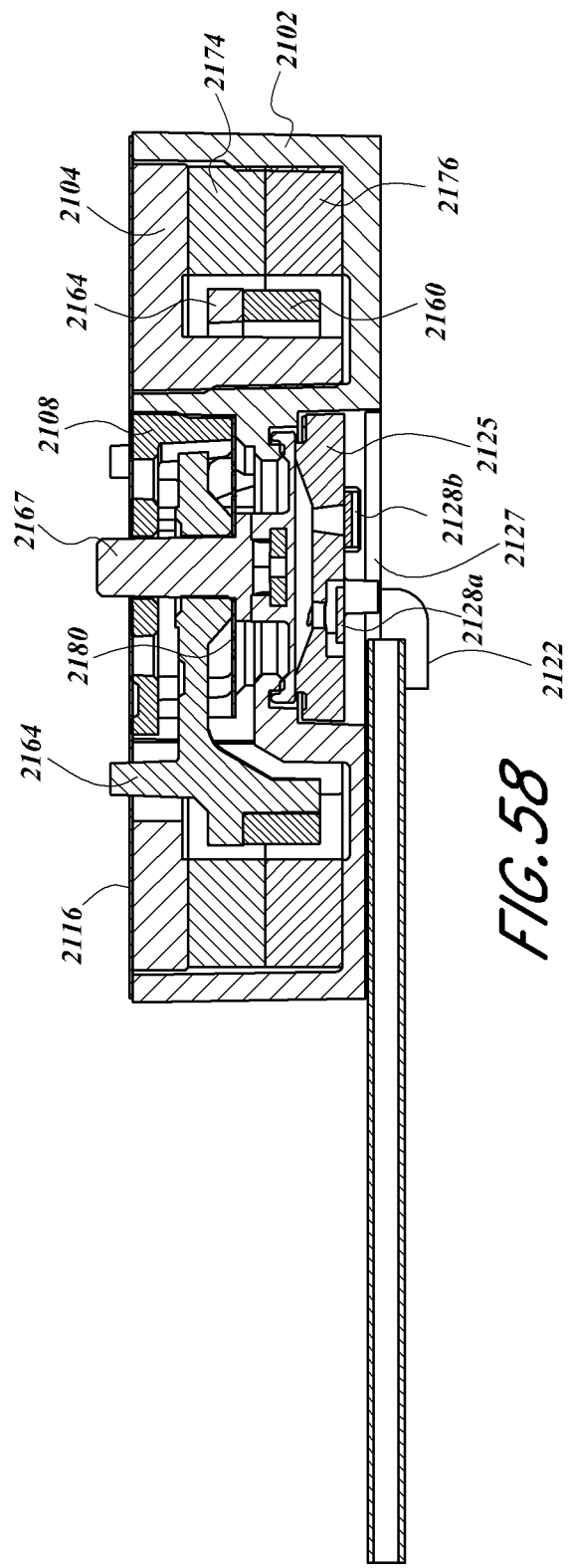

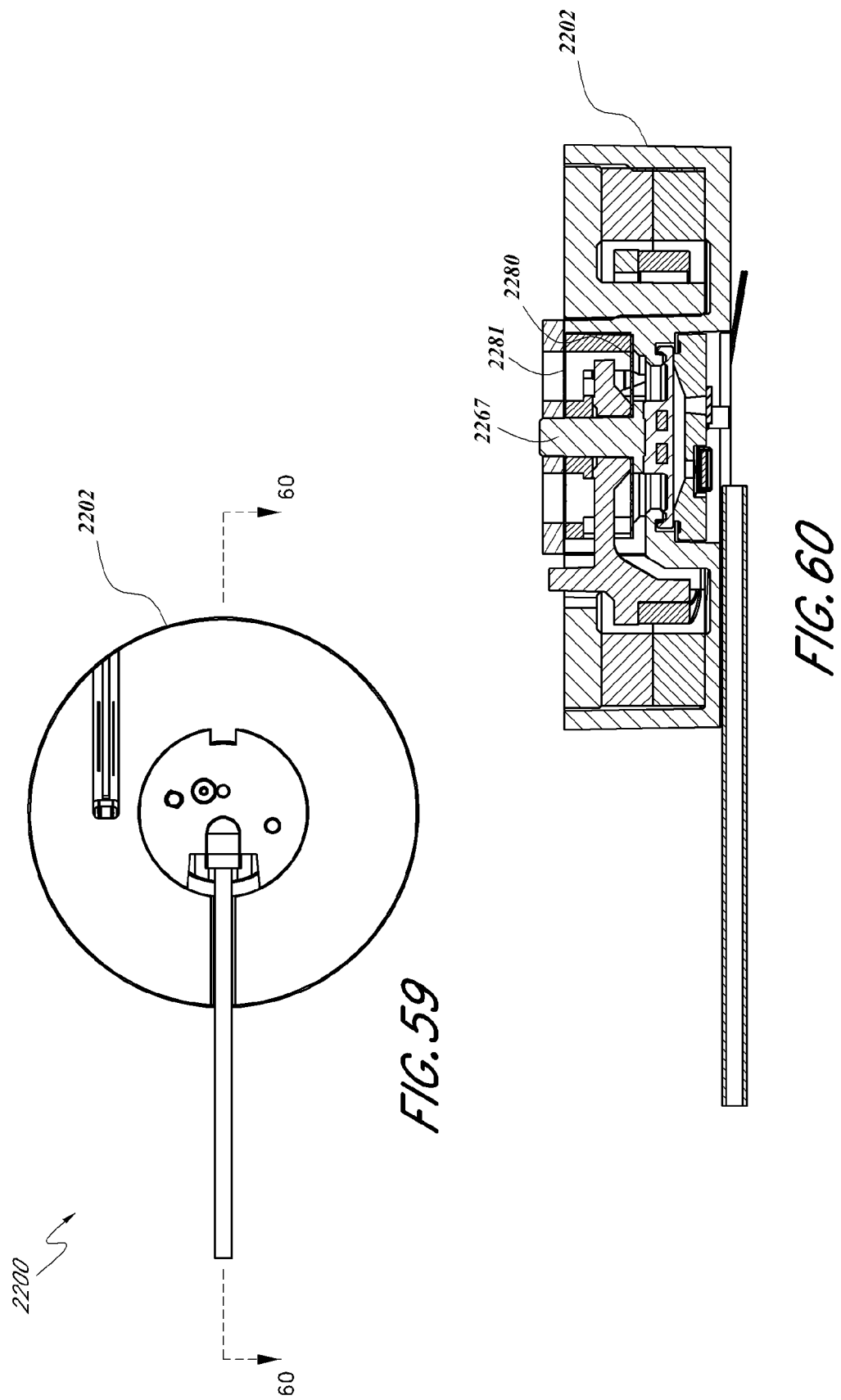

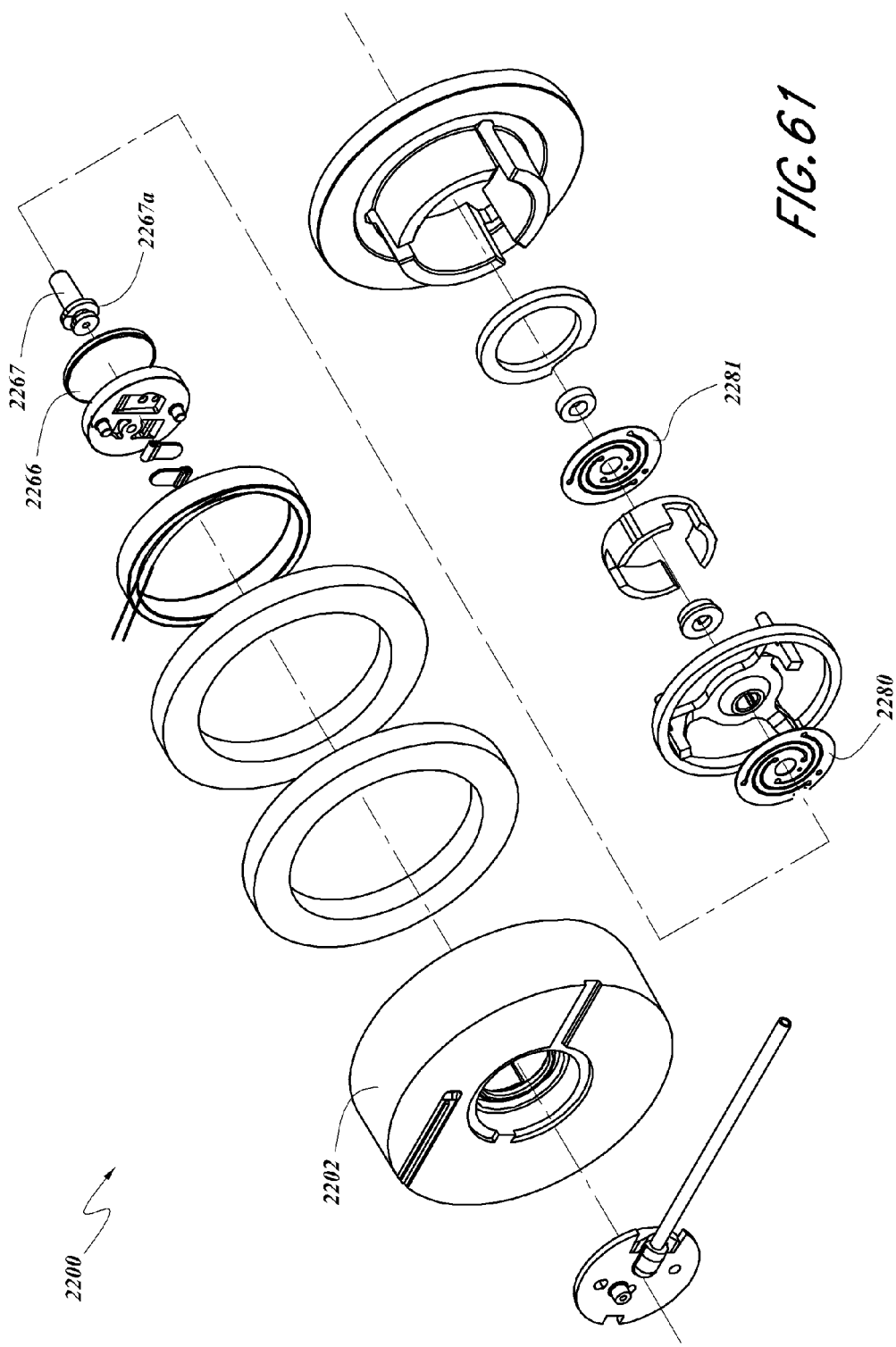

| | | |
|---|---|---|
| End of life (unit)<br>• Illuminates to indicate when device is within 7 days of end of life or illuminates when the 7 day life has expired? (Would there be enough battery power to light the LED after 7 days?) |   |   |
| OK<br>• Illuminates green (pulsing) when product is running normally<br>• Likely to remain as existing "OK" symbol, building on familiarity established with the current Pico product |   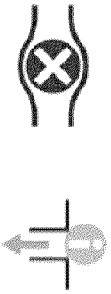 |   |
| Dressing Leak<br>• Indicated pressure loss due to incomplete sealing of the dressing<br>• Likely to remain as existing symbol, building on familiarity established with the current Pico product |    |   |
| Dressing Full<br>• Illuminates to indicate when the dressing filter is blocked and the dressing requires changing.<br>• New feature | 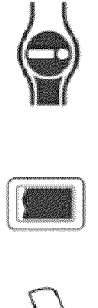  |   |

FIG. 79

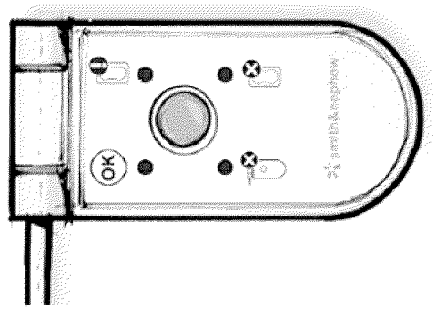
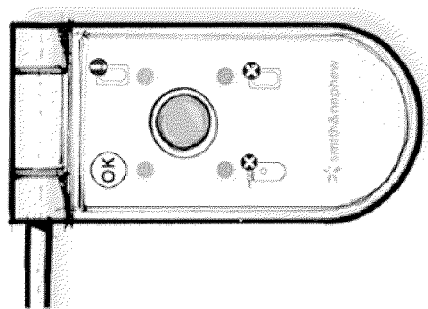
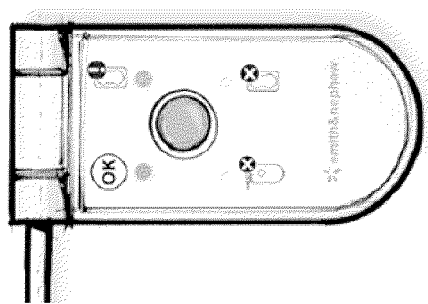
FIG. 84

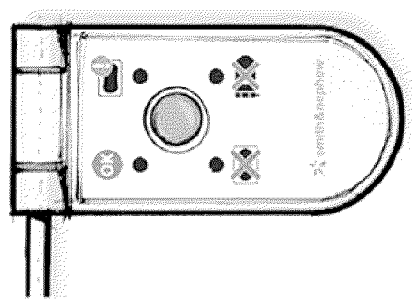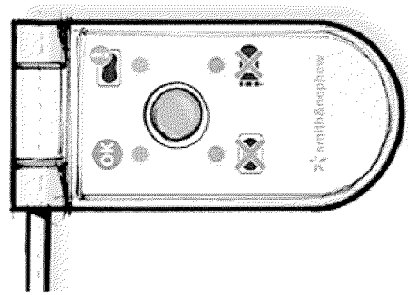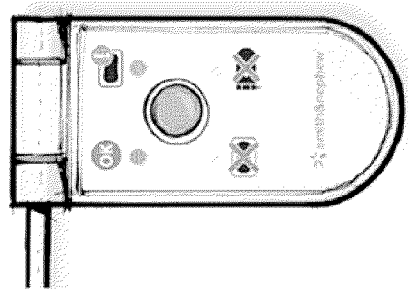
FIG. 85

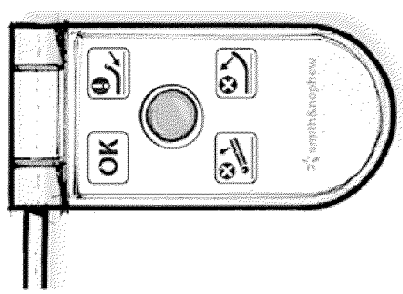
Layout of interface features
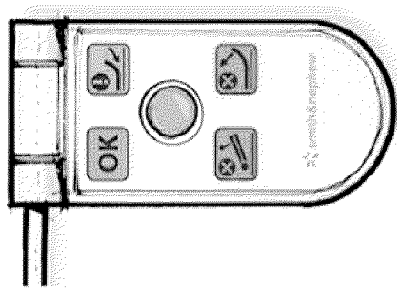
All interface indicators illuminated
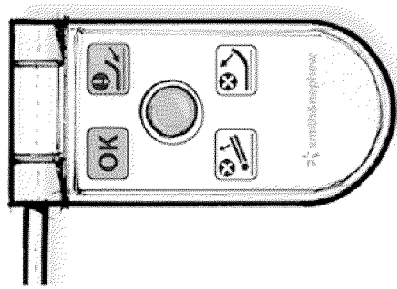
Most common indicator state when device is operational
FIG. 86

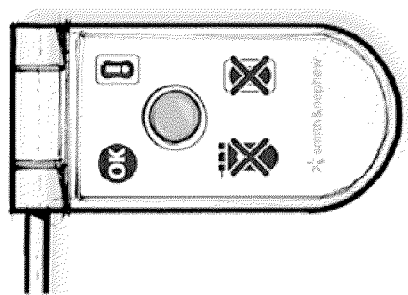
Layout of interface features
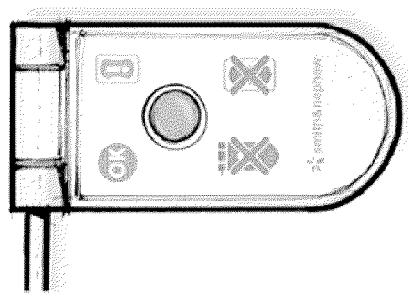
All interface indicators illuminated
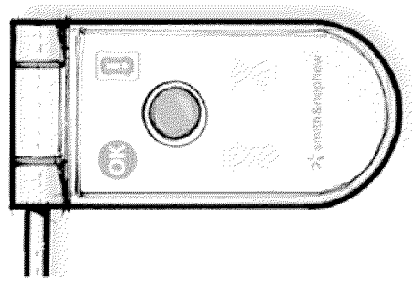
Most common indicator state when device is operational
FIG. 87

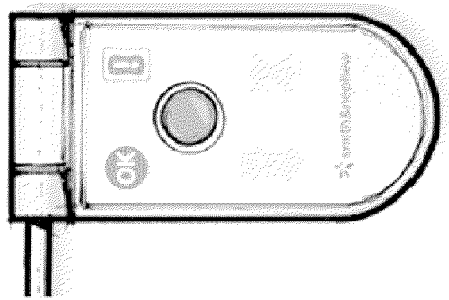
Secret until lit graphic only visible when illuminated from behind
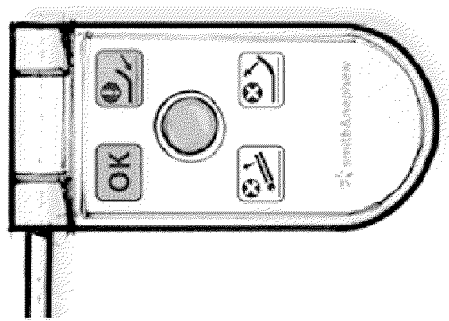
Printed icon artwork with LED light illuminating from behind
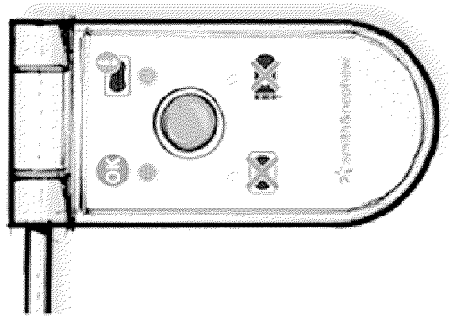
Colour printed icon artwork with LED light pipes
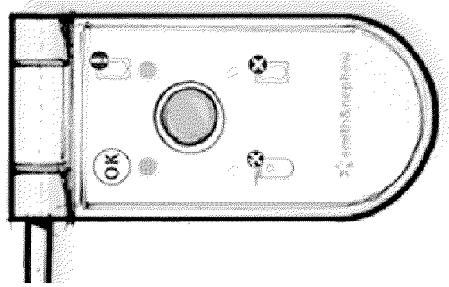
Printed icon artwork with LED light pipes
FIG. 88

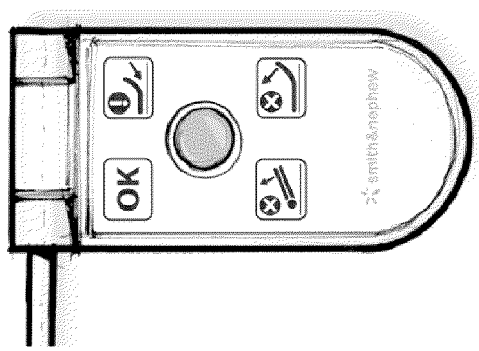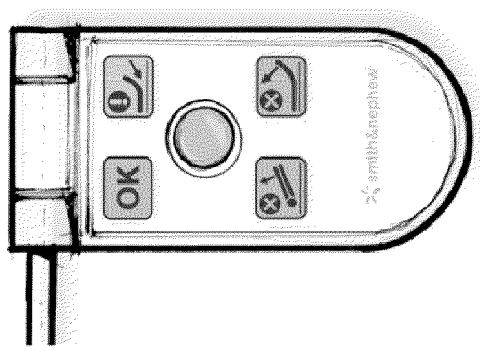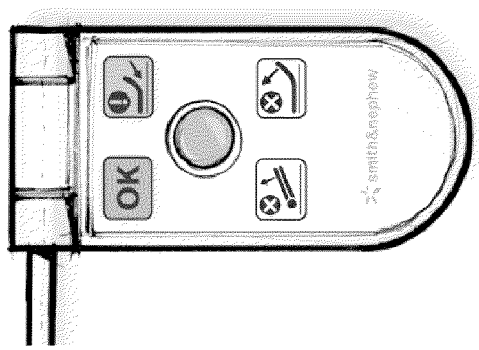
FIG. 93

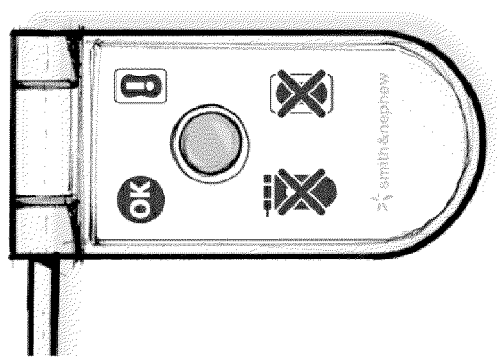
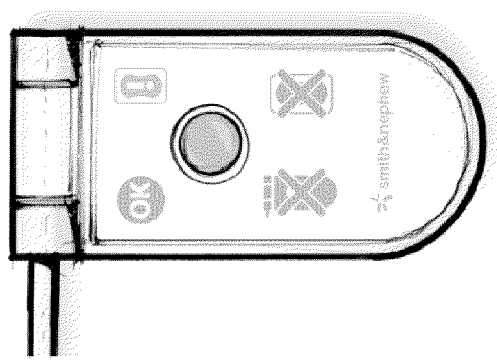
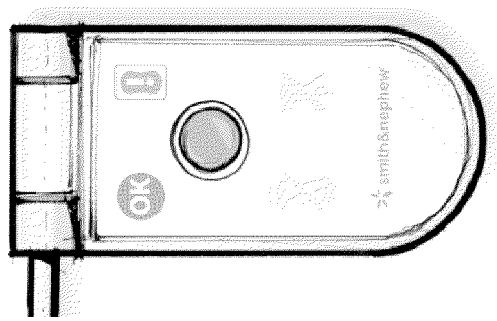
FIG. 94

Initial Concepts

OK' Icon

Illuminates green (pulsing) when product is running normally
Likely to remain as existing "OK" symbol, building on familiarity established with the current Pico product

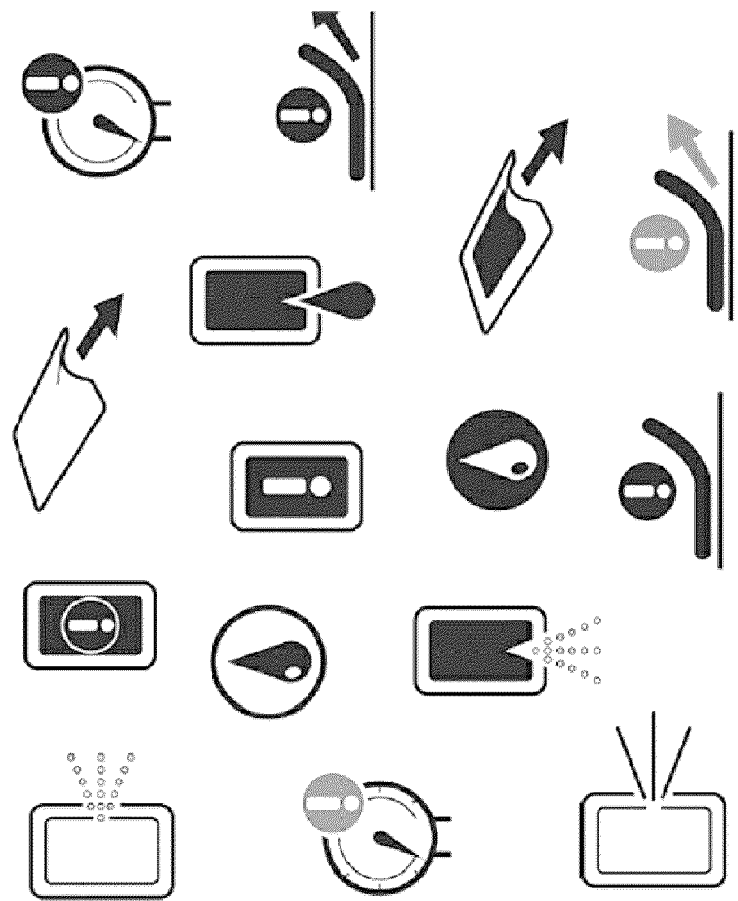
FIG. 96
'Dressing Leak' Icon
- Indicated pressure loss due to incomplete sealing of the dressing
- Likely to remain as existing symbol, building on familiarity established with the current Pico product
- May benefit from some refinement to improve intuitive understanding
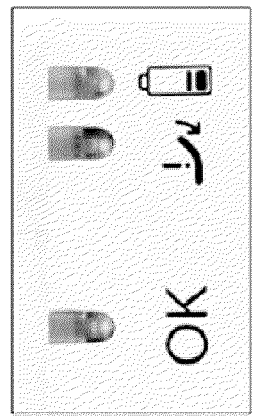

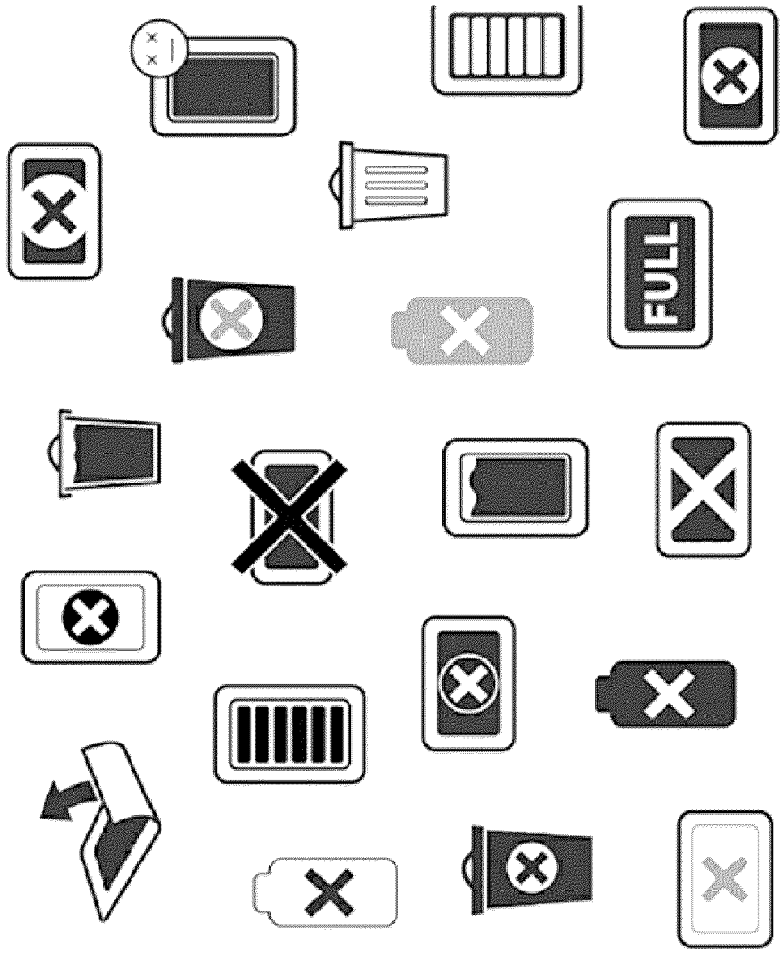
FIG. 97
'End of Life' Icon
- Illuminates to indicate when device is within 7 days of end of life or illuminates when the 7 day life has expired? (Would there be enough battery power to light the LED after 7 days?)
- New feature
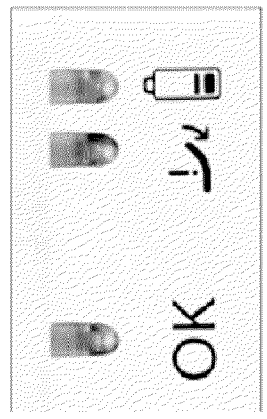

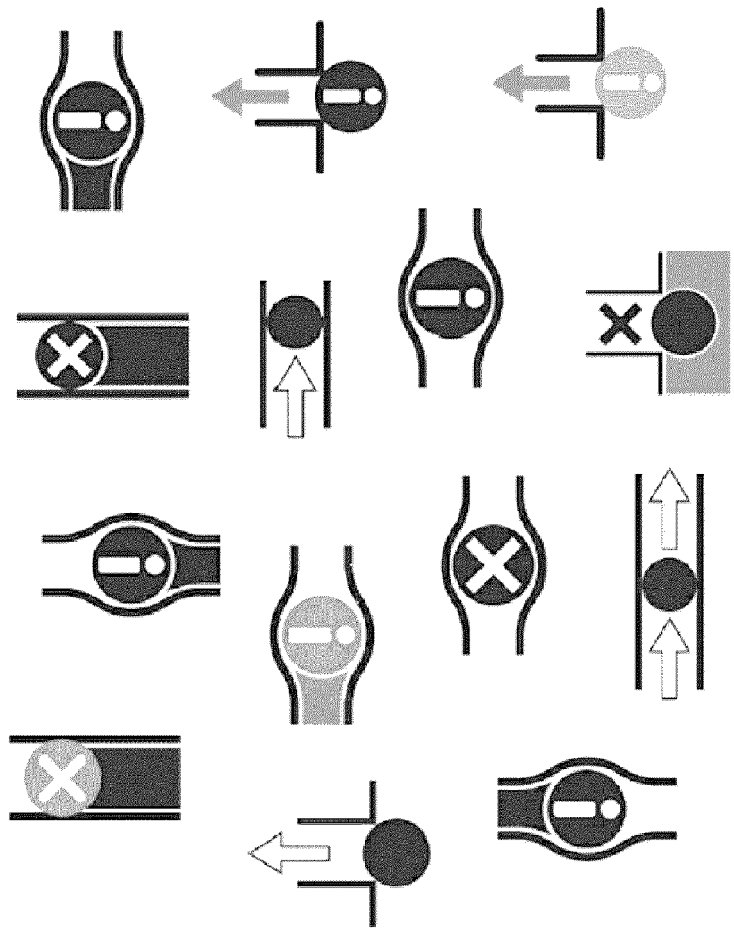
FIG. 98
'Blockage' Icon
- Illuminates to indicate when the dressing filter is blocked and the dressing requires changing.
- New feature
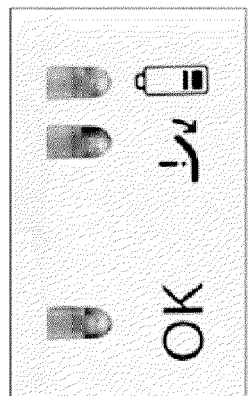

NEGATIVE PRESSURE WOUND THERAPY APPARATUS

CROSS-REFERENCE TO RELATED APPLICATIONS

This application claims the benefit of U.S. Provisional Application Nos. 61/647,397, filed May 15, 2012, 61/678,563, filed Aug. 1, 2012, 61/729,288, filed Nov. 21, 2012, and 61/791,984, filed Mar. 15, 2013, the contents of which are hereby incorporated by reference in their entirety as if fully set forth herein.

INCORPORATION BY REFERENCE

Further components, features, and details of pump assemblies, wound dressings, wound treatment apparatuses and kits, and negative pressure wound treatment methods that may be used with any of the embodiments disclosed in this application are found in the following applications and/or patents, which are hereby incorporated by reference in their entireties as if fully set forth herein:

U.S. patent application Ser. No. 13/287,897, filed Nov. 2, 2011, entitled REDUCED PRESSURE THERAPY APPARATUSES AND METHODS OF USING SAME;

U.S. patent application Ser. No. 13/092,042 (U.S. Patent Publication No. 2011/0282309), filed Apr. 21, 2011, entitled WOUND DRESSING AND METHOD OF USE;

U.S. patent application Ser. No. 11/922,894 (U.S. Patent Publication No. 2009/0123513), filed May 21, 2008, entitled ANTIMICROBIAL BIGUANIDE METAL COMPLEXES;

U.S. Provisional Application No. 61/511,950, entitled METHODS AND APPARATUSES FOR DETECTING LEAKS AND CONTROLLING PUMP OPERATION IN A NEGATIVE PRESSURE WOUND THERAPY SYSTEM, filed Jul. 26, 2011;

PCT Patent Application No. PCT/GB11/000,622 (WO/2011/135284), entitled WOUND DRESSING, filed on Apr. 21, 2011;

PCT Patent Application No. PCT/GB11/000,621 (WO/2011/144888), entitled WOUND PROTECTION, filed on Apr. 21, 2011, PCT Patent Application No. PCT/GB11/000,625 (WO/2011/135285), entitled WOUND DRESSING, filed on Apr. 21, 2011;

PCT Patent Application No. PCT/GB11/000,626 (WO/2011/135286), entitled MULTIPORT DRESSING, filed on Apr. 21, 2011;

PCT Patent Application No. PCT/GB11/000,628 (WO/2011/135287), entitled SUCTION PORT, filed on Apr. 21, 2011;

PCT Patent Application No. PCT/GB11/051,745 (WO/2012/038724), entitled PRESSURE CONTROL APPARATUS, filed on Sep. 16, 2011; and U.S. Patent Application No. 61/678,563, filed Aug. 1, 2011, entitled NEGATIVE PRESSURE WOUND THERAPY APPARATUS.

U.S. patent application Ser. No. 13/287,959 (U.S. Patent Publication No. 2012/0136325), entitled "SYSTEMS AND METHODS FOR CONTROLLING OPERATION OF A REDUCED PRESSURE THERAPY SYSTEM," filed on Nov. 2, 2011;

PCT Patent Application No. PCT/US2011/059016 (WO/2013/015827), entitled "SYSTEMS AND METHODS FOR CONTROLLING OPERATION OF A REDUCED PRESSURE THERAPY SYSTEM," filed on Nov. 2, 2011;

U.S. patent application Ser. No. 13/092,042 (U.S. Patent Publication No. 2011/0282309), entitled "WOUND DRESSING AND METHOD OF USE," filed on Apr. 21, 2011;

PCT International Application No. PCT/US13/30541, filed Mar. 12, 2013, entitled REDUCED PRESSURE APPARATUS AND METHODS; and U.S. Provisional Patent Application No. 61/785,054, entitled "WOUND DRESSING AND METHOD OF TREATMENT," filed on Mar. 14, 2013.

Each and all of the foregoing patent applications are hereby incorporated by reference in their entireties and made part of this disclosure.

BACKGROUND OF THE DISCLOSURE

1. Field of the Disclosure

Embodiments or arrangements disclosed herein relate to methods and apparatuses for dressing and treating a wound with topical negative pressure (TNP) therapy. For example but without limitation, some embodiments disclosed herein relate to treating a wound with reduced pressure provided from a pump kit. Although not required, some embodiments of the pump kit can be sterile. As another non-limiting example, some embodiments disclosed herein relate to apparatuses and methods for controlling the operation of a TNP system.

2. Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

SUMMARY OF SOME EMBODIMENTS

Some embodiments disclosed herein relate to a pump assembly for reduced pressure wound therapy, comprising a housing, a pump motor supported within or by the housing, and a flow pathway through the pump assembly. Though not required, some embodiments may have a one-way flow valve in fluid communication with the pump motor and supported within or by the housing. Some embodiments of the one-way flow valve can be configured to substantially prevent a flow of gas through the flow pathway in a direction of flow away from the pump motor. The pump assembly can have a motor, an inlet and an outlet, a first valve supported by the pump motor or housing and configured to control a flow of a fluid through the inlet, and a second valve supported by the pump motor or housing and configured to control a flow of a fluid through the outlet. In any embodiments disclosed herein, the pump assembly and/or dressing can have one or more sensors therein. For example, in any embodiments disclosed herein, the pump assembly and/or dressing can have a pressure monitor configured to monitor the pressure within the pump housing, dressing, or conduit or chambers within the pump assembly or between the pump assembly and the dressing, or in any combination of such. Additionally, some pump embodiments disclosed herein can use orifices or other features or components to control a flow or rate of flow of fluid through the pump assembly.

Some embodiments disclosed herein relate to a negative pressure therapy kit for reduced pressure wound therapy, comprising a pump assembly comprising a housing, a pump motor supported within the housing, and a controller supported within or by the housing, and at least one switch or button supported by the housing. As used throughout this specification, the phrase "some embodiments" or "In any embodiments disclosed herein" is meant to refer to any embodiment described, illustrated, incorporated by reference, or otherwise disclosed herein. The at least one switch or button can be in communication with the controller and can be accessible to a user so as to permit a user to control one or more modes of operation of the pump assembly. In any embodiments disclosed herein, though not required, the negative pressure therapy kit can comprise a dressing configured to form a substantially fluid tight seal over a wound, a conduit coupleable with the dressing and the pump assembly and configured to provide a substantially or completely enclosed fluid flow pathway from the pump assembly to the dressing, and a first packaging element for packaging the pump assembly, the one or more batteries, the dressing, and the conduit. In any embodiments disclosed herein, the controller can be configured to control an operation of the pump motor, valve, and other components of the pump assembly. Some embodiments of the negative pressure therapy kit can be configured such that the negative pressure therapy kit has been sterilized. The negative pressure therapy kit can be sterilized such that at least an inside and an outside of the housing, the at least one valve, the pump motor, the controller, and the at least one switch or button have been sterilized.

Some embodiments disclosed herein relate to reduced pressure treatment of wounds with a reduced pressure pump assembly. The pump assembly embodiments disclosed herein are not required to be sterilized. However, sterilizing the reduced pressure pump assembly before use and providing the pump assembly and/or dressing or pump kit components in a sterile condition can permit the use of the pump assembly in an operating room (also referred to as an operating theater) or any other location where sterility of the devices is required. For example and without limitation, some embodiments are directed to a sterile pump or dressing kit comprising a sterile pump assembly, a sterile dressing, and a sterile conduit connectable to the dressing and the pump assembly that can be used in an operating room.

Some embodiments disclosed herein relate to a canisterless pump assembly for reduced pressure wound therapy, comprising a housing, a flow pathway through the housing or through the pump assembly, one or more valves in communication with the flow pathway, and a pump motor supported within or by the housing, wherein the pump assembly is canisterless. Some embodiments disclosed herein relate to a canisterless pump assembly for reduced pressure wound therapy, comprising a housing and a pump motor supported within or by the housing. The pump assembly can have a motor, an inlet and an outlet, a first valve supported by the pump assembly and configured to control a flow of a fluid through the inlet, and a second valve supported by the pump and configured to control a flow of a fluid through the outlet. The pump or pump assembly can be canisterless. Further, though not required for all embodiments disclosed herein, and the first and second valves can each have a leakage rate of from approximately 0.1 mL/min to approximately 10 mL/min at nominal working pressures and/or during nominal sterilization pressures, or from 0.1 mL/min or less to 5 mL/min or more, or from 1 mL/min or less to 3 mL/min or more, or between any two values in any of the foregoing ranges at nominal working pressures. In any embodiments disclosed herein, the leakage rate can be from approximately 0.4 mL/min to 0.7 mL/min at nominal working pressures and/or during nominal sterilization pressures.

Some embodiments disclosed herein relate to a sterile pump kit, comprising any of the pump embodiments disclosed herein, a dressing, a conduit coupleable with the dressing and the sterile pump and configured to provide a fluid pathway of reduced pressure to the dressing, one or more batteries, and a first packaging element and a second packaging element configured to be removably coupled with the first packaging element. In any embodiments disclosed herein, at least one of the first and second packaging elements can have recesses for receiving the sterile pump, a dressing, a conduit coupleable with the dressing and the sterile pump and configured to provide a fluid pathway of reduced pressure to the dressing. The sterile pump kit can be been sterilized after the pump, the dressing, the conduit, and the one or more batteries have been supported inside at least one of the first packaging element and the second packaging element.

Some embodiments provide the advantage that the wound dressing can be used to collect wound exudate generated during a negative pressure therapy process. A pump remote from the wound dressing or supported thereby can be connected to the wound dressing and reused (or can be disposable) whilst the wound dressing itself is used to collect wound exudate and may then be disposed of after use. The pump or other source of negative pressure can be connected to the wound dressing through a flexible tubing or conduit. In this arrangement, negative pressure can draw wound exudate and other fluids or secretions away from the wound site. Any of the embodiments disclosed herein are suitable for use with and, hence, can be used with a negative pressure wound therapy system to aid in wound closure and healing in which wound exudate drawn from a wound site during the therapy is collected and stored in a wound dressing and/or in a collection canister.

Some dressing embodiments disclosed herein are configured to have an increased capacity for absorbing wound exudate reducing the frequency with which the dressings must be changed, and to manage the movement of wound exudate through a dressing to avoid blockages occurring that lead to reduced life of the dressing. Some embodiments are configured to provide a wound dressing able to be used with topical negative pressure therapy which helps maintain an open flow path so that therapy can be continued unhindered by blockages caused by build-up of solid matter.

Some embodiments disclosed herein are directed toward the treatment of wounds with negative pressure wound therapy. In particular, any of the dressing embodiments disclosed herein can be used for absorbing and storing wound exudate in conjunction with a pump, such as any of the pump embodiments disclosed herein. Any of the wound dressing embodiments disclosed herein can further comprise a transmission layer configured to transmit wound exudates to an absorbent layer disposed in the wound dressing. Additionally, any of the wound dressing embodiments disclosed herein can be adapted to provide for a port or other fluidic connector configured to retain wound exudate within the wound dressing while transmitting negative pressure to the wound dressing, though such a feature is not required.

According to an embodiment of the present disclosure there is provided a wound treatment apparatus comprising: a wound dressing comprising:
- any of the dressing embodiments disclosed herein;
- any of the pump embodiments disclosed herein; and
- a suction port for applying negative pressure to the wound dressing for the application of topical negative pressure at a wound site, the suction port comprising:
  - a connector portion for connecting the suction port to the pump;
  - a sealing surface for sealing the suction port to the cover layer of the wound dressing; and
  - a liquid impermeable gas permeable filter element arranged to prevent a liquid from entering the connector portion.

According to another embodiment of the present disclosure there is provided a method for the treatment of a wound comprising:
- providing a wound dressing comprising any of the features or combination of features of any of the dressing embodiments disclosed herein, and/or:
  - a transmission layer comprising a 3D knitted or fabric material;
  - an absorbent layer for absorbing wound exudate, the absorbent layer overlying the transmission layer;
  - a cover layer overlying the absorbent layer and comprising an orifice, wherein the cover layer is moisture vapor permeable;
- positioning the dressing over a wound site to form a sealed cavity over the wound site; and
- applying negative pressure to the wound site to draw fluid through the transmission layer into the absorbent layer.

According to another embodiment of the present disclosure there is provided a wound dressing for providing protection at a wound site, comprising any of the features or combination of features of any of the dressing embodiments disclosed herein, and/or:
- a transmission layer comprising a first surface and a further surface spaced apart from the first surface by a relax distance in a relaxed mode of operation; and
- a plurality of spacer elements extending between the first and further surfaces and, in a forced mode of operation, locatable whereby the first and further surfaces are spaced apart by a compression distance less than the relax distance.

According to another embodiment of the present disclosure there is provided a method for providing protection at a wound site, comprising:
- locating a wound dressing comprising any of the components or features of any of the wound dressing embodiments disclosed herein, and/or a transmission layer over a wound site; and
- responsive to a force on the wound dressing, displacing a plurality of spacer elements extending between a first surface and a further surface of the transmission layer whereby;
- a distance between the first and further surfaces is reduced as the spacer elements are displaced.

According to another embodiment of the present disclosure there is provided an apparatus for dressing a wound for the application of topical negative pressure at a wound site, comprising a wound dressing comprising any of the components or features of any of the wound dressing embodiments disclosed herein, and/or:
- a liquid and gas permeable transmission layer;
- an absorbent layer for absorbing wound exudate, the absorbent layer overlying the transmission layer;
- a gas impermeable cover layer overlying the absorbent layer and comprising a first orifice, wherein the cover layer is moisture vapor permeable.

According to a further embodiment of the present disclosure there is provided a method of applying TNP at a wound site, comprising:
- applying negative pressure at an orifice of a cover layer of any wound dressing embodiment disclosed herein, a peripheral region around the wound site being sealed with the wound dressing, such that air and wound exudate are drawn towards the orifice;
- collecting wound exudate, drawn from the wound site, through a transmission layer of the wound dressing, in an absorbent layer of the wound dressing; and
- transpiring a water component of the wound exudate collected in the absorbent layer through the cover layer of the wound dressing.

According to an additional embodiment of the present disclosure there is provided apparatus for dressing a wound for the application of topical negative pressure at a wound site, comprising a wound dressing comprising any of the components or features of any wound dressing embodiment disclosed herein, and/or:
- a liquid and gas permeable transmission layer;
- an absorbent layer for absorbing wound exudate;
- a gas impermeable cover layer overlying the absorbent layer and the transmission layer, the cover layer comprising an orifice connected to the transmission layer; and
- at least one element configured to reduce the rate at which wound exudate moves towards the orifice when a negative pressure is applied at the orifice.

According to another embodiment of the present disclosure there is provided a method of applying TNP at a wound site, comprising:
- applying negative pressure at an orifice of a cover layer of a wound dressing comprising any of the components or features of any wound dressing embodiment disclosed herein, a peripheral region around the wound site being sealed with the wound dressing such that air and wound exudate move towards the orifice;
- collecting wound exudate, from the wound site, through a transmission layer of the wound dressing, in an absorbent layer of the wound dressing; and
- reducing the rate at which wound exudate moves towards the orifice.

According to still another embodiment of the present disclosure there is provided an apparatus for dressing a wound for the application of topical negative pressure at a wound site, comprising a wound dressing comprising any of the components or features of any wound dressing embodiment disclosed herein and/or:
- an absorbent layer for absorbing wound exudate;
- a gas impermeable cover layer overlying the absorbent layer the cover layer comprising at least one orifice configured to allow negative pressure to be communicated through the cover layer in at least two spaced apart regions.

According to an additional embodiment of the present disclosure there is provided a method of applying TNP at a wound site, comprising:
- sealing a cover layer of a wound dressing comprising any of the components or features of any wound dressing embodiment disclosed herein around the wound site;

applying negative pressure at at least one orifice in the cover layer, said at least one orifice configured to allow negative pressure to be communicated through the cover layer in at least two spaced apart regions; and collecting wound exudate, from the wound site, in an absorbent layer of the wound dressing.

According to another embodiment of the present disclosure there is provided a suction port for applying negative pressure to a wound dressing of any of the embodiments disclosed herein or having any of the components or features of any wound dressing embodiment disclosed herein for the application of topical negative pressure at a wound site, the suction port comprising:

a connector portion for connecting the suction port to a source of negative pressure;

a sealing surface for sealing the suction port to a cover layer of a wound dressing; and a liquid impermeable gas permeable filter element arranged to prevent a liquid entering the connector portion.

According to an additional embodiment of the present disclosure there is provided a method of communicating negative pressure comprising a wound dressing of any of the embodiments disclosed herein or having any of the components or features of any wound dressing embodiment disclosed herein for the application of topical negative pressure at a wound site, comprising:

applying negative pressure at a connecting portion of a suction port sealed around a perimeter of an orifice in a cover layer of the wound dressing;

filtering gas drawn from within the wound dressing through a liquid impermeable gas permeable filter element of the suction port.

According to another embodiment of the present disclosure there is provided a method of manufacturing a suction port for applying negative pressure to a wound dressing for the application of topical negative pressure at a wound site, the suction port having a connector portion for connecting the suction port to a source of negative pressure and a sealing surface for sealing the suction port to a cover layer of a wound dressing of any of the embodiments disclosed herein or having any of the components or features of any wound dressing embodiment disclosed herein, the method comprising:

disposing a liquid impermeable gas permeable filter element of the suction port at a location to prevent a liquid entering the connector portion.

According to yet another embodiment of the present disclosure there is provided an apparatus for the application of TNP therapy to a wound site, comprising:

a first layer comprising a plurality of openings each having a first open area;

a further layer spaced apart from the first layer comprising a plurality of further openings each having a further open area; and an air impermeable, moisture vapor permeable cover layer over the first and further layers; wherein a region between the first and further layers comprises a portion of a flow path for air and/or wound exudate flowing from a wound site and said first open area is less than said further open area.

According to still another embodiment of the present disclosure there is provided a method of applying TNP therapy to a wound site, comprising:

via a vacuum pump in fluid communication with a wound dressing of any of the embodiments disclosed herein or having any of the components or features of any wound dressing embodiment disclosed herein located over a wound site, applying a negative pressure at the wound site; and as liquid evaporates through a cover layer of the dressing, preventing blockage of a fluid flowpath region of the wound dressing.

Some embodiments provide a wound dressing of any of the embodiments disclosed herein or having any of the components or features of any wound dressing embodiment disclosed herein able to disconnect shear forces applied to the dressing from the wound site covered by the dressing. As a result damage to the wound can be wholly or at least partially avoided.

Some embodiments provide the advantage that a wound site can be covered with a wound dressing of any of the embodiments disclosed herein or having any of the components or features of any wound dressing embodiment disclosed herein which is simultaneously able to deliver negative pressure wound therapy to a wound site, collect exudate and provide protection from forces operating on the dressing.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing or adjacent to or supported by the wound dressing can be connected to the wound dressing and reused whilst the wound dressing itself is used to collect wound exudate and may then be disposed of after use.

Some embodiments provide a wound dressing and/or method of applying topical negative pressure in which a flowpath through a wound dressing of any of the embodiments disclosed herein or having any of the components or features of any wound dressing embodiment disclosed herein is kept open so that therapy can be continued for as long as desired by a care giver.

Some embodiments prevent solid material, which may cause a blockage, from entering a flowpath region in a wound dressing of any of the embodiments disclosed herein or having any of the components or features of any wound dressing embodiment disclosed herein by using a layer of the dressing to act as a bar to such material.

Some embodiments prevent build-up of solid material in a flowpath region of a wound dressing of any of the embodiments disclosed herein or having any of the components or features of any wound dressing embodiment disclosed herein by ensuring that any solid material that enters into that flowpath region can always escape into a further region of the dressing.

Some embodiments provide the advantage that the build-up of solid material in a flowpath in a wound dressing of any of the embodiments disclosed herein or having any of the components or features of any wound dressing embodiment disclosed herein is avoided by having an absorbent layer close to the flowpath region store liquid over time. This helps keep the environment of the flowpath region moist which helps avoid crusting.

Some embodiments provide the advantage that a wound dressing of any of the embodiments disclosed herein or having any of the components or features of any wound dressing embodiment disclosed herein can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

Embodiments disclosed herein relate to methods and apparatuses for dressing and treating a wound with topical negative pressure (TNP) therapy. For example but without limitation, the embodiments disclosed herein relate to treating a wound with reduced pressure provided from a pump kit. Although not required, any embodiments of the pump kit can be integral, wherein the pump is mounted to or otherwise supported by or adjacent to the dressing. Additionally, although not required, any embodiments of the pump kit can be sterile. As another non-limiting example, some embodiments disclosed herein relate to apparatuses, features, and methods for controlling the operation of a TNP system and/or apparatuses, features, and methods for detecting one or more conditions or parameters of the dressing, such as pressure, temperature, or saturation level, and, although not required, controlling the operation of the pump or other components of the dressing kit accordingly. As another non-limiting example, any embodiments disclosed herein can be configured to provide a visual indication one or more conditions or parameters of the dressing, such as pressure, temperature, or saturation level.

Any of the features, components, or details of any of the arrangements or embodiments disclosed in this application, including those disclosed below, are interchangeably combinable with any other features, components, or details of any of the arrangements or embodiments disclosed herein to form new arrangements and embodiments. With that, the following arrangements are disclosed herein, inter alia.

BRIEF DESCRIPTION OF THE DRAWINGS

Embodiments of the present disclosure will now be described hereinafter, by way of example only, with reference to the accompanying drawings in which:

FIGS. 27H-27I are a side view and an isometric view of the pump assembly embodiment shown in FIG. 27A, respectively, showing a housing of the pump assembly in a partially open position.

FIG. 29A is an enlarged isometric view of a portion of the embodiment of a pump assembly shown in FIG. 28, showing a slider member of an embodiment of a conduit connector in a first, open position.

FIG. 29B is a section view of a portion of the embodiment of a pump assembly shown in FIG. 28, showing a slider member in the first, open position.

FIG. 30A is an enlarged isometric view of a portion of the embodiment of a pump assembly shown in FIG. 28, showing a slider member in a second, closed position.

FIG. 30B is a section view of a portion of the embodiment of a pump assembly shown in FIG. 28, showing a slider member in the second, closed position.

FIGS. 31A, 31B, and 31C are an isometric, side, and end view of an embodiment of a slide member.

FIG. 32 is an exploded view of a portion of another embodiment of a pump assembly having another embodiment of a conduit connector.

FIG. 33A is an enlarged isometric view of a portion of the embodiment of a pump assembly shown in FIG. 32, showing a slider member of an embodiment of a conduit connector in a first, open position.

FIG. 33B is a section view of a portion of the embodiment of a pump assembly shown in FIG. 32, showing a slider member in the first, open position.

FIG. 34A is an enlarged isometric view of a portion of the embodiment of a pump assembly shown in FIG. 32, showing a slider member in a second, closed position.

FIG. 34B is a section view of a portion of the embodiment of a pump assembly shown in FIG. 32, showing a slider member in the second, closed position.

FIGS. 35A, 35B, and 35C are an isometric, side, and end view of another embodiment of a slide member.

FIG. 36 is an exploded view of a portion of another embodiment of a pump assembly having another embodiment of a conduit connector.

FIG. 37A is an enlarged isometric view of a portion of the embodiment of a pump assembly shown in FIG. 36, showing a slider member of an embodiment of a conduit connector in a first, open position.

FIG. 37B is a section view of a portion of the embodiment of a pump assembly shown in FIG. 36, showing a slider member in the first, open position.

FIG. 38A is an enlarged isometric view of a portion of the embodiment of a pump assembly shown in FIG. 36, showing a slider member in a second, closed position.

FIG. 38B is a section view of a portion of the embodiment of a pump assembly shown in FIG. 36, showing a slider member in the second, closed position.

FIGS. 39A, 39B, and 39C are an isometric, side, and end view of another embodiment of a slide member.

FIG. 40H is a side view of the pump assembly embodiment shown in

FIGS. 46A-46G are an isometric view, a top view, a bottom view, a top end view, a bottom end view, a first side view, and a second side view, respectively, of another embodiment of a pump assembly.

FIGS. 47A-47G are an isometric view, a top view, a bottom view, a top end view, a bottom end view, a first side view, and a second side view, respectively, of another embodiment of a pump assembly.

FIG. 58 is a section view of the pump assembly embodiment illustrated in FIG. 54, the section being taken through the center of the pump assembly embodiment.

FIGS. 59 and 60 are a top view and a section view of another embodiment of a pump assembly.

FIG. 61 is an exploded view of the pump assembly embodiment illustrated in FIG. 59.

FIGS. 79-98 illustrate a variety of indicator lights that can be included with any pump assembly disclosed herein.

DETAILED DESCRIPTION OF SOME EMBODIMENTS

Figure 1:
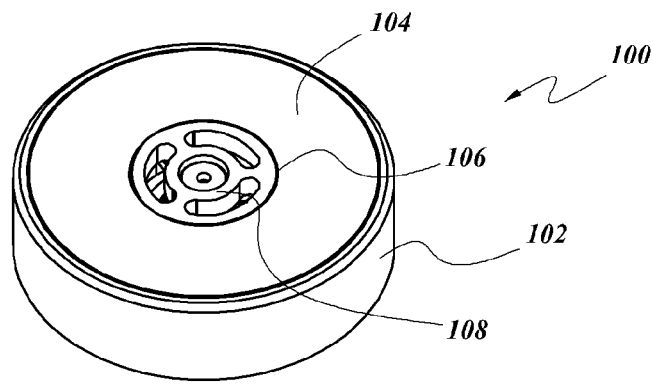
FIG. 1 is a scaled photograph of an embodiment of a pump assembly that can be used to move fluids.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In any embodiments disclosed herein, the components of the TNP system described herein can be particularly suited for incisional wounds that exude a small amount of wound exudate.

It will be understood that embodiments of the present invention are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 in Hg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The negative pressure range for any embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In any embodiments disclosed herein, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even 150 mmHg, can be supplied by the negative pressure apparatus. Other details regarding the operation of the pump assembly are set forth in U.S. patent application Ser. No. 13/092,042, and such embodiments, configurations, details, and illustrations thereof are hereby incorporated by reference in their entireties as if made part of this disclosure.

Any of the embodiments disclosed herein can comprise a pump and/or a pump and dressing kit. However, the pump apparatuses and embodiments of the present disclosure are not limited to use with a dressing or for wound therapy. Any of the pump embodiments disclosed herein can be used independently of the dressing components disclosed herein. Further, any of the pump embodiments disclosed herein can be used, or can be adapted for use, for other purposes outside of negative pressure wound therapy. As such, any of the pump embodiments disclosed herein can be used, or can be adapted for use, to move fluids (gaseous and/or liquid) in any system or application.

Figure 2:
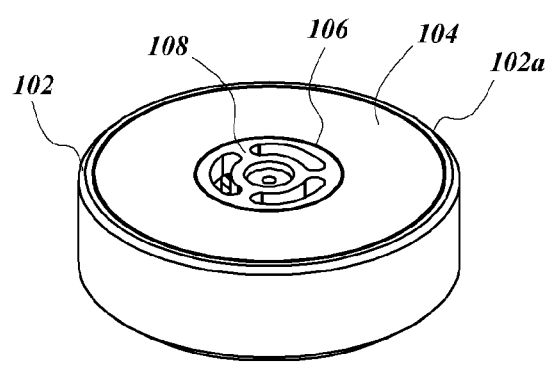
FIG. 2 is an isometric view of the pump assembly embodiment illustrated in FIG. 1, showing a top surface of the pump assembly.
Figure 3:
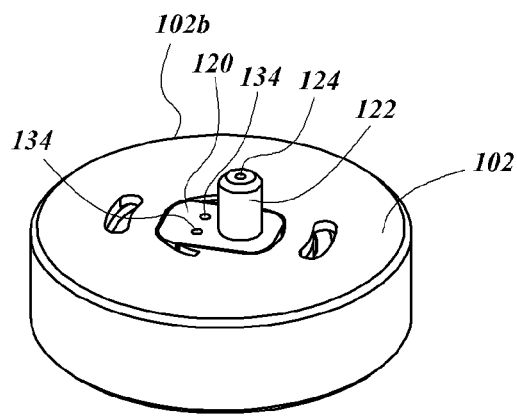
FIG. 3 is an isometric view of the pump assembly embodiment illustrated in FIG. 1, showing a bottom surface of the pump assembly.
Figure 4:
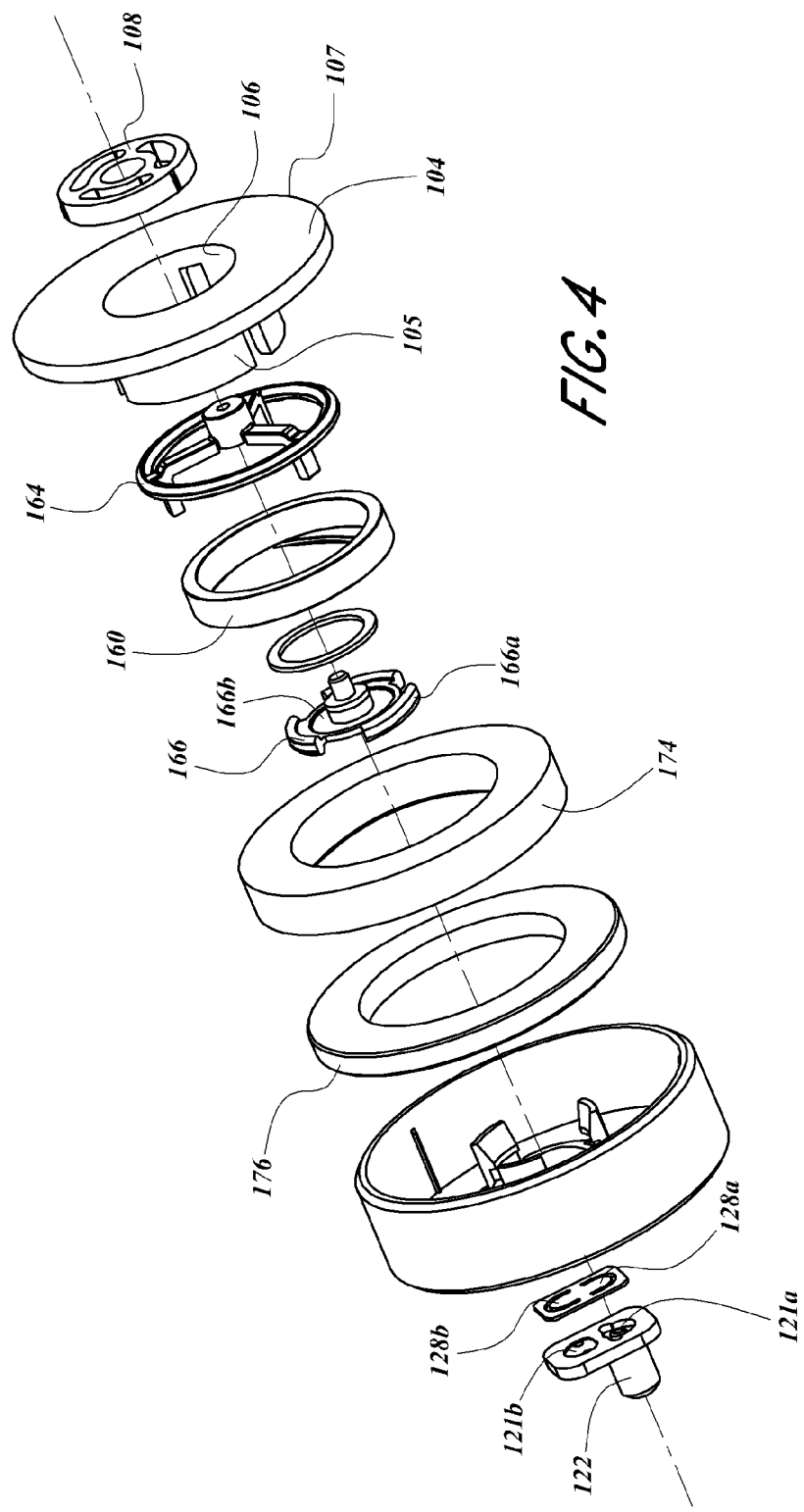
FIG. 4 is an exploded view of the pump assembly embodiment illustrated in FIG. 1.
Figure 5:
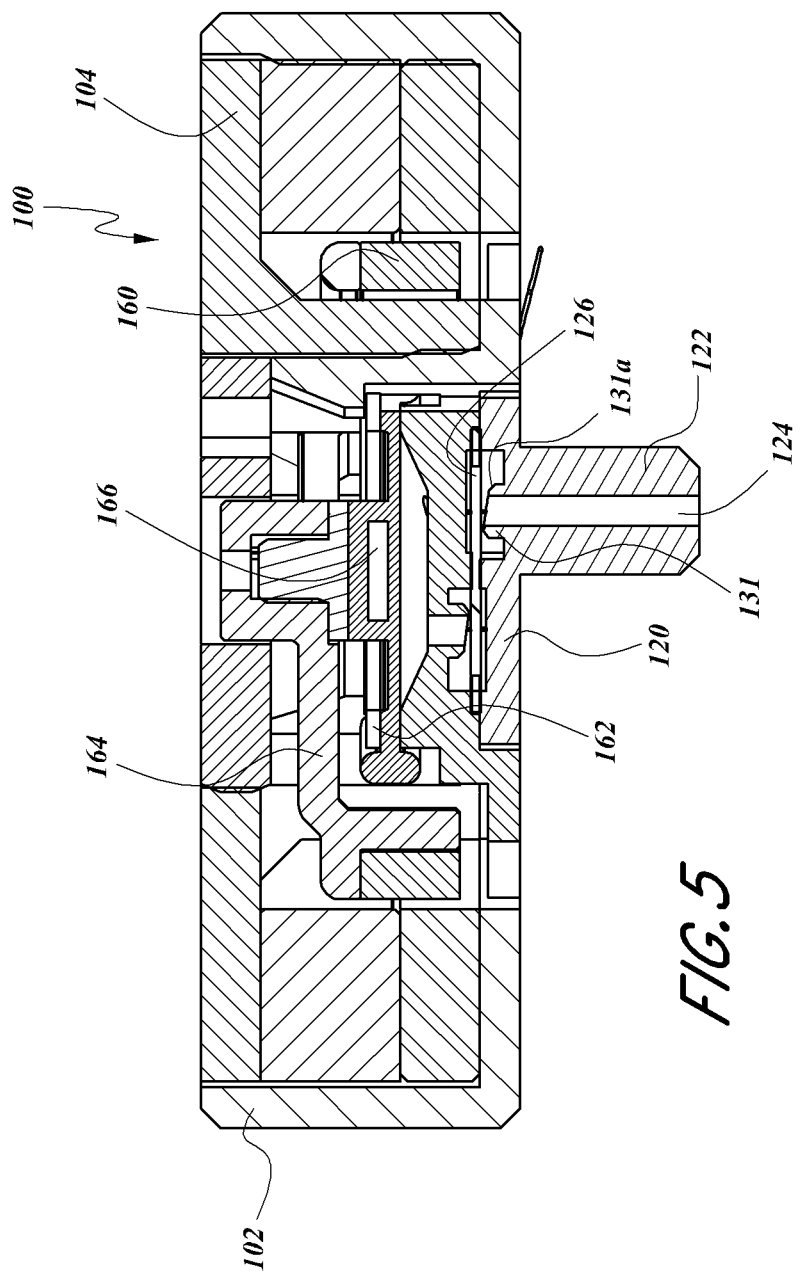
FIG. 5 is a section view of the pump assembly embodiment illustrated in FIG. 1, taken through the axial centerline of the pump assembly embodiment.

FIG. 1 is a scaled photograph of an embodiment of a pump assembly 100 that can be used to move fluids. FIGS. 2 and 3 are isometric views of the pump assembly embodiment illustrated in FIG. 1, showing a top surface of the pump assembly and the bottom surface of the pump assembly, respectively. FIGS. 4 and 5 are an exploded view and a section view of such pump assembly embodiment, the section view being taken through the axial centerline of the pump assembly embodiment.

The pump assembly embodiment 100 can have a compact, small size. In any embodiments disclosed herein, the pump assembly embodiment 100 can have a diameter or lateral size in the range of approximately 26 mm to approximately 27 mm, or between approximately 22 mm or smaller and approximately 28 mm. In any embodiments disclosed herein, the pump assembly embodiment 100 can have a thickness or height of approximately 8 mm, or from approximately 6 and approximately 10 mm. The pump assembly embodiment 100 can be any miniaturized size that is manufacturable, and the overall power output and efficiency meet the needed requirements for the desired application, within or outside of wound therapy. For example, in some pump assembly embodiments that may be suitable for applications requiring miniaturized pumps, the pump can have a diameter or lateral size of approximately 10 mm or less to approximately 15 mm, and a thickness or height of from approximately 3 mm and approximately 6 mm. The sizes and ranges listed herein can apply to any pump embodiment disclosed in this application. Only manufacturing technology limits the lower end of the size scale, although fluid power output and overall efficiency will decrease with decreasing size— but a smaller pump would still be useful in other applications.

As used herein, efficiency can be defined as (fluid power out)/(electrical power in). Additionally, as used herein, unless otherwise specified, the term approximately, as applied to measures of length, weight, time, efficiency rates, percentages, and other similar measures, is meant to refer to a range of plus or minus 15% of the stated value. This embodiment and arrangement of the pump assembly embodiment can be referred to as a "drum" type pump.

The pump assembly embodiment 100 can be produced for a low cost and can operate at high efficiencies, making it beneficial for portable, disposable, and/or single use applications. This pump can be used in an ultra-portable single-use negative-pressure wound therapy (NPWT) device. In any embodiments disclosed herein, the pump assembly embodiment 100 can run for a week on a small primary cell without the need for battery replacement or recharging. Some embodiments of the pump assembly can run up to a week on a 1200 mAh cell, assuming the pump is working for about 20% of the time.

Any pump assembly embodiments disclosed herein can be configured to be capable of producing approximately 118 ml/min of fluid displacement for a power draw of 94 mW. The drive electronics can include a buck-boost convertor to supply a constant voltage from the battery, and a chip to both control the overall system logic and to generate the drive signal for the voice coil actuator (VCA), some pump embodiments disclosed herein will produce a battery life of approximately 7.04 days from the soft-pack $Li/MnO_2$, model CF502445.

In any embodiments disclosed herein, as mentioned, the pump assembly embodiment 100 can be used for negative pressure wound therapy. However, the pump assembly embodiment 100 is not limited to use in NPWT systems. The pump assembly embodiment can be adapted and configured for use in any reduced pressure system or in any system or application in which the movement of gaseous and liquid fluids is desired.

As an overview, the pump assembly embodiment 100 can be configured as a small diaphragm pump with passive valves (such as, but not limited to, flap valves) that can be driven by a VCA. The pump can be designed to work at pressures of 60-80 mm Hg, and can be configured to produce a flow rate of approximately 100 ml min-1, with a minimum efficiency of 15%, in order for the NPWT device to run for a week on a specified battery capacity. In any embodiments disclosed herein, the pump assembly embodiment 100 can be adapted to operate at efficiency levels in excess of 25%.

With reference to FIGS. 1-5, the pump assembly embodiment 100 can have a housing 102 adapted to support and protect many of the components of the pump assembly embodiment 100. An upper pole 104 can be supported at one end (for example, a first end) 102a of the housing 102. In any embodiments disclosed herein, the upper pole 104 can have an opening 106 formed through an axial centerline of the upper pole 104. A bearing 108 can be supported by the upper pole 104, within the opening 106. The bearing 108 or any other components disclosed in this application can be formed by stereolithography, selective laser sintering, molding, or by other suitable processes. Two or more electrical wires 114 can be connected to the pump assembly embodiment 100, configured to provide power to the pump assembly embodiment 100. In particular, the wires 114 can be used to provide electrical current to the coil of the pump assembly. The electrical wires 114 can be routed through one or more openings formed in the housing 102 or other components of the pump assembly embodiment 100.

The housing 102 can support a valve support member 120 at an end (for example, a second end 102b) of the housing 102. The valve support member 120 can support a boss member 122 that can receive a conduit therein or thereover, the boss member 122 having an opening 124 therethrough. The opening 124 can be in fluid communication with one or more passageways inside the pump assembly embodiment 100.

With reference to FIG. 4, the valve support member 120 can support one side of two valve chambers 121, a first inlet valve chamber 121a and a first outlet valve chamber 121b, which will be described in greater detail below. The valve support member 120 can support a flexible valve plate 126 having two flaps 128, one per chamber. The valve plate 126 can have a first flap 128a and a second flap 128b configured to deflect away from the relaxed position of the flaps 128 shown in FIGS. 4-5. In any embodiments disclosed herein, the valve plate 126 and flaps 128, or any other valve plate or flap embodiment disclosed herein, can be formed from a silicone rubber. Any of the valve plate embodiments disclosed in relation to any pump embodiment disclosed herein (meaning, anywhere within this application) can be formed, print-cut, or dye cut from silicone sheet material, or cast or molded from silicone or other suitable materials, and can have any of the following shore hardness values: 20A, 40A, 50A, 60A and 80A. Any of the valve flaps disclosed herein can have one or more score lines therein to improve flexibility.

Figure 6:
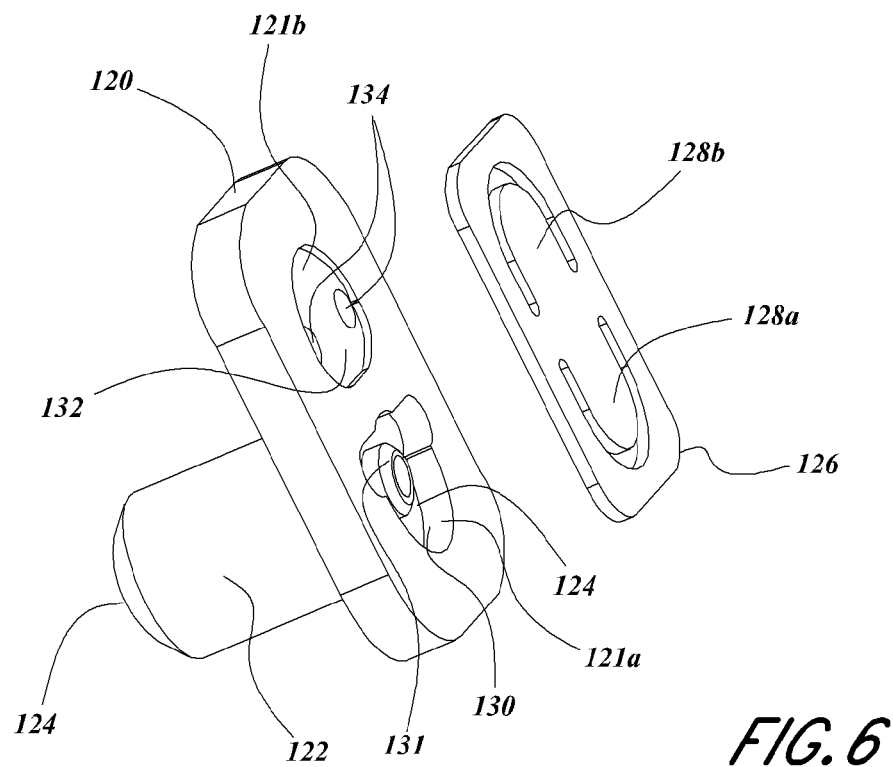
FIG. 6 is an isometric view of the valve support member and the valve plate of the pump assembly embodiment illustrated in FIG. 1.
Figure 7:
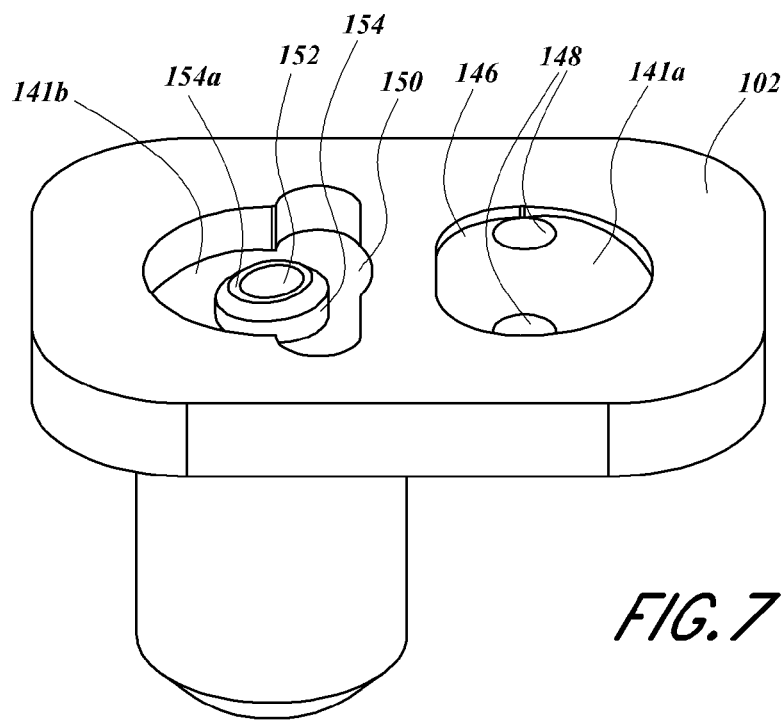
FIG. 7 is an isometric view of a second half or portion of a valve housing that could be formed on the housing, to complete the valve chamber.

FIG. 6 is an isometric view of the valve support member 120 and the valve plate 126 of the embodiment of the pump assembly embodiment 100 illustrated in FIG. 1. FIG. 7 is an isometric view of a second half or portion of a valve housing that could be formed on the housing 102, to complete the valve chamber.

With reference to FIG. 6, the first inlet valve chamber 121a of the valve support member 120 can have a cavity or depression 130 and one or more openings, such as opening 124 in communication with the depression 130 to permit the passage of air from a conduit connected to the boss 122 into the pump assembly embodiment 100 when the flap valve 128a is in an open position (for example, not sealingly covering the opening 124). A boss 131 can be formed within the depression 130 surrounding the opening 124 to provide a sealing surface for the valve flap 128 to selectively seal the opening 124. In any embodiments disclosed herein, the boss 131 can have an angled or curved surface 131a (as shown in FIG. 5) configured to substantially match the profile of the valve flap 128a as the valve flap 128a is deflected from its relaxed position to a position against the surface of the boss 131. This arrangement can improve the seal between the valve flap 128a and the boss 131 to increase the efficiency of the pump assembly embodiment 100.

As shown in FIG. 6, the first outlet valve chamber 121b can have a cavity or depression 132 and one or more openings 134 configured to allow the passage or exit of air from the inside of the depression 132 and the pump assembly embodiment 100 when the valve flap 128b is in an open position. In the embodiment shown in FIG. 6, the valve support member 120 has two openings 134 formed in the first outlet valve chamber 121b.

The housing 102 can have a similar arrangement of inlet and outlet valve chambers as compared to the first inlet and outlet valve chambers 121a, 121b.

With reference to FIG. 7, a second inlet valve chamber 141a supported or defined by the housing 102 can have a cavity or depression 146 and one or more openings 148 in communication with the depression 146 to permit the passage of air from the first inlet valve chamber 121*a* into the second inlet valve chamber 146 when the valve flap 128*a* is in an open position. One or more openings 148 (two being shown) can be formed in the second inlet valve chamber 141*a* to permit air to pass from the second inlet valve chamber 146 into the inside of the pump assembly embodiment 100. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber 141*b* can be supported or defined by the housing 102. The second outlet valve chamber 141*b* can have a depression 150 formed therein and an opening 152 in communication with the second outlet valve chamber 141*b*. A boss 154 can be formed within the depression 150 surrounding the opening 152 to provide a sealing surface for the valve flap 128*b* to selectively seal the opening 152. In any embodiments disclosed herein, similar to the boss 131, the boss 152 can have an angled or curved surface 154*a* configured to substantially match the profile of the valve flap 128*b* as the valve flap 128*b* is deflected from its relaxed position to a position against the surface of the boss 154*a*. This arrangement can improve the seal between the valve flap 128*b* and the boss 1154 to increase the efficiency of the pump assembly embodiment 100. When the valve flap 128*b* is in an open position, air or other fluid within the pump assembly embodiment 100 can pass through the opening 152 into the first outlet valve chamber 121*b* and exit the pump assembly embodiment 100 through the one or more openings 134.

In any embodiments disclosed herein, valve flaps 128*a*, 128*b* can be configured to be unstressed in a neutral position, neither fully open nor fully closed. Therefore, rather than there being a 'cracking pressure' required to open them, In any embodiments disclosed herein, a small back-pressure (e.g., approx. 30 mbar or more) can be used to hold valve flaps 128*a*, 128*b* closed. This can improve efficiency by reducing the pressure force that must be generated by the VCA during the suction stroke. The configuration of the pump assembly embodiment 100 can eliminate or reduce the need for a check valve or other one-way flow restrictor. In any of the embodiments disclosed herein, the valve flaps can operate at a frequency in the range of approximately 120 to approximately 150 Hz.

With reference again to FIG. 4, the pump assembly embodiment 100 can have a coil 160, a retainer 162, and a support 164. The support member 164 or any other components disclosed in this application can be formed by stereolithography, selective laser sintering, molding, or by other suitable processes. The coil 160 can be formed from a length of wound conductive wire, such as without limitation copper wire or amethyst. In any embodiments disclosed herein, the coil 160 or any coil disclosed herein can be formed by winding approximately 160 turns of wire, or from approximately 100 turns or less to 200 turns or more of wire, which can be but is not required to be, 42 gauge (approximately 0.102 mm diameter) wire. The wire used can be self-bonding wire that bonds to adjacent sections of wire upon application of heat. The wire can also be non-self-bonding wire. In any embodiments disclosed herein, approximately 200 turns of wire, or up to approximately 260 turns of wire, can be used to form the coil. Increasing the number of turns of wire In any embodiments disclosed herein of the pump assembly could reduce ohmic losses and could improve the overall efficiency of the pump by between approximately 22% and approximately 24%. As the number of turns of wire is increased, thereby increasing the efficiency of the pump, the size or thickness of the magnet can be decreased, thereby reducing the magnetic field outside of the pump that can potentially interfere with the function of pacemakers and other implanted cardiac devices (ICDs). It was generally determined during experimentation that increasing the number of turns of wire increased the suction stroke and improved the flow rate of the pump assembly.

In operation, the coil 160 is configured to move within a magnetic circuit, and is connected or supported via the support member 164 to a pump diaphragm assembly 166. The diaphragm 166 can be supported and/or fixed at its outer periphery 166*a*, wherein an interior portion 166*b* of the diaphragm assembly 166 is permitted to flex and deflect in either direction away from the relaxed position of the diaphragm assembly 166. In any embodiments disclosed herein, the diaphragm can be clamped and compressed between two rigid surfaces to provide such support. The rigid surfaces can define an annular shape. For example, some embodiments of the diaphragm 166 (or any other diaphragm disclosed herein) can have a moulding and a separate compression ring (made from a rigid plastic, aluminium or other metal, or any other suitable material or composite material). Additionally, some embodiments of the diaphragm 166 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 166 can be sealed at its outer perimeter 166*a*. The diaphragm assembly 166 is configured to elastically return the coil 160 to its relaxed position.

The configuration of the pump assembly embodiment 100 can be similar to that used in low fidelity loudspeakers, which fit a significant amount of magnetic material into a very compact space. With reference to the figures, the pump assembly embodiment 100 can have a magnet 174 positioned between a lower pole 176 and the upper pole 104. In any embodiments disclosed herein, the magnet 174 can be made from sintered Neodymium-Iron-Boron (NdFeB), Neodymium N33, or any other suitable material. This material can be used to maximize field strength and minimize losses, thereby increasing the efficiency of the pump assembly embodiment 100. However, In any embodiments disclosed herein, the magnet 174 can be formed from any suitable magnetic material.

Any of the magnets in any of the embodiments disclosed herein can have any suitable thickness and size, which can depend on the size of one or more of the other components of the pump assembly. For example, In any embodiments disclosed herein, the magnet 174 can have an approximately 25.65 mm outer diameter, an approximately 15 mm inner diameter, and be approximately 6 mm thick. Further, the magnet 174 of some embodiments can have an approximately 25.65 mm outer diameter, an approximately 17 mm inner diameter, and be approximately 3.5 mm thick. The thickness of the magnet In any embodiments disclosed herein can be as small as 2.5 mm.

Additionally, in any embodiments disclosed herein, the upper pole 104 can have a body portion 105 extending away from a planar portion 107 of the upper pole 104. With reference to the cross-sectional view in FIG. 7, the body portion 105 can extend in an axial direction through an axial opening formed in the coil 160, the magnet 174, and the lower pole 176. As will be described in greater detail below, in some embodiments, the body portion can improve the magnetic field of the voice coil actuator and improve the efficiency of the voice coil pump.

Additionally, In any embodiments disclosed herein, shielding components or materials configured to attenuate the magnetic field outside of the pump assembly can be used. For example, materials with very high nickel content (for example, from 50-80%) can be used for magnetic shielding. MuMetal is one material that can be used for this purpose.

Figure 8A:
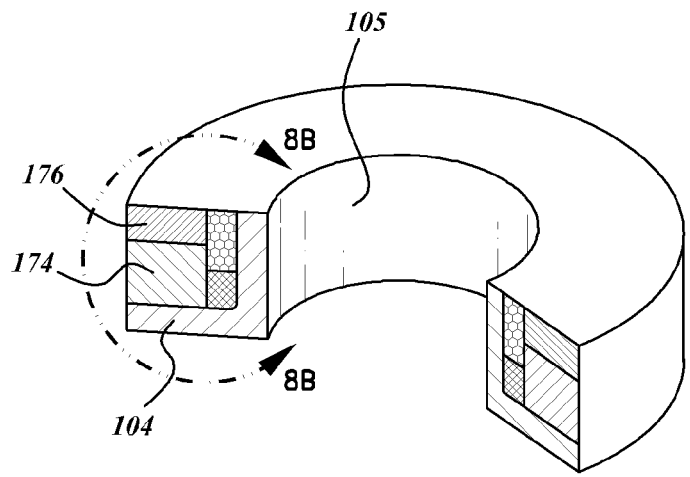
FIG. 8A illustrates one arrangement of a magnetic circuit of the pump assembly embodiment illustrated in FIG. 1.
Figure 8B:
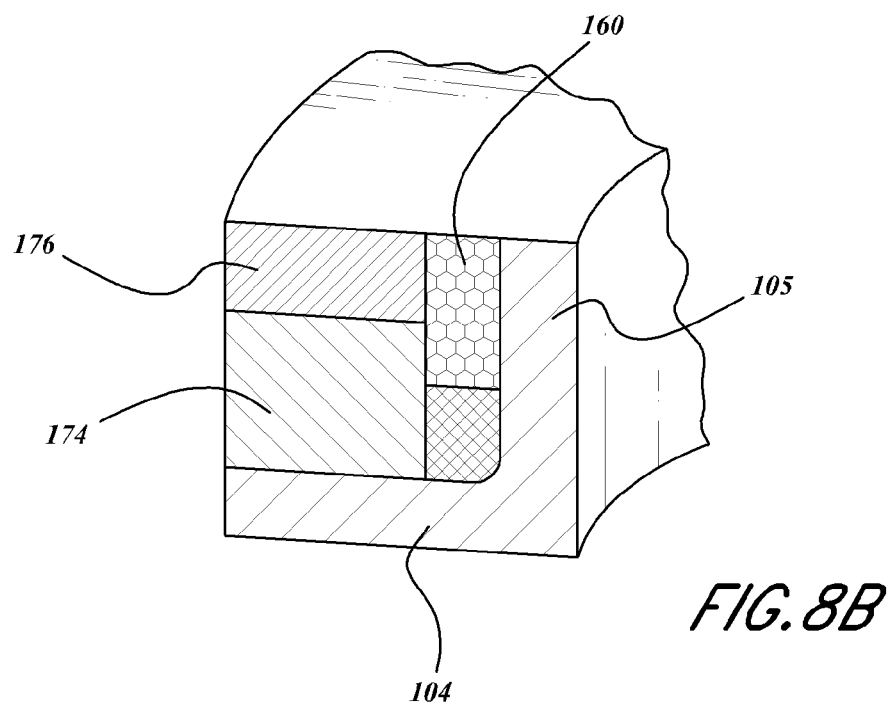
FIG. 8B is an enlarged view of a portion of the arrangement of the magnetic circuit illustrated in FIG. 8A.

One arrangement of a magnetic circuit is shown in FIG. 8. FIG. 8 is a partial cut-away of the an arrangement of a magnetic circuit, with contours of simulated radial magnetic field strength.

Strong magnetic fields can disrupt the function of pacemakers and other ICDs. Boston Scientific, a pacemaker manufacturer, states that 10 Gauss (G) is the maximum safe field that will not interfere with pacemakers. (Boston Scientific, *Portable media players and implantable pacemakers and defibrillators*, http://www.bostonscientific.com/templatedata/imports/HTML/CRM/A_Closer_Look/pdfs/ACL_Portable_MultiMedia_Players_030609.pdf, March 2009). Medtronic, another manufacturer, state that 5 G is the safe field. One paper states that a magnetic field strength of 5-10 G at the pacemaker or ICD has the potential to interact with the device. S. Lee, B. Ransford, K. Fu, K. Tadayoshi, and W. H. Maisel, *Electromagnetic interference (EMI) of implanted cardiac devices by MP*3 *player headphones*, American Heart Association's Scientific Sessions 2008. A fact sheet from the Swiss Federal Office of Public Health (http://www.bag.admin.ch/themen/strahlung/00053/00673/05059/index.html?lang=en) states that modern devices are immune to static fields of up to 10 G, but that older devices with a lower immunity threshold (5-10 G) are still in use.

The thin drum prototype described in greater detail below was measured to have a field strength of approximately 0.7 kG at the surface, dropping to 5 G at a distance of around 55 mm, as measured with a Gauss meter. In its current state, therefore, the pump should not be used within this distance from a pacemaker. If this distance can be reduced significantly (to, e.g., under 1 inch), that would be beneficial.

The arrangement of the pump assembly embodiment 100 can be configured to differ from a typical low fidelity loudspeaker. For example, some embodiments of the pump assembly 100 can differ in the following ways. In the pump assembly embodiment 100, the coil 160 can be configured to underhang below the end of the magnetic circuit. For example, the coil 160 can be configured such that it does not extend above the magnetic circuit. This can improve the efficiency and reduce the overall height of the pump assembly embodiment 100, but can result in the degradation of the linearity of response of the pump assembly embodiment 100.

The coil 160 can have a relatively high number of turns. For example, any coil embodiments disclosed herein, including but not limited to coils 160 and 260 (described below), can have approximately 100 or more turns of wire (which can be copper), or less than 100 turns or wire, or between approximately 100 turns and approximately 160 turns of wire. Some embodiments have as can fit into the space left by the magnetic circuit, based on available or practical wire thicknesses. Generally, the electrical efficiency of the pump assembly will be increased as the number of turns is increased. In any embodiments disclosed herein, the density of the copper can be maximized for the available space, or per unit volume of copper wire in the coil. In any of the embodiments described herein, the wire used for the coil can have a round, flat, square, rectangular, or diamond cross-section. The non-circular cross section shaped wire can result in a more dense copper wire packing and higher electrical efficiency.

Having a relatively high number of turns can give the coil 160 greater structural rigidity and, as mentioned, can maximize the efficiency of the pump assembly embodiment 100. Having a relatively high number of turns in the coil 160 can also limit the frequency of oscillation. The impact of limiting the frequency of oscillation should not affect the performance of the pump assembly embodiment 100 because, In any embodiments disclosed herein, the operating frequency of the pump assembly embodiment 100 can be limited by the responsiveness of the valves, for example, by the responsiveness of the valve flaps 128a, 128b.

Additionally, the pump assembly embodiment 100 will not have a speaker cone that is typically in a low fidelity speaker, which normally serves to control coil motion. In the pump assembly embodiment 100, the diaphragm can be used to center the coil 160, and a linear bearing 108 can be used to limit any wobble of the coil 160 by controlling the movement of the support member 164.

The housing 102, support 114, valve support member 120, retainer 162, and/or support member 164 can be made of a plastic or hard rubber material, metal, or any other suitable material or combination of materials. Such components can be formed by any suitable methods such as casting, any molding process such as injection molding, forging, sintering, machining, or any other suitable process.

Figure 105:
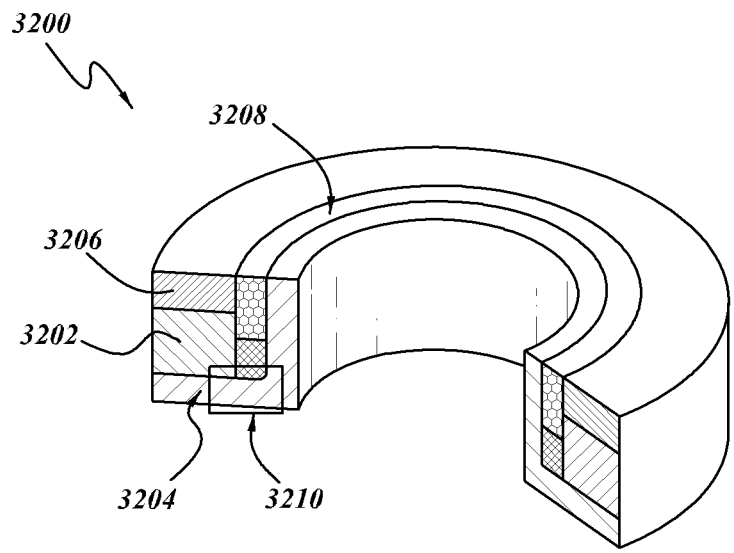
FIG. 105 illustrates another arrangement of a magnetic circuit of the pump assembly embodiment illustrated in FIG. 1.
Figure 106:
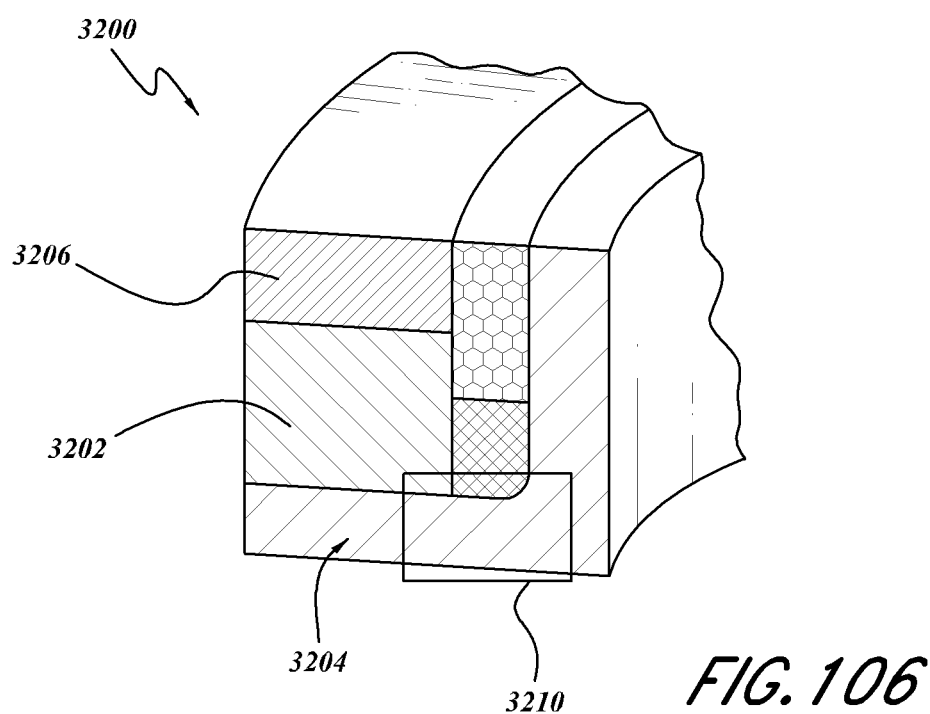
FIG. 106 is enlarged portion of the arrangement of the magnetic circuit of the pump assembly embodiment illustrated in FIG. 1.

FIG. 105 illustrates an arrangement of a magnetic circuit 3200 according to some embodiments. FIG. 105 is a partial cut-away of the an arrangement of the magnetic circuit 3200, with contours of simulated radial magnetic field strength (e.g., in Tesla). This arrangement can be similar to the arrangement illustrated in FIG. 8. The circuit 3200 can include a magnet 3202 positioned between a lower pole 3206 and an upper pole 3204. A coil 3208 can be positioned in a groove in which the coil moves. In any embodiments disclosed herein, the magnetic field can have a north orientation at the bottom of the diagram and a south orientation at the top of the diagram in FIG. 105. In certain embodiments, these directions can be reversed.

As is illustrated, the upper and lower pole pieces 3204 and 3206 are not symmetrical with respect to the coil 3208. In any embodiments disclosed herein, this arrangement of the upper and lower pole pieces can act as a magnetic field "guide" that places the magnetic flux symmetrically with the coil 3208. As is illustrated, the magnetic flux is at its strongest in region 3210 as is evidenced by the density of the flux lines in region 3210. Accordingly, the magnetic field of the magnet 3202, which would normally be centered around the magnet, is shifted to be aligned with the coil 3208. In any embodiments disclosed herein, the entire arrangement illustrated in FIG. 105 contributes to aligning the magnetic field with the coil 3208. In various embodiments, the arrangement and/or placement of the upper pole piece 3204 contributes to aligning the magnetic field with the coil 3208. In any embodiments disclosed herein, such alignment of the magnetic field with the coil 3208 improves efficiency of the voice coil pump.

Figure 9:
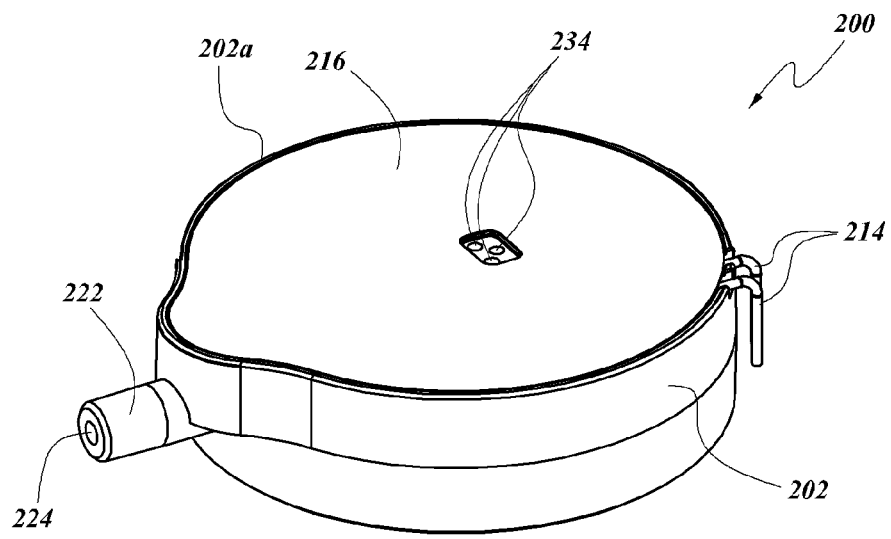
FIG. 9 is an isometric view of another embodiment of a pump assembly, showing a top surface of the pump assembly.
Figure 10:
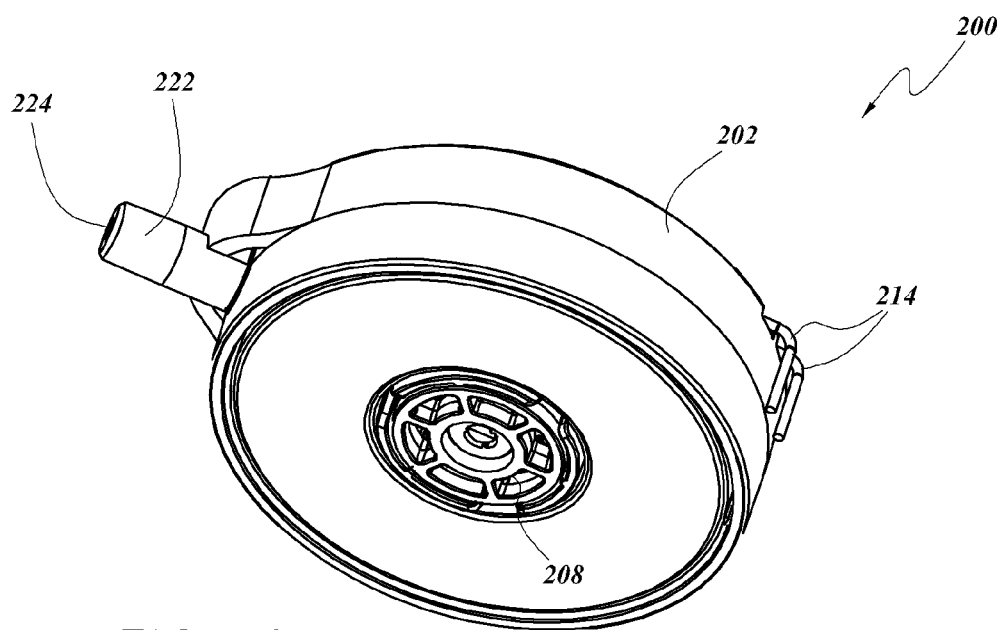
FIG. 10 is an isometric view of the pump assembly embodiment illustrated in FIG. 9, showing a bottom surface of the pump assembly.
Figure 11:
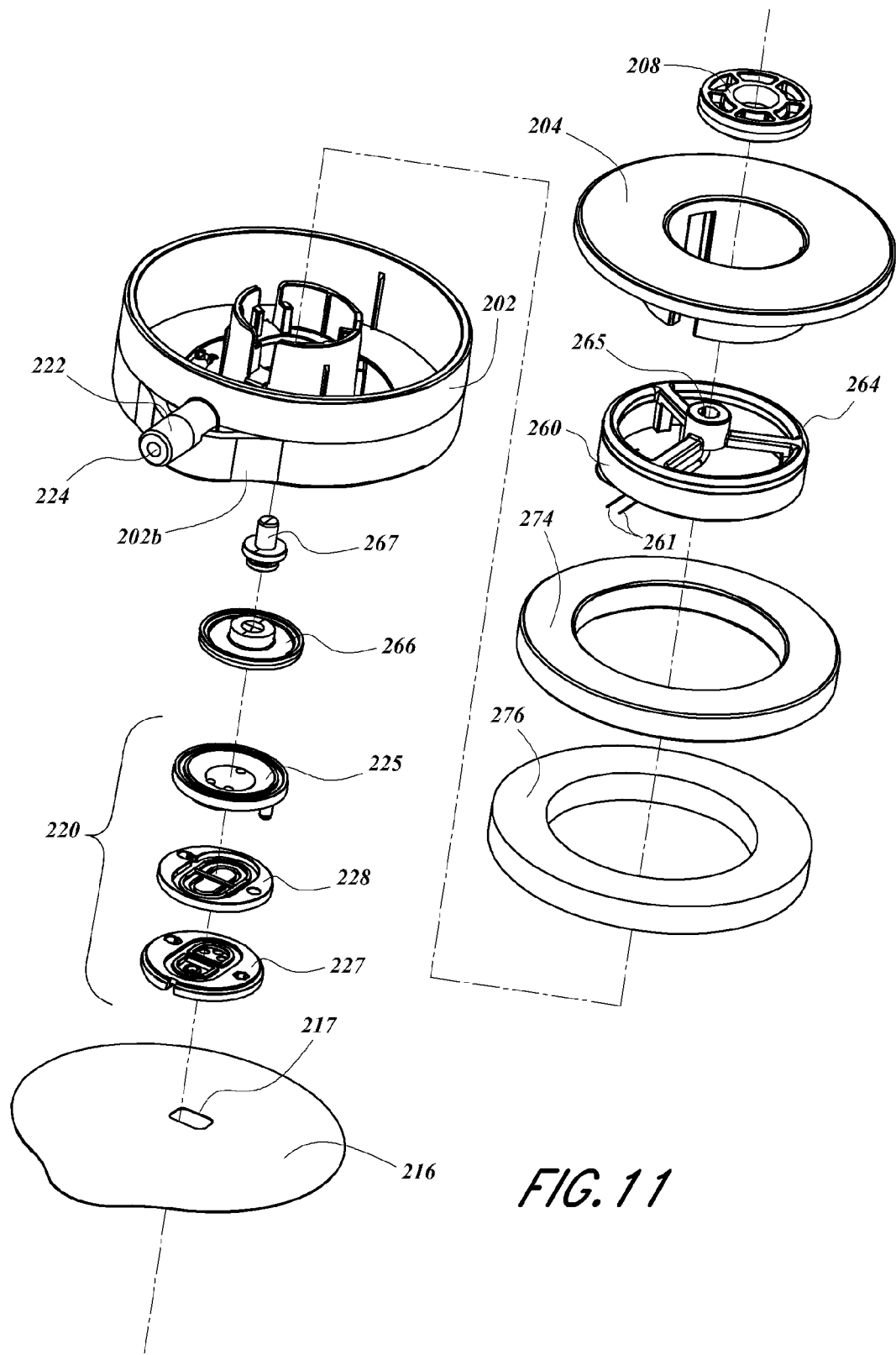
FIG. 11 is an exploded view of the pump assembly embodiment illustrated in FIG. 9, showing the top of the pump assembly.
Figure 12:
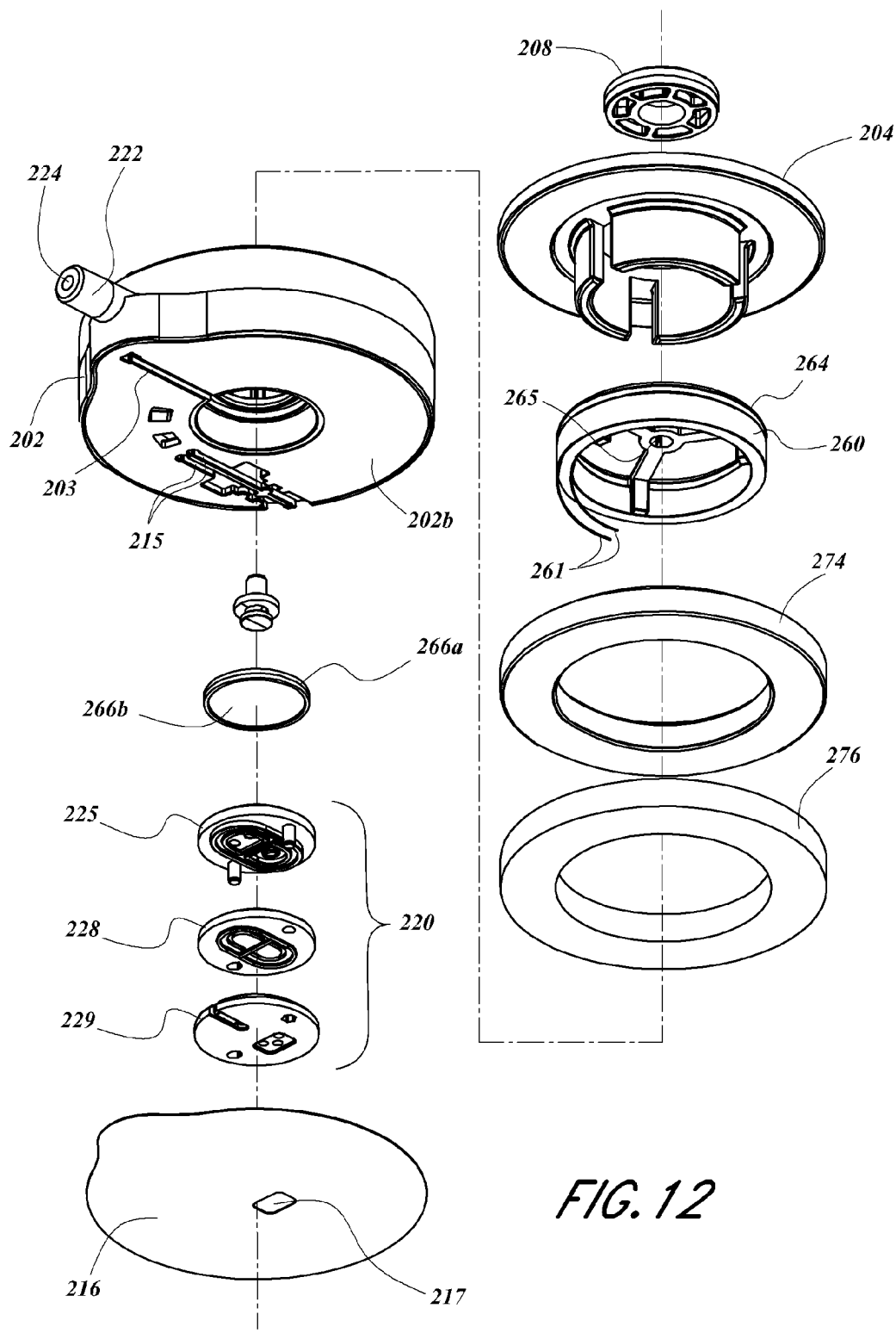
FIG. 12 is an exploded view of the pump assembly embodiment illustrated in FIG. 9, showing the bottom of the pump assembly.

FIGS. 9 and 10 are isometric views of another pump assembly embodiment 200, showing a top surface of the pump assembly and the bottom surface of the pump assembly, respectively. FIGS. 11 and 12 are exploded views of the pump assembly embodiment illustrated in FIG. 9, showing the top of the pump assembly and the bottom of the pump assembly, respectively. The pump assembly embodiment 200 can have a compact, small size and can have any of the same features, components, materials, or other details of the pump assembly embodiment 100 described above, or any of the other pump assembly embodiments disclosed herein.

In any embodiments disclosed herein, the pump assembly embodiment 200 can have a diameter or lateral size in the range of approximately 26-29 mm, or between approximately 25 and approximately 28 mm. In any embodiments disclosed herein, the pump assembly embodiment 200 can have a thickness or height of approximately 8 mm, or between approximately 6 mm and approximately 10 mm. Similar to the pump assembly embodiment 100 above, this embodiment and arrangement of the pump assembly embodiment can also be referred to as a "drum" type pump.

The pump assembly embodiment 200 can be produced for a low cost and can operate at high efficiencies, making it beneficial for portable, disposable, and/or single use applications. In any embodiments disclosed herein, the pump assembly embodiment 200 can run for a week on a small primary cell without the need for battery replacement or recharging. This pump can be used in an ultra-portable single-use negative-pressure wound therapy (NPWT) device, but is not so limited. In any embodiments disclosed herein, as mentioned, the pump assembly embodiment 200 can be used for negative pressure wound therapy. However, the pump assembly embodiment 200 is not limited to use in negative pressure wound therapy systems. The pump assembly embodiment can be adapted and configured for use in any reduced pressure system or in any system or application in which the movement of gaseous and liquid fluids is desired.

The pump assembly embodiment 200 can be designed to work at pressures of 60-80 mm Hg, and can be configured to produce a flow rate of approximately 200 ml min-1, with a minimum efficiency of 15%, in order for the NPWT device to run for a week on a specified battery capacity. In any embodiments disclosed herein, the pump assembly embodiment 200 can be adapted to operate at efficiency levels in excess of 25%.

With reference to FIGS. 9-12, the pump assembly embodiment 200 can have a housing 202 adapted to support and protect many of the components of the pump assembly embodiment 200. An upper pole 204, which can be made from any suitable materials such as mild steel or sintered steel, can be supported at one end (for example, a first end) 202a of the housing 202. In any embodiments disclosed herein, the upper pole 204 can have an opening 206 formed through an axial centerline of the upper pole 204. A bearing 208 can be supported by the upper pole 204, within the opening 206. Two or more electrical wires 214 can be connected to the pump assembly embodiment 200, configured to provide power to the pump assembly embodiment 200. In particular, the wires 214 can be used to provide electrical current to the coil 260 of the pump assembly. The electrical wires 214 can be routed through one or more openings or channels formed in the housing 202, such as channels 215 shown in FIG. 12.

A cover 216 can be positioned over the electrical wires 214 after the electrical wires have been advanced through the channels 215. The cover 216 can be an adhesive backed foil, film, paper, plastic sheet or label, or other similar object. An opening 217 can be formed in the cover 216 to permit air, gas, or other fluid to be exhausted from the pump through the outlet manifold.

Additionally, In any embodiments disclosed herein, the cover 216 can be configured to complete the inlet vacuum channel. In other words, the cover 216 can be configured to separate or seal the vacuum created by the pump from atmosphere. Using a thin label in place of a thicker plastic molded part or otherwise can decrease the height or thickness of the pump as much as possible. Alternatively, some embodiments of the pump assembly can have a thicker cover that can be molded, cast, machined, or formed by any other suitable method.

The housing 202 can support a valve assembly 220 at an end (for example, a second end 202b) of the housing 202. The housing 202 can support a boss member 222 that can receive a conduit therein or thereover, the boss member 222 having an opening 224 therethrough. The opening 224 can be in fluid communication with one or more passageways inside the pump assembly embodiment 200, such as air passageway 203 formed (that can be covered by the cover 216) in the housing 202 that communicates with the air passageway 229 formed in the valve assembly 220.

Figure 14:
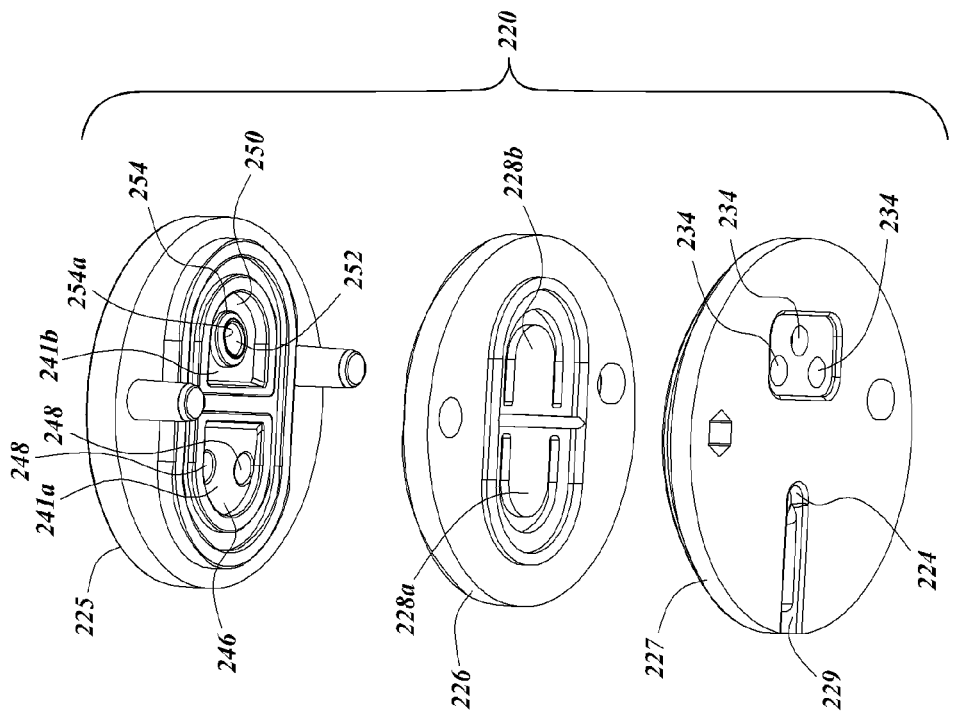
FIG. 14 is an exploded view of the valve assembly of the pump assembly embodiment illustrated in FIG. 9, showing the bottom of the valve assembly.
Figure 13:
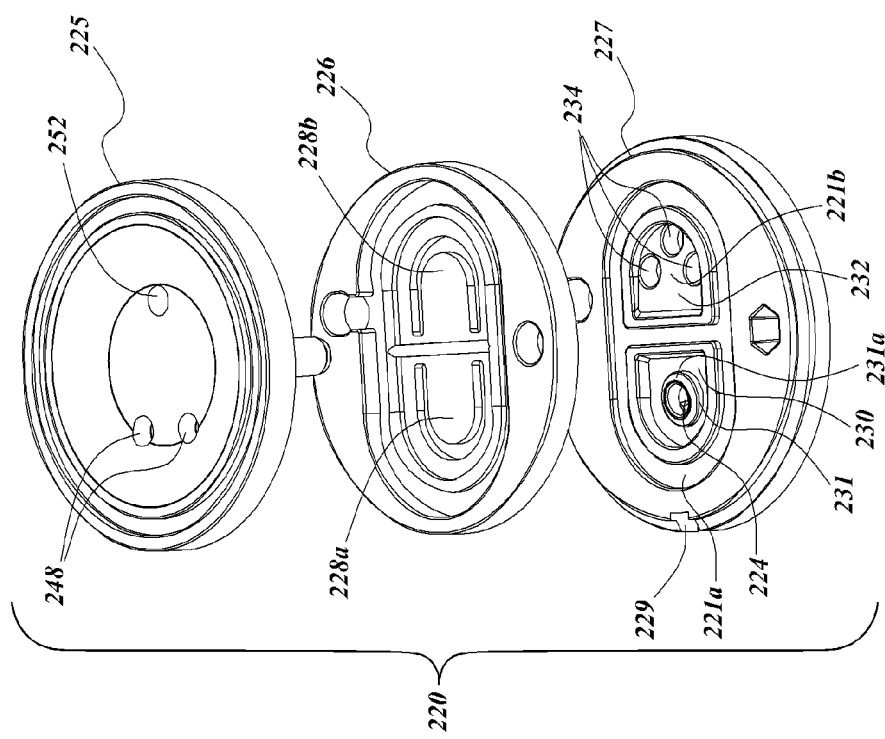
FIG. 13 is an exploded view of a valve assembly of the pump assembly embodiment illustrated in FIG. 9, showing the top of the valve assembly.
Figure 15:
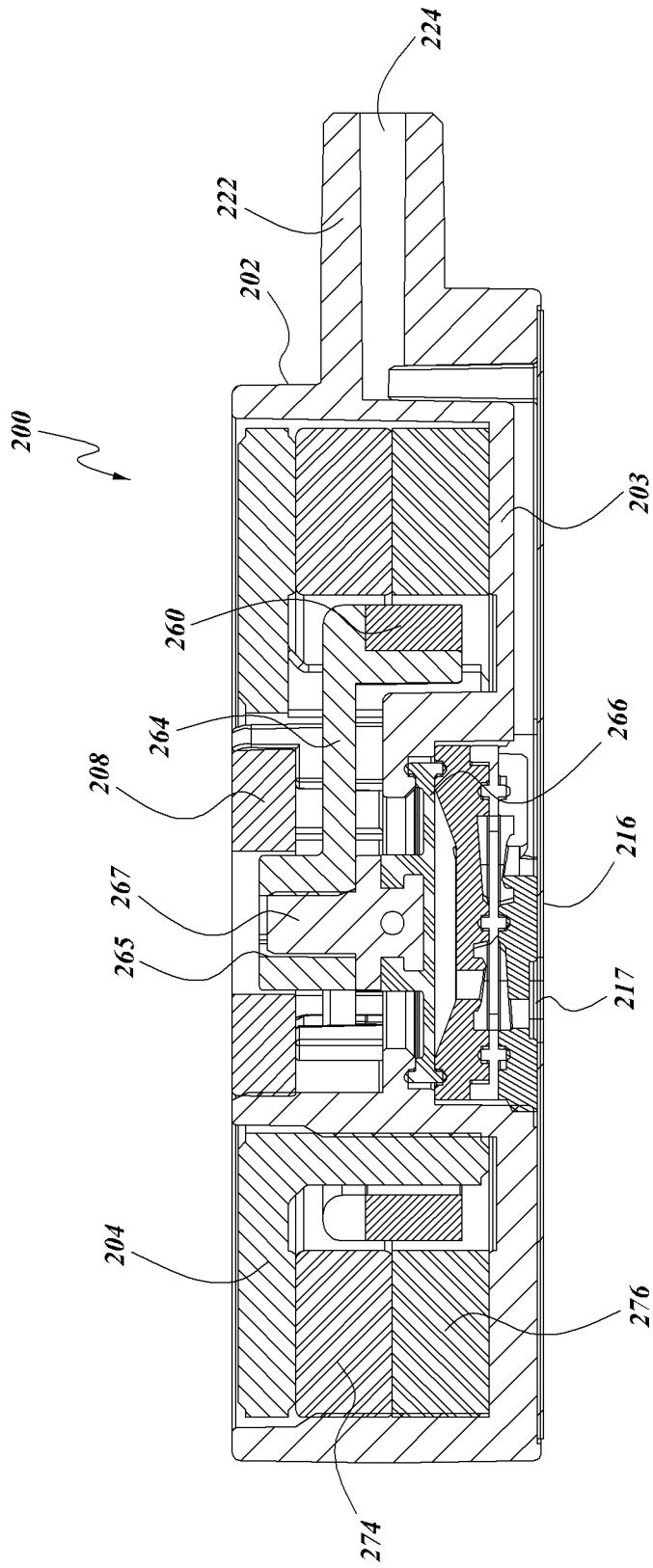
FIG. 15 is a section view of the pump assembly embodiment illustrated in FIG. 9, the section being taken through the center of the pump assembly embodiment.

FIGS. 13 and 14 are exploded views of the valve assembly of the pump assembly embodiment 200 illustrated in FIG. 9, showing the top of the valve assembly and the bottom of the valve assembly, respectively. FIG. 15 is a section view of the pump assembly embodiment 200 illustrated in FIG. 9, the section being taken through the center of the pump assembly embodiment 200. With reference to FIGS. 13 and 14, the valve assembly 220 can have a first valve member 225, a second valve member 227, and a valve plate 226. The valve plate 226 can support two flexible valve flaps 228, a first valve flap 228a for the inlet valve chamber and a second valve flap 228b for the outlet valve chamber. The first flap 228a and the second flap 228b can be configured to deflect away from the relaxed position of the flaps 228 shown in FIGS. 4-5.

The first inlet valve chamber 221a of the second valve member 227 can have a cavity or depression 230 and one or more openings, such as opening 224 in communication with the depression 230 to permit the passage of air from the channel 229 into the pump assembly embodiment 200 when the flap valve 228a is in an open position. A boss 231 can be formed within the depression 230 surrounding the opening 224 to provide a sealing surface for the valve flap 228 to selectively seal the opening 224. In any embodiments disclosed herein, the boss 231 can have an angled or curved surface 231a (as shown in FIG. 5) configured to substantially match the profile of the valve flap 228a as the valve flap 228a is deflected from the relaxed position against the surface of the boss 231. This arrangement can improve the seal between the valve flap 228a and the boss 231 to increase the efficiency of the pump assembly embodiment 200.

In use, for any of the embodiments disclosed herein, as the voltage supplied to the coil oscillates between a positive voltage and a negative voltage, the coil (which can be fixed to the support member and the diaphragm) can oscillate up and down in the pump between the two poles. The oscillation of the diaphragm can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm returns toward the valve support, the volume of airspace decreases, causing the air pressure to increase. This forces air out of the chamber through the outlet valve, while the inlet valve is sealed closed.

The first outlet valve chamber 221b of the second valve member 227 can have a cavity or depression 232 and one or more openings 234 configured to allow the passage or exit of air from the inside of the depression 232 and the pump assembly embodiment 200 when the valve flap 228b is in an open position. In the embodiment shown in FIGS. 9-14, the valve assembly 220 has three openings 234 formed in the first outlet valve chamber 221b. The housing 202 can have a similar arrangement of inlet and outlet valve chambers as compared to the first inlet and outlet valve chambers 221a, 221b.

With reference to FIGS. 13 and 14, a second inlet valve chamber 241a supported by the first valve member 225 can have a cavity or depression 246 and one or more openings 248 in communication with the depression 246 to permit the passage of air from the first inlet valve chamber 221a into the second inlet valve chamber 246 when the valve flap 228a is in an open position (e.g., not sealingly covering the opening 224). One or more openings 248 (two being shown) can be formed in the second inlet valve chamber 241a to permit air to pass from the second inlet valve chamber 246 into the inside of the pump assembly embodiment 200. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber 241b can be supported by first valve member 225. The second outlet valve chamber 241b can have a depression 250 formed therein and an opening 252 in communication with the second outlet valve chamber 241b. A boss 254 can be formed within the depression 250 surrounding the opening 252 to provide a sealing surface for the valve flap 228b to selectively seal the opening 252. In any embodiments disclosed herein, similar to the boss 231, the boss 252 can have an angled or curved surface 254a configured to substantially match the profile of the valve flap 228b as the valve flap 228b is deflected from the relaxed position against the surface of the boss 254a. This arrangement can improve the seal between the valve flap 228b and the boss 254 to increase the efficiency of the pump assembly embodiment 200. When the valve flap 228b is in an open position, air or other fluid within the pump assembly embodiment 200 can pass through the opening 252 into the first outlet valve chamber 221b and exit the pump assembly embodiment 200 through the one or more openings 234.

In any embodiments disclosed herein, valve flaps 228a, 228b can be configured to be unstressed in a neutral position, neither fully open nor fully closed. Therefore, rather than there being a 'cracking pressure' required to open them, In any embodiments disclosed herein, a small back-pressure (for example, approx. 30 mbar or more) can be used to hold valve flaps 228a, 228b closed. This improves efficiency by reducing the pressure force that must be generated by the VCA during the suction stroke.

The pump assembly embodiment 200 can have a coil 260 comprising electrical wires 261, a retainer 264, and a support 264. The coil 260 can be formed from a length of wound conductive wire, such as without limitation copper wire. In operation, the coil 260 is configured to move within a magnetic circuit, and is connected or supported via the support member 264 to a pump diaphragm assembly 266. In any embodiments disclosed herein, an opening 265 formed in the support member 264 can be configured to receive a boss or protrusion 267 of the diaphragm assembly 266 so the pump diaphragm assembly 266 can be coupled with the support member 264. The diaphragm 266 can be supported and fixed at its outer periphery 266a, wherein an interior portion 266b of the diaphragm assembly 266 is permitted to flex and deflect in either direction away from the relaxed position of the diaphragm assembly 266. The diaphragm assembly 266 is configured to elastically return the coil 260 to its relaxed position.

The diaphragm 266 can be supported and/or fixed along all or a portion of its outer periphery 266a, wherein an interior portion 266b of the diaphragm assembly 266 is permitted to flex and deflect in either direction away from the relaxed position of the diaphragm assembly 266. In any embodiments disclosed herein, the diaphragm can be clamped and compressed between two rigid surfaces to provide such support. The rigid surfaces can define an annular shape. For example, some embodiments of the diaphragm 266 (or any other diaphragm disclosed herein) can have a moulding and a separate compression ring (made from a rigid plastic, aluminium or other metal, or any other suitable material or composite material). Additionally, some embodiments of the diaphragm 266 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 266 can be sealed at its outer perimeter 266a. The diaphragm assembly 266 is configured to elastically return the coil 160 to its relaxed position. Any of the pump embodiments disclosed herein (i.e., in this application) can be formed from cast or molded silicone, polyurethane, thermoplastic polyurethane, and/or other suitable materials, having a hardness value of approximately 20A, 30A, 40A, 50A, 55A, or more.

The configuration of the pump assembly embodiment 200 can be similar to that used in low fidelity loudspeakers, which fit a significant amount of magnetic material into a very compact space. With reference to the figures, the pump assembly embodiment 200 can have a magnet 274 positioned between a lower pole 276 and the upper pole 204. In any embodiments disclosed herein, the magnet 274 can be made from sintered Neodymium-Iron-Boron (NdFeB). This material can be used to maximize field strength and minimize losses, thereby increasing the efficiency of the pump assembly embodiment 200. However, In any embodiments disclosed herein, the magnet 274 can be formed from any suitable magnetic material. In any embodiments disclosed herein, the lower pole can be approximately 1.5-2.0 mm thick and can be made from any suitable material, such as mild steel.

One arrangement of a magnetic circuit is shown in FIG. 8. FIG. 8 is a cut-away of an arrangement of a magnetic circuit, with contours of simulated radial magnetic field strength.

The arrangement of the pump assembly embodiment 200 can be configured to differ from a typical low fidelity loudspeaker. For example, some embodiments of the pump assembly 200 can differ in the following ways. In the pump assembly embodiment 200, the coil 260 can be configured to underhang below the end of the magnetic circuit. For example, the coil 260 can be configured such that it does not extend above the magnetic circuit. This can improve the efficiency and reduce the overall height of the pea 200, but can result in the degradation of the linearity of response of the pump assembly embodiment 200.

The coil 260 can have a relatively high number of turns. Having a relatively high number of turns can give the coil 260 greater structural rigidity and can maximize the efficiency of the pump assembly embodiment 200. Additionally, the pump assembly embodiment 200 will not have a speaker cone that is typically in a low fidelity speaker, which normally serves to control coil motion. In the pump assembly embodiment 200, the diaphragm can be used to center the coil 260, and a linear bearing 208 can be used to limit any wobble of the coil 260 by engaging the protrusion 267 and controlling the movement of the support member 264.

The housing 202, support 214, valve assembly 220, retainer 262, and/or support member 264 can be made of a plastic or hard rubber material, metal, or any other suitable material or combination of materials. Such components can be formed by any suitable methods such as casting, any molding process such as injection molding, forging, sintering, machining, or any other suitable process.

In any embodiments disclosed herein, as in any of the illustrated embodiments, the pump assembly can be of a sufficiently small and portable size to be supported on a user's body or in a user's clothing. For example, any of the pump assemblies disclosed herein can be sized to be attached using adhesive medical tape or otherwise to a person's skin or to a dressing in a comfortable location, adjacent to or on the dressing or otherwise. Further, any of the pump assembly embodiments disclosed herein can be sized to fit within a person's pants or shirt pocket, or can be tethered to a person's body using a lanyard, pouch, or other suitable device or article.

In any embodiments disclosed herein, the pump assembly can be powered by one or more batteries (for example, two batteries, or as described in any other embodiments described herein) and can weigh less than 80 grams, including the weight of the batteries. In any embodiments disclosed herein, the pump assembly can have any desired number of batteries and can weigh from approximately 70 grams to approximately 90 grams, or from approximately 75 grams to approximately 100 grams, or between any values within the foregoing ranges. For example, the weight and/or size of the pump assembly could be reduced by reducing the battery size and/or weight (to, for example, AAA sized batteries, or smaller) or the pump size and/or weight. Any embodiments of the pump assembly can be powered by any suitable electrical source, including a main supply of electricity.

Any of the pump assemblies described herein can have a layer of open foam or other material wrapped at least partially around an outside surface of the pump to reduce the noise and/or vibration produced by the pump. One or more labels can be affixed to an outside surface of the housing of any pump assembly disclosed herein, not only to seal the internal components, but also to recite printed information. Additionally, In any embodiments disclosed herein, the pump can have one or more weights, cushions, foam (such as a viscoelastic foam), plastic (such as ABS, polyurethane, urethane, or otherwise), or other pads, panels, sheets, or segments supported by the pump or positioned adjacent to one or more outside surfaces of the pump. Any embodiments can have mass based or compliant damping materials. Such components or materials (not illustrated) can damp vibration and/or attenuate noise produced by the pump.

Any of the pump assemblies disclosed herein can have a flow manifold and a one-way flow valve in communication with a fluid flow pathway within the pump assembly. The one-way flow valve (also referred to as a check valve) can be a diaphragm valve made from silicone or any other suitable elastomeric or soft material, including without limitation, polyurethane, viton, nitrile rubber, neoprene, Teflon, and other suitable materials. Other suitable valves for the one-way flow valve are, for example and without limitation, umbrella valves, ball valves, reed valves, duckbill valves. In any embodiments disclosed herein, the leakage rate of the one-way flow valve can be approximately 0.05 mL/minute or less. In any embodiments disclosed herein, the one-way flow valve can be positioned within the pump assembly or in place of one of the valves positioned within the pump assembly.

Any of the pump assembly embodiments disclosed herein can be powered by one or more batteries. The batteries can be lithium chloride or any other suitable batteries that are suitable for exposure to ethylene dioxide and/or other sterilization gases. The batteries can be supported outside of the pump housing so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Any embodiments of the dressings disclosed herein can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

As described in U.S. patent application Ser. No. 13/092,042, which disclosure is hereby incorporated by reference as if fully set forth herein, a lower surface of any of the wound dressing embodiments for use with the pump assembly disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation may be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of some embodiments of such an arrangement can be between approximately 367 $gm^{-2}/24$ hrs to approximately 405 $gm^{-2}/24$ hrs, or a mean moisture vapour permeability of 382 $gm^{-2}/24$ hrs.

Additionally, any of the dressing embodiments disclosed herein can have an anti-microbial agent or substance incorporated into the dressing or coated on one or more surfaces of the dressing. For example, without limitation, a wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 2008, which application is incorporated by reference herein as if made part of this disclosure, PHMB, chlorohexadine, peroxide, hypochloride, or other bleaches therein or thereon. Further, an absorbent layer of any dressing embodiments disclosed herein can have silver sulphur diazine or any of the previously mentioned substances or active agents therein or thereon. These may be used separately or together. These respectively can eliminate micro-organisms in the wound and micro-organisms in the absorption matrix. As a still further option, other active components, for example, pain suppressants such as ibuprofen or healing agents can be incorporated into the dressing. Also agents which enhance cell activity, such as growth factors or that inhibit enzymes, such as matrix metalloproteinase inhibitors, such as tissue inhibitors of metalloproteinase (TIMPS) or zinc chelators, can be incorporated into the dressing. Odor trapping elements such as activated carbon, cyclodextrine, zeolite or the like can also be included in the absorbent layer or other portions or components of the dressing, or above the filter layer.

Any embodiments of the wound therapy apparatuses disclosed herein can be manufactured in a wide variety of different models or versions, wherein the size of the dressing can be varied to accommodate a wide range of wound sizes. For example, without limitation, any of the embodiments disclosed herein can have any of the following sizes of dressings and wound pads or other absorbent elements.

| Approximate Dressing Size | Approximate Wound Pad Size |
|---|---|
| 10 cm × 30 cm (4 in × 11.75 in) | 5 cm × 20 cm (2 in × 8 in) |
| 15 cm × 15 cm (6 in × 6 in) | 10 cm × 10 cm (4 in × 4 in) |
| 15 cm × 20 cm (6 in × 8 in) | 10 cm × 15 cm (4 in × 6 in) |
| 10 cm × 20 cm (4 in × 8 in) | 5 cm × 10 cm (2 in × 4 in) |
| 20 cm × 20 cm (8 in × 8 in) | 15 cm × 15 cm (6 in × 6 in) |

In any embodiments disclosed herein, it may be preferable for the wound site to be filled partially or completely with a wound packing material. This wound packing material is optional, but may be desirable in certain wounds, for example deeper wounds. The wound packing material can be used in addition to the other components of overlay or overlay kit. The wound packing material generally can comprise a porous and conformable material, for example foam (including reticulated foams), and gauze. Preferably, the wound packing material is sized or shaped to fit within the wound site so as to fill any empty spaces. The wound dressing can then be placed over the wound site and wound packing material overlying the wound site. When a wound packing material is used, once the wound dressing is sealed over the wound site, TNP can be transmitted from a pump through or under the wound dressing, through the wound packing material, and to the wound site. This negative pressure draws wound exudate and other fluids or secretions away from the wound site. Some embodiments of the overlay or dressing can be substantially impervious to air flow and the flow of bacteria or other contaminants through the overlay layer, while being pervious to vapor transmission.

Any embodiments of the pump and dressing embodiments disclosed herein can be configured or adapted for sterilization before delivery to the hospital, operating room or theatre, or to the medical practitioner using such devices such that the sterile pump and/or a sterile pump/dressing kit can be applied immediately following the surgical or operating procedures. One advantage of this is that the surgeon can release the patient from the operating room knowing that the reduced pressure pump is operating and that the reduced pressure therapy has been started at the earliest point in time possible. A further advantage of applying the dressing kit immediately following the surgical or other procedure is that doing so can reduce the chance of infection by eliminating a subsequent dressing change that may otherwise be required in the ward. In other words, for those patients where a dressing (but not a pump) is applied in the operating theatre and then a problem is found thereafter, such as a leak or other issue with the dressing, if the dressing is required to be removed to be repositioned, replaced, or otherwise after the patient is released from the operating theater, the patient's wound may be exposed to infection risk when the dressing is repositioned, replaced, or otherwise outside of the operating theater.

However, with the embodiments disclosed herein, if the pump is applied and tested while the patient is in the operating theater, any issues with the dressing that may require the dressing to be removed, repositioned, or otherwise, can be handled in the sterile operating room environment, thereby significantly reducing or eliminating the risk of exposure to pathogens, bacteria, or other contaminants. Further, it is generally not possible for a hospital to sterilize a traditional pump once it has been received by the hospital, and therefore the hospital may resort to bagging the pumps in sterile bags but risk compromising the operating room sterile field with this approach, particularly once the device is turned on and pathogens, bacteria, or other contaminants that may be inside the pump are release due to the operation of the pump.

Any of the pump assembly embodiments disclosed herein can be configured to be amenable to gas sterilization, having features, components, and other characteristics that make the pump amenable to full sterilization gas exposure and penetration throughout the components of the pump. For example, without limitation, one or more pump valves or flap valves can be selected or configured to permit a sufficient flow of sterilization gas therethrough such that the entire fluid pathway within the pump can be exposed to the sterilization gas. As will be explained in greater detail below, In any embodiments disclosed herein, the pump can have other components, such as without limitation, strategically positioned one way flow valves, to complement the other valves within the pump, which can improve the efficiency of the pump by reducing leakage through the flow pathway within the pump assembly.

Additionally, where provided, the sterile pump/dressing kit can also be designed and configured to be amenable to gas sterilization. As described below, the sterile pump/dressing kit can be configured such that all of the components comprising the sterile pump/dressing kit, including the pump assembly, are packaged together in at least a first packaging element before sterilization, permitting all of the components to be sterilized together. Furthermore, as will be described, the components comprising the sterile pump/dressing kit can be arranged in the packaging such that at least some of the components can be removed in a predefined order, making it easier for the surgeon or medical practitioner to assemble and apply the dressing to the patient.

The pump assembly can be configured such that a sterilization gas, such as ethylene dioxide, can penetrate into the housing of the pump assembly such that the internal components of the pump assembly are exposed to the sterilization gas during normal sterilization processes. Typically, the pump will be exposed to the sterilization gas in a chamber that has been substantially evacuated of air or any other gas, so that the sterilization gas is drawn into the pump housing and into the other spaces and chambers within the pump assembly.

There are a number of benefits to being able to begin treatment of a wound in the operating theater, including without limitation providing a substantially sealed barrier over the wound while the wound is in a sterile condition and environment that will inhibit or prevent bacteria or other contaminants from getting into the wound. Additionally, initiating the reduced pressure treatment at the earliest stage possible is also advantageous to healing of the wound.

Additionally, embodiments disclosed or incorporated by reference herein, such as those disclosed in U.S. patent application Ser. No. 13/287, U.S. patent application Ser. No. 13/092,042, Great Britain Patent Application Nos. 1015656.0, 1006986.2, 1006983.9, 1006985.4, 1006988.8, and 1008347.5 comprise improved wound dressing components. All embodiments, components, features, and other details of such disclosures are hereby incorporated by reference herein as if made part of this disclosure, and can be used in place of or in combination with any of the components, features, and other details of the embodiments disclosed herein. For example, In any embodiments disclosed herein, the wound dressing can be configured to act as a buffer to help prevent compression or shear forces exerted on the wound dressing, for example due to patient movement, from harming a healing wound. Embodiments of the wound dressing may act as a waste canister to collect and store wound exudate removed from a wound site, and also relate to the management of solid build-up in a wound dressing covering a wound site whilst TNP therapy is applied. Further, embodiments disclosed herein relate to a method and suction port for applying negative pressure to a wound dressing and a method of manufacturing a suction port and wound dressing.

Moreover, some embodiments disclosed or incorporated by reference herein are directed to systems that include negative pressure therapy apparatuses and dressings, and methods and algorithms for operating such negative pressure therapy apparatuses for use with negative pressure therapy dressings. In any embodiments disclosed herein, a negative pressure therapy apparatus comprises a pump assembly configured to, inter alia, provide negative pressure to a wound. Some embodiments of pump assemblies disclosed herein comprise novel and inventive control logic configured to control the operation of the pump assembly. Any embodiments of the drum pumps disclosed herein can be configured such that their maximum pressure level produced by the pumps is less than the threshold value that is capable of injuring a user. For example, some drum pump embodiments disclosed herein can be configured so that it is impossible for the drum pump to produce vacuum levels that can harm a user.

For example, some embodiments comprise novel and inventive control logic configured to control the operation of a pump assembly in response to monitoring and detecting various operating conditions, such as presence and/or severity of a leak or leaks in the system, rate of flow of fluid (e.g., air, liquid and/or solid exudate, etc.) aspirated from a wound, and the like. In any embodiments disclosed herein, the control logic can be configured to detect a leak or leaks in a system (e.g., leak or leaks in the dressing that is in fluid communication with the pump, leak or leaks in the seal created by the dressing over the wound, etc.) as well as to control the operation of the pump assembly when such leak or leaks are detected. In any embodiments disclosed herein, the pump assembly can be configured to distinguish between at least a normal or low leak (e.g., a leak that has a relatively low flow rate), a high leak (e.g., a leak that has a relatively high flow rate), and a very high leak (e.g., a leak that has a relatively very high flow rate). Some embodiments can further be configured to also distinguish between the aforementioned leaks and an extremely high leak.

In any embodiments disclosed herein, the pump assembly can comprise a source of negative pressure, such as a miniature, disposable pump, powered by a power source, such as a battery source. The pump assembly can be configured to provide therapy for a predetermined period of time, such as approximately 1 day, 2-10 days, etc. In any embodiments disclosed herein, the pump assembly can be required to provide uninterrupted therapy for such period of time. In any embodiments disclosed herein, the pump assembly can be configured to deactivate itself a predetermined period of time (e.g., 7 days) after an initial activation. The algorithms or logic disclosed herein can help the pump assembly operate more efficiently and conserve power, for example but without limitation, battery power.

In any embodiments disclosed herein, the system can be configured to provide "play/pause" functionality and/or logic via a switch, button, etc. located on the exterior of the pump assembly's housing or any other suitable place where it can be accessed by the user. Play/pause functionality can allow the user to suspend and/or restart therapy (e.g., pause and/or restart the pump). The pump assembly can be configured to automatically restart therapy following a certain predetermined or variable pause interval. The pump assembly can be configured to automatically restart therapy upon expiration of such interval and/or indicate to the user expiration of such interval.

In any embodiments disclosed herein, the system can be configured to provide indication, alarms, etc. to the user reflecting operating conditions. The system can include visual, audible, tactile, and other types of indicators and/or alarms configured to signal to the user various operating conditions. Such conditions include system on/off, standby, pause, normal operation, dressing problem, leak, error, and the like. The indicators and/or alarms can include speakers (including a speaker made using some or all of the relevant components of the pump motor), displays, light sources, etc., and/or combinations thereof. For example, indication can be provided by activating or deactivating the source of negative pressure, reducing negative pressure level generated by the source of negative, lowering the amount of power used by the source of negative pressure, etc. or any combination thereof. Additionally, for example, the pump itself can be used to create audio alarm sounds, buzzing sensations, pulsing sensations, etc.

In any of the apparatus embodiments disclosed herein, the pump assembly can be a canisterless pump assembly (meaning that the pump assembly does not have an exudate or liquid collection canister). However, any of the pump embodiments disclosed herein can be configured to include or support a canister. Additionally, in any of the apparatus embodiments disclosed herein, any of the pump assembly embodiments can be mounted to or supported by the dressing, or adjacent to the dressing. The dressing may be placed over a wound (not illustrated) as described in greater detail in U.S. patent application Ser. No. 13/092,042, which disclosure is hereby incorporated by reference and made part of this disclosure, and a conduit may then be connected to the dressing. Any dressing disclosed herein can have any of the materials, sizes, components, or other details of any of the dressing embodiments disclosed in U.S. patent application Ser. No. 13/092,042, and such embodiments and illustrations thereof are hereby incorporated by reference in their entireties as if made part of this disclosure. The conduit or any other conduit disclosed herein can be formed from polyurethane, PVC, nylon, polyethylene, silicone, or any other suitable material.

Figure 16:
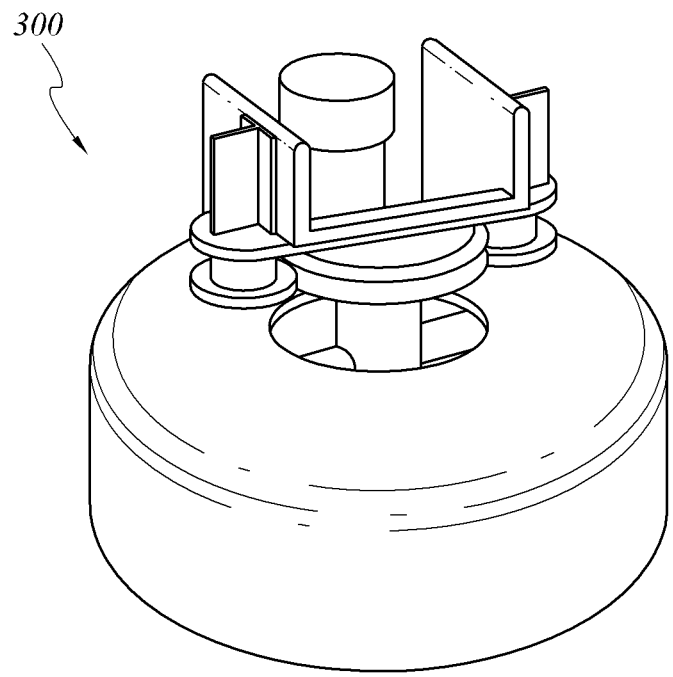
FIG. 16 is an illustration of a first drum pump (also referred to herein as a thick pump) that was built for experimental purposes.

Two examples of voice coil pump assemblies were constructed and tested. First, an embodiment of a thicker drum pump assembly 300, as illustrated in FIG. 16, was constructed. This assembly used an off-the-shelf, 25.65 mm outer diameter, 15 mm inner diameter, 6 mm high NdFeB ring magnet. The pump did not fit inside this ring, so the pump head with diaphragm and valves were separated out of the housing and separate from the magnet for this experimental setup.

Figure 17:
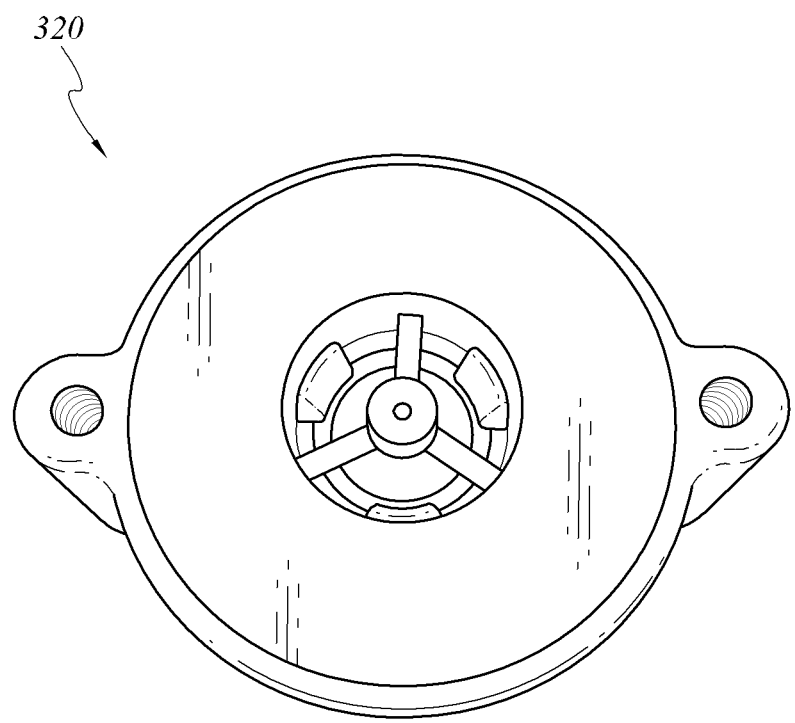
FIG. 17 is a photograph of a second drum pump (also referred to herein as a thin pump) that was built for experimental purposes.

Additionally, a thin drum style pump, such as the embodiment of the drum pump 320 as illustrated in FIG. 17, was constructed. The embodiment of the thin drum pump 320 comprises NdFeB magnets ground down to the target size. The magnets were machined using a combination of grinding and wire erosion. In both cases, the pole pieces were machined from mild steel, which has a high magnetic saturation. For this application, saturation is more important than permeability, and eddy currents are not an issue. Therefore, typical transformer steels may not be suitable or optimized for the pump embodiments disclosed herein.

In the two example voice coil pumps that were constructed, the valve chambers were machined from aluminum. Machined aluminum has a poor surface finish compared with typical high-volume injection-molded plastic parts. The poor surface finished of the aluminum parts may negatively affect the sealing performance and capabilities of the valves if not properly controlled. The valve chambers of any of the pump embodiments disclosed herein, such as those of pump assembly embodiments 100 or 200, can be made from injection molded plastic to improve the efficiency of the pumps. In addition, tolerances of machining are high compared with the total valve flap travel (which, in the constructed examples, was approximately 0.25 mm). The machined features can also deviate slightly from the ideal design for reasons of machinability.

The valve plate and diaphragm of the example pumps can be made from cast elastomers, using machined aluminum molds. Again, this may also negatively affect the surface finish of the valve flaps. Valve flaps in both silicone and polyurethane were tested, with a range of shore hardness values: 20A, 40A, 60A and 80A. Diaphragms were tested in both 30A and 40A silicone.

Figure 18:
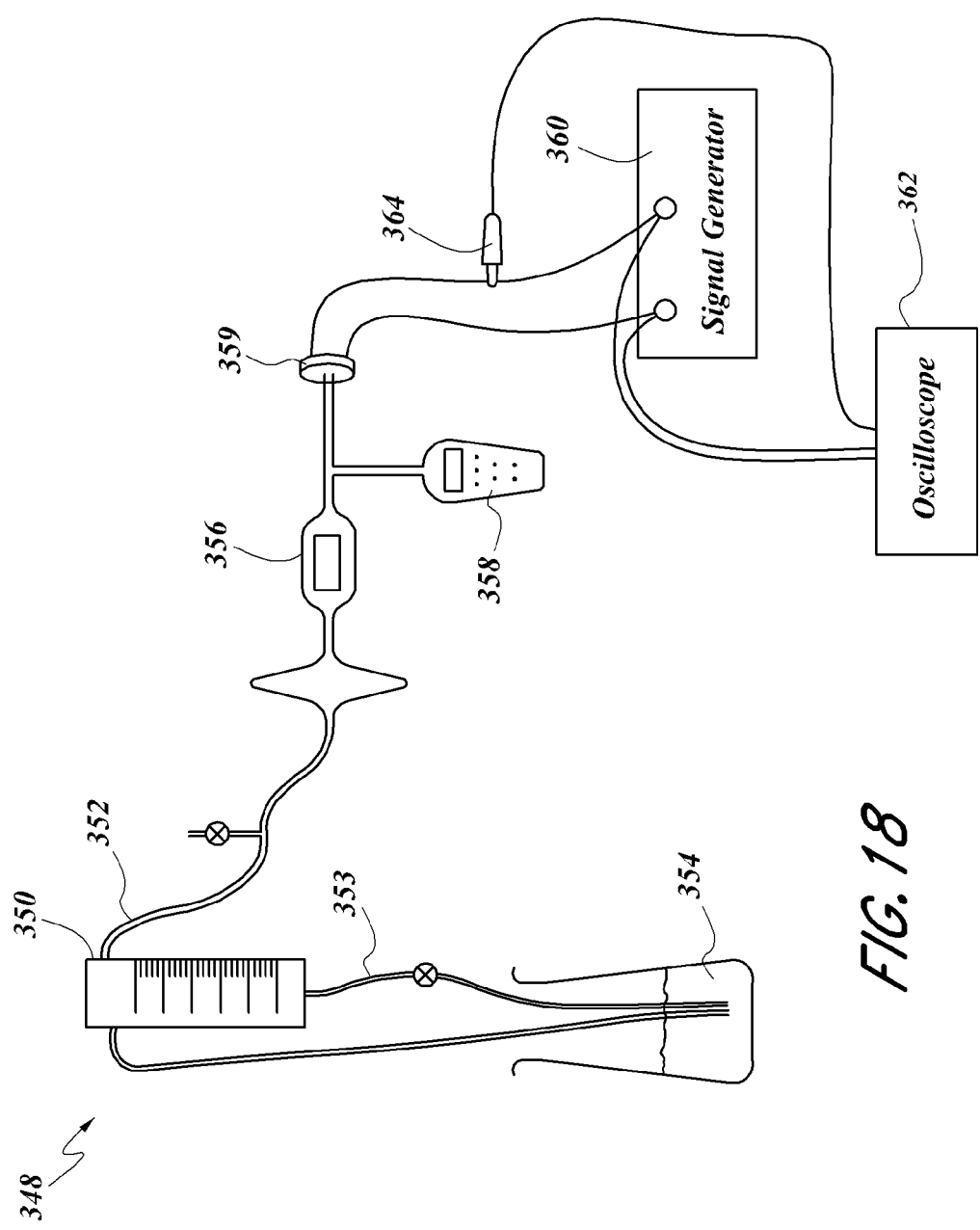
FIG. 18 shows a an illustration of the experimental test setup used to test the first, thick, and the second, thin, experimental pump assemblies.

FIG. 18 shows a schematic of the experimental test setup 348 used to test the thick experimental pump assembly embodiment 300 and the thin experimental pump assembly embodiment. A graduated cylinder 350 was used as a reservoir of air at constant pressure. Tubing 352 runs from the top of the cylinder to a water reservoir 354, and as air is drawn from the graduated cylinder 350, so water is drawn up the tubing 353 to replace it. The constant head of water maintains the pressure within the cylinder at 80 mm Hg below atmospheric pressure (approximately 10% vacuum).

The air is drawn through a TSI 4140 flow meter 356 (a thermal-mass flow meter). This flow meter 356 has an accuracy of ±5 sccm (standard cubic centimeters per minute) for flows of 10-250 sccm. In addition, the flow rate can be independently verified by measuring the rate at which water flows into the graduated cylinder, with an accuracy of ±4% (assuming flows around 100 ml min$^{-1}$, measured over approximately 1 minute). Pressure is determined by the head of water. However, it is also verified with a calibrated manometer 358, and also with a pressure meter built into the TSI 4140 flow meter. The tubing used is 6 mm ID except for the final section from manometer to pump, which is 2.5 mm ID. At the flow rates observed, and over the tubing lengths used, this does not give any significant pressure loss.

The VCA 359 is driven from a signal generator 360. The signal generator output is fed to an oscilloscope 362, monitoring the driving voltage, and a current clamp 364 monitors the current fed to the VCA 359. This data is logged by computer, which multiplies the two signals to determine instantaneous power draw, and averages the power draw over 2.5 seconds (250-500 cycles, for frequencies of 100 Hz-200 Hz, the frequencies used in testing).

The following metrics were used to evaluate pump performance:
Flow rate at approximately 80 mm Hg pressure (the maximum pressure that the NPWT system is expected to draw)
Efficiency, defined as (fluid power out)/(electrical power in). Fluid power is the product of pressure differential and flow rate.

The following experimental outputs were gathered. In both prototypes, peak flow rate was achieved with the 30 A silicone diaphragm and the 60 A polyurethane valve plate, driven by an offset square wave, and peak efficiency was achieved with the same mechanical configuration but driven by an offset sinusoidal or sine wave. The biased signal was, essentially, powering the pump in suction, and then providing a small 'nudge' to expel the air.

The drive signal in any pump embodiments disclosed herein, including those disclosed below, can be offset to increase the power of the stroke in one direction more than the other. For example, In any embodiments disclosed herein, it has been determined that the amount of force required to move the diaphragm in an air intake direction is greater than the amount of force required to move the diaphragm in an air offtake or outflow direction. Therefore, the voltage of the drive signal can be offset to supply more power to the motor during the intake portion of the stroke than the offtake portion of the stroke. Alternatively, any of the pump embodiments can be configured such that the diaphragm or one or more springs (elastomeric, plastic, metallic, or otherwise) bias the diaphragm in one direction more than another, for example, more in the intake direction than the outflow direction such that the pump can operate at optimal efficiency with a symmetrical drive signal (i.e., a non-offset drive signal).

Increasing the diaphragm hardness to 40 A made the pump behave in a more 'resonant' fashion: peak performance required an unbiased signal.

A 40 A valve plate was more tolerant of imperfections in valve housing geometry, but does not respond so quickly, and is therefore less efficient than the 60A valve when the geometry is close enough to design. Note that the prototype valve housings were aluminium machinings, whose dimensions and surface finish are poorly controlled relative to the plastic mouldings envisaged for full production.

The 20A valve plate did not respond quickly enough to produce a reasonable flow, and the 80A valve plate was too stiff for the valves to operate at all.

Experimental results for the thick pump assembly are listed below in Table 1.

Peak efficiencies achieved were 28.4%, for a flow rate of 60 ml min$^{-1}$ at the target pressure. Peak flow rate at the target pressure was 105 ml min$^{-1}$, at an efficiency of 24.1%.

TABLE 1

Thick drum experimental results

|  | Peak efficiency | Peak flow rate |
| --- | --- | --- |
| Pressure/mm Hg | 78.8 | 78.8 |
| Driving signal waveform | Offset sine | Offset square |
| Frequency/Hz | 120 | 120 |
| Peak +ve voltage | 2.7 | 3.0 |
| Peak −ve voltage | 1.3 | 1.0 |
| Power draw/mW | 37 | 76 |
| Diaphragm material | 30 shore A silicone | 30 shore A silicone |
| Valve material | 60 shore A PU | 60 shore A PU |
| Flow rate/ml min$^{-1}$ | 60 | 105 |
| Efficiency | 28.4% | 24.1% |
| Flow rate per power drawn/ml min$^{-1}$ mW$^{-1}$ | 1.62 | 1.38 |

Experimental results for the thin drum pump assembly are listed below in Table 2.

Peak efficiencies achieved were 22.3%, for a flow rate of 118 ml min$^{-1}$ at the target pressure.

Peak flow rate at the target pressure was 137 ml min$^{-1}$, at an efficiency of 22.3%.

Figure 19:
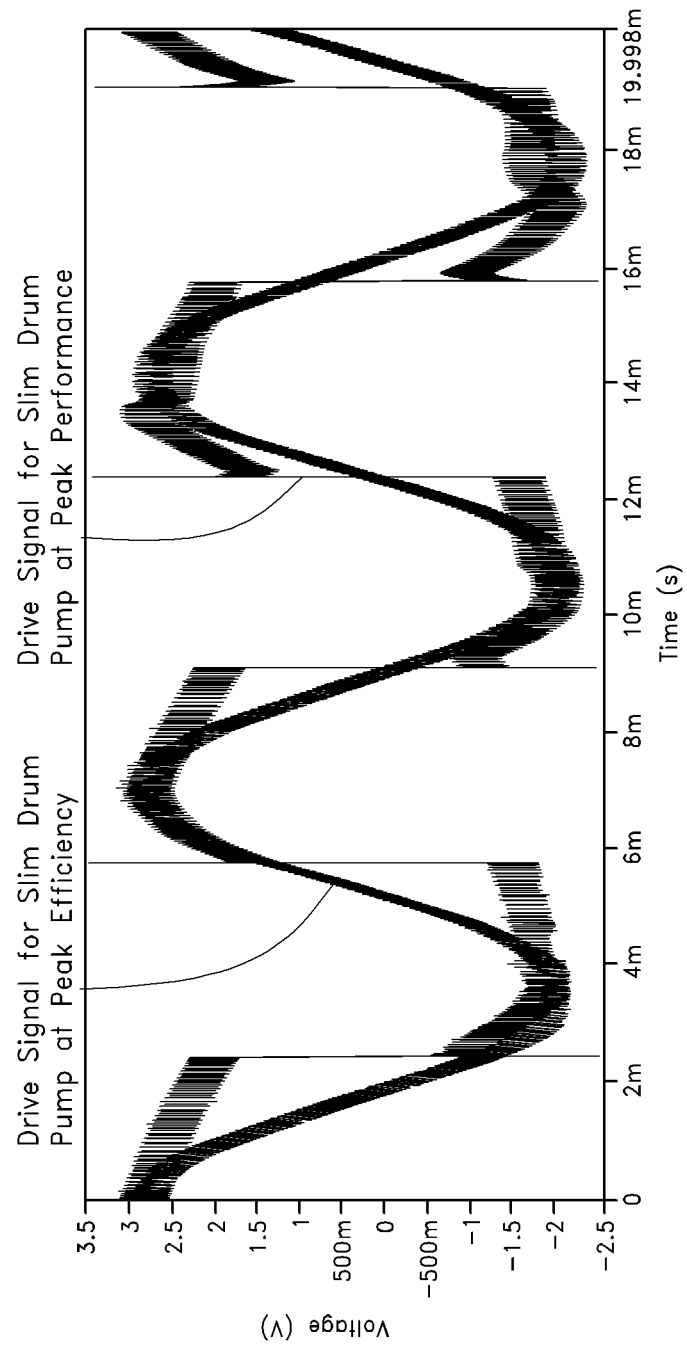
FIGS. 19 and 20 show the measured drive signal and current draw for second thin drum pump for the two cases described in Table 2.
Figure 20:
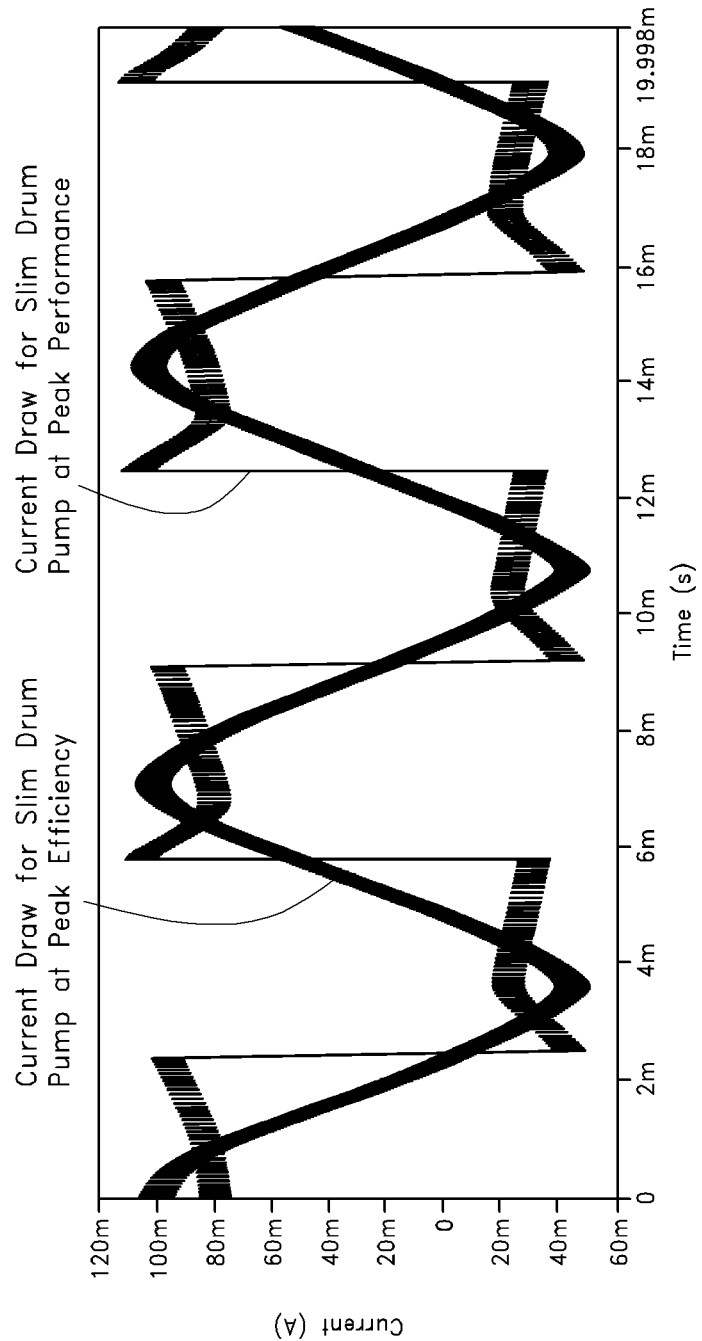
Figure 21:
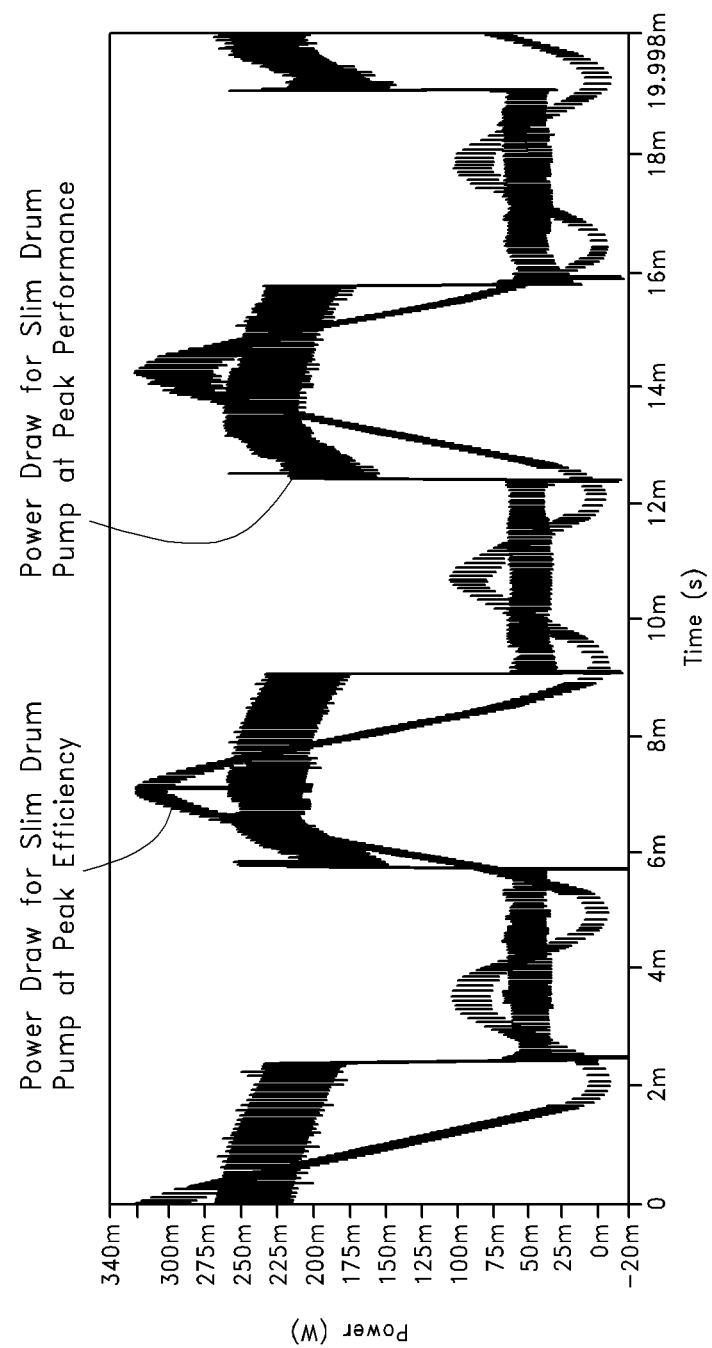
FIG. 21 shows the instantaneous power draw of the second, thin pump.

FIGS. 19 and 20 show the measured drive signal and current draw for the second, thin drum pump for the two cases described in Table 2. FIG. 21 shows the instantaneous power draw of the second, thin pump, which peaks at 320 mW for the sine signal. Note that one half of the signal contains almost all of the power draw (225 mW vs 50 mW, for the square wave signal): this is the 'suction' stroke. Expelling the air to atmosphere requires very little power.

Any of the voice coil actuated pump embodiments disclosed herein can be driven by a signal generator. For example, without limitation, any of the voice coil actuated pump embodiments disclosed herein can be driven by an offset square wave (for example, +3.0 V/−1.0 V), a square wave with a non-50-% duty cycle, an offset sine wave, a symmetric sine wave, a pulsed wave having pulses in either direction (e.g. 35% at +3.0V, 15% rest, 15% −3.0V, 35% rest), pulses in either direction with 'suck' pulse more than half the cycle (e.g. 75% at +3.0V, 25% −3.0V), or any other suitable drive signal.

Figure 22:
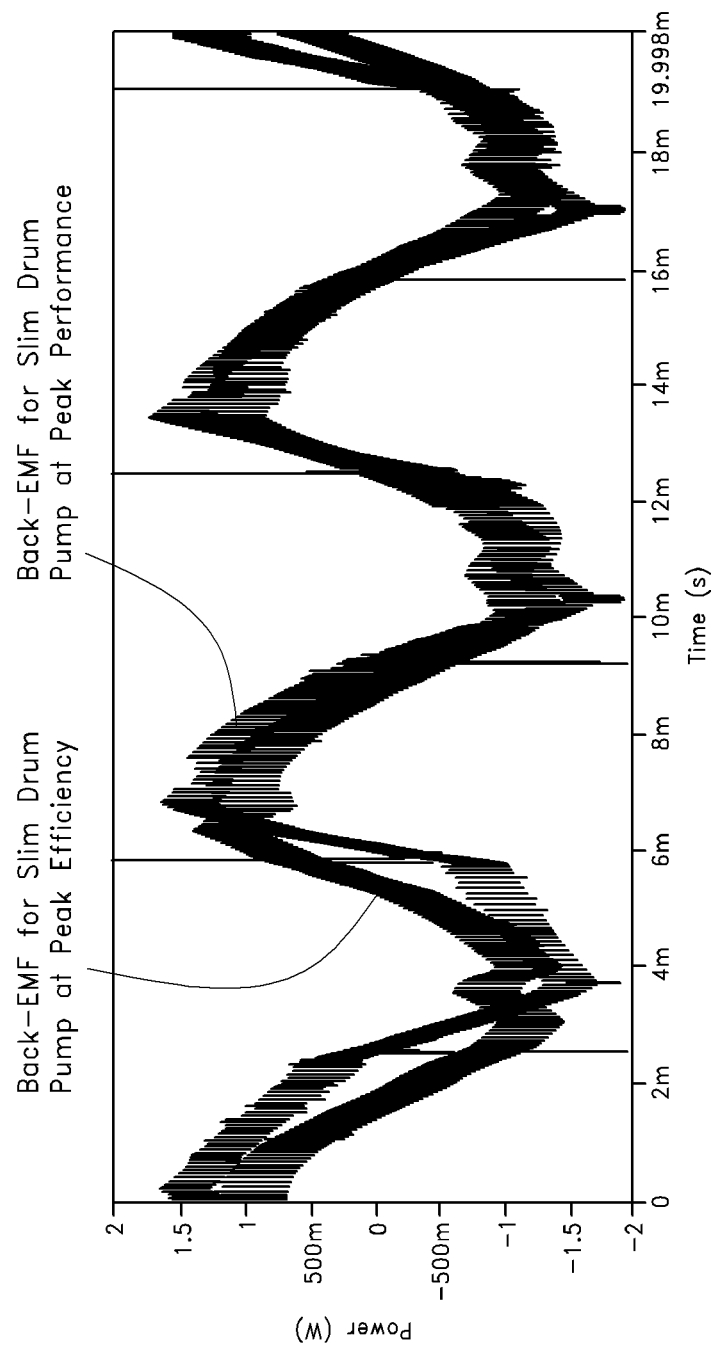
FIG. 22 illustrates the back EMF across the coil of the second, thin pump.

FIG. 22 illustrates the back EMF across the coil, based on a measured coil resistance of 19.5Ω. This is approximately proportional to instantaneous coil velocity, and shows that despite the significant difference in the power draw signal shapes, the motion of the pump is very similar in the two cases.

TABLE 2

Slim drum experimental results

|  | Peak efficiency | Peak flow rate |
| --- | --- | --- |
| Pressure/mm Hg | 80.3 | 80.3 |
| Driving signal waveform | Offset sine | Offset square |
| Frequency/Hz | 140 | 150 |
| Peak +ve voltage | 4.0 | 3.5 |
| Peak −ve voltage | 2.0 | 1.5 |
| Power draw/mW | 94 | 135 |
| Diaphragm material | 30 shore A silicone | 30 shore A silicone |
| Valve material | 60 shore A PU | 60 shore A PU |
| Flow rate/ml min$^{-1}$ | 118 | 138 |
| Efficiency | 22.3% | 18.2% |
| Flow rate per power drawn/ml min$^{-1}$ mW$^{-1}$ | 1.25 | 1.02 |

The following is a discussion of the experimental results. For both thick and thin drum embodiments, there was a single prototype, with valve mating surfaces made from machined aluminium. There were no specific alignment features to aid valve block assembly. Therefore, dismantling and reassembling the valve block typically had a large effect on performance, and it is anticipated that production surface finishes and tolerances would improve performance further.

However, the efficiencies achieved are very good for a vacuum pump on this scale, more than double the peak efficiency obtainable from the pump used in the current-generation ultra-portable NPWT device.

Further reductions in winding losses can be realised, by using production coil winding equipment. Currently, self-bonding wire is used, which is comparatively bulky. If normal insulated wire is used, the coil density can be increased by 50%, leading to a 33% reduction in resistive losses. System simulations suggest that the VCA losses are around 40% of total power draw, and therefore the peak efficiency of Fat Drum could rise to 33%, and the efficiency of Slim Drum could increase to 26%. This would be in addition to gains from improved valve performance (noted above).

Figure 99:
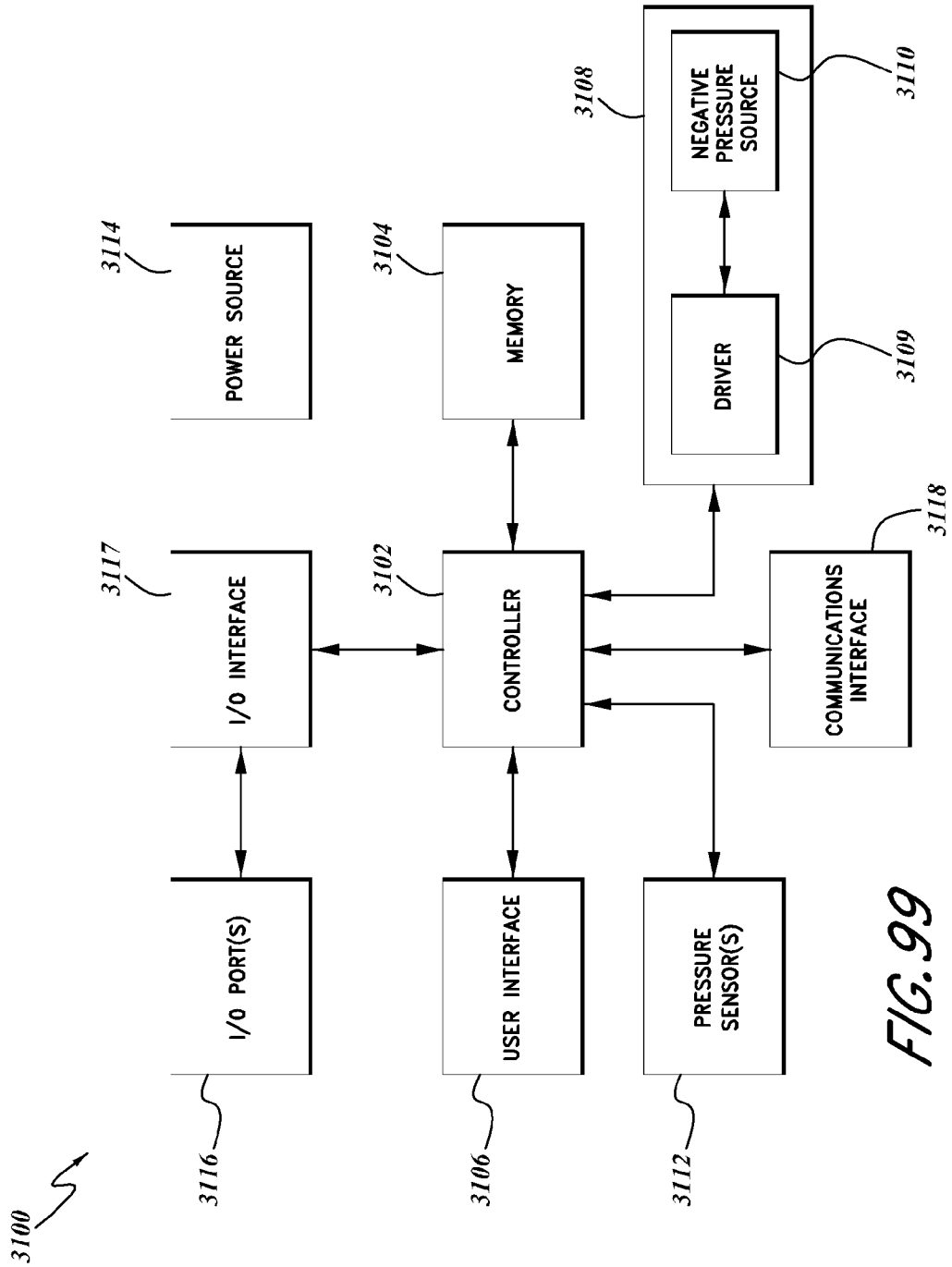
FIG. 99 is an electrical component schematic of an embodiment of a pump assembly.

FIG. 99 is an electrical component schematic 3100 of an embodiment of the pump assembly 100 or any pump assembly embodiment disclosed herein, particularly the voice coil actuated drive pumps. Electrical components can operate to accept user input, provide output to the user, operate the pump assembly and the source of negative pressure, provide network connectivity, and so on. Electrical components can be mounted on one or more PCBs (not shown). The pump assembly can include a controller or processor 3102. In any embodiments disclosed herein, the controller 3102 can be a general purpose processor, such as a low-power processor. In other embodiments, the controller 3102 can be an application specific processor. In any embodiments disclosed herein, the controller 3102 can be configured as a "central" processor in the electronic architecture of the pump assembly, and the controller 3102 can coordinate the activity of other controllers, such as a user interface controller 3106, I/O interface controller 3117, negative pressure control module 3108, communications interface controller 3118, and the like.

The pump assembly can also include a user interface controller or processor 3106 configured to operate one or more components for accepting user input and providing output to the user, such buttons, indicators (e.g., LEDs), displays, etc. Input to the pump assembly and output from the pump assembly can controlled via one or more input/output (I/O) ports 3116 controlled by an I/O interface module or controller 3117. For example, the I/O module 3117 can receive data from one or more I/O ports 3116, such as serial, parallel, hybrid ports, expansion ports, and the like. In any embodiments disclosed herein, I/O ports 3116 include one or more of USB ports, SD ports, Compact Disc (CD) drives, DVD drives, FireWire ports, Thunderbolt ports, PCI Express ports, and the like. The controller 3102, along with other controller or processors, can store data in one or more memory modules 3104, which can be internal and/or external to the schematic 3100. Any suitable type of memory can be used, including volatile and/or non-volatile memory, such as RAM, ROM, magnetic memory, solid-state memory, Magnetoresistive random-access memory (MRAM), and the like. The pump assembly can be powered by a power source 3114, which can comprise one or more disposable or rechargeable batteries, mains, etc. The power source 3114 can be internal or external to the schematic 3100.

A negative pressure or pump control module 3108 can be configured to control the operation of a negative pressure source 3110. The negative pressure source 3110 can be a voice coil pump. Other suitable pumps include diaphragm pumps, peristaltic pumps, rotary pumps, rotary vane pumps, scroll pumps, screw pumps, liquid ring pumps, diaphragm pumps operated by a piezoelectric transducer, and the like. The pump control module 3108 can include a driver module 3109 configured to control the operation of the negative pressure source 3110. For example, the driver module 3109 can provide power to the negative pressure source 3110. Power can be provided in a form of a voltage and/or current signal. In any embodiments disclosed herein, the driver module 3109 controls the negative pressure source 3108 using pulse-width modulation (PWM). A control signal for driving the negative pressure source 3108 (or pump drive signal) can be a 0-100% duty cycle PWM signal.

The controller 3102 can receive information from one or more sensors 3112 placed in a suitable location in a fluid flow path. In any embodiments disclosed herein, the controller 3102 can measure pressure in the fluid flow path, using data received from one or more pressure sensors 3112, calculate the rate of fluid flow, and control the negative pressure source 3110 so that desired level of negative pressure is achieved in a wound cavity or under the dressing. The desired level of negative pressure can be pressure set or selected by a user. Pressure measured by the one or more sensors can be provided to the controller 3102 so that the controller can determine and adjust the pump drive signal to achieve the desired negative pressure level. In any embodiments disclosed herein, the tasks associated with controlling the negative pressure source 3110 can be offloaded to the pump control module 3108, which can include one or more controllers or processors.

In any embodiments disclosed herein, it may be advantageous to utilize multiple processors for performing various tasks. In any embodiments disclosed herein, a first processor can be responsible for user activity and a second processor can be responsible for controlling the negative pressure source. This way, the activity of controlling the negative pressure source, which may necessitate a higher level of responsiveness, can be offloaded to a dedicated processor and, thereby, will not be interrupted by user interface tasks, which may take longer to complete because of interactions with the user.

A communications interface controller or processor 3118 can be configured to provide wired and/or wireless connectivity. The communications processor 3118 can utilize one or more antennas (not shown) for sending and receiving data. In any embodiments disclosed herein, the communications processor 3118 can provide one or more of the following types of connections: Global Positioning System (GPS) technology, cellular or other connectivity, such as 2G, 3G, LTE, 4G, WiFi, Internet connectivity, Bluetooth, zigbee, RFID, and the like. Additionally, any embodiments disclosed herein can be configured to synchronize, upload, or download data to and/or from the pump apparatus to and/or from a portable data device, such as a tablet, smart phone, or other similar devices.

Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. In any embodiments disclosed herein, the communications processor 3118 can provide dual GPS/cellular functionality. Cellular functionality can, for example, be 3G functionality. In such cases, if the GPS module is not be able to establish satellite connection due to various factors including atmospheric conditions, building or terrain interference, satellite geometry, and so on, the device location can be determined using the 3G network connection, such as by using cell identification, triangulation, forward link timing, and the like. In any embodiments disclosed herein, the pump assembly can include a SIM card, and SIM-based positional information can be obtained.

In any embodiments disclosed herein, the performance and efficiency of the pump can be improved by selecting a suitable signal or waveform for driving the coil (e.g., coil 160 of the pump assembly). A suitable driving waveform can be applied to the coil by the controller (e.g., by the driver module 3109). For example, a suitable waveform can be applied to the voice coil actuator (or pump motor). In any embodiments disclosed herein, the pressure differential across a diaphragm of a pump (e.g., diaphragm 166) when the diaphragm is drawing against vacuum (or removing gas from the fluid flow pathway) can be determined as the sum of the pressure drop across the valves and the vacuum level under the dressing. For example, In any embodiments disclosed herein, the negative pressure range can be approximately −80 mmHg, which means that the vacuum level of up to 80 mm Hg can affect the pressure drop across the diaphragm. When the diaphragm is expelling removed gas (e.g., expelling removed air to the atmosphere), the pressure differential across the diaphragm can be determined as the pressure drop across the valves. In other words, when gas is being expeled, the pressure differential across the diaphragm is substantially equivalent to the pressure drop across the valves.

Figure 23:
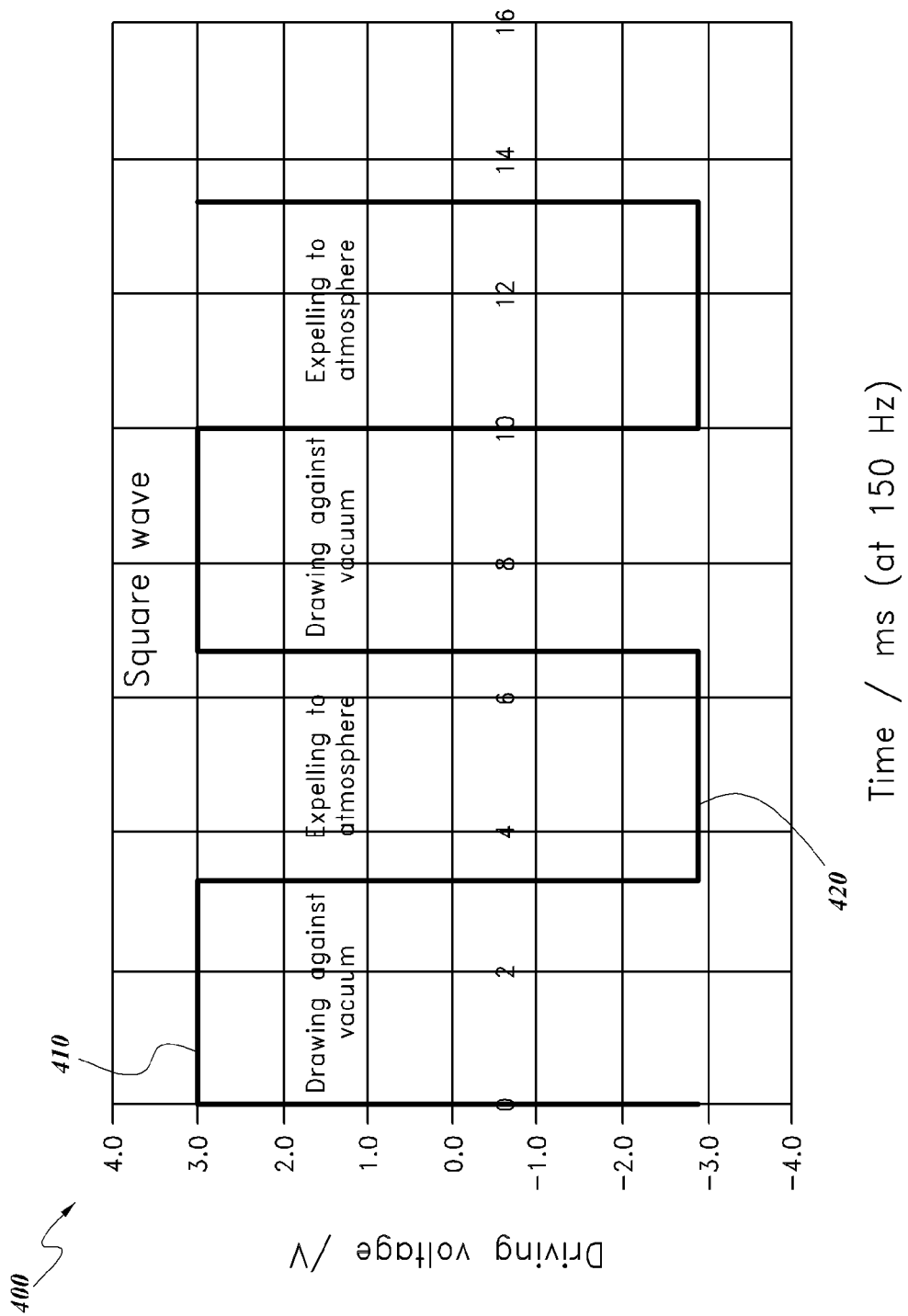
FIGS. 23-26 illustrate waveforms of various signals for driving a diaphragm.

In any embodiments disclosed herein, the force for expelling removed gas can be smaller than the force for drawing vacuum (e.g., removing gas from the fluid flow pathway). If a symmetric signal, such as a square wave or sine wave of equal positive and negative amplitude is applied to the coil, the diaphragm may oscillate about a point that is not its relaxed center state, which may reduce the total diaphragm travel. One such signal is illustrated in FIG. 23, which depicts a symmetric square wave voltage signal 400 that can be applied to the coil. In any embodiments disclosed herein, symmetric signals, such as that depicted in FIG. 23, can be used to drive the coil, which thereby causes the diaphragm to flex and deflect. Although a voltage waveform is depicted, it will be understood that waveform of current applied to the coil can be alternatively or additionally illustrated. As is shown, symmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 410) and to expel the removed gas (depicted as region 420). As is illustrated, the waveforms applied in regions 410 and 420 are identical with the exception of the reversal of voltage magnitude (e.g., so that the diaphragm oscillates in opposite directions in regions 410 and 420). In any embodiments disclosed herein, other suitable magnitudes of voltage can be used, such as between −1.0 V and 1.0V, −2.0 V and 2.0 V, −4.0 V and 4.0 V, and so on. In any embodiments disclosed herein, increasing the voltage can increase the flow rate of the pump assembly, but can result in greater energy losses in the coil, which can decrease the operating efficiency of the pump.

Any suitable frequency of the driving waveform can be used, such as frequencies less than or greater than 150 Hz.

In any embodiments disclosed herein, driving the coil with using a symmetrical waveform can reduce the performance and efficiency of the pump. Such reduction in performance and efficiency can be avoided by utilizing a stiffer diaphragm (e.g., so that deflection resulting from the vacuum level under the dressing is negligible). However, In any embodiments disclosed herein, its may be advantageous to have the natural frequency of the diaphragm-coil assembly match the frequency at which the valves perform substantially optimally. In such cases, increasing the diaphragm stiffness may require the use of valves to having a faster response or may require the use of a heavier coil (which can increase the vibration felt by a user and may also generate more operational noise). In addition, with increase in the diaphragm stiffness, more energy is put into it in each oscillation cycle, which may cause greater hysteric losses in the diaphragm elastomer.

In any embodiments disclosed herein, in order to achieve substantially optimal efficiency, a soft diaphragm can be driven by a biased drive signal(s). Such signal(s) can, In any embodiments disclosed herein, combine an oscillating force to drive the diaphragm and a constant force for countering the pressure differential due to the vacuum under the dressing. The diaphragm can achieve full travel, which can be important for effective and efficient operation of the pump.

Figure 24:
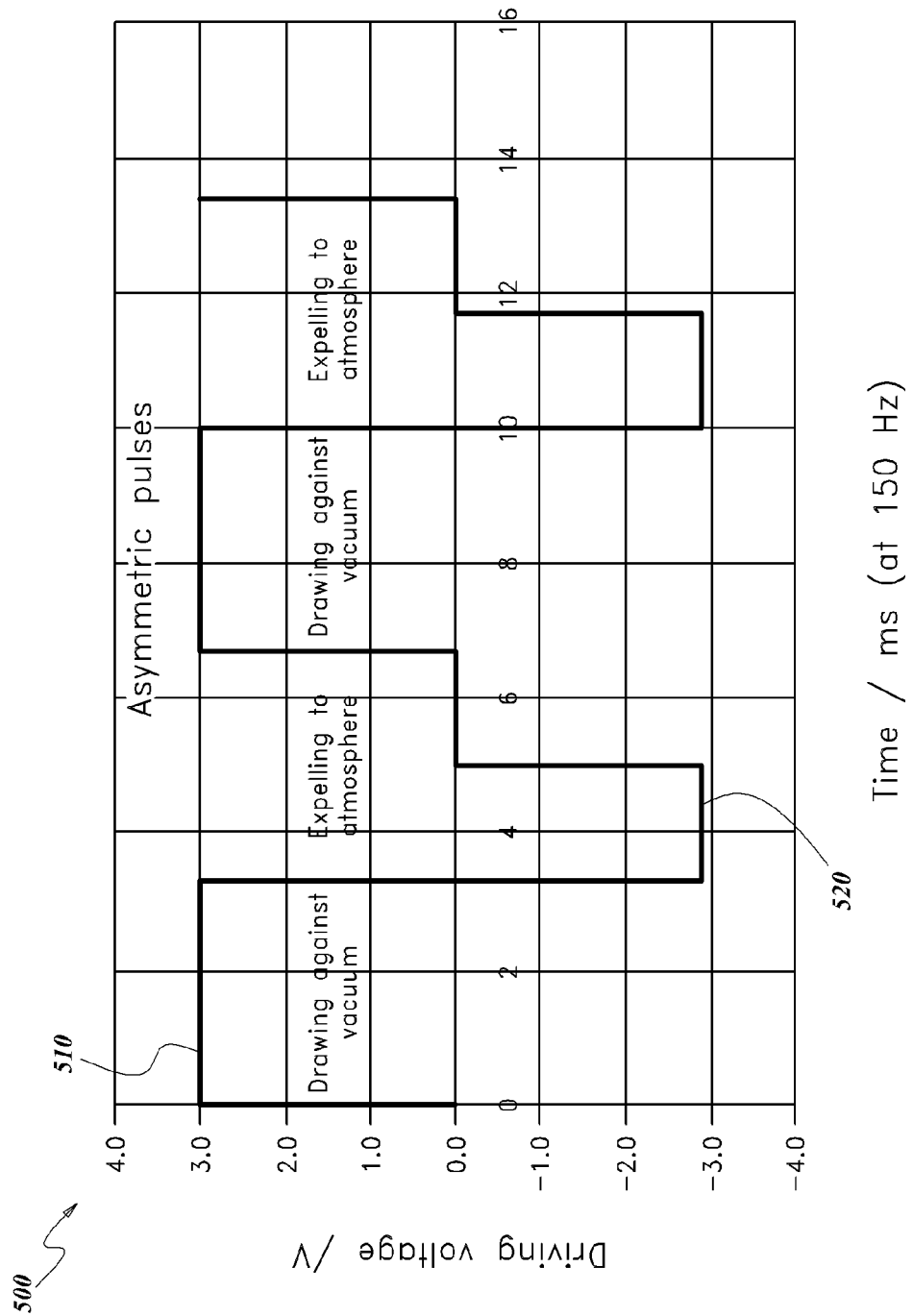
Figure 25:
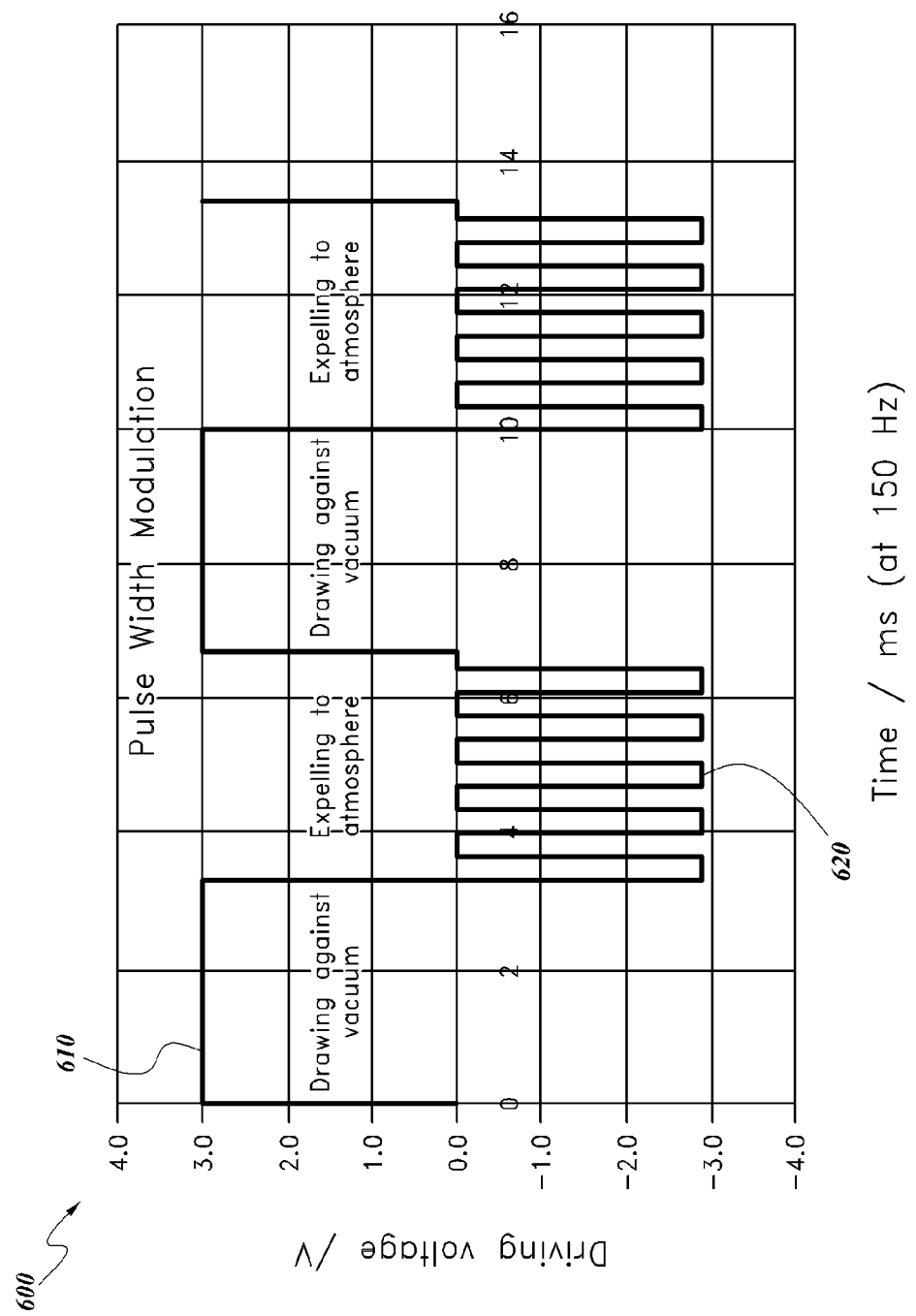
Figure 26:
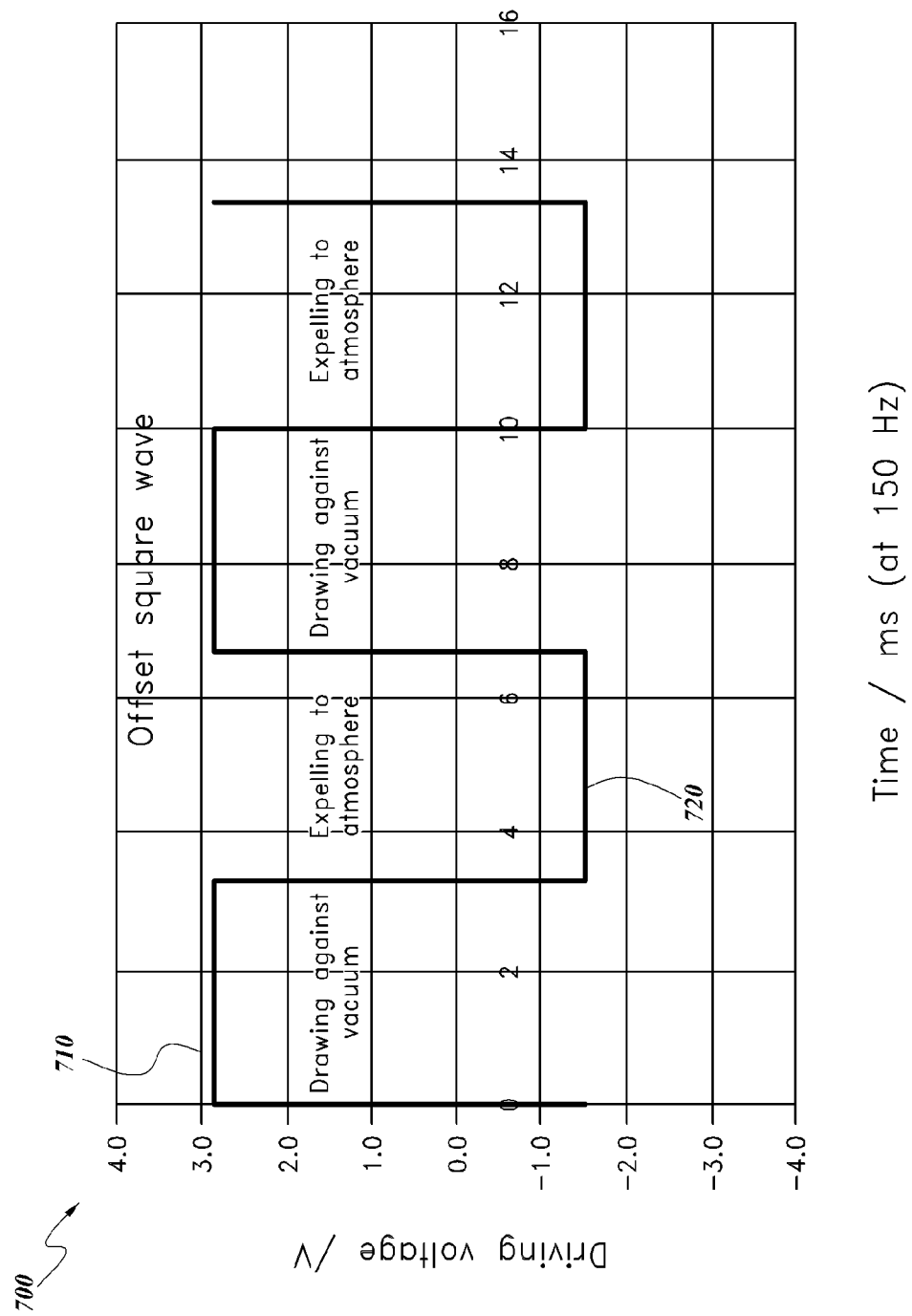

Examples of biased drive signals are illustrated in FIGS. 24-26. FIG. 24 illustrates an asymmetric pulse voltage signal 500 that can be applied to the coil. In any embodiments disclosed herein, the signal depicted in FIG. 24 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 510) and to expel the removed gas (depicted as region 520). As is illustrated, the waveforms applied in regions 510 and 520 are not the same. Less power (e.g., average power, total power, etc.) is applied to the coil in region 520 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz.

FIG. 25 illustrates a pulse width modulated voltage signal 600 that can be applied to the coil. In any embodiments disclosed herein, the signal depicted in FIG. 25 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 610) and to expel the removed gas (depicted as region 620). As is illustrated, the waveforms applied in regions 610 and 620 are not the same. Due to pulse width modulation of the waveform, less power (e.g., average power, total power, etc.) is applied to the coil in region 620 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz.

FIG. 26 illustrates an offset square wave voltage signal 700 that can be applied to the coil. In any embodiments disclosed herein, the signal depicted in FIG. 26 can be used to drive the coil, which thereby causes the diaphragm to flex and deflect. Although a voltage waveform is depicted, it will be understood that waveform of current applied to the coil can be alternatively or additionally illustrated. As is shown, asymmetrical voltage signal of magnitude between −3.0 V and 3.0 V is applied to the coil at a frequency of 150 Hz, which can cause the diaphragm to flex and deflect so that the diaphragm oscillates to draw vacuum (depicted as region 710) and to expel the removed gas (depicted as region 720). As is illustrated, the waveforms applied in regions 710 and 720 are not the same. Due to pulse width modulation of the waveform, less power (e.g., average power, total power, etc.) is applied to the coil in region 720 (e.g., when gas is expelled), thereby causing less force to be applied to the diaphragm when gas is expelled. In any embodiments disclosed herein, other suitable magnitudes of voltage can be used, such as between −1.0 V and 1.0V, −2.0 V and 2.0 V, −4.0 V and 4.0 V, and so on. Any suitable frequency of the driving waveform can be used, such as frequencies less than or greater than 150 Hz. It will be appreciated that other suitable drive signals can be used in other embodiments. For example, pulse duration modulated waveforms, offset sinusoidal waveforms, offset sawtooth waveforms, assymetric sinusoidial waveforms, assymetrical sawtooth waveforms, etc. can be used.

Figure 100:
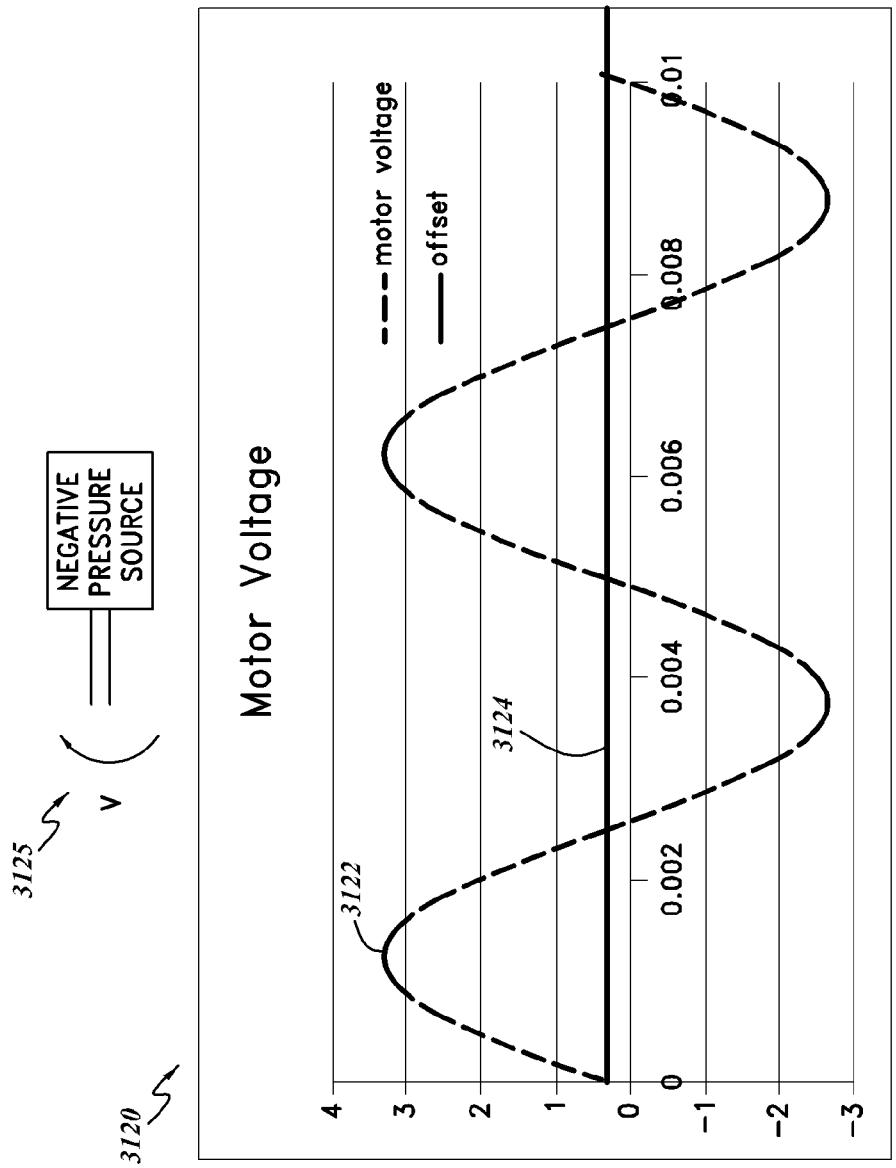
FIGS. 100-103 illustrate sinusoidal waveforms for driving a diaphragm according to some embodiments.

In any embodiments disclosed herein, in order to achieve a substantially optimal pumping efficiency, a soft diaphragm can be driven by an offset sinusoidal drive signal. For example, the driving signal can be applied to the voice coil actuator of the pump, thereby causing the diaphragm to flex and deflect. FIG. 100 illustrates an offset sine waveform 3120 that can be applied to the coil according to some embodiments. The x-axis represents time and the y-axis represents voltage. The sine wave 3122 is offset from 0 V as is shown by line 3124, which is about 0.4 V. Any suitable offset can be used, such as 0.05 V, 0.1 V, 0.65 V, etc. The sine wave 3122 can be applied to the pump (and the diaphragm) as is illustrated in 3125. In one embodiment, the sine wave 3122 can be applied to the voice coil actuator, thereby causing the voice coil to move and the diaphragm to flex and deflect. The sine wave 3120 can be a signal of a suitable magnitude, such as 5.3 V, less than 5.3V, or more than 5.3 V. Although the illustrated sine wave 3120 is a voltage signal, a current signal can be used for driving the diaphragm. The sine wave 3120 can be of a suitable frequency, such as from approximately 50 Hz to approximately 200 Hz, or from approximately 25 Hz or less to approximately 300 Hz or more. Other frequencies can be used, such as frequencies below 50 Hz and above 200 Hz.

In any embodiments disclosed herein, driving the diaphragm with a sine wave signal, such as the offset sine wave 3122, increases the efficiency of the negative pressure source. For example, because the sine wave 3122 has a single frequency, that frequency only stimulates a single vibrational or resonance mode of the pump (e.g., the first vibrational mode of the pump is stimulated provided that the other modes have a higher natural or resonant frequency). Efficiency can be optimized if the pump only moves or resonates at a single frequency. For instance, the axial spring stiffness of the diaphragm and the offset of the sine wave can be optimized for greater efficiency. In addition, little or no driving energy may be absorbed by components other than the diaphragm, such as rubber components. In contrast, In any embodiments disclosed herein, a square wave driving signal is more difficult to optimize because the square wave comprises decaying frequency components that are multiples of a base frequency. These higher frequency components can excite higher vibrational modes of the system, which can make the overall behaviour of the pump less predictable and more difficult to optimize. In any embodiments disclosed herein, using a square wave driving signal generates higher flow at a cost of lower efficiency.

In any embodiments disclosed herein, non-offset sine wave drive signals can be used. In various embodiments, other periodic signals such as cosine waves, tangent waves, square, triangular waves, sawtooth waves, pulse duration modulated waveform, and the like can be used to drive the diaphragm. Signals driving the diaphragm can be symmetrical or assymetrical and/or offset or not offset. In certain embodiments, non-periodic driving signals are used.

Figure 101:
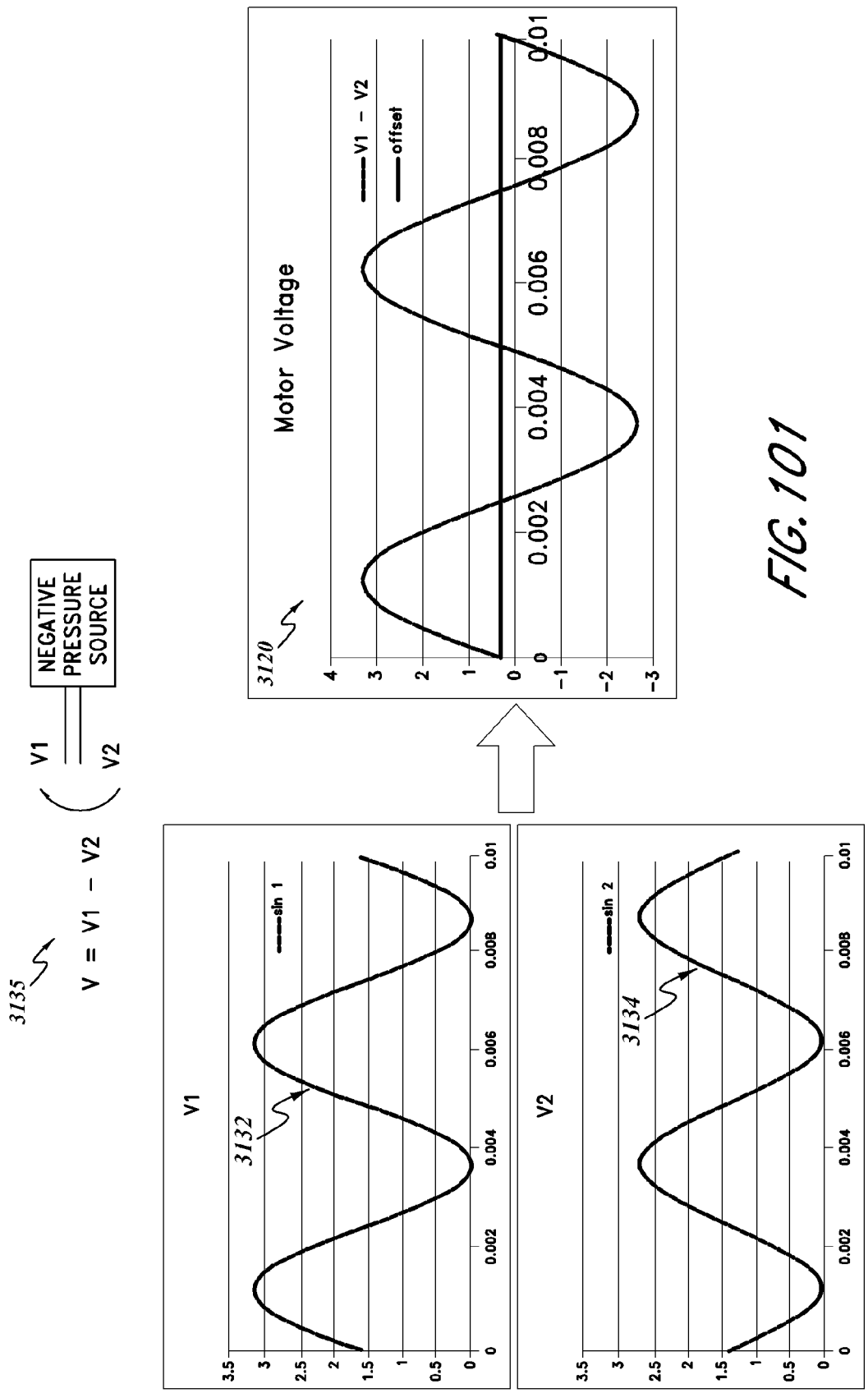

FIG. 101 illustrates generation of the sine wave 3122 according to some embodiments. Two 180 degree phase shifted sine waves 3132 and 3134 can be combined to generate the sine wave 3122. The sine waves 3132 and 3134 can have different amplitudes, such as peak-to-peak amplitudes. In any embodiments disclosed herein, sine wave 3134 is subtracted from sine wave 3132 and applied to the diaphragm as is illustrated in 3135. In any embodiments disclosed herein, the sine waves 3132 and 3134 can be phase shifted with respect to each other with any suitable phase shift value selected from the range between 0 and 360 degrees. In various embodiments, sine waves 3132 and 3134 can be combined in any linear or non-linear manner.

Figure 102:
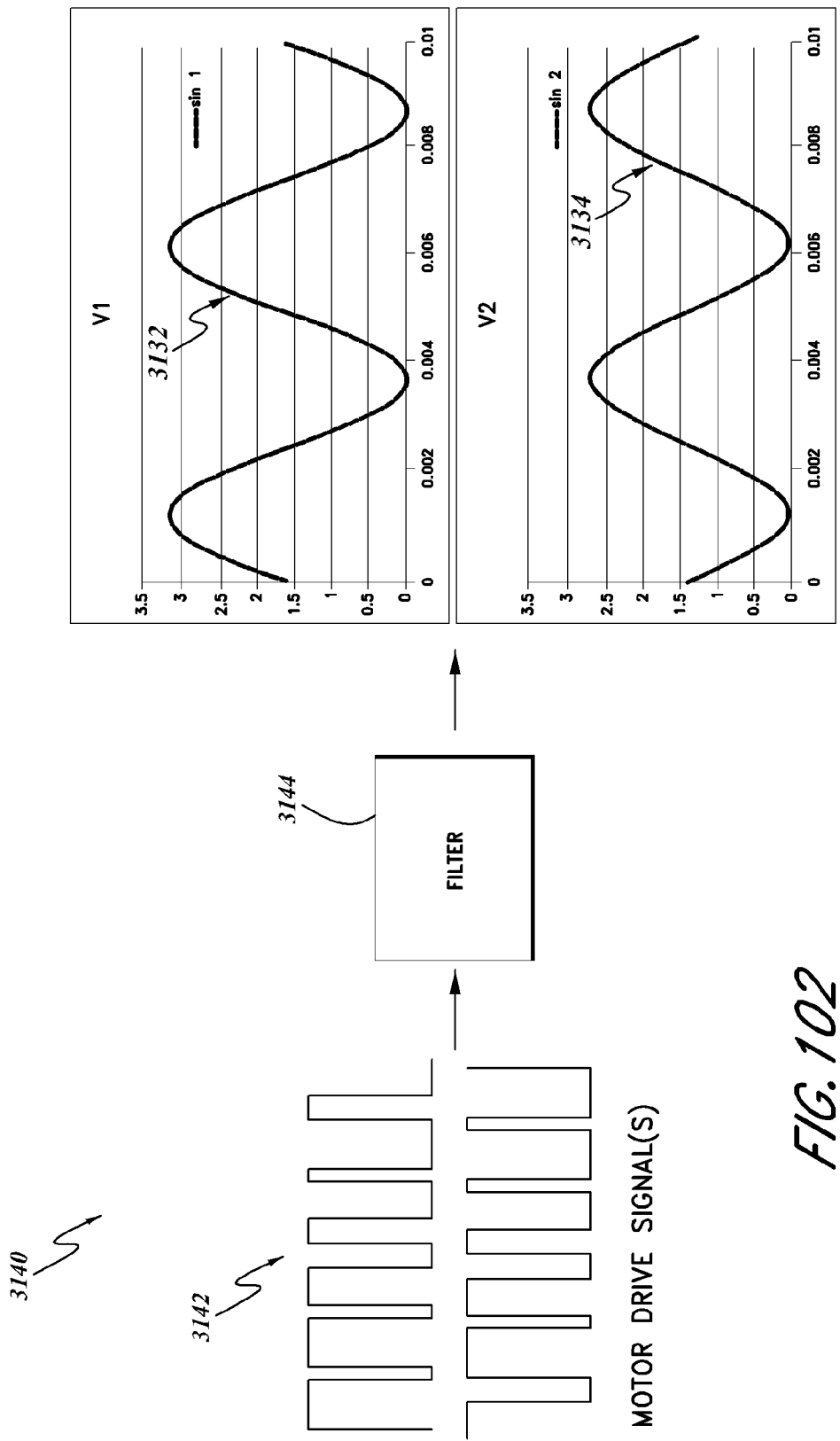

FIG. 102 illustrates generation of the sine waves 3132 and 3134 according to some embodiments. One or more PWM drive signals 3142 can be generated by the driver module 3109. These signals, which can be represented as a combination of square waves at different frequencies, are filtered by a filter 3144, which can be a low-pass filter. In any embodiments disclosed herein, filtering the one or more PWM drive signals 3142 produces the sine waves 3132 and 3134. In any embodiments disclosed herein, two PWM drive signals 3142 are used to produce the sine waves 3132 and 3134. Each of the PWM drive signals 3142 can be a signal having appropriate characteristics, such as amplitude, for generating the respective sine wave signal 3132 or 3134.

In any embodiments disclosed herein, the voice coil actuator or motor is used as the filter 3144. The voice coil motor can behave as a resonant circuit, such as an LC or RLC circuit, that has low-pass filter characteristics. In one embodiment, the motor can have the following characteristics: resistance R=20Ω, inductance L=1 mH, and time constant τ=50 μs. In any embodiments disclosed herein, a suitable separate filter 3144 can be used. In certain embodiments, the filter 3144 can have high pass, band pass, band stop, and/or notch characteristics. In any embodiments disclosed herein, the sine wave 3122 can be generated directly from the one or more PWM signals.

Figure 103:
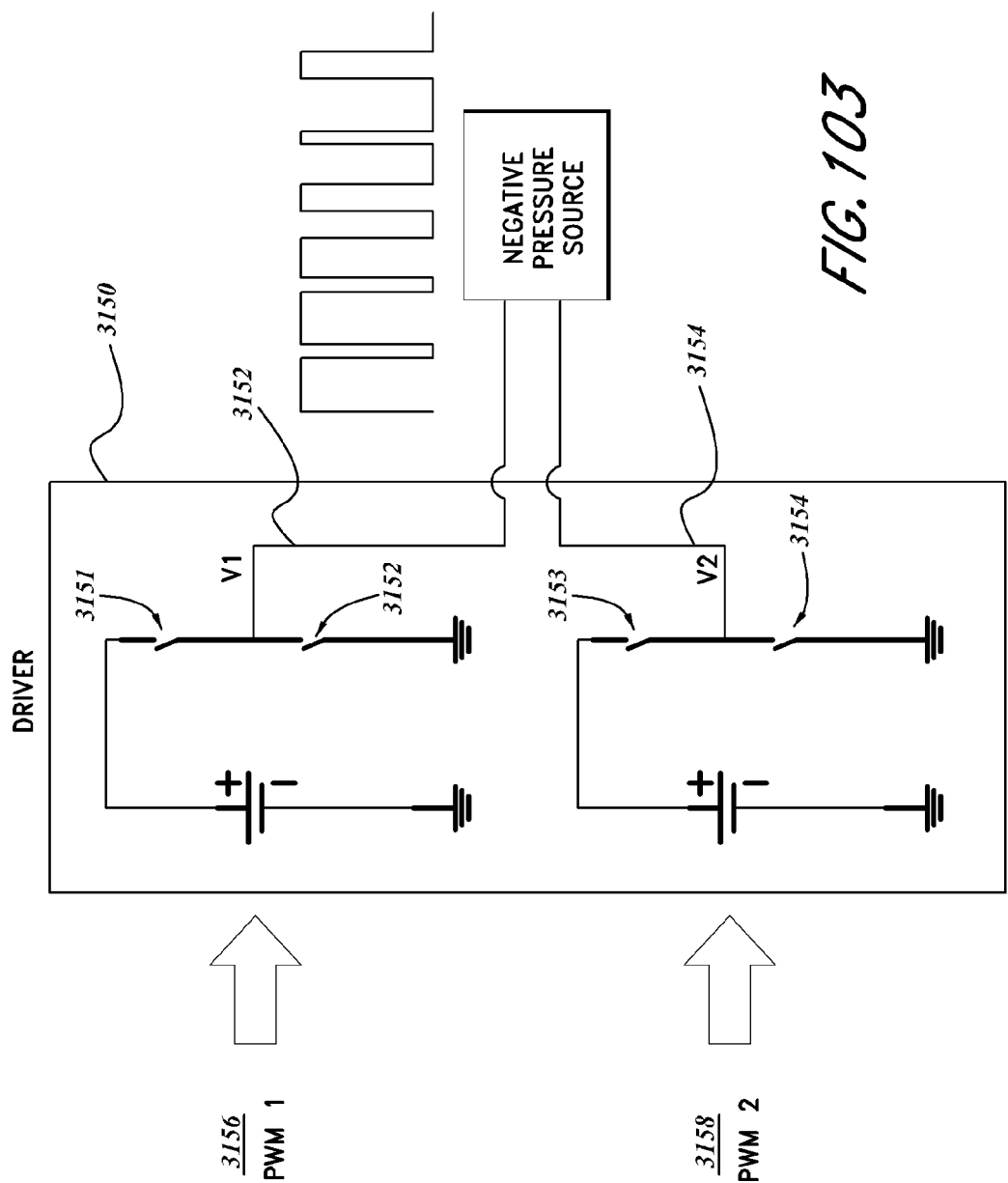

FIG. 103 illustrates a circuit 3150 for generating one or more PWM drive signals, such as signals 3142, used to generate the sine waves 3132 and 3134 according to some embodiments. The circuit 3150 can be part of the driver module 3109. The circuit 3150 includes switches 3151, 3152, 3153, and 3154, which can be transistor switches. Two PWM control signals 3156 and 3158 are used to drive the respective pair of switches 3151, 3152 and 3153, 3154. The PWM control signals 3156 and 3158 can cause the switches to toggle, which produces the desired one or more PWM drive signals for driving the pump. PWM control signals 3156 and 3158 can be generated by the controller 3102. In any embodiments disclosed herein, the circuit 3150 can be an H bridge circuit. In various embodiments, using the circuit 3150 results in pumping efficiency of approximately 90% or higher.

In any embodiments disclosed herein, linear driving can be used to generate the one or more PWM signals used to generate the sine waves 3132 and 3134. One example of linear driving is using a digital-to-analog converter (DAC) in conjunction with an amplifier, such as an audio amplifier (e.g., class A, class B, class C, class D, etc. amplifier). A digital controller, such as the controller 3102, can generate a digital control signal, such as a PWM signal, that is converted into an analog signal by the DAC. The analog signal output by the DAC can be amplified by the amplifier and can be used for driving the motor. In any embodiments disclosed herein, using switching driving, such as that illustrated in circuit 3150, provides a higher efficiency than that achieved with linear driving.

Figure 104:
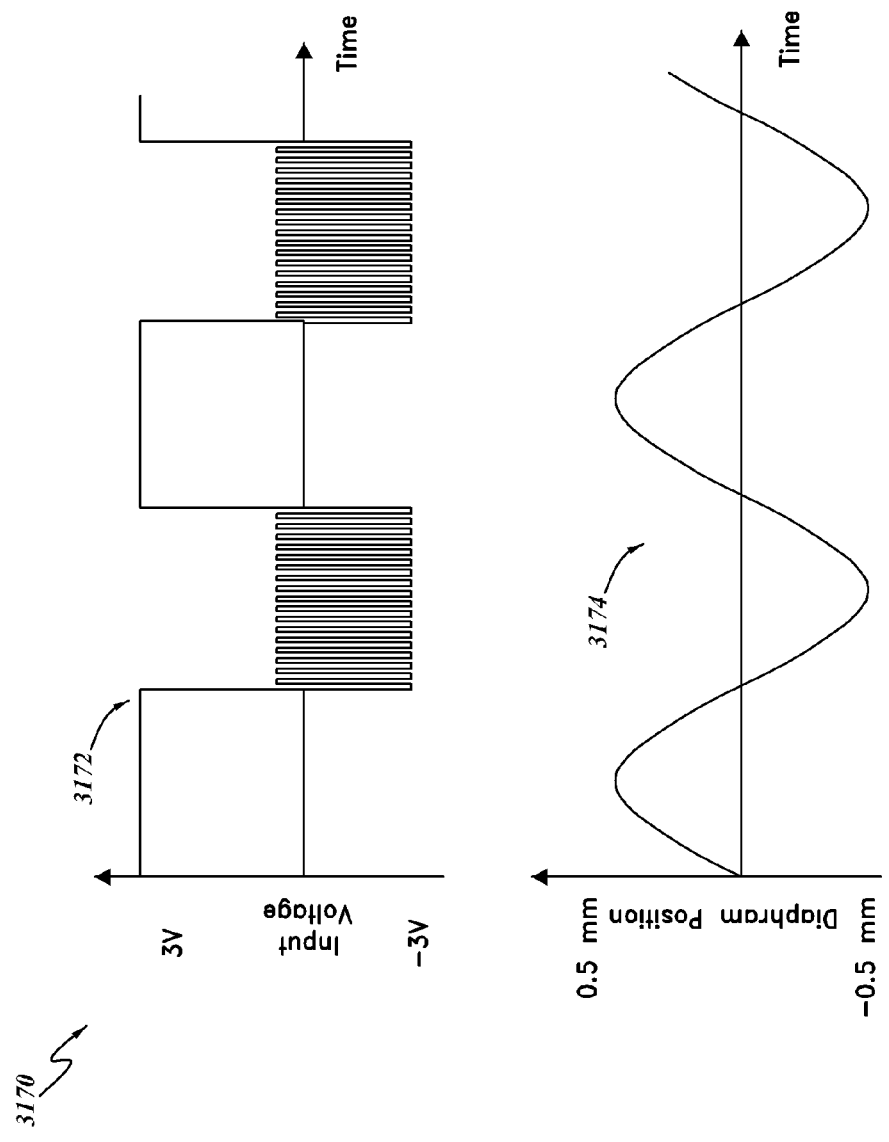
FIG. 104 illustrates position of a diaphragm according to an embodiment of a pump assembly.

FIG. 104 illustrates a diagram 3170 of a position of the diaphragm according to an embodiment of a pump assembly. Graph 3172 illustrates a driving signal applied to the pump. In any embodiments disclosed herein, the driving signal is offset as is illustrated in graph 3172. For example, the positive portion of the driving signal can have a peak amplitude of +3 V, and the negative portion of the driving signal can have a peak amplitude of −1.5 V. As explained above, In any embodiments disclosed herein, the force for expelling removed gas can be smaller than the force for drawing vacuum, and using an offset driving signal can improve pumping efficiency. In certain embodiments, a non-offset driving signal is used. In any embodiments disclosed herein, applying the driving signal 3172 results in the diaphragm moving as is illustrated by 3174. The diaphragm oscillates between +0.5 mm and −0.5 mm with respect to a resting position. In any embodiments disclosed herein, the diaphragm can oscillate between any other suitable position, such as positions greater or lesser than +0.5 mm and −0.5 mm.

FIGS. 27A-27G are an isometric view, a top view, a bottom view, a top end view, a bottom end view, a first side view, and a second side view, respectively, of an embodiment of a pump assembly 800. The pump assembly 800 can have a casing 802 that can be used or adapted to support any suitable type of pump motor or actuator. This can include, without limitation, any of the voice coil actuated pump embodiments disclosed herein (such as, without limitation, pump disclosed above), a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combination of the foregoing pumps. In any embodiments disclosed herein, the pump housing 802 can be configured to support the components of the pump directly therein such that some or a portion of the components of the pump housing that may otherwise be on the pump can be eliminated, with the housing 802 providing the necessary support for pump components. Any of the pump assembly embodiments disclosed herein, including without limitation pump assembly 800, can be used with any of the dressing embodiments disclosed herein or otherwise.

In any of the pump assembly embodiments disclosed herein, as in the embodiment illustrated in FIGS. 27A-27G, the pump assembly can be a canisterless pump assembly (meaning that the pump assembly does not have an exudate or liquid collection canister). However, any of the pump embodiments disclosed herein can be configured to include or support a canister, either within the pump casing, attached to or supported by the pump casing, or otherwise. Additionally, in any of the apparatus embodiments disclosed herein, any of the pump assembly embodiments can be mounted to or supported by the dressing, or adjacent to the dressing. The dressing may be positioned and sealed over any suitable wound, as described in greater detail in U.S. patent application Ser. No. 13/092,042, which disclosure is hereby incorporated by reference and made part of this disclosure, and a conduit may then be connected to the dressing.

Dressing embodiments that are usable with the pump assembly 800, or any other pump assembly embodiment disclosed herein, can have any of the materials, sizes, components, or other details of any of the dressing embodiments disclosed in U.S. patent application Ser. No. 13/092, 042, and such embodiments and illustrations thereof are hereby incorporated by reference in their entireties as if made part of this disclosure. The conduit used to communicate the reduced pressure from the pump assembly to the dressing, or any other conduit disclosed herein, can be formed from polyurethane, PVC, nylon, polyethylene, silicone, or any other suitable material.

As mentioned, some embodiments of the apparatus are designed to operate without the use of an exudate canister. The dressing can be configured to have a film having a high water vapour permeability to enable the evaporation of surplus fluid, and can have a superabsorbing material contained therein to safely absorb wound exudate. Some embodiments of the apparatus are designed for single-use therapy and can be disposed of in an environmentally friendly manner after an approximately maximum usage of from seven to eleven days. The pump can be programmed to automatically terminate therapy after a desired number of days, e.g., after seven days, further operation of the pump will not be possible. Some embodiments are designed for longer or repeated usage, and can be configured to support an exudate canister.

In any embodiments disclosed herein, as in the illustrated embodiment, the pump assembly 800 can be of a sufficiently small and portable size to be supported on a user's body or in a user's clothing. For example, the pump assembly 800 can be sized to be attached using adhesive medical tape or otherwise to a person's skin in a comfortable location, adjacent to or on the dressing or otherwise. Further, the pump assembly 800 can be sized to fit within a person's pants or shirt pocket, or can be tethered to a person's body using a lanyard, pouch, or other suitable device or article.

Figure 27A:
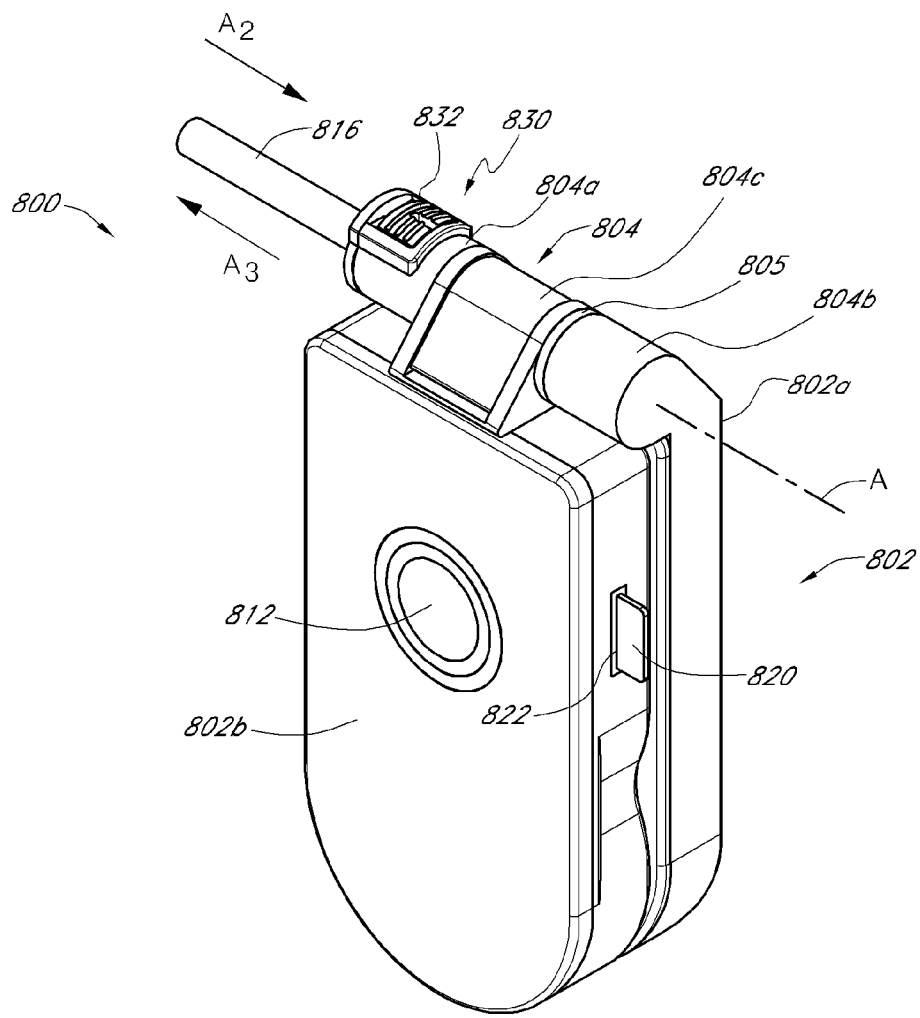
FIGS. 27A-27G are an isometric view, a top view, a bottom view, a top end view, a bottom end view, a first side view, and a second side view, respectively, of an embodiment of a pump assembly.
Figure 27B:
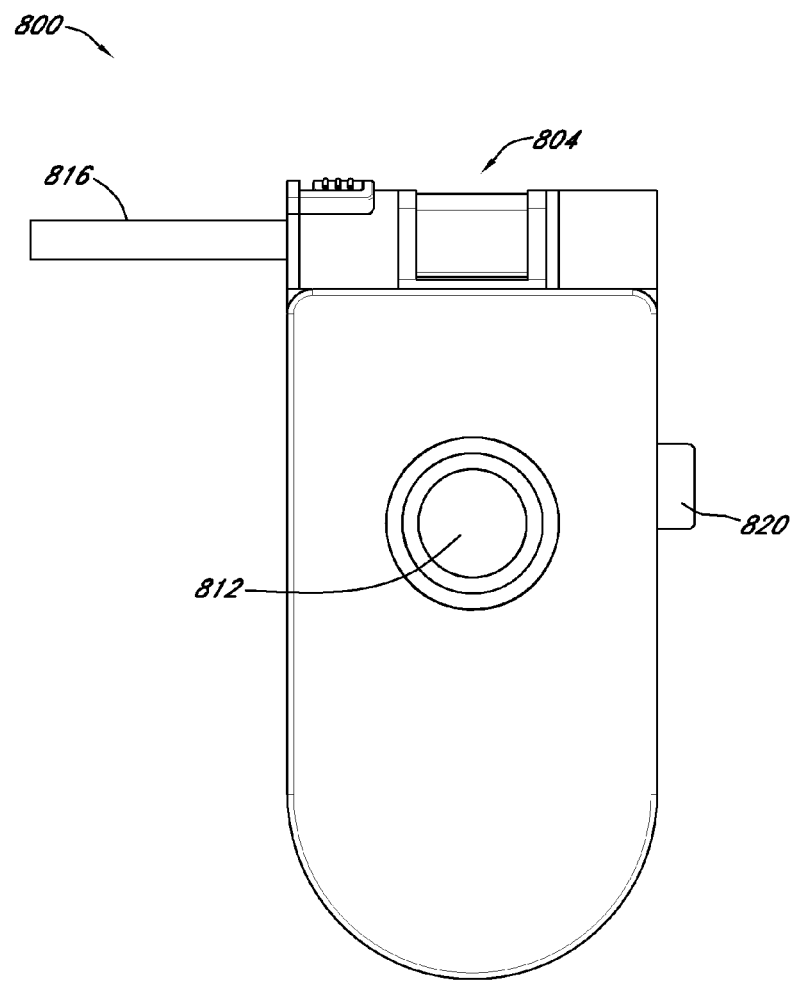
Figure 27C:
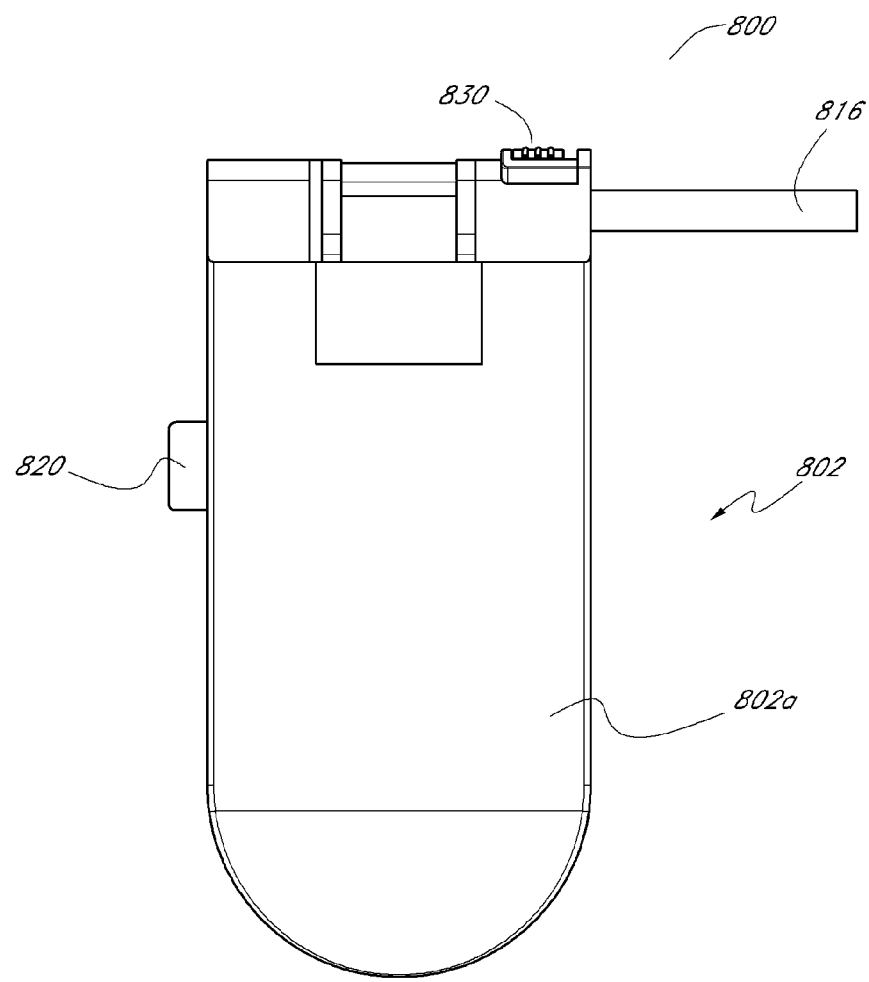
Figure 27D:
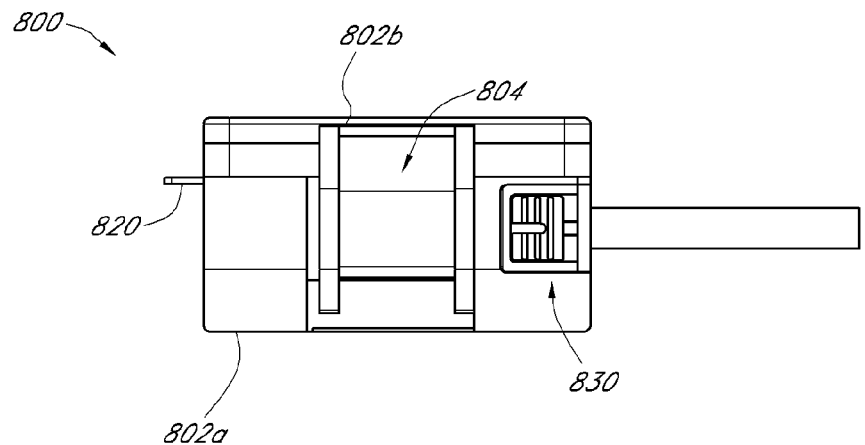
Figure 27E:
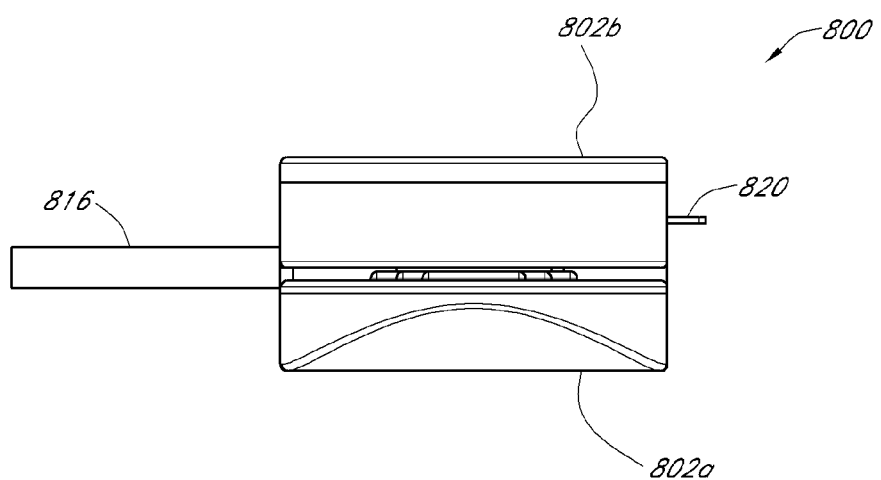
Figure 27F:
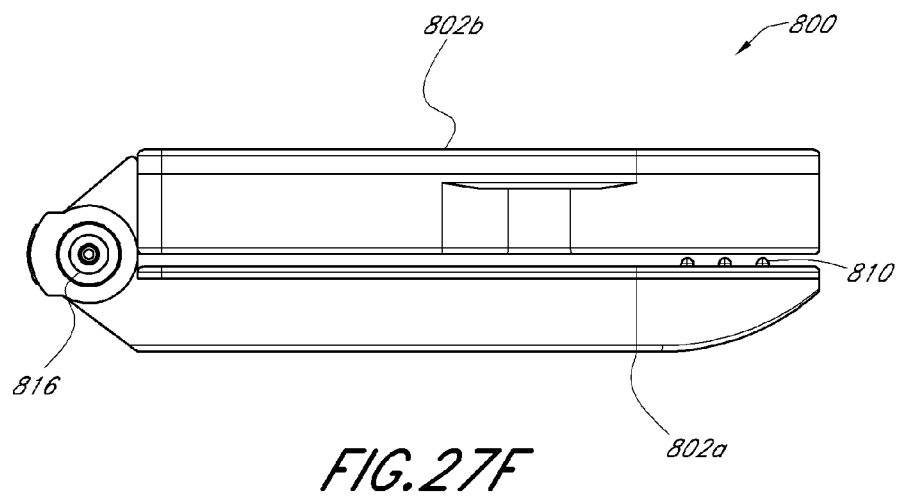
Figure 27G:
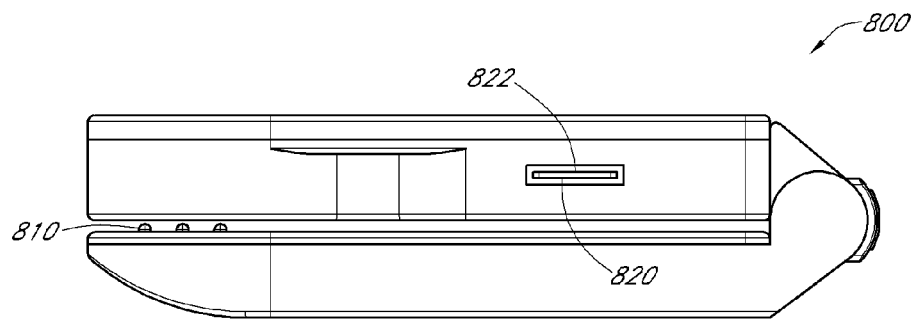
Figure 27H:
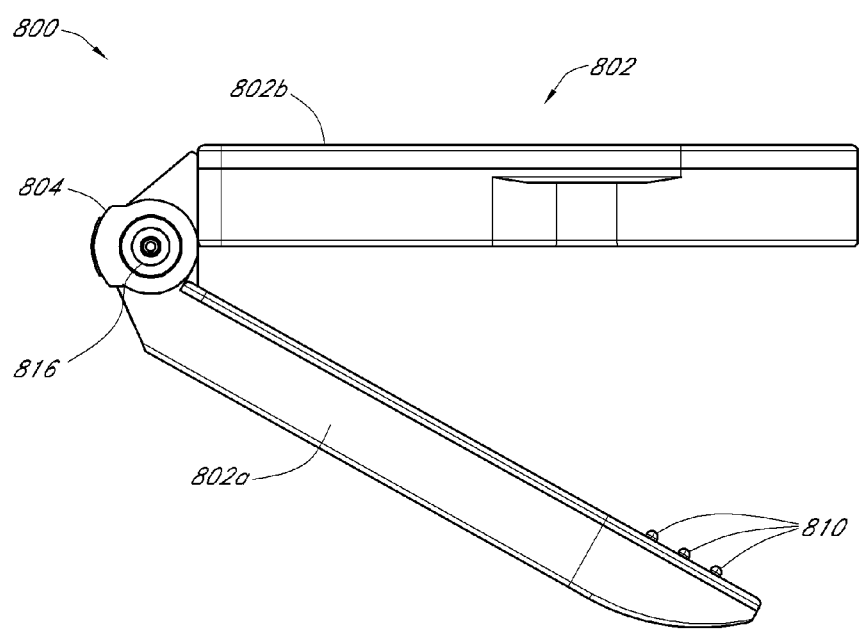
Figure 271:
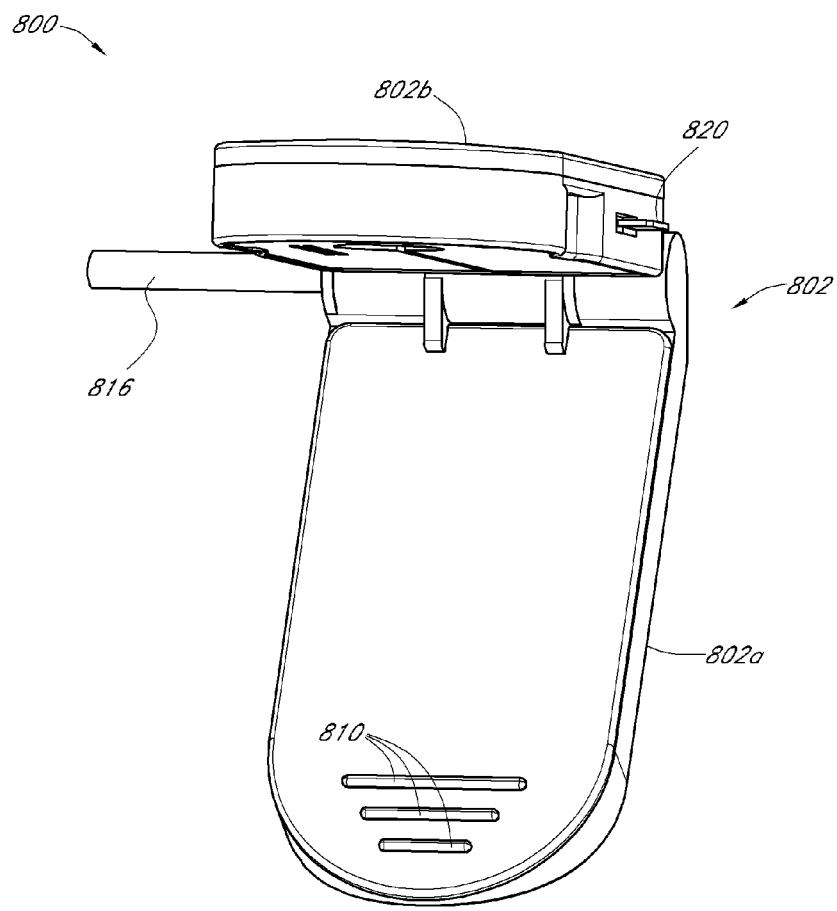

The housing 802 of the pump assembly 800 can have a first portion or element 802a and a second portion or element 802b. With reference to FIGS. 27H-27I, the first portion 802a and the second portion 802b of the housing 802 can be rotatably connected to one another by a hinge 804. The hinge 804 can permit the first portion 802a to rotate about an axis A within a particular angular range relative to the second portion 802b. The hinge 804 can be biased toward a closed position, as illustrated in FIG. 27A, such that the two portions 802a, 802b form a clip or a clamp. In this configuration, the housing 802 can be clipped to a person's clothing, such as in a pocket, over a belt, to a flap or in a pouch or a pocket on the dressing, or otherwise. For example, the first portion 802a can be positioned on the inside of a pouch, pocket, or otherwise, and the second portion 802b can be positioned outside of the pouch, pocket, or otherwise. The bias can be created with a coil spring, a bent spring, or otherwise, and can cause the housing 802 to grip the flap or pocket. The clamping force can be low enough that a user can open the housing from the clamped position, but strong enough so that it will remain clamped about the pocket, flap, or other material.

The hinge 804 can have a first hinge portion 804a and a second hinge portion 804b supported by the first housing portion 802a. A complementary hinge 804c supported by the second housing portion 802b can be positioned between the first and second hinge portions 804a, 804b and rotatable about axis A1 relative to one another.

One or both of the first portion 802a and the second portion 802b can have gripping features to help prevent the pump housing from sliding off of the flap or other material that the pump housing 802 is clipped onto. For example and without limitation, with reference to FIGS. 27H-27I, a plurality of protrusions 810 can be supported by or molded onto the first housing portion 802a and/or the second housing portion 802b to help grip the flap or other material that the housing is clipped to or clamped over.

A control button 812 can be used to control the operation of the pump assembly 800. For example, the button 812 can be used to activate the pump motor, pause the pump motor, clear indication or alarm signals, or be used for any other suitable purpose for controlling an operation of the pump assembly 800. The button can be a push style button that can be positioned on an outside, front surface of the housing.

Additionally, the housing can have any combination of indication lights, as described more fully below. The lights, which can be LED lights, can be configured to alert a user to a variety of operating and/or failure conditions of the pump assembly 800, including alerting the user to normal or proper operating conditions, pump failure, power supplied to the pump or power failure, the condition or voltage level of the batteries, detection of a leak within the dressing or flow pathway, suction blockage, or any other similar or suitable conditions or combinations thereof. The indicator lights can be positioned on an outside, front surface of the housing.

The pump assembly 800 can be configured to receive and support a conduit 816 used to communicate the reduced pressure provided by the pump housing 800 to the dressing. In any embodiments disclosed herein, the conduit 816 can be supported by the housing 800 such that the conduit cannot be removed by the user, so as to prevent the user from inadvertently disconnecting the conduit from the pump housing 800 or from inadvertently causing a leak with the tubing. In any embodiments disclosed herein, the conduit 816 can be removably supported by an opening in the housing or by the tube connector features and embodiments described herein. For example, any pump assembly embodiments disclosed herein can have a tube connector configured to removably or non-removably secure the conduit to the pump assembly.

In any pump embodiments disclosed herein, a tubing connector can be supported by the housing 802, such as tubing connector 830. In some embodiments, the tubing connector 830 can be configured to securely attach an end of the tubing 816 to the housing 802.

Figure 28:
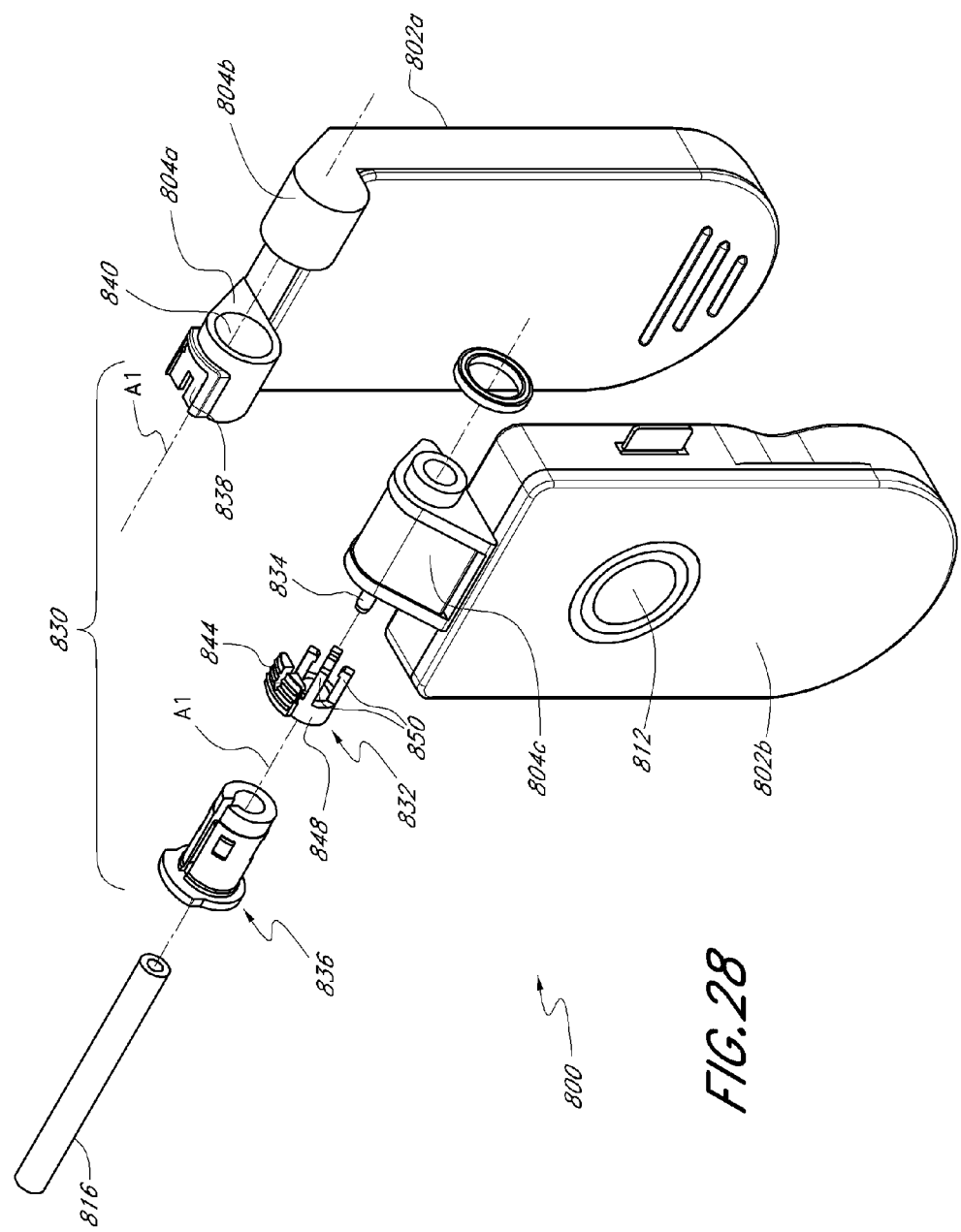
FIG. 28 is an exploded view of a portion of an embodiment of a pump assembly.

For example, as shown in FIG. 28, which is an exploded view of a portion of the pump assembly embodiment 800 shown in FIG. 27A, any pump assembly embodiments disclosed herein can have a tube connector 830 comprising a slider member 832, a boss 834 that can be supported by the third hinge portion 804c, a support member 836 for supporting the slider member 832, and a receiving element 838 formed on or supported by the first hinge portion 804a. In an assembled state, the slider member 832 and the support member 836 can be supported within an opening 840 formed in the first hinge portion 804a. The boss member 834 can be configured to receive an end portion of the conduit, such as but not limited to round tubing. A pad portion 844 of the slider member 832 can be configured to translate in the receiving portion 838. With reference to FIG. 27A, moving the slider member 832 in a first direction (represented by arrow A2 in FIG. 27A) will put the connector 830 in a second, locked position over the conduit 816, such that the conduit is securely attached to the housing 802, or at least inhibited from being removed from the housing 802. Moving the slider member 832 in a second, opposite direction (represented by arrow A3 in FIG. 27A) will put the connector 830 in an open or first position over the conduit 816, such that the conduit can be removed. The connector 830 is shown in the open or first position in FIG. 27A.

FIGS. 29A and 29B are an isometric and section view, respectively, of a portion of the embodiment of a pump assembly 800 shown in FIG. 28, showing a slider member 832 of an embodiment of a conduit connector 830 in a first, open position. With reference to FIGS. 29A and 29B, when the slide member 832 is in a first position, the one or more legs 850 of the slide member 832 can be forced against the inclined surfaces 859 so as to spread radially away from the conduit member 816 such that the protrusions 852 at the distal ends of the legs 850 are forced radially away from the conduit member, thereby permitting the conduit member 816 to be removed from the connector 830.

FIGS. 30A and 30B are an isometric and section view, respectively, of a portion of the embodiment of a pump assembly 800 shown in FIG. 28, showing a slider member 832 in a second, closed position. In this position, because the protrusions or tabs 852 at the ends of the one or more legs 850 have been moved apart from the inclined surfaces 859, the protrusions 852 can squeeze against the tubing or conduit 816 to hold or secure the conduit in the connector 830. The legs 850 can be biased to exert a radial inward force on the tubing 816 when no external force is applied to the legs 850.

Additionally, as shown in FIG. 32, which is an exploded view of a portion of the pump assembly embodiment 800 shown in FIG. 27A, any pump assembly embodiments disclosed herein can have a tube connector 860 comprising a slider member 862, a boss 834 that can be supported by the third hinge portion 804c, a support member 866 for supporting the slider member 832, and a receiving element 868 formed on or supported by the first hinge portion 804a. In an assembled state, the slider member 862 and the support member 866 can be supported within an opening 840 formed in the first hinge portion 804a. The boss member 864 can be configured to receive an end portion of the conduit, such as but not limited to round tubing. A pad portion 874 of the slider member 862 can be configured to translate in the receiving portion 868.

FIGS. 33A and 33B are an isometric and section view, respectively, of a portion of the embodiment of a pump assembly 800 shown in FIG. 32, showing a slider member 832 of an embodiment of a conduit connector 830 in a first, open position. With reference to FIG. 33A, moving the slider member 862 in a first direction (represented by arrow A1 in FIG. 33A) will put the connector 860 in a second, locked position over the conduit 816, such that the conduit is securely attached to the housing 802, or at least inhibited from being removed from the housing 802. Moving the slider member 862 in a second, opposite direction (represented by arrow A2 in FIG. 34A) will put the connector 860 in an open or first position over the conduit 816, such that the conduit can be removed. The connector 860 is shown in the open or first position in FIG. 33A.

With reference to FIGS. 33A and 33B, when the slide member 832 is in a first position, a protrusion (such as the annular protrusion 872 formed on the body 878) will be positioned so as to not surround the boss 834. FIGS. 34A and 34B are an isometric and section view, respectively, of a portion of the embodiment of a pump assembly 800 shown in FIG. 32, showing a slider member 862 in a second, closed position. In this position, because the protrusions or tabs 872 supported by the body portion 878 of the slider member 862 have been moved so as to surround the conduit positioned over the boss 834, the protrusions 834 can squeeze against the conduit and squeeze the wall of the conduit between the boss 834 and the tabs 872 to secure the conduit to the boss 834.

Additionally, as shown in FIG. 36, which is an exploded view of a portion of the pump assembly embodiment 800 shown in FIG. 27A, any pump assembly embodiments disclosed herein can have a tube connector 880 comprising a slider member 882, a boss 834 that can be supported by the third hinge portion 804c, a support member 883 for supporting the slider member 882, and a receiving element 884 formed on or supported by the first hinge portion 804a. In an assembled state, the slider member 882 and the support member 883 can be supported within an opening 840 formed in the first hinge portion 804a. The boss member 834 can be configured to receive an end portion of the conduit, such as but not limited to round tubing. A pad portion 885 of the slider member 882 can be configured to translate in the receiving portion 884. With reference to FIG. 37A, moving the slider member 882 in a first direction (represented by arrow A1 in FIG. 27A) will put the connector 880 in a second, locked position over the conduit 816, such that the conduit is securely attached to the housing 802, or at least inhibited from being removed from the housing 802. Moving the slider member 882 in a second, opposite direction (represented by arrow A2 in FIG. 38A) will put the connector 880 in an open or first position over the conduit 816, such that the conduit can be removed. The connector 880 is shown in the open or first position in FIG. 37A.

FIGS. 37A and 37B are an isometric and section view, respectively, of a portion of the embodiment of a pump assembly 800 shown in FIG. 28, showing a slider member 882 of an embodiment of a conduit connector 880 in a first, open position. With reference to FIGS. 37A and 37B, when the slide member 882 is in a first position, the one or more legs 887 of the slide member 882 can be spaced apart from the inclined surfaces 889 so as to permit the legs 887 to remain in a relaxed position relative to the conduit 816 such that the protrusions 888 at the distal ends of the legs 887 are relaxed and do not substantially engage the conduit 816, thereby permitting the conduit member 816 to be removed from the connector 880.

FIGS. 38A and 38B are an isometric and section view, respectively, of a portion of the embodiment of a pump assembly 800 shown in FIG. 28, showing a slider member 882 (shown in more detail in FIGS. 39A-39C) in a second, closed position. In this position, because the protrusions or tabs 888 at the ends of the one or more legs 887 have been forced against the inclined surface 889, the inclined surface can force the ends of the 887, having the protrusions 888 thereon, radially inward against the conduit 816 such that the protrusions 888 can squeeze against the tubing or conduit 816 to hold or secure the conduit in the connector 880. The legs 887 can be biased to extend radially outward away from the tubing 816 when no external force is applied to the legs 887.

The operation or activation of any of the pump embodiments disclosed herein can be alternatively or additionally controlled by the use of one or more pull tabs, sliding switches, or other similar features coupled with one or more switches, buttons, controllers, etc. of the pump assembly. For example, with reference to FIGS. 27A-27I, in any embodiments disclosed herein, a pull tab 820 can be supported by an opening 822 formed in the housing 802. In this arrangement, the pull tab 820 can be configured to be positioned between the battery terminals and batteries, or between other components in the electrical circuit. In any embodiments disclosed herein, the packaging supporting the dressing can be configured such that such tab or isolator must be positioned between the components in the electrical circuit to ensure that the batteries are not electrically connected to the pump assembly or other components during sterilization or prior to activation. The pump assembly 800 can be configured such that, the pump cannot be operated or activated when the pull tab 820 is positioned within the opening 822 (so as to open a portion of the electrical or power circuit that necessary for the operation of the pump). To use the pump, the user must remove the pull tab 820 from the opening 822. The pump can then be operated automatically, or can be operated by depressing one or more buttons (such as button 812) or moving one or more switches.

The pump assembly 800 or any pump assembly embodiment disclosed herein can be configured such that the pump device (such as, without limitation, a voice coil actuated pump device) is supported in the first housing portion 802a. The battery can be supported in the first or the second housing portion 802a, or, in the case of multiple batteries supported by the pump device, in both. In other words, one battery can be supported in the first housing portion 802a and one batter can be supported in the second housing portion 802b. When two or more batteries are used, such batteries can provide power simultaneously or sequentially, or both. The housing 802 can be configured such that a user can access and replace the batteries without the use of tools. In any embodiments disclosed herein, the housing 802 can be configured such that a user cannot gain access to the batteries without the use of tools or without opening the housing.

A control board, such as a printed circuit board assembly (PCBA), can be configured to mechanically support and electrically connect various electrical/electronic components of the pump assembly, including the battery or batteries, the pump device, the control button, a pressure monitor in communication with the pump device or the conduit or otherwise, and/or any indicator lights or audible alarms. The PCBA can be single-sided or double-sided. The control board can be supported within the first or the second housing portion 802a, 802b.

In any embodiments disclosed herein, as in the illustrated embodiment, the pump device and the control board can be supported in the first housing portion 802a and the battery can be supported in the second housing portion 802b. In any embodiments disclosed herein, the pump device can be supported in the first housing portion 802a, the control board can be supported in the second housing portion 802b, and the battery can be supported in the second housing portion 802b. Electrical wires or connectors can be routed from the first to the second housing portion through the hinge 804.

In any embodiments disclosed herein, though not required, the pump assembly can be configured such that a sterilization gas, such as ethylene dioxide, can penetrate into the housing 802 to expose the internal components of the pump assembly 800 to the sterilization gas during normal sterilization processes. Typically, the pump will be exposed to the sterilization gas in a chamber that has been substantially evacuated of air or any other gas, so that the sterilization gas is drawn into the pump housing 802 and into the other spaces, channels, and chambers within the pump assembly 800.

In any embodiments disclosed herein, the pump assembly can be powered by one or more batteries (for example, two batteries) and can weigh approximately 84 grams, or less than 90 grams, including the weight of the batteries. In any embodiments disclosed herein, the pump assembly 800 can have any desired number of batteries and can weigh from approximately 80 grams to approximately 90 grams, or from approximately 75 grams to approximately 100 grams, or between any values within the foregoing ranges. For example, the weight and/or size of the pump assembly 800 could be reduced by reducing the battery size and/or weight by using, for example, AAA sized batteries, lithium batteries, printed or flexible batteries, or smaller), or by reducing the pump size and/or weight.

Further, any embodiments of the pump assembly 800 (or any pump assembly embodiments disclosed herein) can be sized to have a total volume defined by an outside surface of the pump of approximately 92.5 cubic centimeters (approximately 5.6 cubic inches), or 92.5 cubic centimeters (5.6 cubic inches) or less, or between 75 cubic centimeters or less and 115 cubic centimeters or more, or between 85 cubic centimeters and 100 cubic centimeters. Additionally, the pump assembly 800 can be further miniaturized using techniques known to one of ordinary skill in the art to sizes in the range of approximately 40 cubic centimeters, or 40 cubic centimeters or less, or between 30 cubic centimeters or less and 60 cubic centimeters or more. Any pump assembly embodiments disclosed herein can be sized to have a total volume of between 2 cubic inches or less and 6.5 cubic inches or more, or from approximately 4 cubic inches to approximately 6 cubic inches, or between any values within the foregoing ranges.

The pump assembly 800 can have an overall outside size that is approximately 7.2 cm×approximately 6.4 cm×approximately 2.1 cm (or 7.2 cm×6.4 cm×2.1 cm), or a maximum of approximately 8.5 cm×approximately 8.5 cm×approximately 3 cm. Additionally, the pump assembly 800 can have an overall outside size that is approximately 5.5 cm×approximately 4.8 cm×approximately 1.5 cm (or 5.5 cm×4.8 cm×1.5 cm). As mentioned, the size and weight of the pump assembly 800 can be optimized, as it is in the embodiments disclosed herein, to make it more comfortable to wear or carry by the user, thereby affording increased mobility.

The negative pressure range for some embodiments of the present disclosure can be approximately −80 mmHg, or between about −20 mmHg and −200 mmHg. Note that these pressures are relative to normal ambient atmospheric pressure thus, −200 mmHg would be about 560 mmHg in practical terms. In any embodiments disclosed herein, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even 150 mmHg, can be supplied by the pump assembly. Other details regarding the operation of the pump assembly 800 are set forth in U.S. patent application Ser. No. 13/092,042, and such embodiments, configurations, details, and illustrations thereof are hereby incorporated by reference in their entireties as if made part of this disclosure.

As mentioned, the pump assembly 800 can be powered by one or more batteries. The batteries can be lithium chloride or any other suitable batteries that are suitable for exposure to ethylene dioxide and/or other sterilization gases. The batteries can be supported outside of the pump housing 120 so as to minimize or eliminate the chance of an electrical spark which could cause an explosion in the presence of the sterilization gas or an explosive gas during the sterilization process when supported in the packaging element or elements. Additionally, where there are a plurality of batteries, the batteries can be spaced apart or otherwise separated in the packaging to prevent any power loss or sparking of the batteries during the sterilization process or otherwise before usage.

Any pump embodiments disclosed herein can be as light as approximately 8 grams or less, or approximately 10 grams, or between approximately 6 grams and 15 grams, or between any values within the foregoing range. The pump can have a pump capacity of approximately 500 mL per minute, or between approximately 100 mL per minute or less and approximately 600 mL per minute or more, or between approximately 300 mL per minute and approximately 500 mL per minute, or between any values within the foregoing ranges. In any embodiments disclosed herein, the pump assembly 800 could comprise two or more pumps, including two or more voice coil actuated pumps. For example, the pump assembly 800 could have a first pump having a high flow rate, configured to provide a rapid drawdown of the space between the wound overlay and the wound, and a second, smaller capacity pump configured to maintain the level of reduced pressure of the space between the wound overlay and the wound after the initial draw down. In any embodiments disclosed herein, the pump flow rate can be approximately 20 times the leak alarm flow rate, which can be set at approximately 15 milliliters per minute.

As mentioned, any pump assembly embodiment disclosed herein can have a pressure monitor. The pressure monitor can be supported by the control board and can be configured to monitor a level of pressure in the fluid flow passageway. The pressure monitor can be configured to protect the motor from exceeding a predefined threshold pressure. In any embodiments disclosed herein, the pressure monitor can be calibrated to not exceed 175+/−50 mmHg. In any embodiments disclosed herein, the pressure monitor can be calibrated to not exceed 235 mmHg. The pressure monitor can be configured to cut power to the motor if the pressure reading reaches a predetermined value, and be configured to resume when the pressure level drops below the predetermined value or a second predetermined value that can be higher or lower than the first predetermined value. Additionally, the pump assembly 800 can be programmed to prevent such over-pressurization. The pump assembly 800 can be configured such that the software provides the primary mechanism for preventing over-pressurization, and the pressure monitor can provide backup over-pressurization protection.

The pump device can have a layer of open foam or other material wrapped at least partially around an outside surface of the pump to reduce the noise and vibration produced by the pump. One or more labels can be affixed to an outside surface of the housing 802. In any embodiments disclosed herein, the label can be used to seal one side or more than one side an air conduit that is part of the pump assembly. Additionally, In any embodiments disclosed herein, the pump can have one or more weights, cushions, foam (such as a viscoelastic foam), plastic (such as ABS, polyurethane, urethane, or otherwise), or other pads, panels, sheets, or segments supported by the pump or positioned adjacent to one or more outside surfaces of the pump. Some embodiments can have mass based or compliant damping materials. Such components or materials (not illustrated) can damp vibration and/or attenuate noise produced by the pump.

For example, one or more weights (made from steel, metal, or any other suitable material) can be supported or attached to an outside surface of the pump device or any other pump embodiment disclosed herein. The steel weights can weigh approximately 1.8 grams, 3.8 grams, or 5.8 grams, or between 1 gram and 10 grams or more, or between 1.5 grams and 6 grams. Two or more weights can be supported or attached to an outside surface of the pump or any other pump embodiment disclosed herein. Two steel weights each weighing approximately 1.8 grams, 3.8 grams, or 5.8 grams, or between 1 gram and 10 grams or more, or between 1.5 grams and 6 grams, can be attached to an outside surface of the pump. Each of the two plates can be positioned on opposite sides of the motor, or otherwise. In any embodiments disclosed herein, four steel weights each weighing approximately 1.8 grams, 3.8 grams, or 5.8 grams, or between 1 gram and 10 grams or more, or between 1.5 grams and 6 grams, can be attached to an outside surface of the pump. The plates can be arranged such that two plates are positioned on each of two opposite sides of the motor, or otherwise. In any embodiments disclosed herein, weights can be positioned adjacent to three or more sides of the pump including, for example and without limitation, the sides and top surfaces of the pump.

FIGS. 40A-40G are an isometric view, a top view, a bottom view, a top end view, a bottom end view, a first side view, and a second side view, respectively, of another embodiment of a pump assembly 900. Any embodiments of the pump assembly 900 can have any of the same features, components, weights, dimensions, shapes, or other details of any other pump assembly embodiment disclosed herein, including without limitation the pump assembly embodiment 800 disclosed above. Additionally, the pump assembly embodiment 900 can be used with any of the dressing embodiments disclosed herein or otherwise. However, In any embodiments disclosed herein, the pump assembly 900 can have a number of differences as compared to other pump assemblies disclosed herein.

For example, a control button or switch 912 can be supported on a side wall surface of the second housing portion 902*b*. Additionally, pump assembly can have any number of indicator lights, such as indicator lights 916, positioned on an outside, front surface of the housing.

Figure 40A:
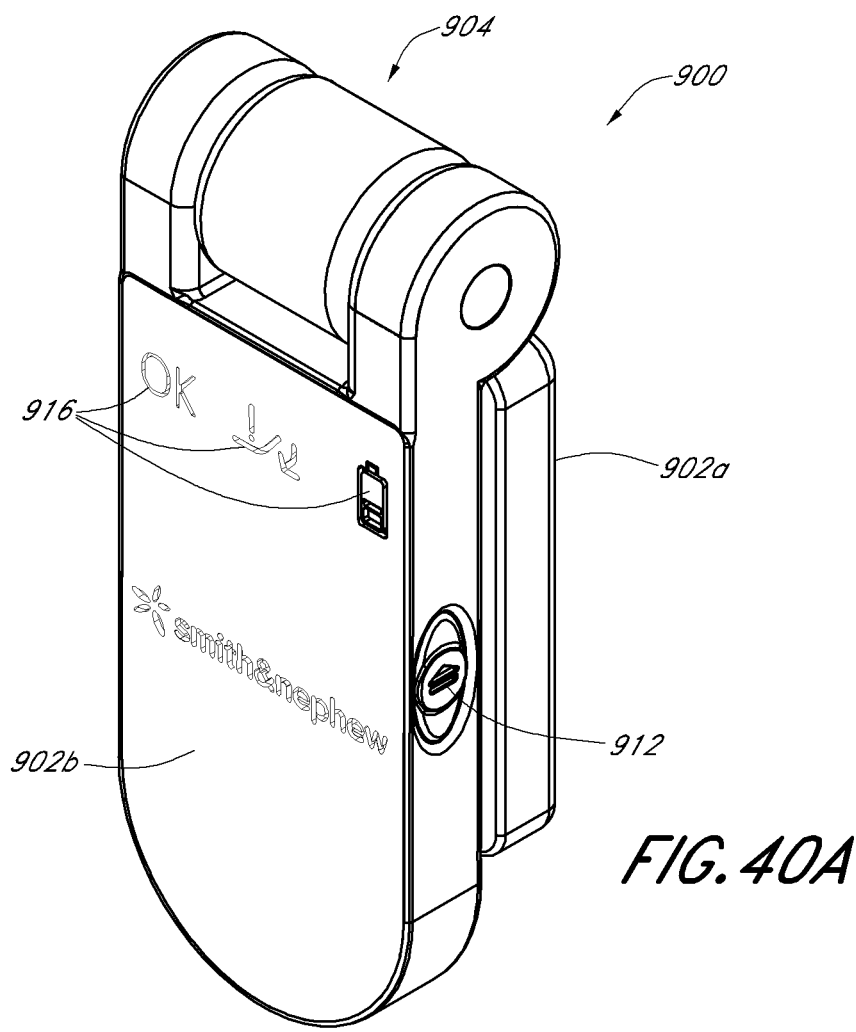
FIGS. 40A-40G are an isometric view, a top view, a bottom view, a top end view, a bottom end view, a first side view, and a second side view, respectively, of another embodiment of a pump assembly.
Figures 40B, 40C:
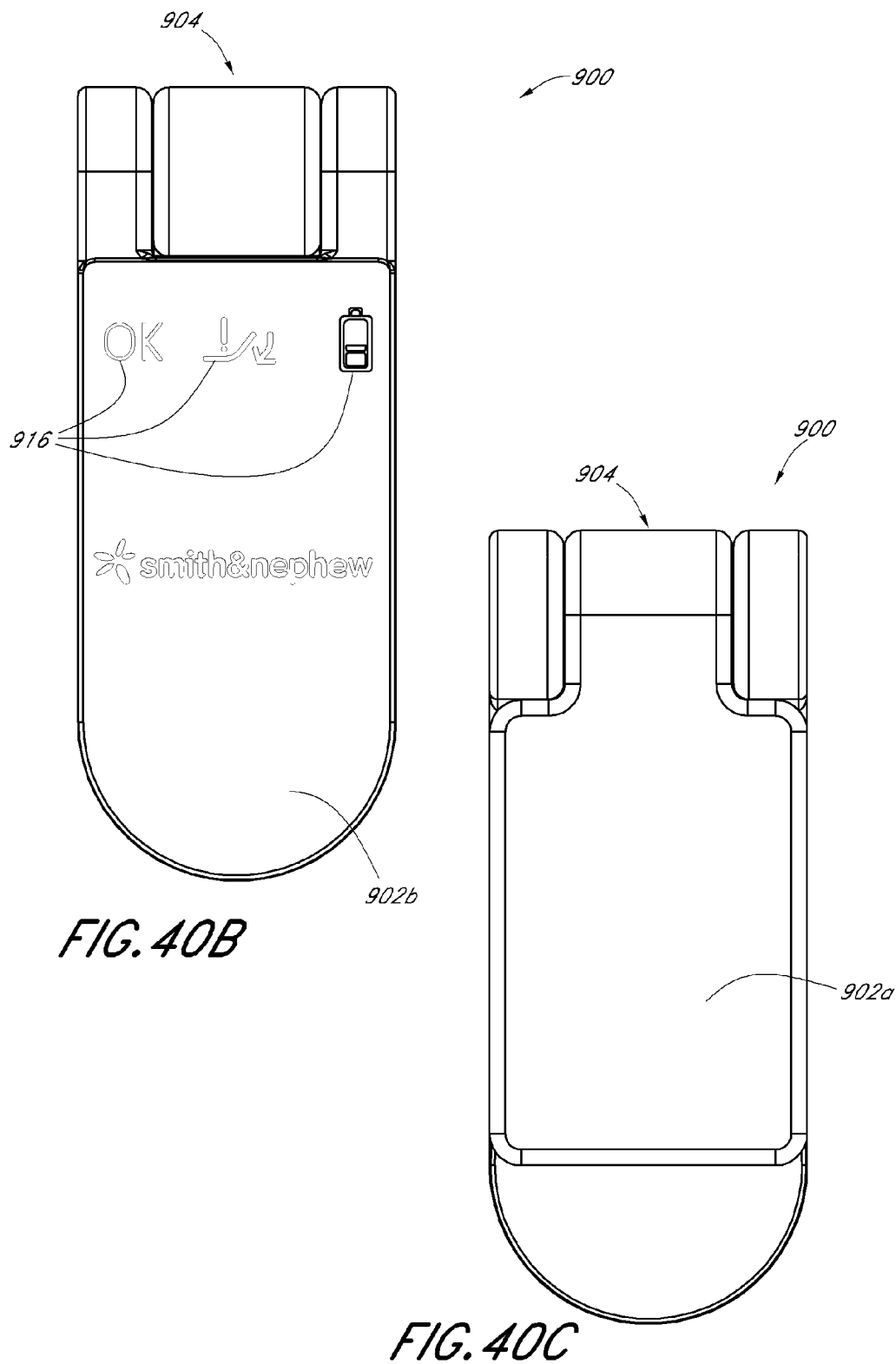
Figure 40D:
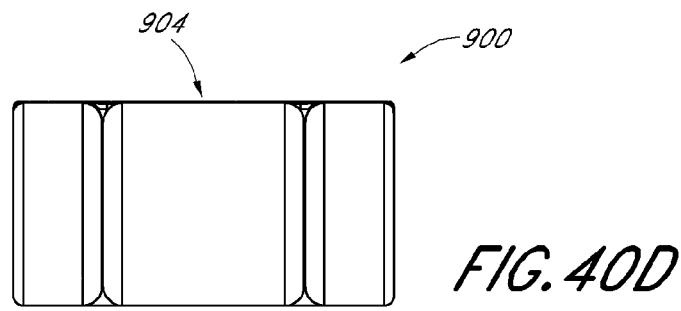
Figure 40E:
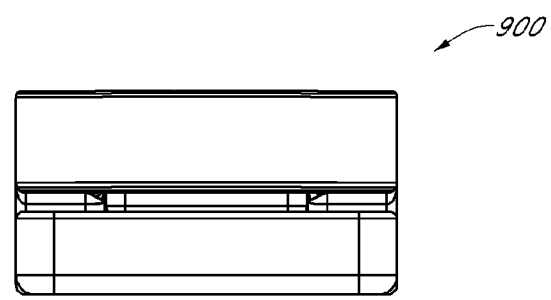
Figure 40F:
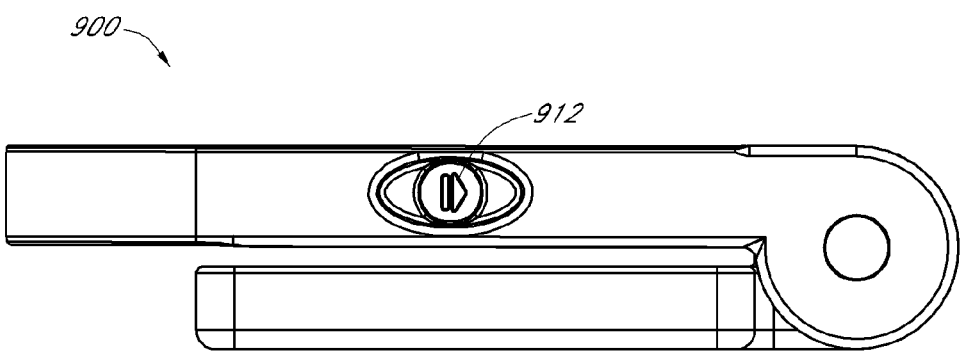
Figure 40G:
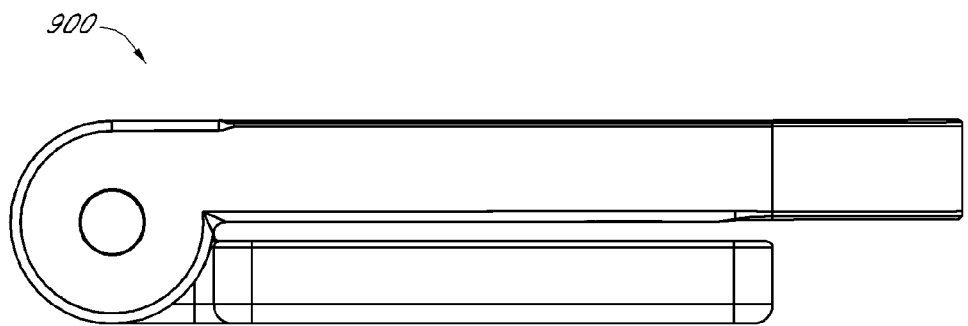
Figure 40H:
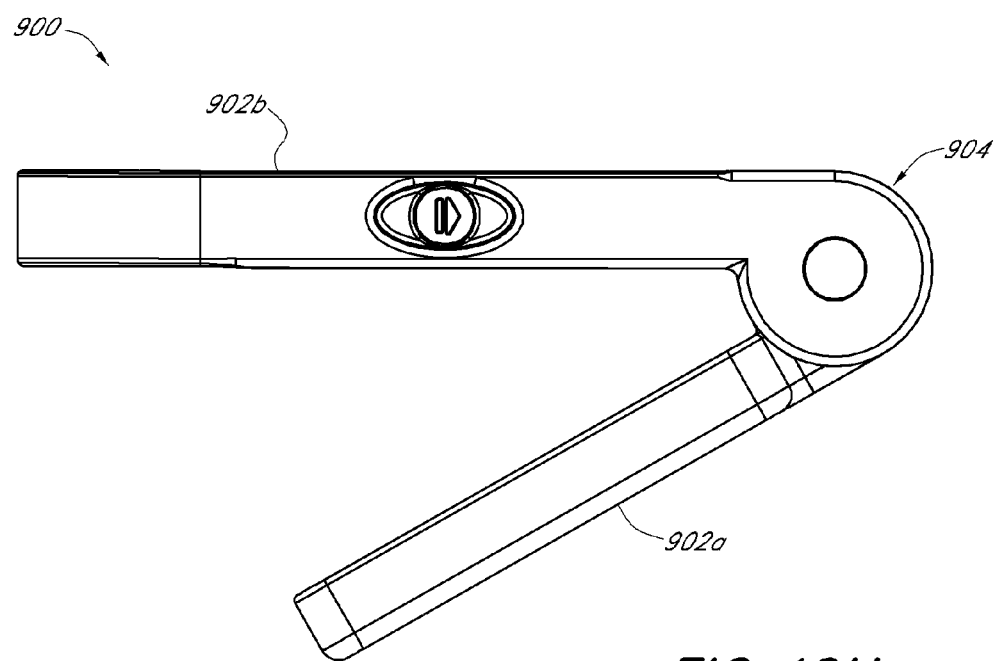
Figure 41A:
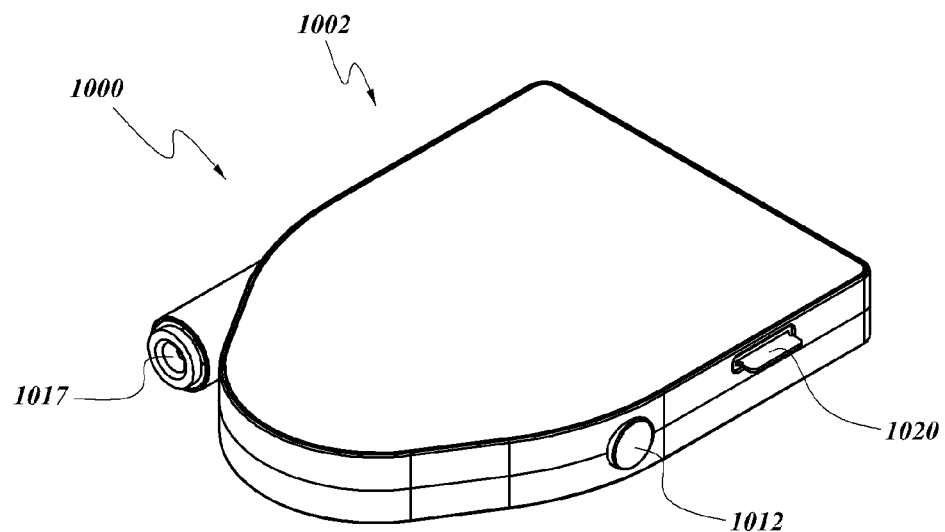
FIGS. 41A-41G are an isometric view, a top view, a bottom view, a top end view, a bottom end view, a first side view, and a second side view, respectively, of an embodiment of a pump assembly.
Figure 41B:
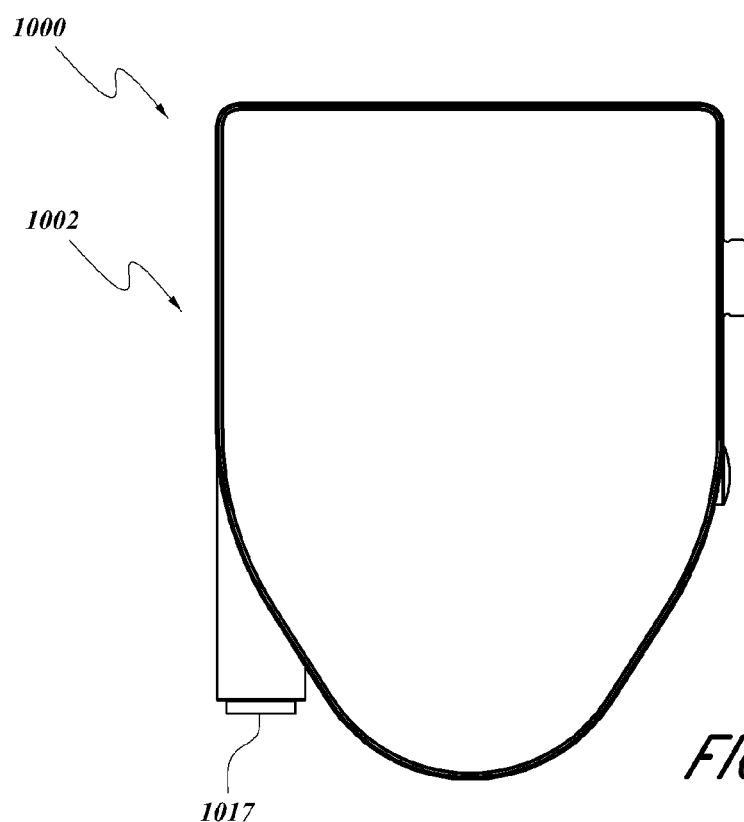
Figure 41C:
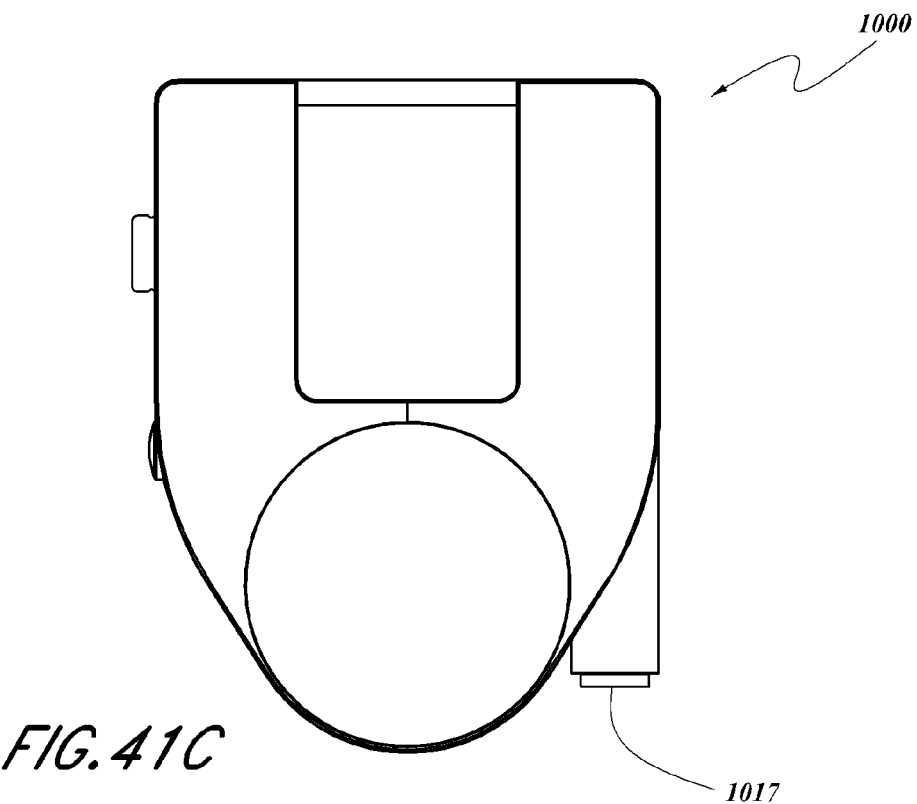
Figure 41D:
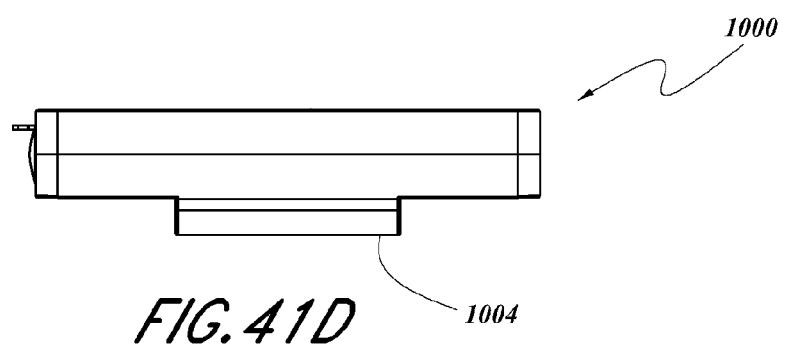
Figure 41E:
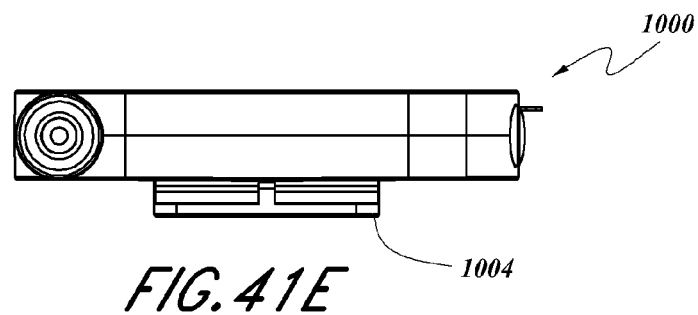
Figure 41F:
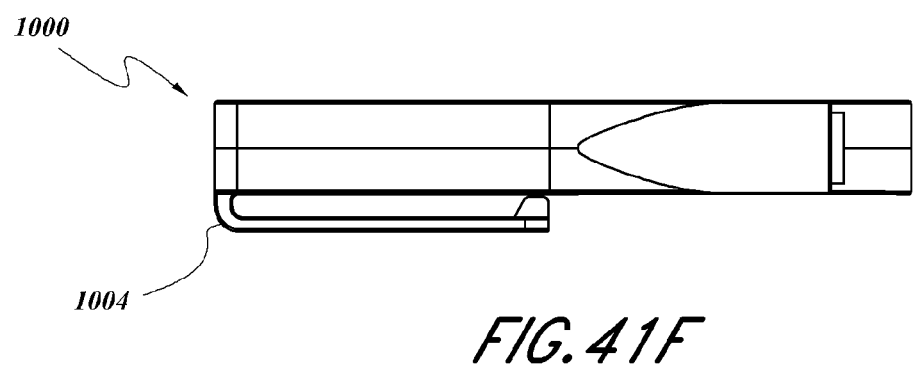
Figure 41G:
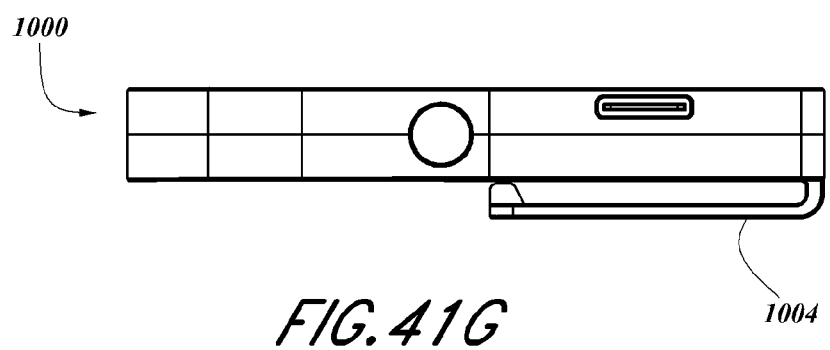
Figure 42A:
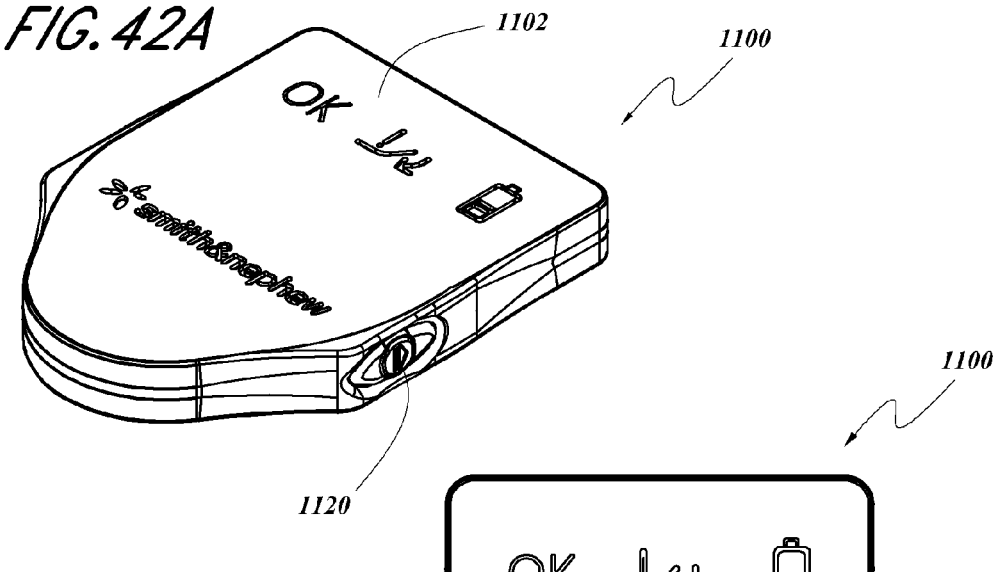
FIGS. 42A-42G are an isometric view, a top view, a bottom view, a top end view, a bottom end view, a first side view, and a second side view, respectively, of another embodiment of a pump assembly.
Figure 42B:
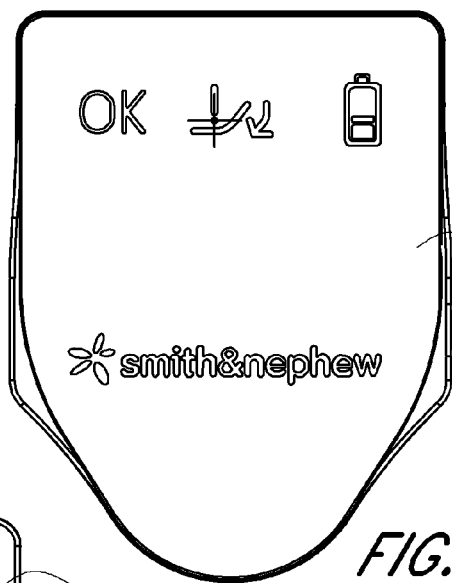
Figure 42C:
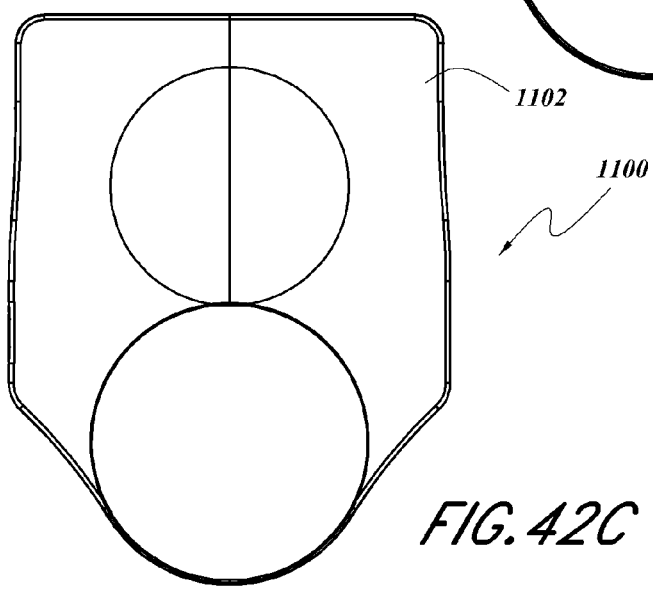
Figure 42D:
Figure 42E:
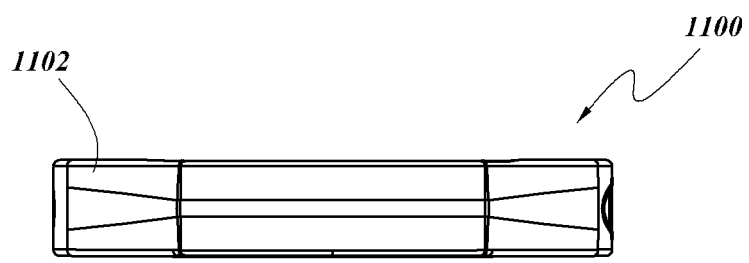
Figure 42F:
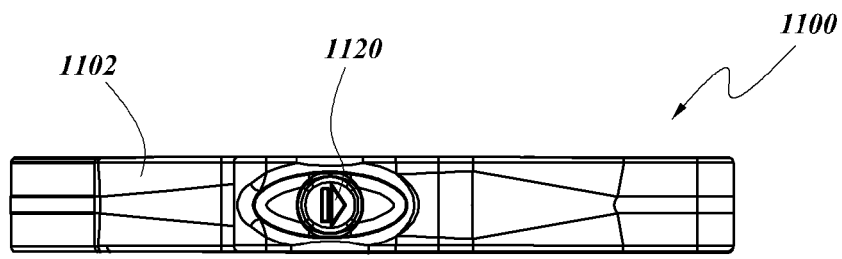
Figure 42G:
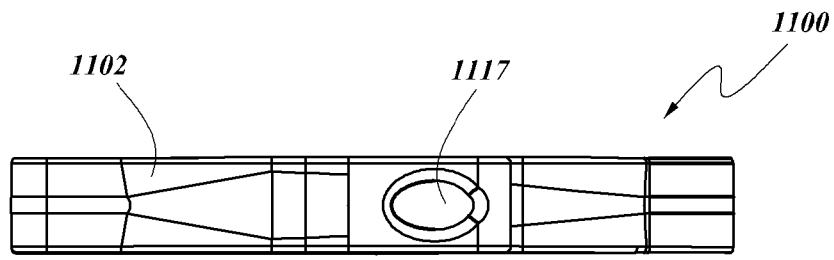
Figure 43A:
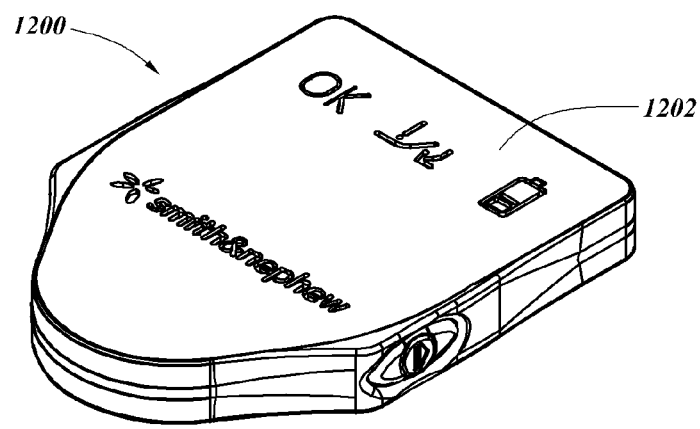
FIGS. 43A-43G are an isometric view, a top view, a bottom view, a top end view, a bottom end view, a first side view, and a second side view, respectively, of another embodiment of a pump assembly.
Figure 43B:
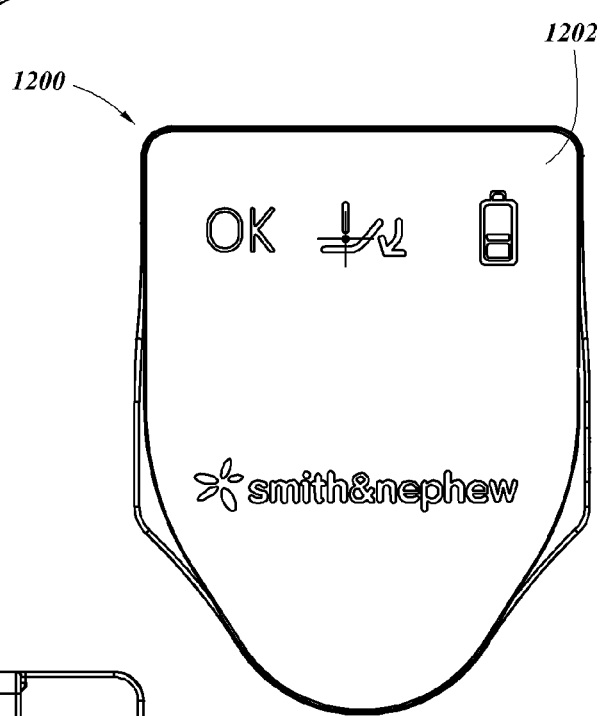
Figure 43C:
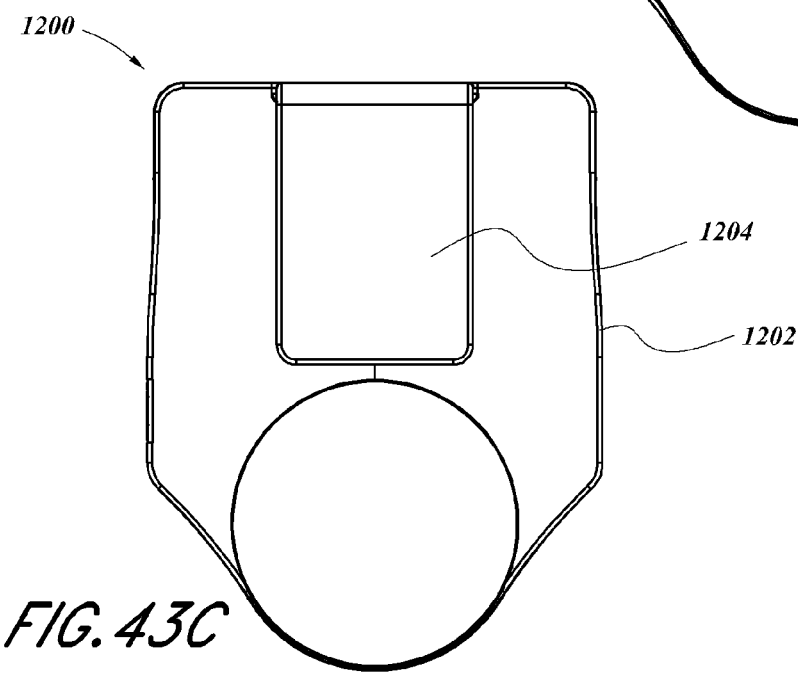
Figure 43D:
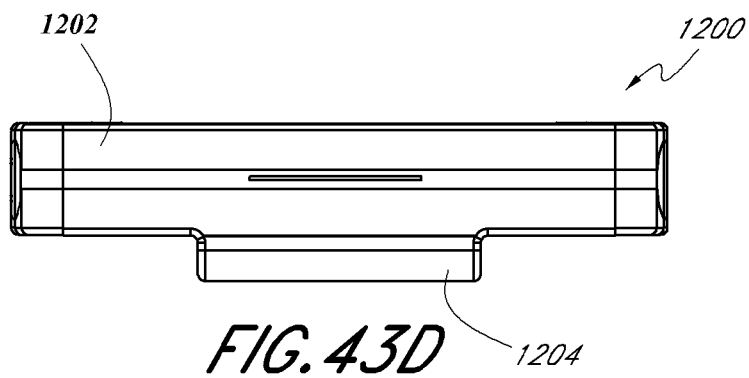
Figure 43E:
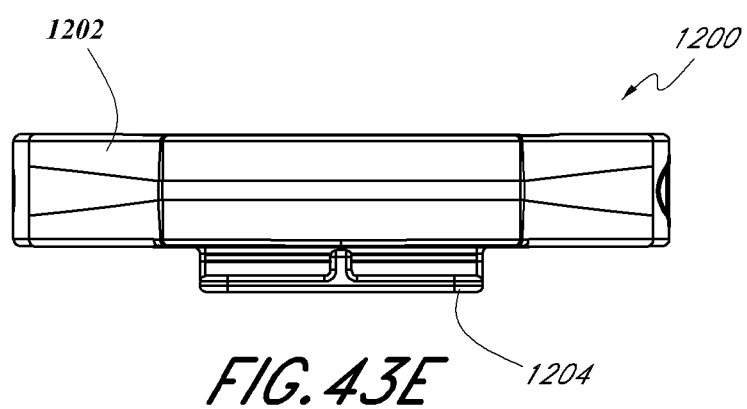
Figure 43F:
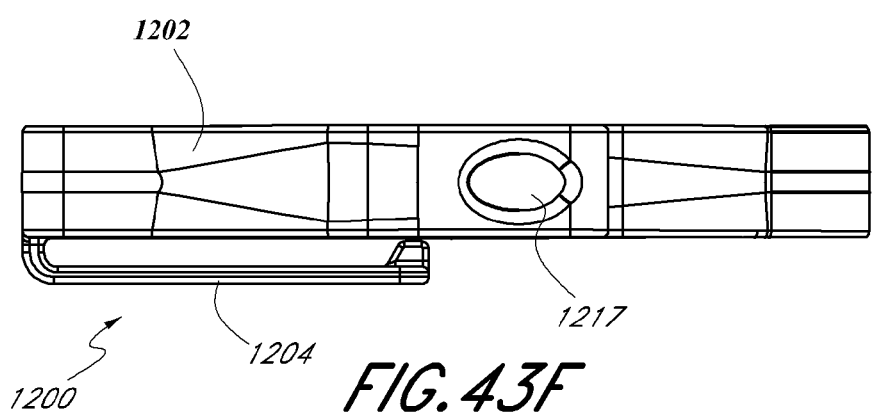
Figure 43G:
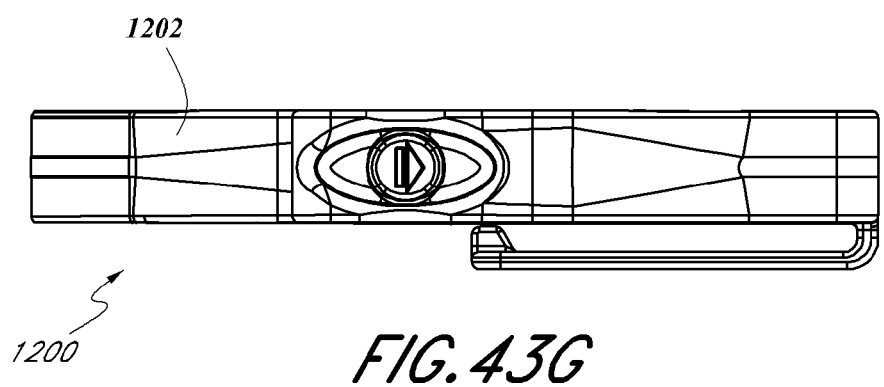
Figure 44A:
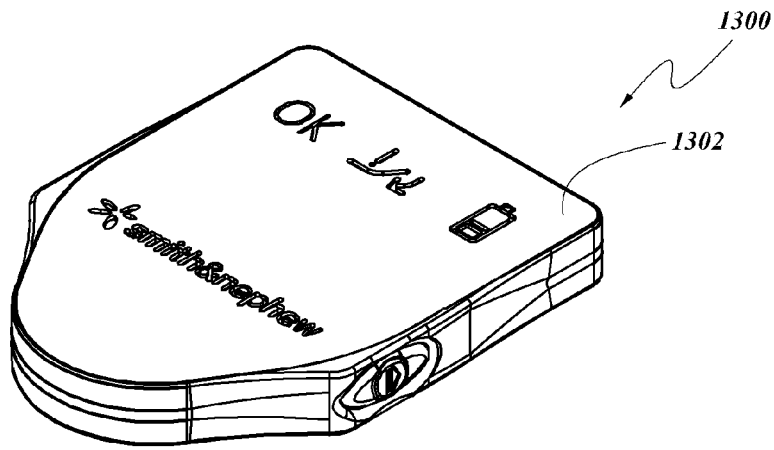
FIGS. 44A-44G are an isometric view, a top view, a bottom view, a top end view, a bottom end view, a first side view, and a second side view, respectively, of another embodiment of a pump assembly.
Figure 44B:
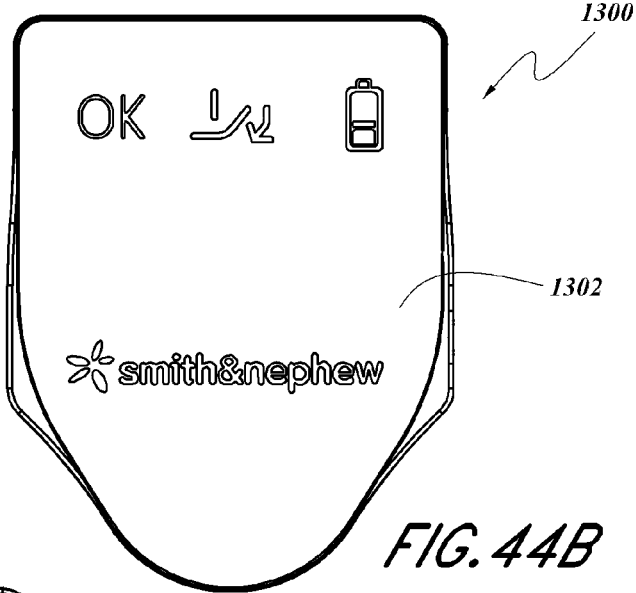
Figure 44C:
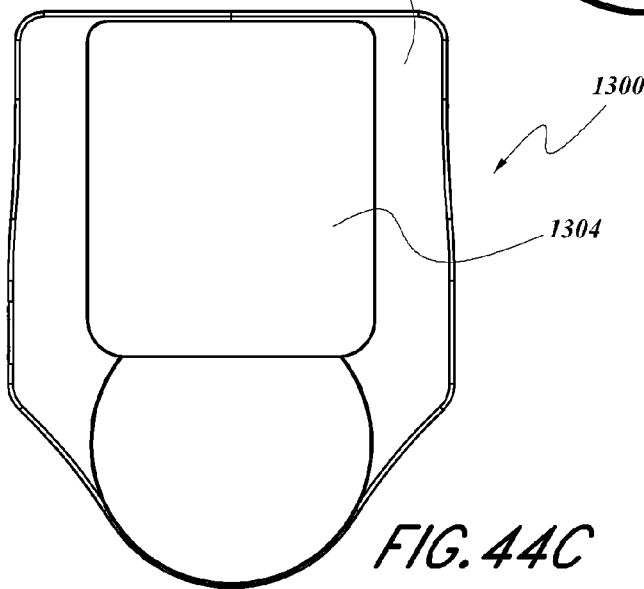
Figure 44D:
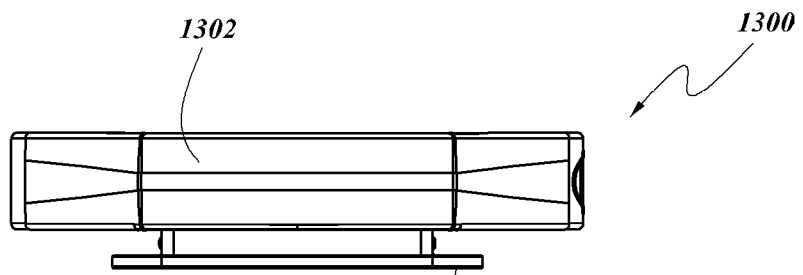
Figure 44E:
Figure 44F:
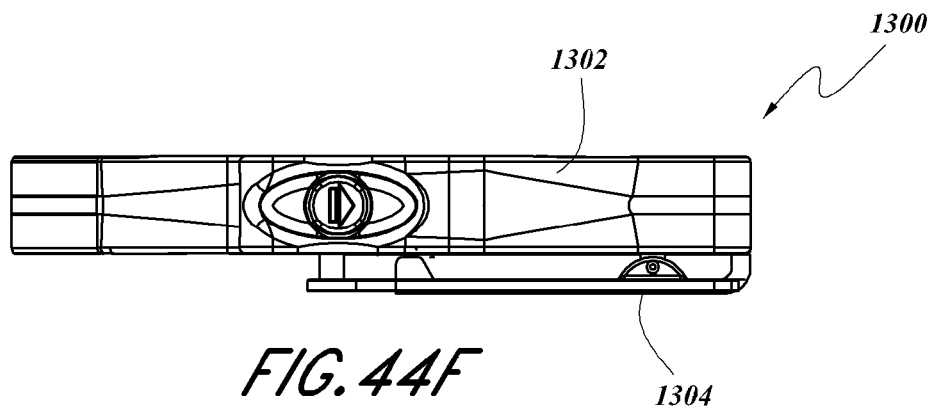
Figure 44G:
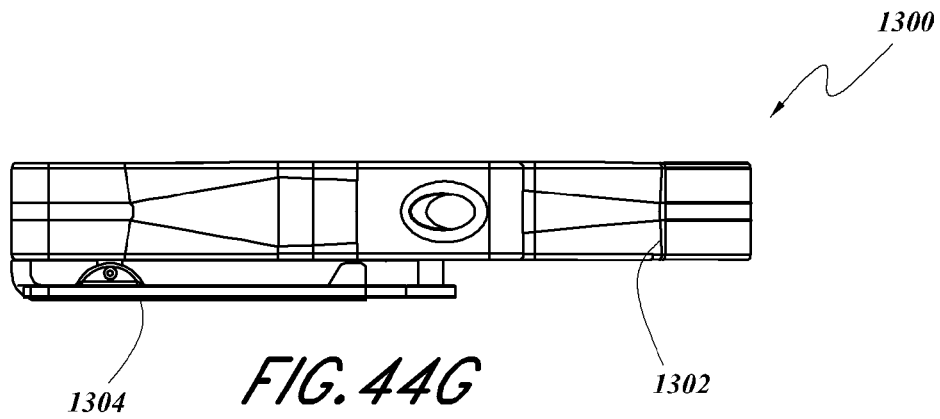
Figure 45A:
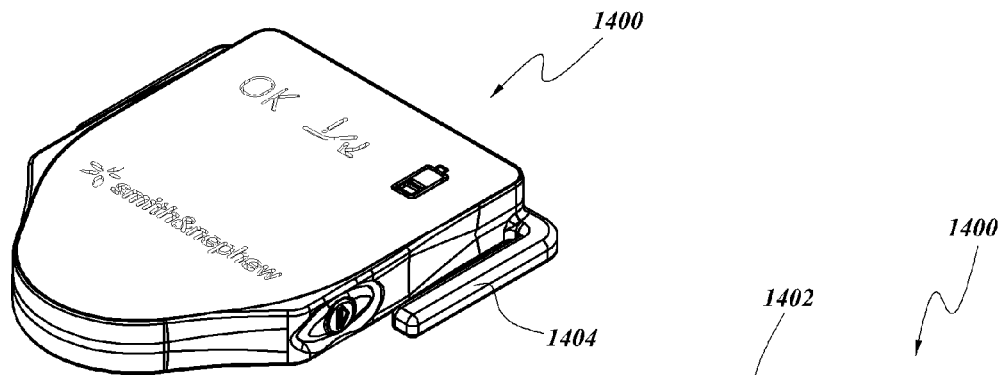
FIGS. 45A-45G are an isometric view, a top view, a bottom view, a top end view, a bottom end view, a first side view, and a second side view, respectively, of another embodiment of a pump assembly.
Figure 45B:
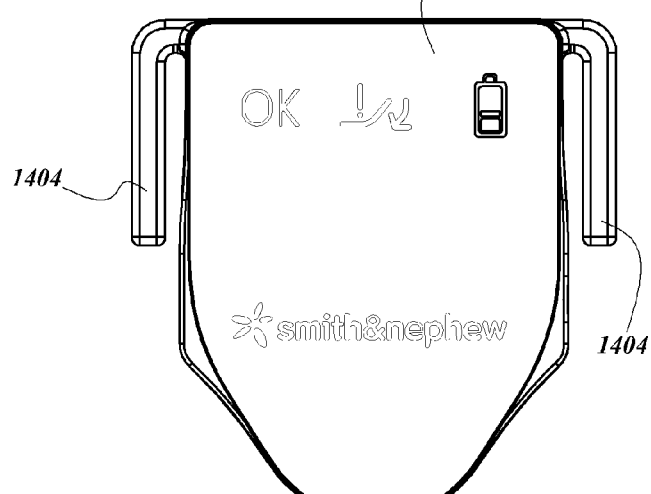
Figure 45C:
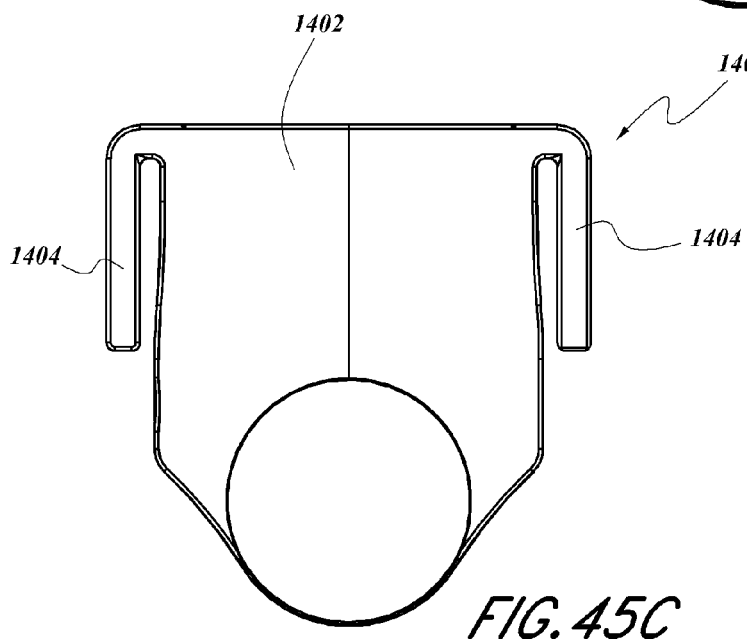
Figure 45D:
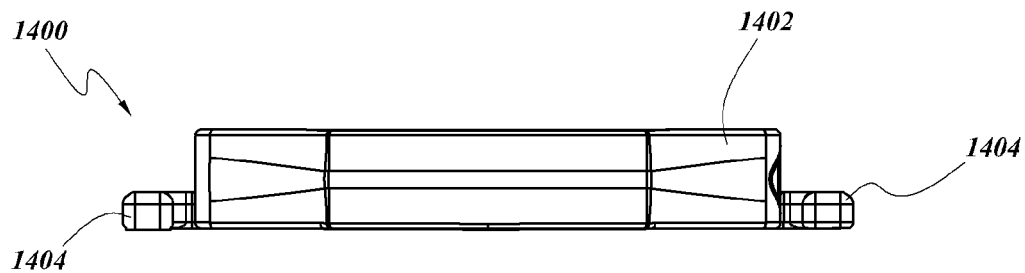
Figure 45E:
Figure 45F:
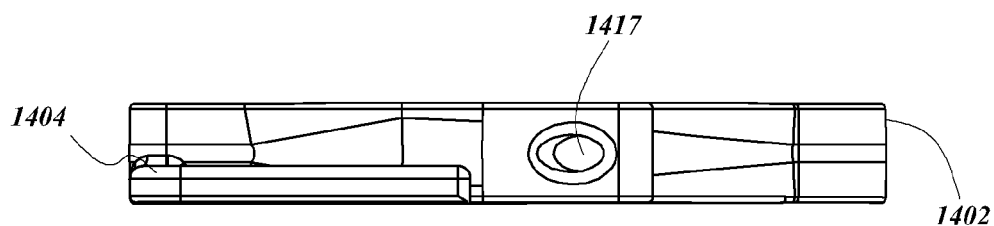
Figure 45G:
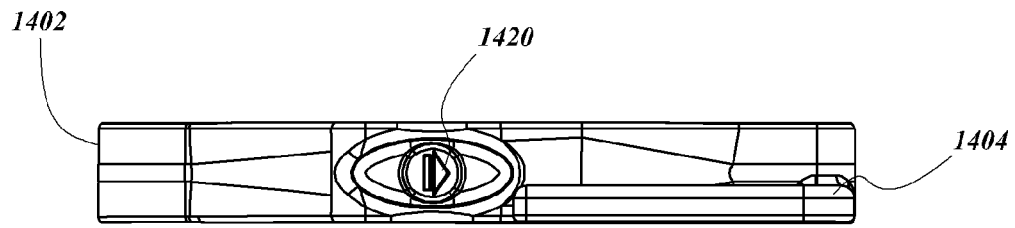
Figure 46D:
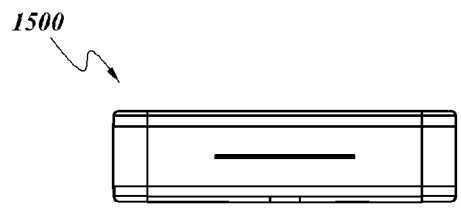
Figure 46E:
Figure 46F:
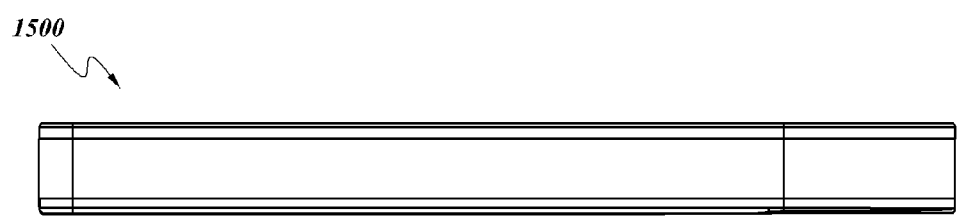
Figure 46G:
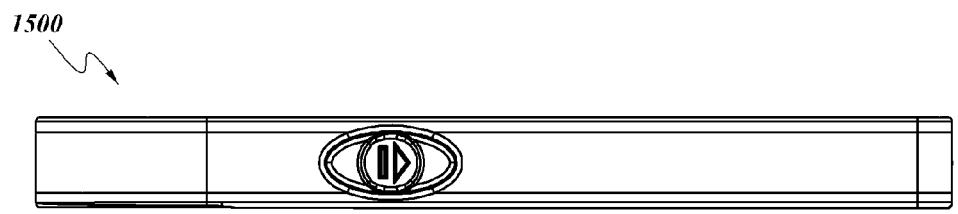
Figure 47D:
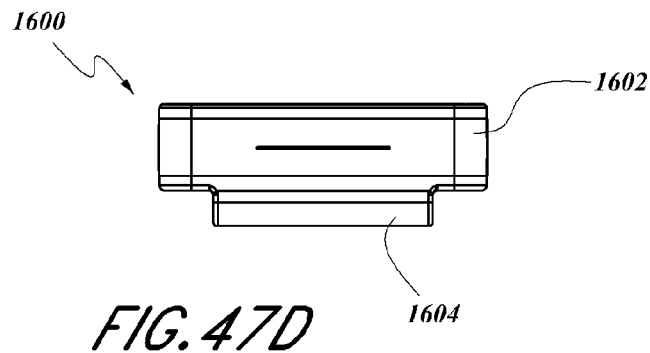
Figure 47E:
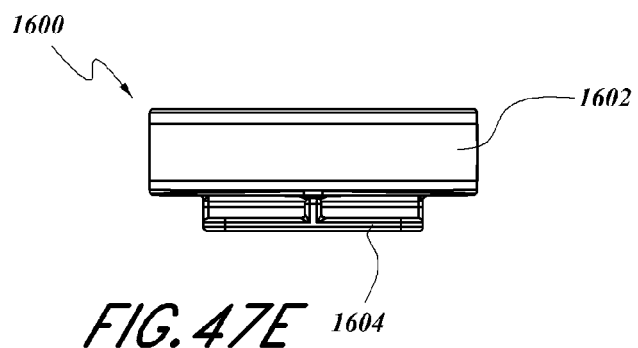
Figure 47F:
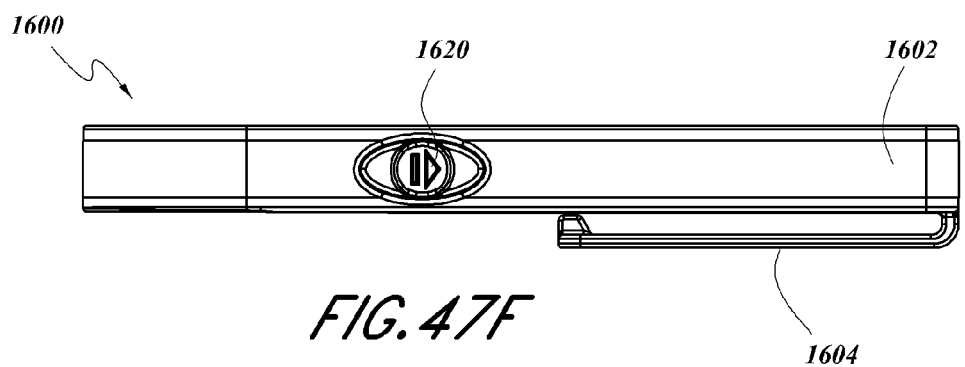
Figure 47G:
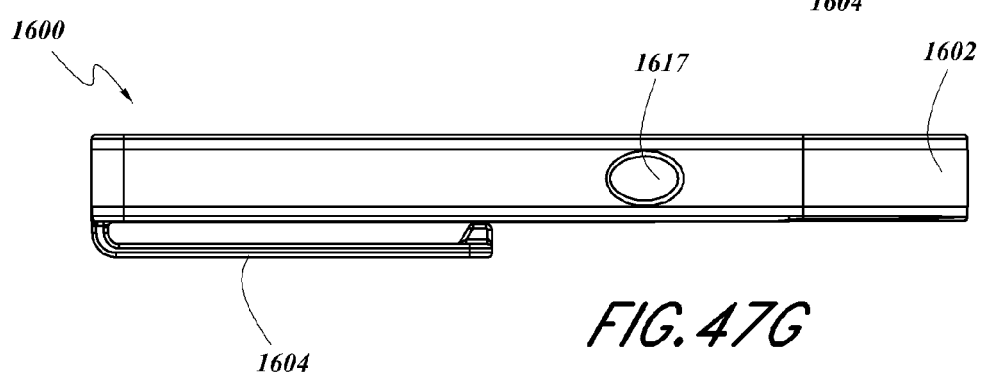
Figure 48A:
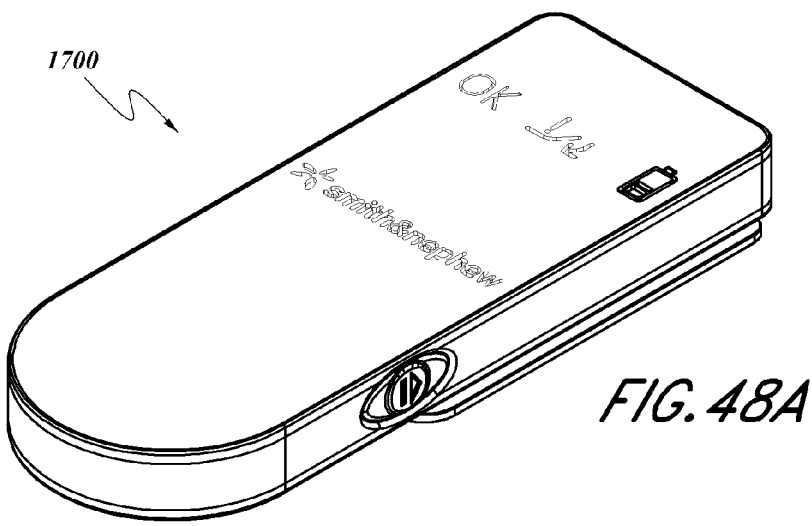
FIGS. 48A-48G are an isometric view, a top view, a bottom view, a top end view, a bottom end view, a first side view, and a second side view, respectively, of another embodiment of a pump assembly.
Figures 48B, 48C:
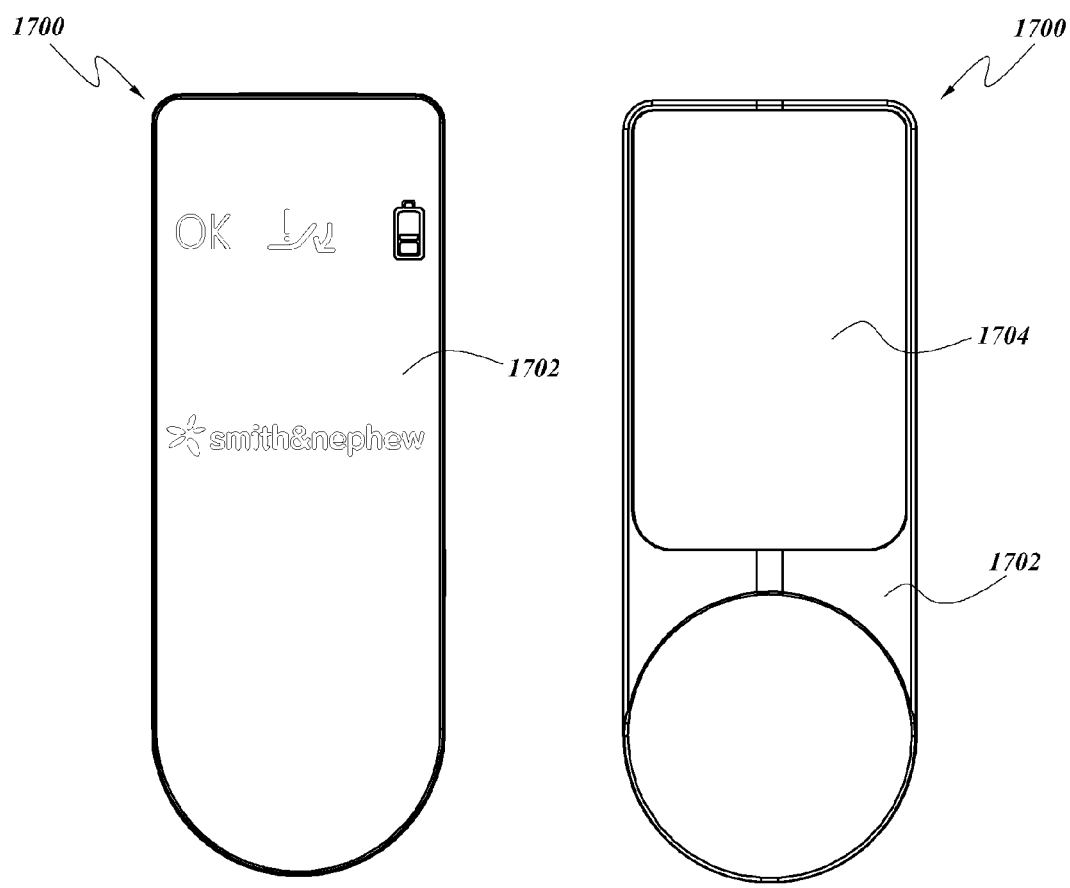
Figure 48D:
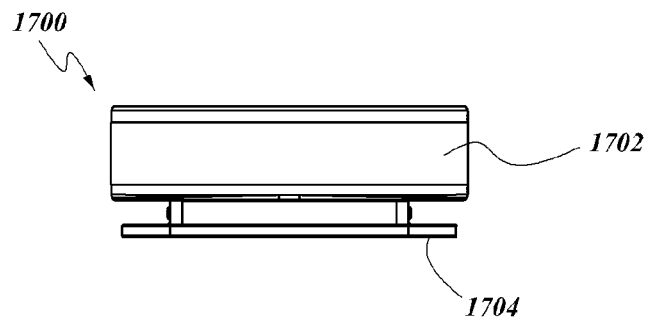
Figure 48E:
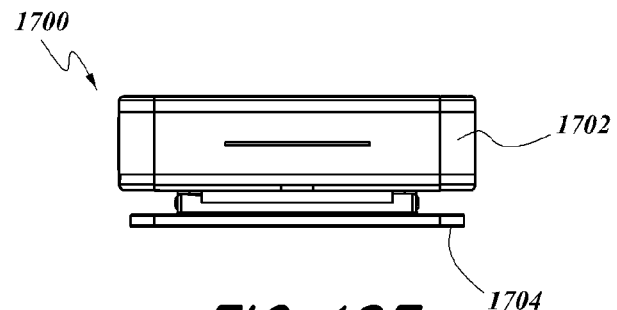
Figure 48F:
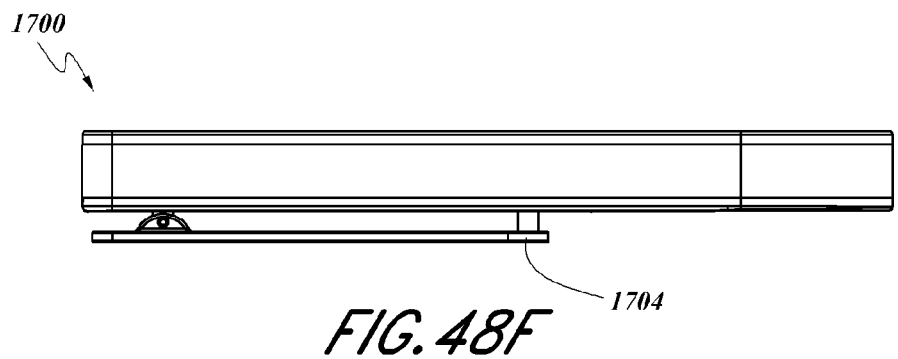
Figure 48G:
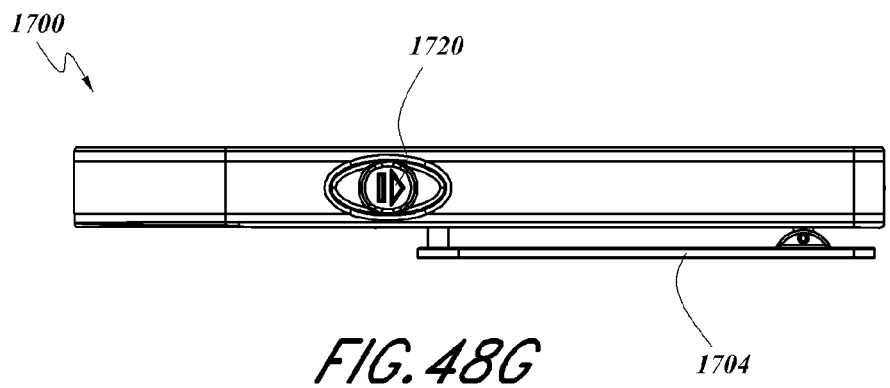

With reference to FIG. 40H, the first portion 902a and the second portion 902b of the housing 902 can be rotatably connected to one another by a hinge 904. The hinge 904 can permit the first portion 902a to rotate about an axis A within a particular angular range relative to the second portion 902b. The hinge 904 can be biased toward a closed position, as illustrated in FIG. 29A, such that the two portions 902a, 902b form a clip or a clamp. In this configuration, the housing 902 can be clipped to a person's clothing, such as in a pocket, over a belt, to a flap or in a pouch or a pocket on the dressing, or otherwise. For example, the first portion 902a can be positioned on the inside of a pouch, pocket, or otherwise, and the second portion 902b can be positioned outside of the pouch, pocket, or otherwise. The bias can be created with a coil spring, a bent spring, or otherwise, and can cause the housing 902 to grip the flap or pocket. The clamping force can be low enough that a user can open the housing from the clamped position, but strong enough so that it will remain clamped about the pocket, flap, or other material.

FIGS. 41A-41G are an isometric view, a top view, a bottom view, a top end view, a bottom end view, a first side view, and a second side view, respectively, of another embodiment of a pump assembly 1000. Any embodiments of the pump assembly 1000 can have any of the same features, components, weights, dimensions, shapes, or other details of any other pump assembly embodiment disclosed herein, including without limitation the pump assembly embodiment 800 disclosed above. Additionally, the pump assembly embodiment 1000 can be used with any of the dressing embodiments disclosed herein either directly, by incorporation by reference, as part of Appendix A included in Application Ser. No. 61/791,984, or otherwise. Therefore, any use of the term "disclosed herein" in this disclosure is meant to refer to any embodiments described or illustrated in this application, incorporated by reference herein, and/or attached to Application Ser. No. 61/791,984 as an appendix. However, in any embodiments disclosed herein, the pump assembly 1000 can have a number of differences as compared to other pump assemblies disclosed herein.

With reference to FIGS. 41A-41G, the pump assembly 1000 can have a housing 1002 that only has one portion. In this configuration, control button, the pump device, battery power, and control board will be supported within one housing portion. As with the pump assembly 800, an actuation tab (i.e., pull tab) 0 can be used to prevent inadvertent operation of the pump device before the pump assembly 1000 is ready for treatment. In any embodiments disclosed herein, the housing 1002 can have an opening 1017 configured to receive a conduit for communication of reduced pressure to a dressing. A clip 1004 can be supported by the housing 1002, the clip 1004 being configured to enable a user to removably clip the pump assembly to a pocket, pouch, or other flap.

FIGS. 42A-42G are an isometric view, a top view, a bottom view, a top end view, a bottom end view, a first side view, and a second side view, respectively, of another embodiment of a pump assembly 1100. Any embodiments of the pump assembly 1100 can have any of the same features, components, weights, dimensions, shapes, or other details of any other pump assembly embodiment disclosed herein, including without limitation the pump assembly embodiment 800 disclosed above. Additionally, the pump assembly embodiment 1100 can be used with any of the dressing embodiments disclosed herein or otherwise. However, In any embodiments disclosed herein, the pump assembly 1100 can have a number of differences as compared to other pump assemblies disclosed herein.

With reference to FIGS. 42A-42G, the pump assembly 1100 can have a housing 1 that only has one portion. In this configuration, control button, the pump device, battery power, and control board will be supported within one housing portion. In any embodiments disclosed herein, an actuation tab (not shown) can be used to prevent inadvertent operation of the pump device before the pump assembly 1100 is ready for treatment. In any embodiments disclosed herein, the housing 1 can have an opening 1117 configured to receive a conduit for communication of reduced pressure to a dressing. A clip 1004 can be supported by the housing 1002, the clip 1004 being configured to enable a user to removably clip the pump assembly to a pocket, pouch, or other flap.

FIGS. 43A-43G are an isometric view, a top view, a bottom view, a top end view, a bottom end view, a first side view, and a second side view, respectively, of another embodiment of a pump assembly 1200. FIGS. 44A-44G are an isometric view, a top view, a bottom view, a top end view, a bottom end view, a first side view, and a second side view, respectively, of another embodiment of a pump assembly 1300. FIGS. 45A-45G are an isometric view, a top view, a bottom view, a top end view, a bottom end view, a first side view, and a second side view, respectively, of another embodiment of a pump assembly 1400.

Any embodiments of the pump assembly 1200, 1300, or 1400 can have any of the same features, components, weights, dimensions, shapes, or other details of any other pump assembly embodiment disclosed herein, including without limitation the pump assembly embodiment 1100 disclosed above. Additionally, any embodiments of the pump assembly 1200, 1300, or 1400 can be used with any of the dressing embodiments disclosed herein or otherwise.

However, In any embodiments disclosed herein, the pump assembly 1200, the pump assembly 1300, or the pump assembly 1400 can have a number of differences as compared to other pump assemblies disclosed herein. For example, without limitation, the pump assembly 1200 can have a clip 1204 supported by the housing 1202, the clip 1204 being configured to clip the pump assembly to a pocket, pouch, belt, flap, or otherwise. Similarly, without limitation, the pump assembly 1300 can have a clip 1304 supported by the housing 1302, the clip 1304 being configured to clip the pump assembly to a pocket, pouch, belt, flap, or otherwise. The clip 1304 can have a rotatable hinge having a spring or other biasing mechanism to bias the clip 1304 to a closed position. Further, without limitation, the pump assembly 1400 can have a pair of tabs 1404 configured to clip the pump assembly to a pocket, pouch, belt, flap, or otherwise.

FIGS. 46A-46G are an isometric view, a top view, a bottom view, a top end view, a bottom end view, a first side view, and a second side view, respectively, of another embodiment of a pump assembly 1500. Any embodiments of the pump assembly 1500 can have any of the same features, components, weights, dimensions, shapes, or other details of any other pump assembly embodiment disclosed herein, including without limitation the pump assembly embodiments 800 or 1100 disclosed above. Additionally, the pump assembly embodiment 1500 can be used with any of the dressing embodiments disclosed herein or otherwise. However, In any embodiments disclosed herein, the pump assembly 1500 can have a number of differences as compared to other pump assemblies disclosed herein.

FIGS. 47A-47G are an isometric view, a top view, a bottom view, a top end view, a bottom end view, a first side view, and a second side view, respectively, of another embodiment of a pump assembly 1600. FIGS. 48A-48G are an isometric view, a top view, a bottom view, a top end view, a bottom end view, a first side view, and a second side view, respectively, of another embodiment of a pump assembly 1700.

Any embodiments of the pump assembly 1600 or 1700, or any other pump assembly embodiments disclosed herein, can have any of the same features, components, weights, dimensions, shapes, or other details of any other pump assembly embodiment disclosed herein, including without limitation the pump assembly embodiments 1100 or 1500 disclosed above. Additionally, any embodiments of the pump assembly 1600 or 1700 can be used with any of the dressing embodiments disclosed herein or otherwise.

However, in any embodiments disclosed herein, the pump assembly 1600 and the pump assembly 1700 can have a number of differences as compared to other pump assemblies disclosed herein. For example, without limitation, the pump assembly 1600 can have a clip 1604 supported by the housing 1602, the clip 1604 being configured to clip the pump assembly to a pocket, pouch, belt, flap, or otherwise. Similarly, without limitation, the pump assembly 1700 can have a clip 1704 supported by the housing 1702, the clip 1704 being configured to clip the pump assembly to a pocket, pouch, belt, flap, or otherwise. The clip 1704 can have a rotatable hinge having a spring or other biasing mechanism to bias the clip 1704 to a closed position.

Additionally, any of the pump assembly or pump device embodiments disclosed herein can be configured to have one or more of the indicator lights illustrated in any of FIGS. 38-58. For example and without limitation, the housing of any of the pump assemblies disclosed herein can support one or more indicator lights of the type and design illustrated in any of such figures.

Figure 49:
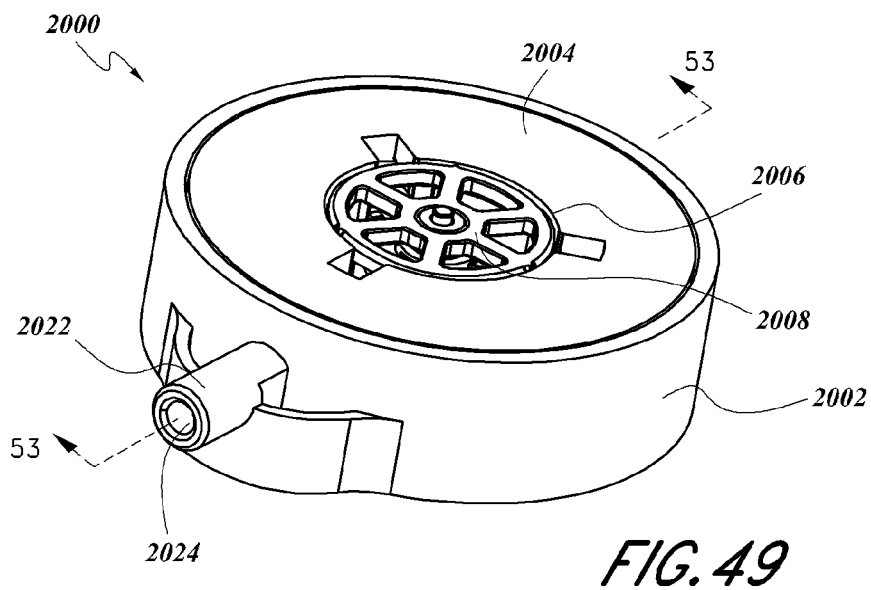
FIG. 49 is an isometric view of another embodiment of a pump assembly, showing a top surface of the pump assembly.
Figure 50:
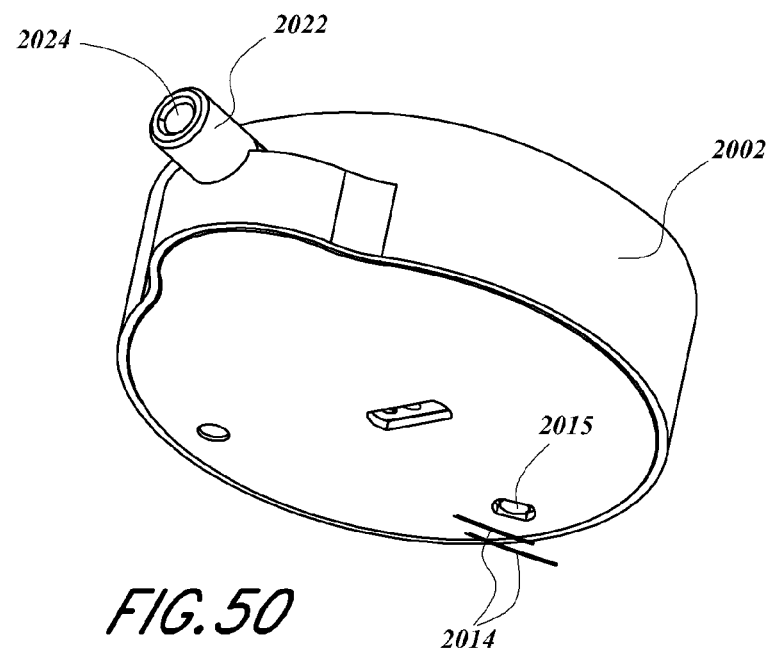
FIG. 50 is an isometric view of the pump assembly embodiment illustrated in FIG. 49, showing a bottom surface of the pump assembly.
Figure 51:
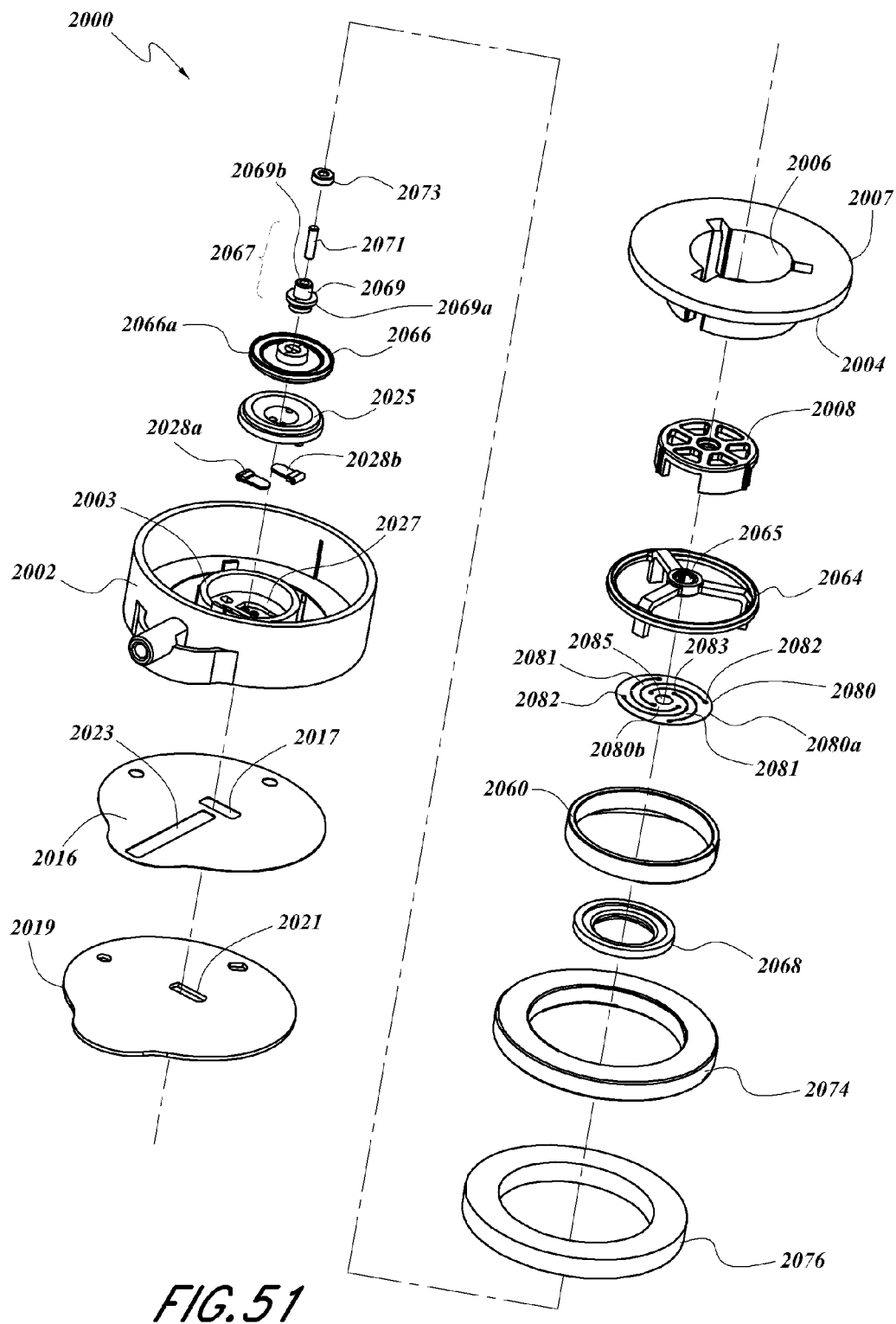
FIG. 51 is an exploded view of the pump assembly embodiment illustrated in FIG. 49, showing the top of the pump assembly.
Figure 52:
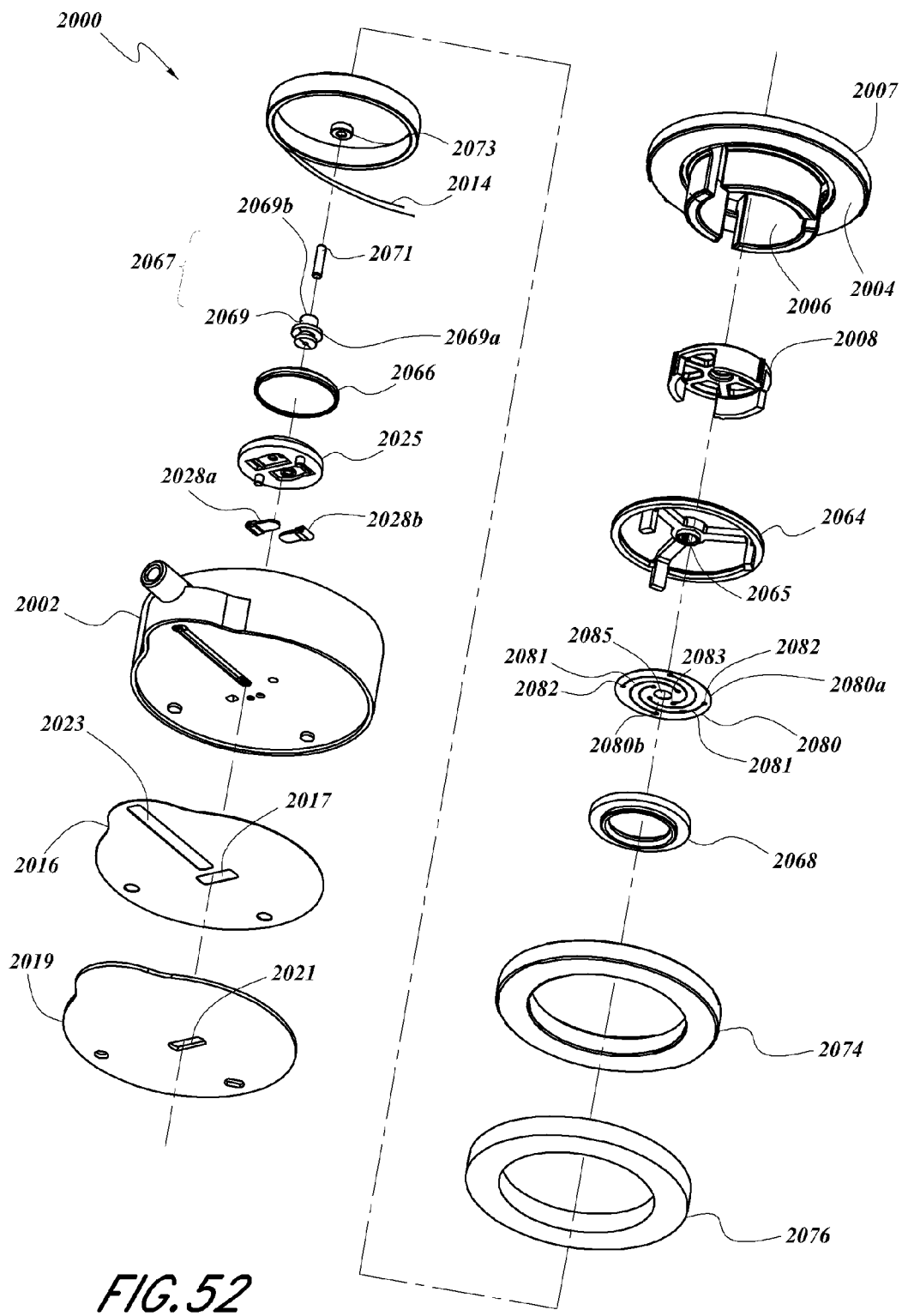
FIG. 52 is an exploded view of the pump assembly embodiment illustrated in FIG. 49, showing the bottom of the pump assembly.
Figure 53:
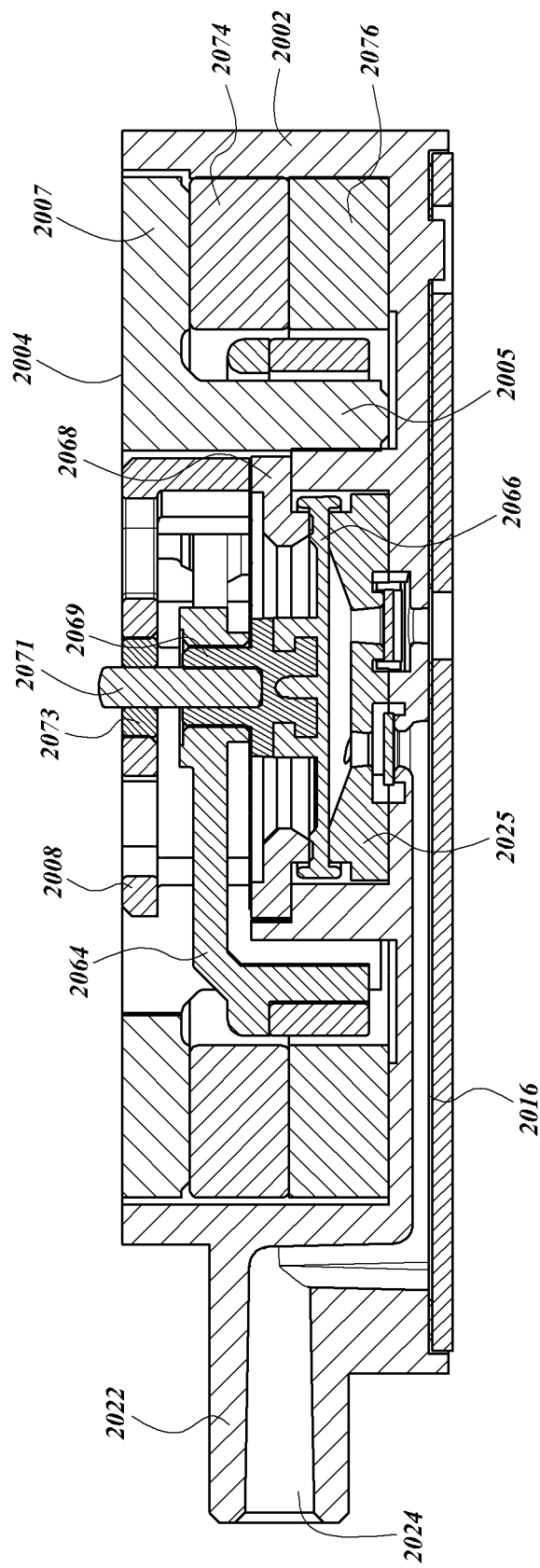
FIG. 53 is a section view of the pump assembly embodiment illustrated in FIG. 49, the section being taken through the center of the pump assembly embodiment.

FIGS. 49 and 50 are isometric views of another embodiment of a pump assembly 2000, showing a top surface of the pump assembly and the bottom surface of the pump assembly, respectively. FIGS. 51 and 52 are exploded views of the pump assembly embodiment illustrated in FIG. 49, showing the top of the pump assembly and the bottom of the pump assembly, respectively. FIG. 53 is a section view of the pump assembly embodiment illustrated in FIG. 49, the section being taken through the center of the pump assembly embodiment. The pump assembly embodiment 2000 can have a compact, small size and can have any of the same features, sizes, components, materials, or other details of the pump assembly embodiment 200 described above, or any of the other pump assembly embodiments disclosed herein.

In any embodiments disclosed herein, the pump assembly 2000 can have a diameter or lateral size in the range of approximately 26-29 mm, or between approximately 25 and approximately 28 mm. In any embodiments disclosed herein, the pump assembly embodiment 2000 can have a thickness or height of approximately 8 mm, or between approximately 6 mm and approximately 10 mm.

The pump assembly embodiment 2000 can be produced for a low cost and can operate at high efficiencies, making it beneficial for portable, disposable, and/or single use applications. In any embodiments disclosed herein, the pump assembly embodiment 2000 can run for a week on a small primary cell without the need for battery replacement or recharging. This pump can be used in an ultra-portable single-use negative-pressure wound therapy (NPWT) device, but is not so limited. In any embodiments disclosed herein, as mentioned, the pump assembly embodiment 2000 can be used for negative pressure wound therapy. However, the pump assembly embodiment 2000 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2000 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2000 can be adapted to operate at efficiency levels in excess of 25%.

The pump assembly embodiment 2000 can have a housing 2002 adapted to support and protect many of the components of the pump assembly embodiment 2000. An upper pole 2004, which can be made from any suitable materials such as mild steel or sintered steel, can be supported at one end (for example, a first end) 2002a of the housing 2002. In any embodiments disclosed herein, the upper pole 2004 can have an opening 2006 formed through an axial centerline of the upper pole 2004. A bearing 2008 can be supported by the upper pole 2004, within the opening 2006. Two or more electrical wires 2014 can be connected to the pump assembly embodiment 2000, configured to provide power to the pump assembly embodiment 2000. In particular, the wires 2014 can be used to provide electrical current to the coil 2060 of the pump assembly. The electrical wires 2014 can be routed through one or more openings or channels formed in the housing 2002, such as channels 2015 shown in FIG. 50 or in any other opening formed in the housing.

A cover 2016 (also referred to herein as a first cover) can be positioned over the electrical wires 2014 after the electrical wires have been advanced through the channels 2015. The cover 2016 can be an adhesive backed foil, film, paper, plastic sheet or label, or other similar object. An opening 2017 can be formed in the cover 2016 to permit air, gas, or other fluid to be exhausted from the pump through the outlet manifold or opening. Additionally, in any embodiments, a second channel or opening 2023 can be formed in the cover 2016 to form an inlet conduit for the pump. A second cover 2019 can be positioned over the first cover 2016, the second cover 2019 having an opening 2021 therein for exhaust gas. The second cover 2019 can be used to close or substantially seal one or more openings, such as the opening 2023 for an inlet conduit, formed in the cover 2016.

Additionally, in any embodiments disclosed herein, the first cover 2016 and/or the second cover 2019 can be configured to complete the inlet vacuum channel. In other words, the cover 2016 can be configured to separate or seal the vacuum created by the pump from atmosphere. Using a thin label, such as the cover 2016, in place of a thicker plastic molded part or otherwise can decrease the height or thickness of the pump as much as possible. Alternatively, some embodiments of the pump assembly can have a thicker cover that can be molded, cast, machined, or formed by any other suitable method.

The housing 2002 can support a valve assembly 2020 at an end (for example, a second end 2002b) of the housing 2002. The housing 2002 can support a boss member 2022 that can receive a conduit therein or thereover, the boss member 2022 having an opening 2024 therethrough. The opening 2024 can be in fluid communication with one or more passageways inside the pump assembly embodiment 2000, such as air passageway 2003 formed (that can be covered by the cover 2016) in the housing 2002 that communicates with the air passageway 2029 formed in the valve assembly 2020.

With reference to FIGS. 51 and 52, the valve assembly 2020 can have a first valve member 2025, and a second valve member 2027 (that can be formed into the housing 2002). The valve plate 2026 can support two flexible valve flaps 2028, a first valve flap 2028a for the inlet valve chamber and a second valve flap 2028b for the outlet valve chamber. The first flap 2028a and the second flap 2028b can be configured to deflect away from the relaxed position of the flaps 2028 shown to block passage of air through the valve assembly 2020 during operation of the pump, or possibly even during sterilization of the pump.

As with the other valve plates or valve assembly embodiments disclosed herein, a first inlet valve chamber of the second valve member 2027 can have a cavity or depression and one or more openings, such as an opening in communication with the depression to permit the passage of air from the channel into the pump assembly embodiment 2000 when the flap valve 2028a is in an open position. In any pump assembly embodiments disclosed herein, the valve plate can provide a sealing surface for the valve flap 2028 to selectively seal against to seal the opening 2024. In any embodiments disclosed herein, the sealing surface for any of the valves can have an angled or curved surface configured to substantially match the profile of the valve flap 2028a as the valve flap 2028a is deflected from the relaxed position against the sealing surface. This arrangement can improve the seal between the valve flap 2028a and the sealing surface to increase the efficiency of the pump assembly embodiment 2000. In some embodiments, the sealing surface can be straight and not angled or curved.

In use, for any of the embodiments disclosed herein, as the voltage supplied to the coil oscillates between a positive voltage and a negative voltage, the coil (which can be fixed to the support member and the diaphragm) can oscillate up and down in the pump between the two poles 2004 and 2076. The oscillation of the diaphragm 2066 can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm 2066 returns toward the valve support, the volume of airspace decreases, causing the air pressure to increase. This forces air out of the chamber through the outlet valve, while the inlet valve is sealed closed.

The first outlet valve chamber of the second valve member 2027 can have a cavity or depression and one or more openings configured to allow the passage or exit of air from the inside of the depression and the pump assembly embodiment 2000 when the valve flap 2028b is in an open position. In some embodiments, the valve assembly 2020 can have one, two, three, or more openings formed in either of the inlet and outlet valve chambers. The housing 2002 can have a similar arrangement of inlet and outlet valve chambers as compared to the first inlet and outlet valve chambers.

A second inlet valve chamber supported by the first valve member 2025 can have a cavity or depression and one or more openings in communication with the depression to permit the passage of air from the first inlet valve chamber into the second inlet valve chamber when the valve flap is in an open position (e.g., not sealingly covering the opening 2024). One or more openings can be formed in the second inlet valve chamber to permit air to pass from the second inlet valve chamber into the inside of the pump assembly embodiment 2000. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber can be supported by first valve member 2025. The second outlet valve chamber can have a depression formed therein and an opening in communication with the second outlet valve chamber. In any embodiments disclosed herein, similar to the boss 2031, the boss 2052 can have an angled or curved surface configured to substantially match the profile of the valve flap as the valve flap is deflected from the relaxed position against the surface of the boss. This arrangement can improve the seal between the valve flap and the boss or sealing surface to increase the efficiency of the pump assembly embodiment 2000. When the valve flap 2028b is in an open position, air or other fluid within the pump assembly embodiment 2000 can pass through the opening into the first outlet valve chamber and exit the pump assembly embodiment 2000 through the one or more openings.

In any embodiments disclosed herein, valve flaps 2028a, 2028b can be configured to be unstressed in a neutral position, neither fully open nor fully closed. Therefore, rather than there being a 'cracking pressure' required to open them, In any embodiments disclosed herein, a small backpressure (for example, approx. 30 mbar or more) can be used to hold valve flaps 2028a, 2028b closed. This improves efficiency by reducing the pressure force that must be generated by the VCA during the suction stroke.

The pump assembly embodiment 2000 can have a coil 2060 comprising electrical wires 2014, and a support member 2064. The coil 2060 can be formed from a length of wound conductive wire, such as without limitation copper wire. In operation, the coil 2060 can be configured to move within a magnetic circuit, and can be supported via a support member to a pump diaphragm assembly 2066. In any embodiments disclosed herein, an opening 2065 formed in the support member 2064 can be configured to receive a shaft assembly or protrusion 2067 (which can comprise a base portion 2069 and a shaft portion 2071) of the diaphragm assembly 2066 so the pump diaphragm assembly 2066 can be coupled with the support member 2064. The diaphragm 2066 can be supported and fixed at its outer periphery 2066a, wherein an interior portion 2066b of the diaphragm assembly 2066 is permitted to flex and deflect in either direction away from the relaxed position of the diaphragm assembly 2066. The diaphragm assembly 2066 is configured to elastically return the coil 2060 to its relaxed position.

The housing 2002 can have a generally cylindrical protrusion or wall 2003 that can engage the outer periphery 2066a of the diaphragm. A bearing or bushing 2008 that can have extending cylindrical walls can support the outer periphery 2066a from the opposite side as compared to the wall 2003 of the housing.

The diaphragm 2066 can be supported and/or fixed along all or a portion of its outer periphery 2066a, wherein an interior portion 2066b of the diaphragm assembly 2066 is permitted to flex and deflect in either direction away from the relaxed position of the diaphragm assembly 2066. In any embodiments disclosed herein, the diaphragm can be clamped and compressed between two rigid surfaces to provide such support. The rigid surfaces can define an annular shape. For example, some embodiments of the diaphragm 2066 (or any other diaphragm disclosed herein) can have a moulding and a separate compression ring (made from a rigid plastic, aluminium or other metal, or any other suitable material or composite material). Additionally, some embodiments of the diaphragm 2066 (or any other diaphragm disclosed herein) can have one plastic or other frame or moulding on each side of the flexible diaphragm membrane. The mouldings and the flexible diaphragm membrane can be held together with adhesive, mechanical connections between the mouldings, ultrasonically welding, or by any other suitable method. In any embodiments disclosed herein, the diaphragm can have a single frame or moulding having a channel therein configured to receive and support a peripheral edge of the flexible diaphragm membrane. Additionally, In any embodiments disclosed herein, the diaphragm 2066 can be sealed at its outer perimeter 2066a. The diaphragm assembly 2066 is configured to elastically return the coil 160 to its relaxed position. Any of the pump embodiments disclosed herein (i.e., in this application) can be formed from cast or molded silicone, polyurethane, thermoplastic polyurethane, EPDM, and/or other suitable materials, having a hardness value of approximately 20A, 30A, 40A, 50A, 55A, or more.

Any embodiments disclosed herein can also have a flat spring member 2080 positioned adjacent to the diaphragm. In some embodiments, the spring member 2080 can be positioned against a flange portion 2069a of the base portion 2069 of the diaphragm assembly 2066. In some embodiments, the spring member 2080 can be positioned at a top portion 2069b of the base portion 2069 of the diaphragm assembly 2066, or can be positioned in any desired locations. In some embodiments, the spring member 2080 can be sized and configured to provide frequency tuning or adjustment to the resonance frequency of the diaphragm and/or the components of the oscillating coil assembly. In some embodiments, the spring member 2080 can be configured to maintain the radial alignment of the diaphragm assembly 2066 with the remainder of the pump assembly (to inhibit wobble of the diaphragm member or otherwise), or both to maintain alignment and to provide resonance frequency adjustment. The spring member 2080 can be made from stainless steel, spring steel, or any other suitable material.

In any embodiments disclosed herein, the spring member 2080 can have a thickness of approximately 0.08 mm, or from approximately 0.06 mm to approximately 0.2 mm, or between any two values in the foregoing range. In any embodiments, an outside diameter of the spring member 2081 can be approximately 9.75 mm, or from approximately 6.0 mm or less to approximately 11.0 mm. In some embodiments, the gap between the arms can be approximately 0.2 mm wide.

Additionally, in any pump embodiments disclosed herein, the spring member 2080 can have a plurality of arms 2081. The arms 2081 in any embodiment can be straight, can be radially oriented, or can be curved or helically shaped, as in the illustrated embodiment. To reduce stress concentrations and to improve the flexibility of the arms 2081, openings 2083 can be formed in the spring member 2081 adjacent to the ends of the arms. In any embodiments, as in the illustrated embodiment, the spring member 2080 can have four arms. In other embodiments, as in other embodiments disclosed herein, the spring member can have three arms, or five or more arms. The arms can be flexible and can be configured to provide the spring-like displacement between an outer portion 2080a of the spring member 2080 and an inner portion 2080b of the spring member 2080. An opening 2085 can be positioned at a center of the spring member 2081 for receiving the shaft portion 2071.

The pump assembly embodiment 2000 can have a magnet 2074 positioned between a lower pole 2076 and the upper pole 2004. In any embodiments disclosed herein, the magnet 2074 can be made from sintered Neodymium-Iron-Boron (NdFeB), from Neodymium N33, or any other suitable material. Any of the pole pieces disclosed herein can be formed from soft iron or any suitable material. This material can be used to maximize field strength and minimize losses, thereby increasing the efficiency of the pump assembly embodiment 2000. However, In any embodiments disclosed herein, the magnet 2074 can be formed from any suitable magnetic material. In any embodiments disclosed herein, the lower pole can be approximately 1.5-2.0 mm thick and can be made from any suitable material, such as mild steel.

The arrangement of the pump assembly embodiment 2000 can be configured to differ from a typical low fidelity loudspeaker. For example, some embodiments of the pump assembly 2000 can differ in the following ways. In the pump assembly embodiment 2000, the coil 2060 can be configured to underhang below the end of the magnetic circuit. For example, the coil 2060 can be configured such that it does not extend above the magnetic circuit. This can improve the efficiency and reduce the overall height of the pea 2000, but can result in the degradation of the linearity of response of the pump assembly embodiment 2000.

The coil 2060 can have a relatively high number of turns. Having a relatively high number of turns can give the coil 2060 greater structural rigidity and can maximize the efficiency of the pump assembly embodiment 2000. Additionally, the pump assembly embodiment 2000 will not have a speaker cone that is typically in a low fidelity speaker, which normally serves to control coil motion. In the pump assembly embodiment 2000, the diaphragm can be used to center the coil 2060, and a linear bearing 2008 can be used to limit any wobble of the coil 2060 by engaging the protrusion 2067 and controlling the movement of the support member 2064.

The housing 2002, support 2014, valve assembly 2020, retainer 2062, and/or support member 2064 can be made of a plastic or hard rubber material, metal, or any other suitable material or combination of materials. Such components can be formed by any suitable methods such as casting, any molding process such as injection molding, forging, sintering, machining, or any other suitable process.

Figure 54:
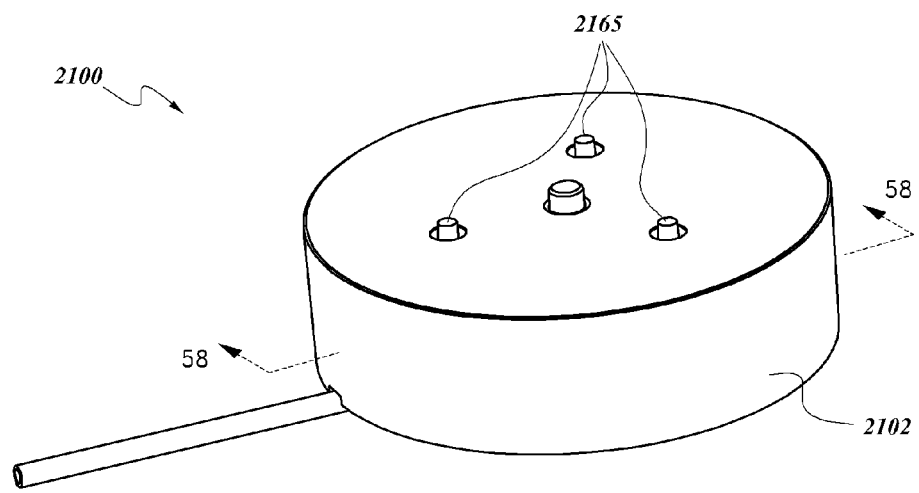
FIGS. 54 and 55 are isometric views of another embodiment of a pump assembly, showing a top surface of the pump assembly and the bottom surface of the pump assembly, respectively.
Figure 55:
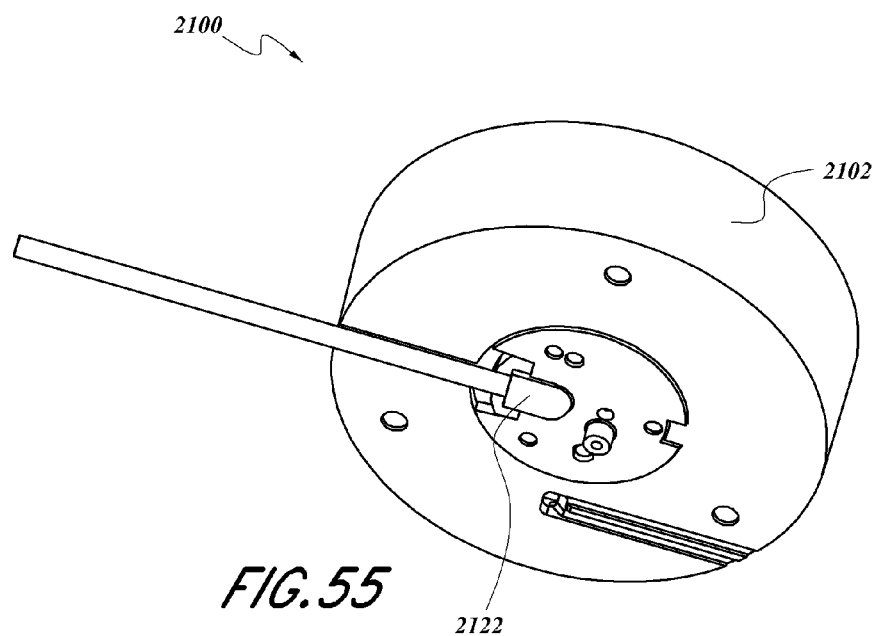
Figure 56:
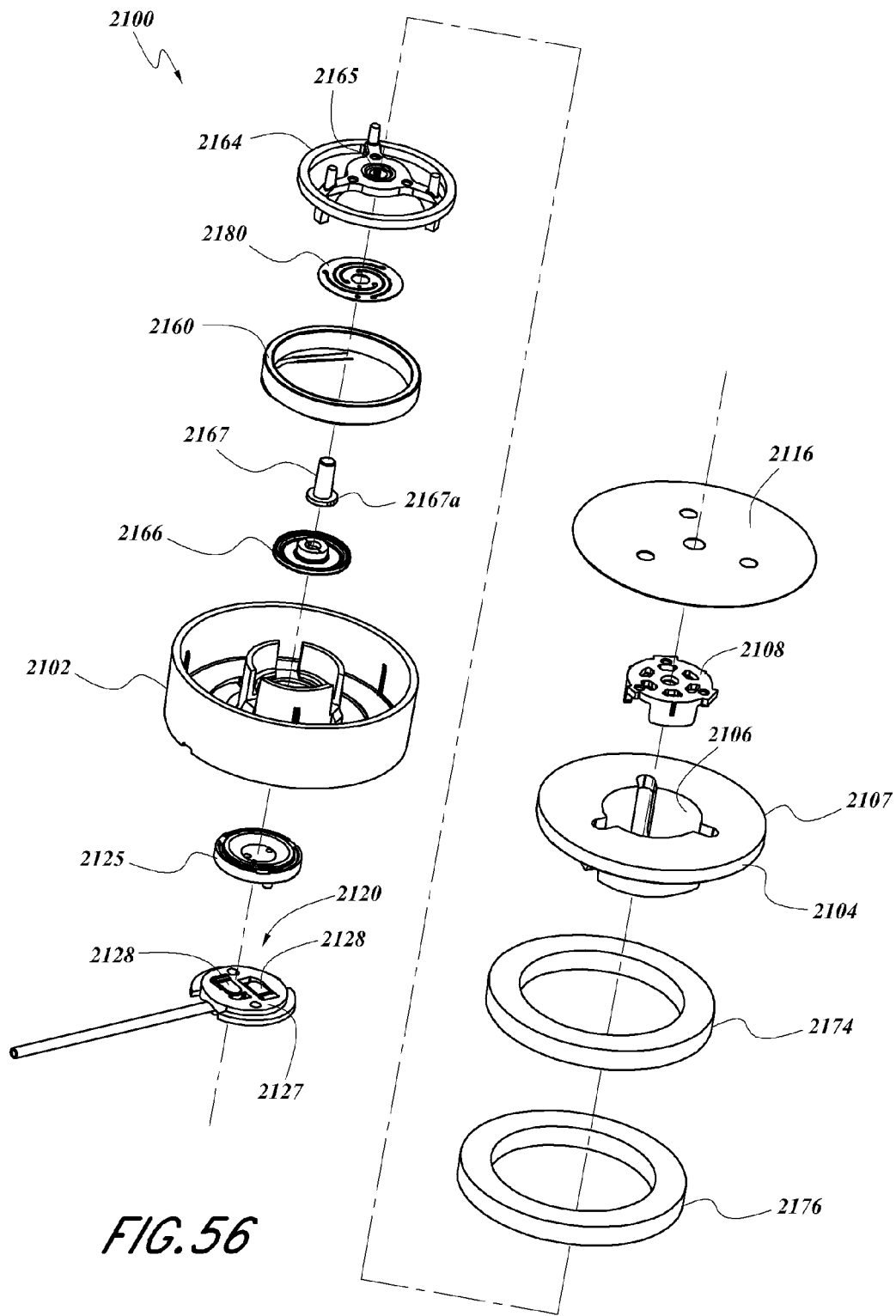
FIGS. 56 and 57 are exploded views of the pump assembly embodiment illustrated in FIG. 54, showing the top of the pump assembly and the bottom of the pump assembly, respectively.
Figure 57:
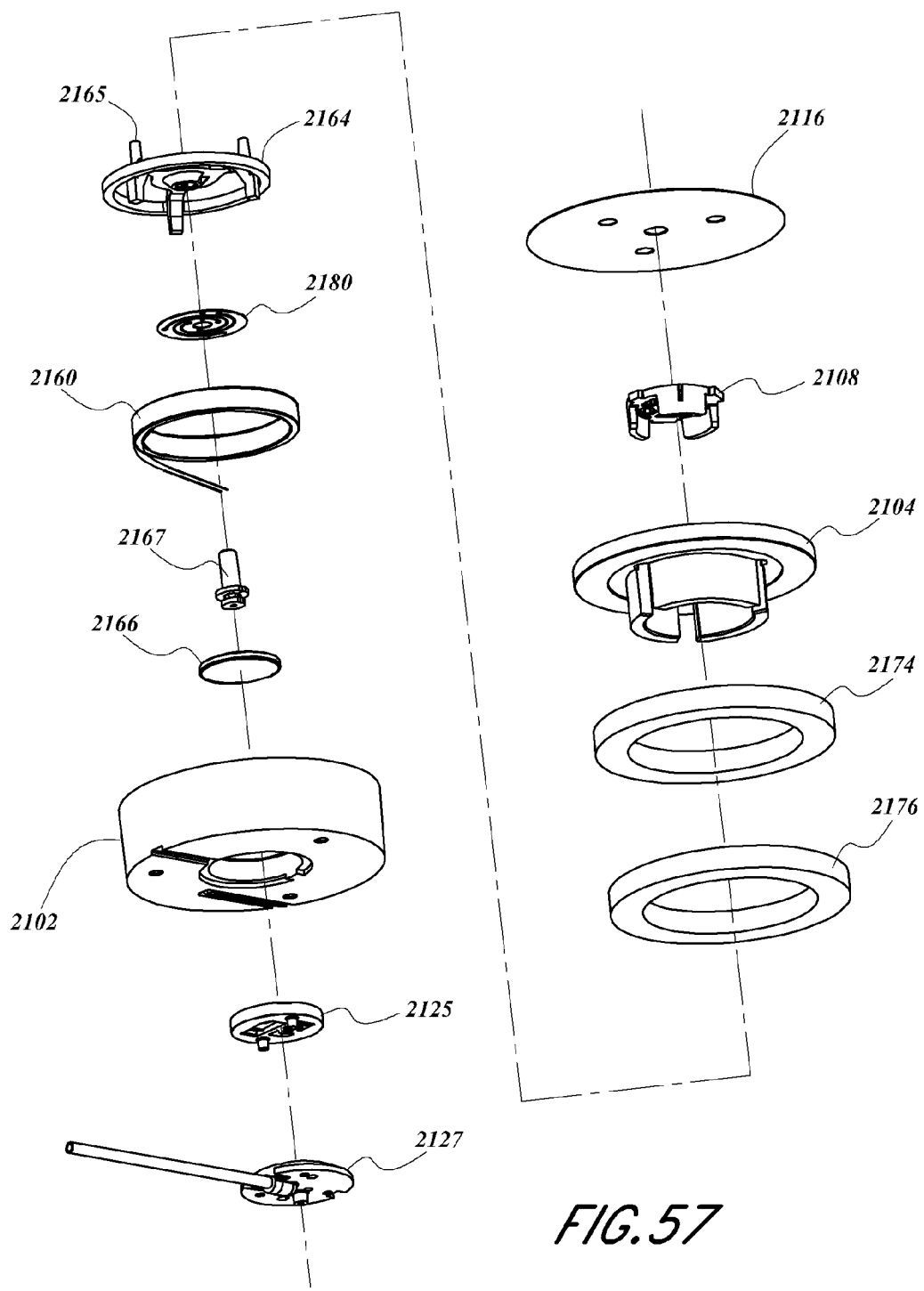

FIGS. 54 and 55 are isometric views of another embodiment of a pump assembly 2100, showing a top surface of the pump assembly and the bottom surface of the pump assembly, respectively. FIGS. 56 and 57 are exploded views of the pump assembly embodiment illustrated in FIG. 54, showing the top of the pump assembly and the bottom of the pump assembly, respectively. FIG. 58 is a section view of the pump assembly embodiment illustrated in FIG. 54, the section being taken through the center of the pump assembly embodiment. The pump assembly embodiment 2100 can have a compact, small size and can have any of the same features, sizes, components, materials, or other details of the pump assembly embodiment 210 described above, or any of the other pump assembly embodiments disclosed herein.

In any embodiments disclosed herein, the pump assembly 2100 can have a diameter or lateral size in the range of approximately 26-29 mm, or between approximately 25 and approximately 28 mm. In any embodiments disclosed herein, the pump assembly embodiment 2100 can have a thickness or height of approximately 8 mm, or between approximately 6 mm and approximately 10 mm.

The pump assembly embodiment 2100 can be produced for a low cost and can operate at high efficiencies, making it beneficial for portable, disposable, and/or single use applications. In any embodiments disclosed herein, the pump assembly embodiment 2100 can run for a week on a small primary cell such as a 1200 mAh battery without the need for battery replacement or recharging. This pump can be used in an ultra-portable single-use NPWT device, but is not so limited. In any embodiments disclosed herein, as mentioned, the pump assembly embodiment 2100 can be used for negative pressure wound therapy. However, the pump assembly embodiment 2100 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2100 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2100 can be adapted to operate at efficiency levels in excess of 25%.

The pump assembly embodiment 2100 can have a housing 2102 adapted to support and protect many of the components of the pump assembly embodiment 2100. An upper pole 2104, which can be made from any suitable materials such as mild steel or sintered steel, can be supported at one end (for example, a first end) 2102a of the housing 2102. In any embodiments disclosed herein, the upper pole 2104 can have an opening 2106 formed through an axial centerline of the upper pole 2104. A bearing 2108 can be supported by the upper pole 2104, within the opening 2106. In any embodiments disclosed herein, one or more channels can be formed in the housing for routing wires or conduit, or to create an air passageway.

A cover 2116 (also referred to herein as a first cover) can be positioned over an end portion of the housing 2102. The cover 2116 can be an adhesive backed foil, film, paper, plastic sheet or label, or other similar object. An opening 2117 can be formed in the cover 2116 to permit air, gas, or other fluid to be exhausted from the pump through the outlet manifold.

The valve assembly 2120 can have a first valve member 2125 and a second valve member 2127 that can also have a conduit connection thereon. The valve plate 2126 can support two flexible valve flaps 2128, a first valve flap 2128a for the inlet valve chamber and a second valve flap 2128b for the outlet valve chamber. The first flap 2128a and the second flap 2128b can be configured to deflect away from the relaxed position of the flaps 2128 shown to block passage of air through the valve assembly 2120 during operation of the pump, or possibly even during sterilization of the pump.

The first outlet valve chamber of the second valve member 2127 can have a cavity or depression and one or more openings configured to allow the passage or exit of air from the inside of the depression and the pump assembly embodiment 2100 when the valve flap 2128b is in an open position. In some embodiments, the valve assembly 2120 can have one, two, three, or more openings formed in either of the inlet and outlet valve chambers. The housing 2102 can have a similar arrangement of inlet and outlet valve chambers as compared to the first inlet and outlet valve chambers.

A second inlet valve chamber supported by the first valve member 2125 can have a cavity or depression and one or more openings in communication with the depression to permit the passage of air from the first inlet valve chamber into the second inlet valve chamber when the valve flap is in an open position (e.g., not sealingly covering the opening 2124). One or more openings can be formed in the second inlet valve chamber to permit air to pass from the second inlet valve chamber into the inside of the pump assembly embodiment 2100. In any of the pump embodiments disclosed herein, the inlet valve chamber and/or the outlet valve chamber, on either side of the flap valve, can have one, two, three, ore more openings configured to permit air to pass therethrough.

Similarly, a second outlet valve chamber can be supported by first valve member 2125. The second outlet valve chamber can have a depression formed therein and an opening in communication with the second outlet valve chamber. In any embodiments disclosed herein, similar to the boss 2131, the boss 2152 can have an angled or curved surface configured to substantially match the profile of the valve flap as the valve flap is deflected from the relaxed position against the surface of the boss. This arrangement can improve the seal between the valve flap and the boss or sealing surface to increase the efficiency of the pump assembly embodiment 2100. When the valve flap 2128b is in an open position, air or other fluid within the pump assembly embodiment 2100 can pass through the opening into the first outlet valve chamber and exit the pump assembly embodiment 2100 through the one or more openings.

The pump assembly embodiment 2100 can have a coil 2160 comprising electrical wires 2114, and a support member 2164. The support member 2164 can have legs 2165 extending through openings in the housing 2102. The coil 2160 can be formed from a length of wound conductive wire, such as without limitation copper wire. In operation, the coil 2160 can be configured to move within a magnetic circuit, and can be supported via a support member to a pump diaphragm assembly 2166.

The diaphragm 2166 can be supported and/or fixed along all or a portion of its outer periphery 2166a, wherein an interior portion 2166b of the diaphragm assembly 2166 is permitted to flex and deflect in either direction away from the relaxed position of the diaphragm assembly 2166. In any embodiments disclosed herein, the diaphragm can be clamped and compressed between two rigid surfaces to provide such support. The rigid surfaces can define an annular shape. For example, some embodiments of the diaphragm 2166 (or any other diaphragm disclosed herein) can have a moulding and a separate compression ring (made from a rigid plastic, aluminium or other metal, or any other suitable material or composite material). Additionally, some embodiments of the diaphragm 2166 (or any other diaphragm disclosed herein) can have one plastic or other frame or moulding on each side of the flexible diaphragm membrane. The diaphragm assembly 2166 is configured to elastically return the coil 160 to its relaxed position. Any of the pump embodiments disclosed herein (i.e., in this application) can be formed from cast or molded silicone, polyurethane, thermoplastic polyurethane, EPDM, and/or other suitable materials, having a hardness value of approximately 20A, 30A, 40A, 50A, 55A, or more.

Any embodiments disclosed herein can also have a flat spring member 2180 positioned adjacent to the diaphragm. In some embodiments, the spring member 2180 can be positioned against a flange portion 2167a of the base portion 2167 of the diaphragm assembly 2166. In some embodiments, the spring member 2180 can be positioned at a top portion 2167b of the base portion 2167 of the diaphragm assembly 2166, or can be positioned in any desired locations. In some embodiments, the spring member 2180 can be sized and configured to provide frequency tuning or adjustment to the resonance frequency of the diaphragm and/or the components of the oscillating coil assembly. In some embodiments, the spring member 2180 can be configured to maintain the axial alignment of the diaphragm assembly 2166 with the remainder of the pump assembly, or both to maintain alignment and to provide resonance frequency adjustment. The spring member 2180 can be made from stainless steel, spring steel, or any other suitable material.

The pump assembly embodiment 2100 can have a magnet 2174 positioned between a lower pole 2176 and the upper pole 2104, any of which components can be made from any of the materials disclosed herein.

FIGS. 59 and 60 are a top view and a section view of another embodiment of a pump assembly 2200. FIG. 61 is an exploded view of the pump assembly embodiment illustrated in FIG. 59. The pump assembly embodiment 2200 can have a compact, small size and can have any of the same features, sizes, components, materials, or other details of the pump assembly embodiment 2100 described above, or any of the other pump assembly embodiments disclosed herein.

Additionally, with reference to FIGS. 60 and 61, the pump assembly embodiment 2200 can have two flat springs 2280 and 2281 supported by the housing along the length of the shaft 2267 for the diaphragm 2266. A first flat spring 2280 can be positioned at a base of the shaft 2267 and can be configured to provide alignment (via radial support or otherwise) and resonance frequency adjustment for the diaphragm shaft 2267 and the diaphragm 2266. A second spring member 2281 can be positioned closer to a distal end of the shaft 2267 and can be configured to provide radial support to the diaphragm shaft 2267.

Figure 62:
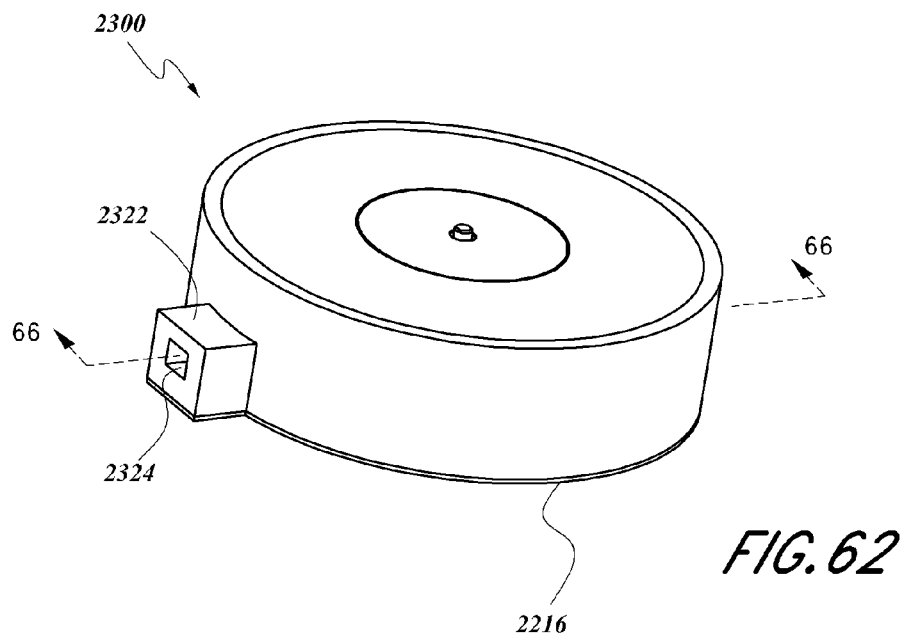
FIGS. 62 and 63 are isometric views, showing the top and the bottom sides of another embodiment of a pump assembly.
Figure 63:
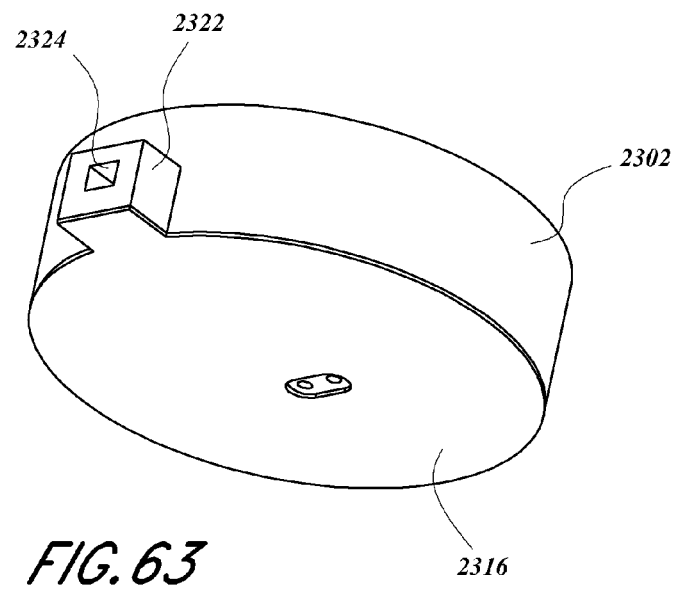
Figure 64:
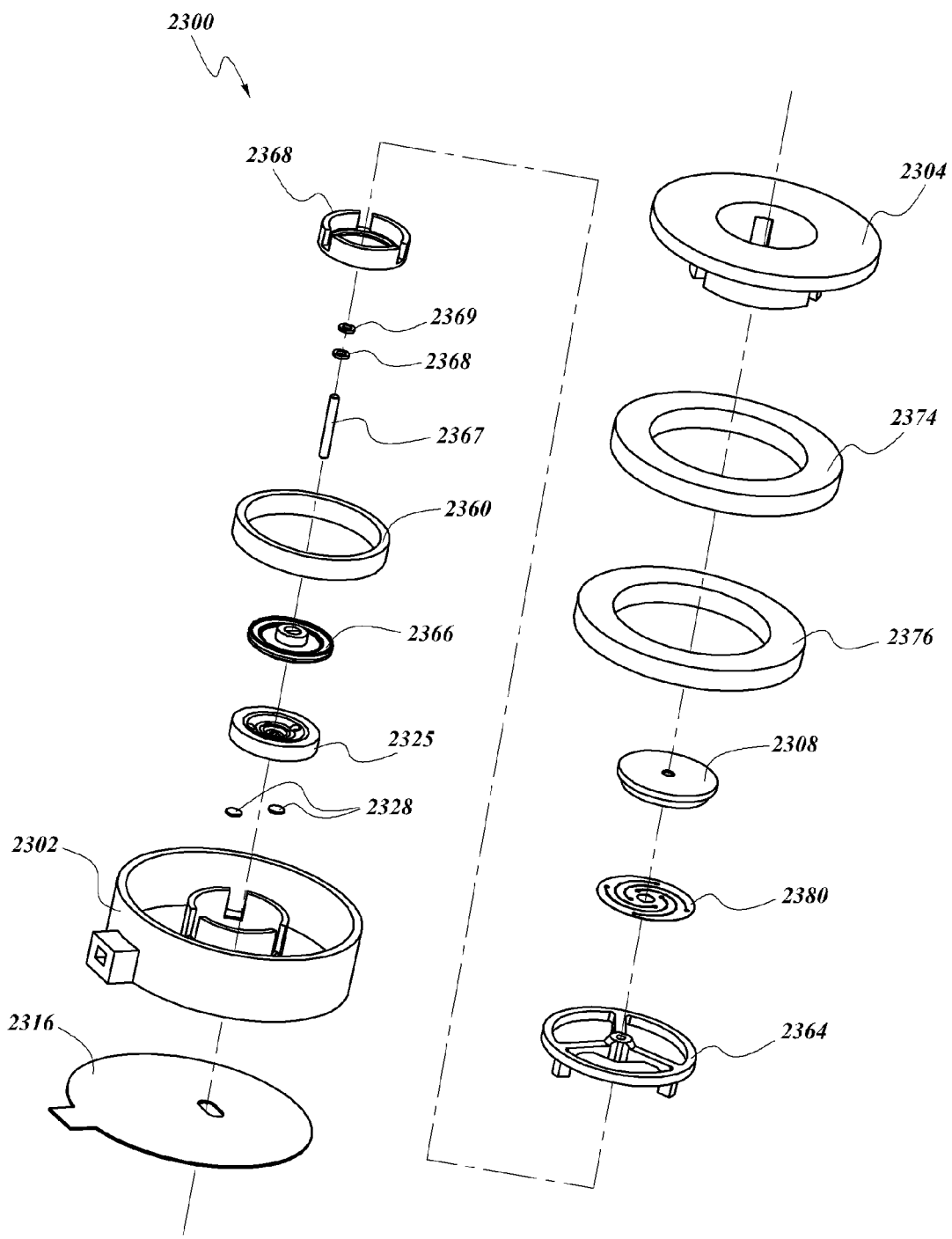
FIGS. 64 and 65 are exploded views of the pump assembly embodiment illustrated in FIG. 62.
Figure 65:
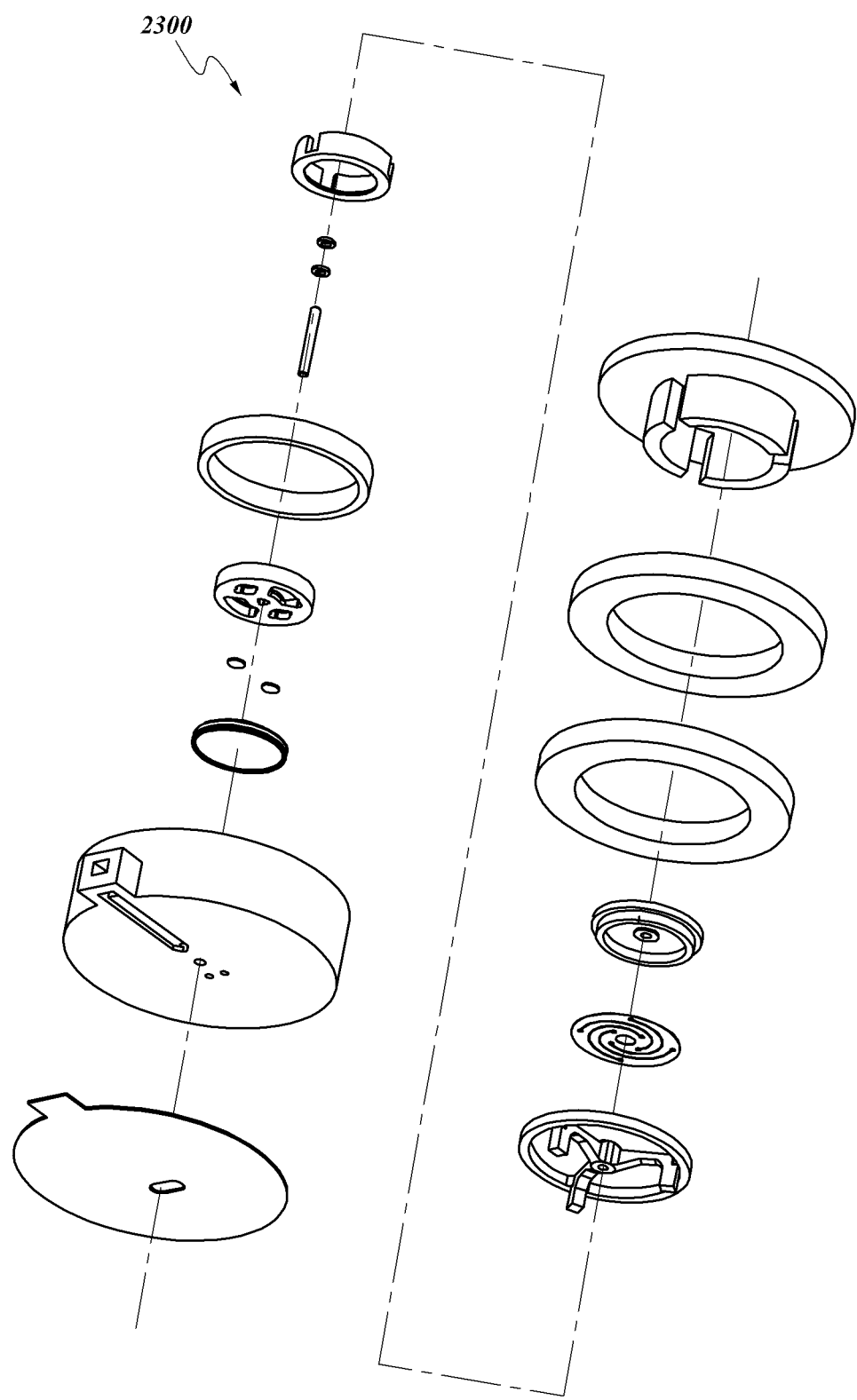
Figure 66:
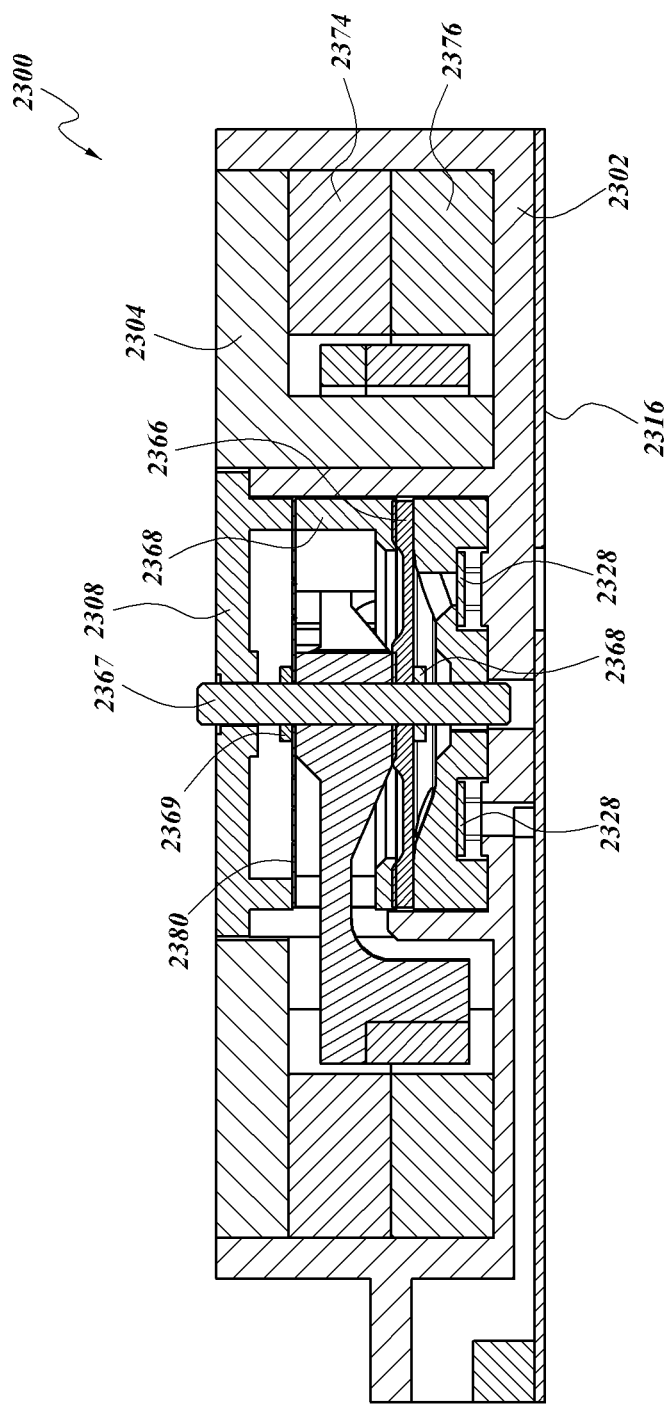
FIG. 66 is a section view of the pump assembly embodiment illustrated in FIG. 62.

FIGS. 62 and 63 are isometric views, showing the top and the bottom sides of another embodiment of a pump assembly 2300. FIGS. 64 and 65 are exploded views of the pump assembly embodiment illustrated in FIG. 62, and FIG. 66 is a section view. The pump assembly embodiment 2300 can have a compact, small size and can have any of the same features, sizes, components, materials, or other details of the pump assembly embodiment 2100 and/or 2200 described above, or any of the other pump assembly embodiments disclosed herein.

Additionally, the pump assembly embodiment 2300 can have a flat spring 2380 positioned above the support member 2364 for alignment of the diaphragm member 2366 and the shaft 2367 that is coupled with the diaphragm member 2366 using one or more rings 2368 and 2369.

Additionally, in any embodiments herein, the valve flaps 2328 can have a round, disc-like shape and can be supported within the first valve member 2325 between the housing 2302 and the first valve member 2325. A bushing 2368 can be positioned between the diaphragm 2366 and the upper busing 2308. The bushing 2368 can be configured to support a perimeter of the diaphragm 2366 against a perimeter of the first valve plate 2325 within the housing 2302.

Figure 67:
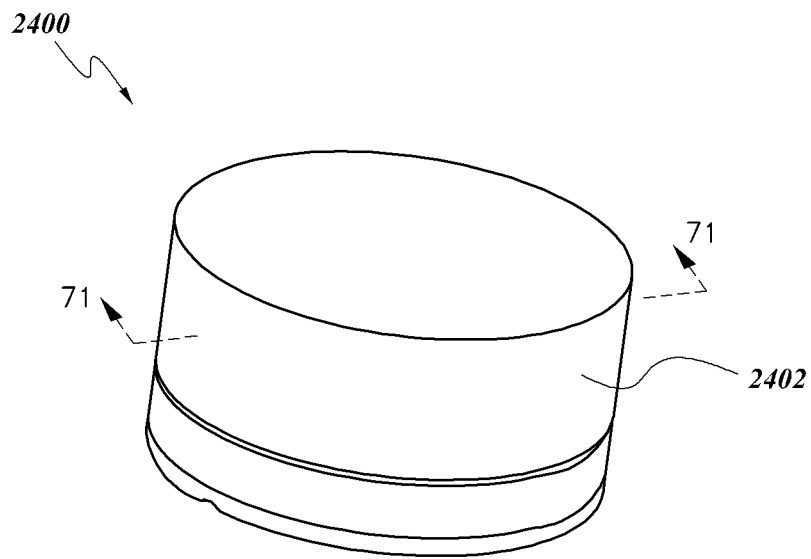
FIGS. 67 and 68 are isometric views of another embodiment of a pump assembly, showing a top surface of the pump assembly and the bottom surface of the pump assembly, respectively.
Figure 68:
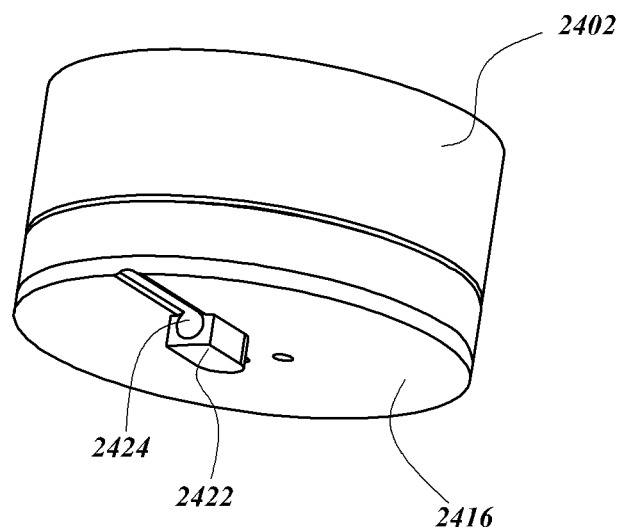
Figure 69:
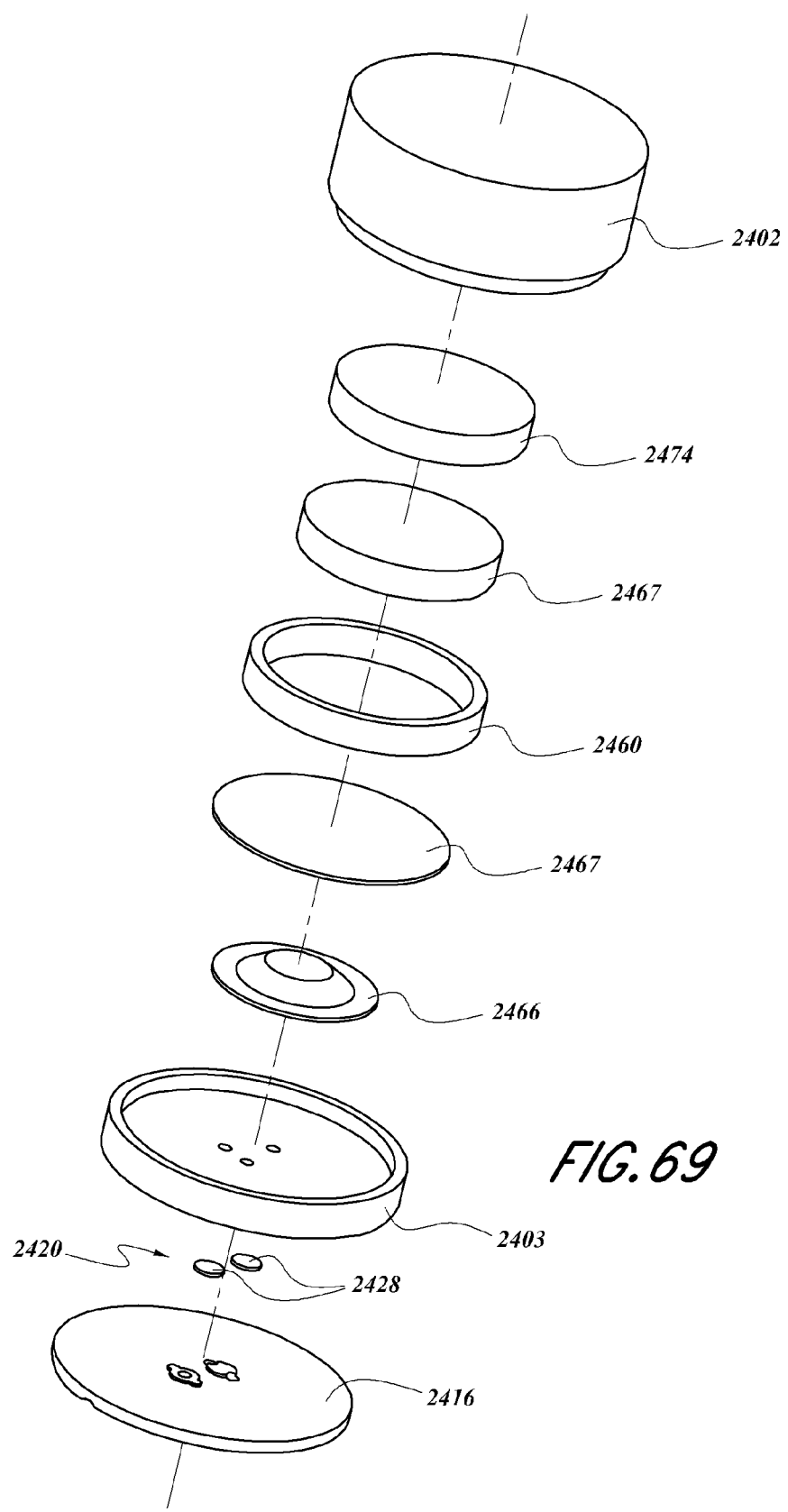
FIGS. 69 and 70 are exploded views of the pump assembly embodiment illustrated in FIG. 67, showing the top of the pump assembly and the bottom of the pump assembly, respectively.
Figure 70:
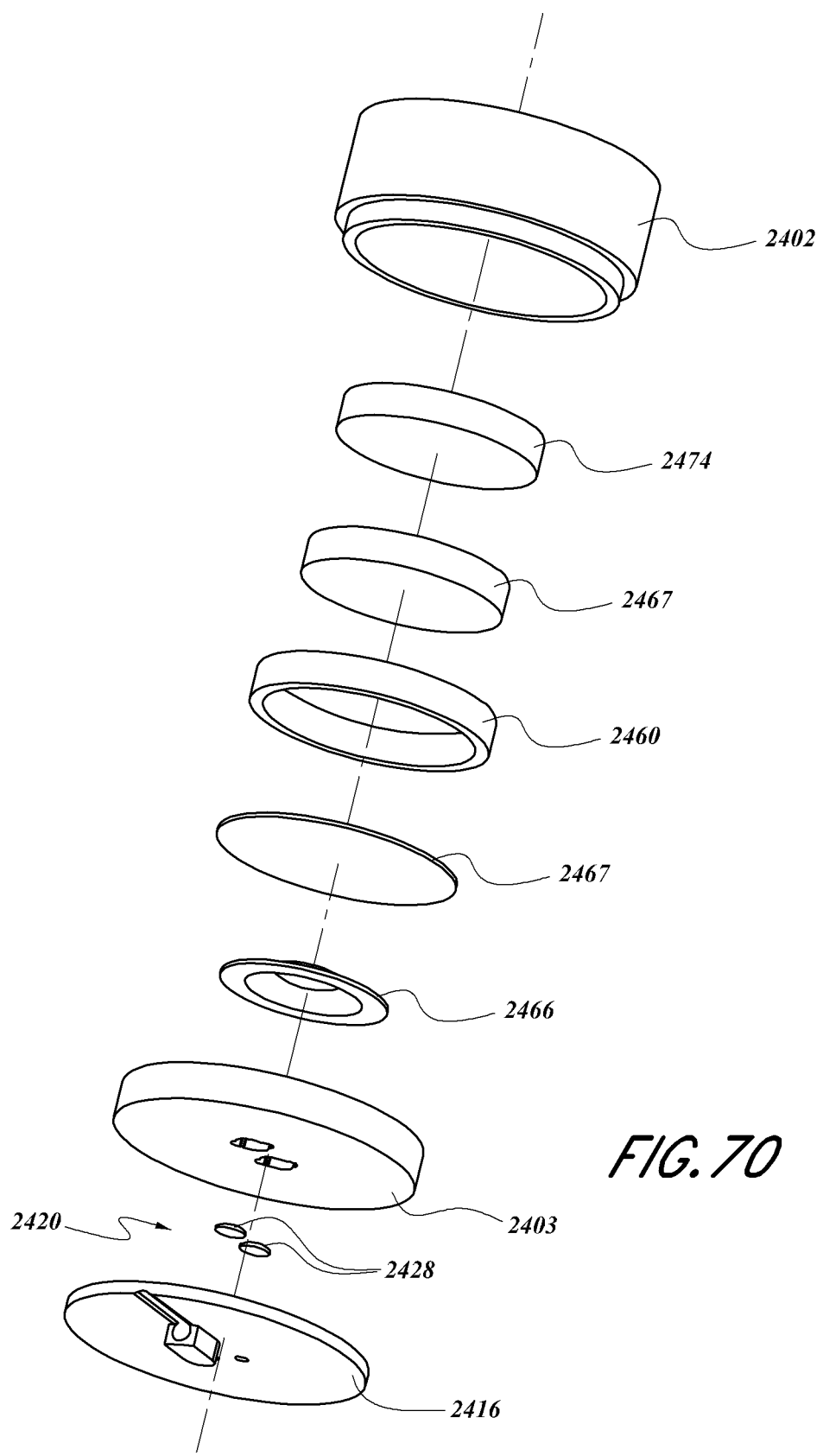
Figure 71:
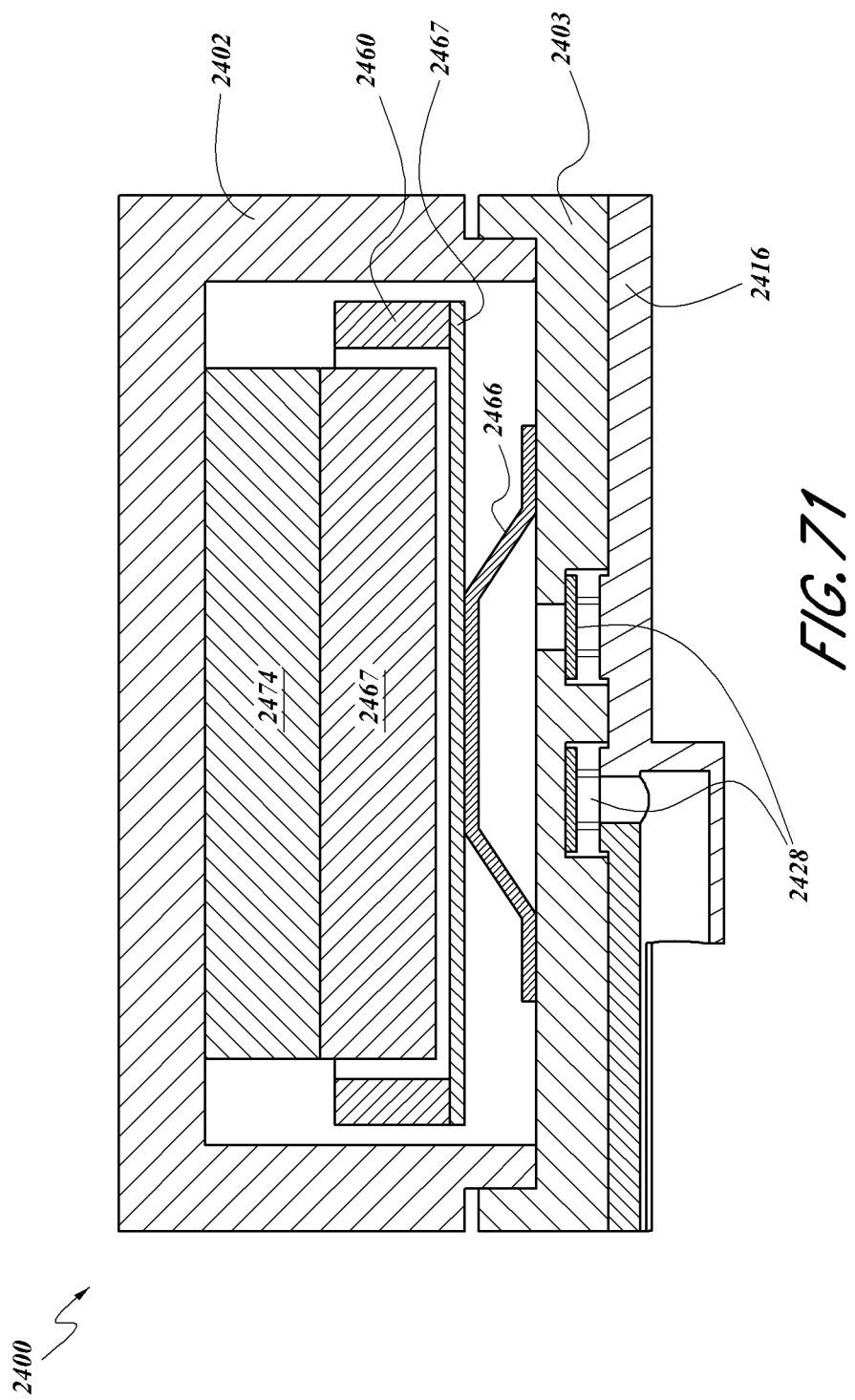
FIG. 71 is a section view of the pump assembly embodiment illustrated in FIG. 67, the section being taken through the center of the pump assembly embodiment.
Figure 72:
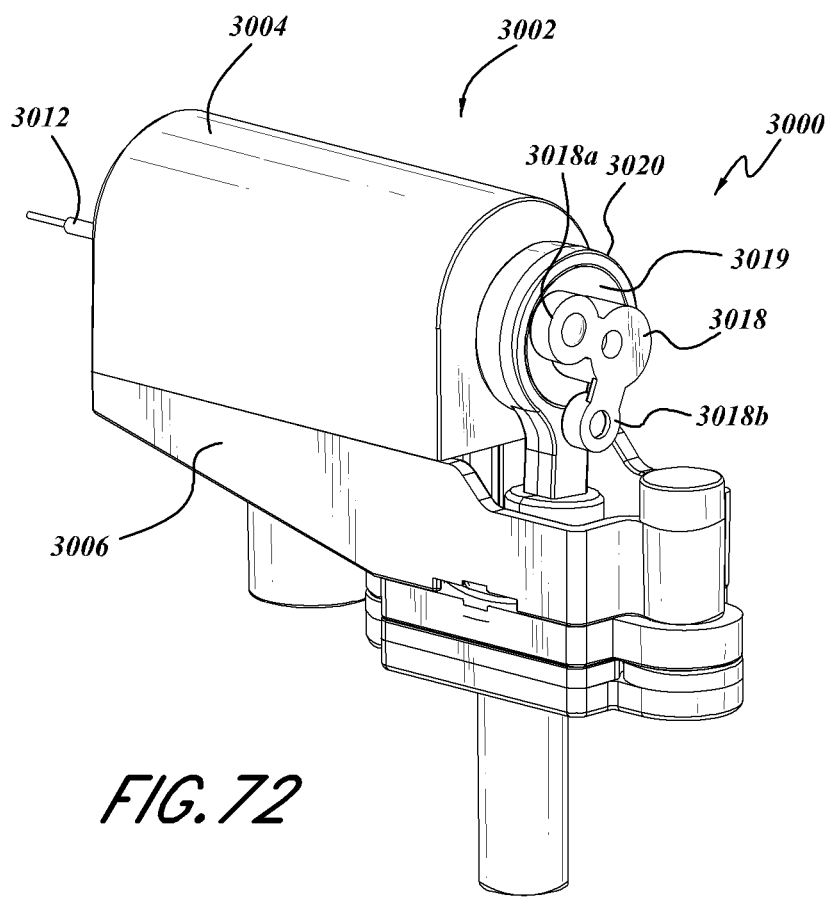
FIG. 72 is an isometric view of another embodiment of a pump assembly that can be used to provide reduced pressure to a wound dressing.
Figure 73:
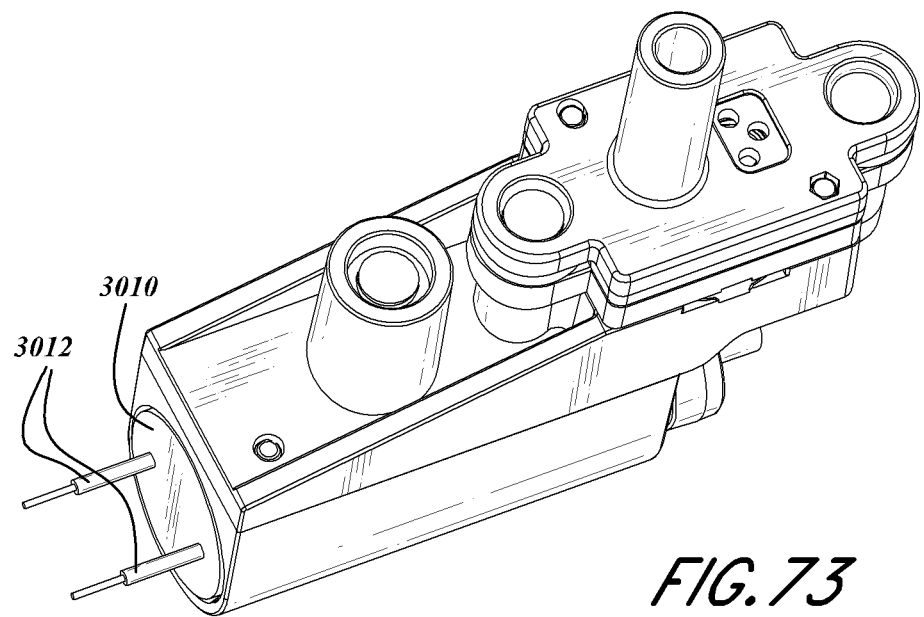
FIG. 73 is another isometric view of the embodiment of the pump assembly shown in FIG. 72.
Figure 74:
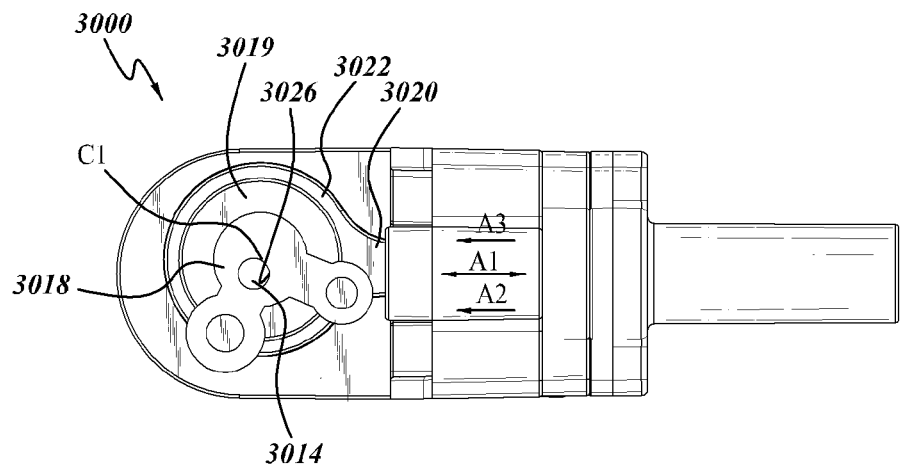
FIG. 74 is a front view of the embodiment of the pump assembly shown in FIG. 72.
Figure 75:
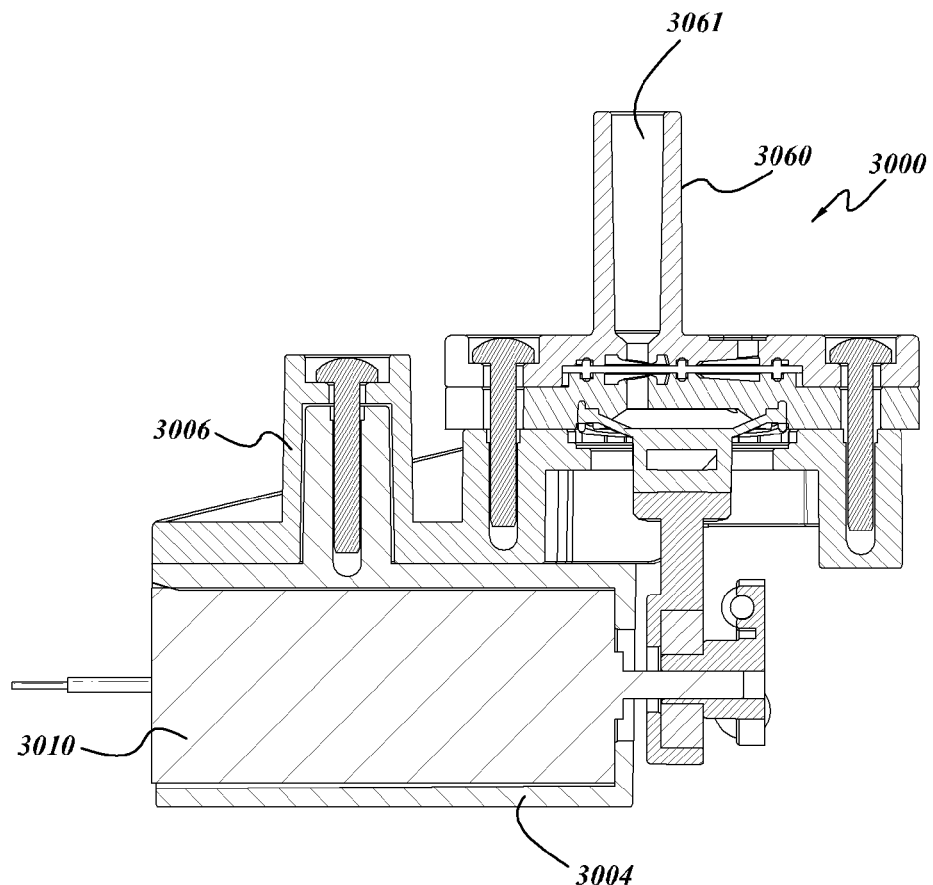
FIG. 75 is a sectional view of the embodiment of the pump assembly the pump assembly shown in FIG. 72.
Figure 76:
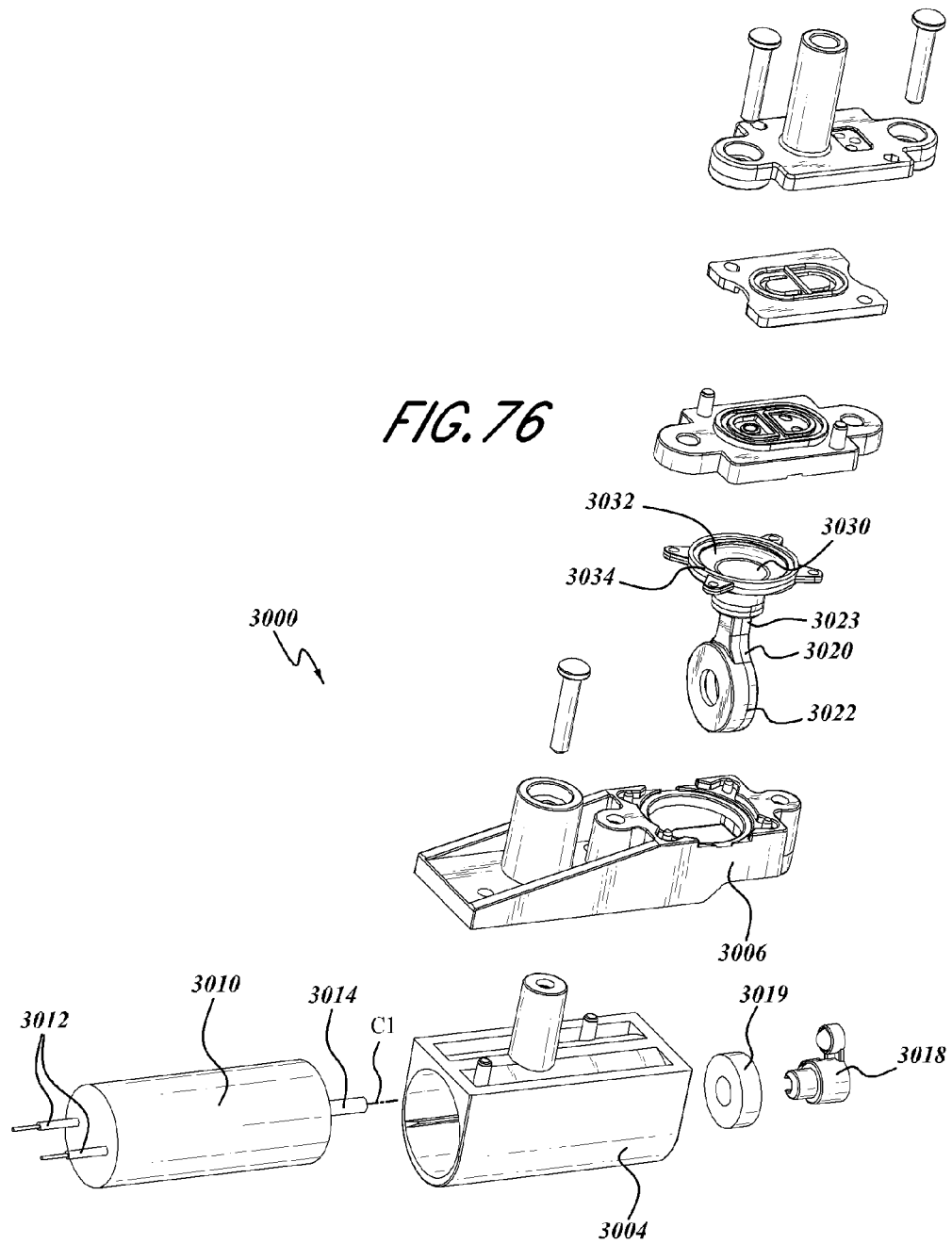
FIG. 76 is an exploded assembly view of the embodiment of the pump assembly shown in FIG. 72.

FIGS. 67 and 68 are isometric views of another embodiment of a pump assembly 2400, showing a top surface of the pump assembly and the bottom surface of the pump assembly, respectively. FIGS. 69 and 70 are exploded views of the pump assembly embodiment illustrated in FIG. 67, showing the top of the pump assembly and the bottom of the pump assembly, respectively. FIG. 71 is a section view of the pump assembly embodiment illustrated in FIG. 67, the section being taken through the center of the pump assembly embodiment. The pump assembly embodiment 2400 can have a compact, small size and can have any of the same features, sizes, components, materials, or other details of the pump assembly embodiment 240 described above, or any of the other pump assembly embodiments disclosed herein.

In any embodiments disclosed herein, the pump assembly 2400 can have a diameter or lateral size in the range of approximately 26-29 mm, or between approximately 25 and approximately 28 mm. In any embodiments disclosed herein, the pump assembly embodiment 2400 can have a thickness or height of approximately 15 mm, or between approximately 10 mm and approximately 18 mm.

The pump assembly embodiment 2400 can be produced for a low cost and can operate at high efficiencies, making it beneficial for portable, disposable, and/or single use applications. In any embodiments disclosed herein, the pump assembly embodiment 2400 can run for a week on a small primary cell such as a 1200 mAh battery without the need for battery replacement or recharging. This pump can be used in an ultra-portable single-use NPWT device, but is not so limited. In any embodiments disclosed herein, as mentioned, the pump assembly embodiment 2400 can be used for negative pressure wound therapy. However, the pump assembly embodiment 2400 is not limited to use in negative pressure wound therapy systems. The pump assembly embodiment can be adapted and configured for use in any reduced pressure system or in any system or application in which the movement of gaseous and liquid fluids is desired.

The pump assembly embodiment 2400 can be designed to work at pressures of 60-80 mm Hg or more, and can be configured to produce a flow rate of approximately 200 ml min-1, with a minimum efficiency of 15%, in order for the NPWT device to run for a week on a specified battery capacity. In any embodiments disclosed herein, the pump assembly embodiment 2400 can be adapted to operate at efficiency levels in excess of 25%.

The pump assembly embodiment 2400 can have a housing 2402 adapted to support and protect many of the components of the pump assembly embodiment 2400. An upper pole (which can be the upper casing for the housing), which can be made from any suitable materials such as mild steel or sintered steel. A cover 2416 (also referred to herein as a first cover) can be positioned over an end portion of the housing 2402. The cover 2416 can be an adhesive backed foil, film, paper, plastic sheet or label, or other similar object. An opening can be formed in the cover in communication with a port member 2422 having an opening 2424 therein to permit air, gas, or other fluid to be exhausted from the pump through the outlet manifold.

The valve assembly 2420 can have a first valve member or plate that can be formed into a bottom portion 2403 of the housing 2402. The pump can have two round or disc shaped valve flaps 2428, a first valve flap 2428 for the inlet valve chamber and a second valve flap 2428 for the outlet valve chamber. The first flap 2428 and the second flap 2428 can be configured to translate away from the openings in the valve plates to block passage of air through the valve assembly 2420 during operation of the pump, or possibly even during sterilization of the pump.

The diaphragm 2466 can be supported and/or fixed along all or a portion of its outer periphery 2466a, wherein an interior portion 2466b of the diaphragm assembly 2466 is permitted to flex and deflect in either direction away from the relaxed position of the diaphragm assembly 2466. In some embodiments, the diaphragm can simply rest against the planar surface of the housing portion 2466. In any embodiments disclosed herein, the diaphragm can be clamped and compressed between two rigid surfaces to provide such support.

The pump assembly embodiment 2400 can have a magnet 2474 positioned between a lower pole 2476 and the upper pole 2404, any of which components can be made from any of the materials disclosed herein. In use, for any of the embodiments disclosed herein, as the voltage supplied to the coil oscillates between a positive voltage and a negative voltage, the coil can oscillate up and down in the pump between the two poles 2004 and 2076. The coil can be in contact with plate 2467, which can in turn contact the diaphragm, so that the diaphragm can cyclically compress and extend as the coil oscillates.

Thus, the oscillation of the diaphragm 2066 can cause the volume within the pump to increase or decrease and, hence, cause the pressure within the pump to decrease or increase. A pressure decrease within the pump chamber can draw air into the pump chamber and open the inlet manifold (or flap), while the flap on the outlet manifold can seal the outlet manifold closed. Then, as the diaphragm 2466 returns toward the valve support, the volume of airspace decreases, causing the air pressure to increase. This forces air out of the chamber through the outlet valve, while the inlet valve is sealed closed.

In any embodiments disclosed herein, as in any of the illustrated embodiments, the pump assembly can be of a sufficiently small and portable size to be supported on a user's body or in a user's clothing. For example, any of the pump assemblies disclosed herein can be sized to be attached using adhesive medical tape or otherwise to a person's skin or to a dressing in a comfortable location, adjacent to or on the dressing or otherwise. Further, any of the pump assembly embodiments disclosed herein can be sized to fit within a person's pants or shirt pocket, or can be tethered to a person's body using a lanyard, pouch, or other suitable device or article.

FIGS. 72-78 are isometric, front, sectional, and exploded views of another embodiment of a pump assembly 3000 that can be used to provide reduced pressure to a wound dressing. The pump assembly 3000 can be referred to as a crank pump assembly. In any embodiments disclosed herein, the pump assembly can have a housing 3002 to support the pump components. The housing can have a first housing portion 3004 couplable with a second housing portion 3006. The first housing portion 3006 can support an electric motor 3010 having electrical wires 3012 for connection to a power source, the control board, or otherwise. The motor shaft 3014 can projects from the motor along the axial centerline of the motor 3010. Any suitable control board, including any control board of any of the other pump embodiments disclosed herein, can be used to control the operation of the pump motor. Additionally, any embodiments of the pump assembly 3000 can be configured to have any of the components, features, power sources, sizes, materials, or other details of any of the other pump embodiments disclosed herein.

In any embodiments disclosed herein, the pump 3000 can have a mass of approximately 5 grams, and an efficiency of approximately 12%. As mentioned above, efficiency can be defined as (fluid power out)/(electrical power in). The pump motor 3010 can be a DC electric motor, having a diameter of 6 mm, 7 mm, 8 mm, or 10 mm, or any suitable size. In any embodiments disclosed herein, the motor can be a DC electric micro-motor such as any of the following manufactured by Precision Microdrives: PMD 107-001, PMD 108-105, or PMD 110-002.

In any embodiments disclosed herein, the end of the motor shaft 3014 can be coupled with a shaft connector 3018. A bushing or bearing 3019 can be supported on the connector 3018. The bushing 3019 can be used to couple the connector 3018 with a pump shaft 3020. In particular, the bushing 3019 can be received within a recess formed within a first portion 3022 of the pump shaft 3020.

To enable the reciprocating motion for the pump shaft 3020, the shaft connector 3018 can have an opening 3026 that is configured to receive the shaft 3014 therein. The opening 3026 can be positioned eccentrically relative to the axial centerline C1 of the motor shaft 3014. In this configuration, with the connector 3018 having the eccentric opening 3026, the bushing 3019 and the head portion 3022 of the pump shaft will be eccentrically positioned relative to the motor shaft 3014 such that, as the motor shaft 3014 rotates the connector 3018 and the bushing 3019, the pump shaft 3020 will experience reciprocating motion in an axial direction (represented by arrow A1 in FIG. 74).

Some embodiments of the pump assembly 3000 can be configured such that the pump shaft 3020 reciprocates (i.e., travels) approximately 0.6 mm in either direction. In any embodiments disclosed herein, the pump assembly 3000 can be configured such that the pump shaft 3020 reciprocates approximately 1.0 mm in either direction, or approximately 1.4 mm in either direction, or within a range between 0.6 mm and 1.4 mm or to or from any values within this range.

In any embodiments disclosed herein, the connector 3018 can support one or more weights at an eccentric position to balance the pump and/or offset and attenuate vibration produced by the eccentrically supported pump shaft 3020. For example, the connector 3018 can have a first tab 3018a and/or a second tab 3018b used to support weights thereby. The weights can be formed from steel or any other suitable material suitable for reducing the vibration produced by the pop during operation. In the illustrated embodiment, the weights are spherically shaped, such a small steel BBs or shot.

In any embodiments disclosed herein, the pump assembly 3000 can have a flexible diaphragm 3030 supported within the housing 3002. With reference to the illustrated embodiment, the diaphragm 3030 can be coupled with a second end portion 3023 of the pump shaft 3020. In this configuration, as the pump shaft 3020 reciprocates in the axial direction, the movement of the pump shaft 3020 will cause corresponding and simultaneous displacement or deflection of the flexible diaphragm 3030. The displacement of the diaphragm 3030 within the sealed space 3032 defined by the diaphragm 3030, the gasket seal or ring 3034, and the first valve plate 3035 (also referred to herein as a valve nozzle or first valve nozzle) will cause the pressure within such sealed space 3032 (that is to say, with the exception of the ports and valves that will be discussed in greater detail below) to cyclically increase and decrease in response to the position of the diaphragm. For example, as one of ordinary skill in the art would understand, moving the shaft 3020 and hence diaphragm 3030 in a first direction (defined by arrow A2 in FIG. 74) will compress the air within the space 3032 to increase the pressure within such space 3032. Similarly, moving the shaft 3020 and hence diaphragm 3030 in a second direction (defined by arrow A3 in FIG. 74) will increase the volume and temporally decrease the pressure within the space 3032.

In any embodiments disclosed herein, the valve and valve plate arrangement of the pump embodiment 3000 illustrated in FIGS. 72-78 can have any of the same features, components, or other details of any other pump embodiments disclosed herein. In any embodiments disclosed herein, the valve assembly 3033 can have a first valve plate 3035 that can have a first side 3035a and a second side 3035b, and a plurality of openings or apertures therethrough. For example, in the illustrated embodiment, an first inflow opening 3042 (also referred to as a first inflow opening) can be used to permit the passage of air into the space 3032. Two or more openings 3044 (which can be outflow or exhaust openings) can be used to permit the flow of air out of the space 3032.

Figure 77:
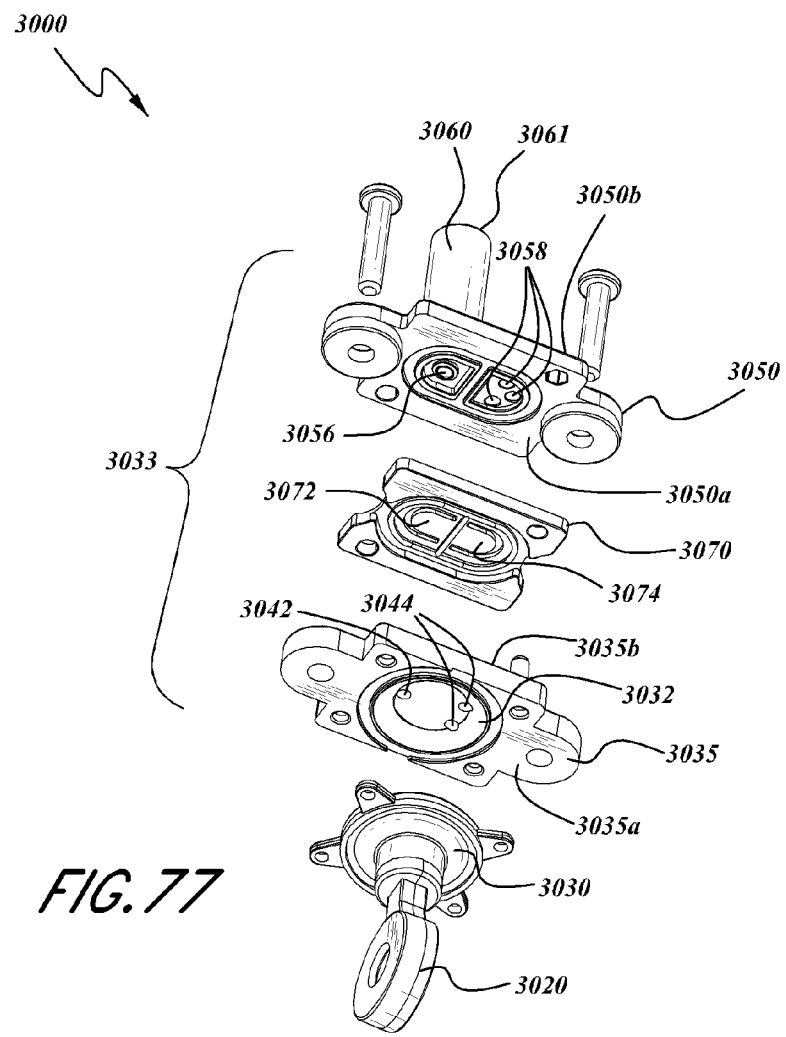
FIG. 77 is an enlarged exploded view of the embodiment of the pump assembly shown in FIG. 72.
Figure 78:
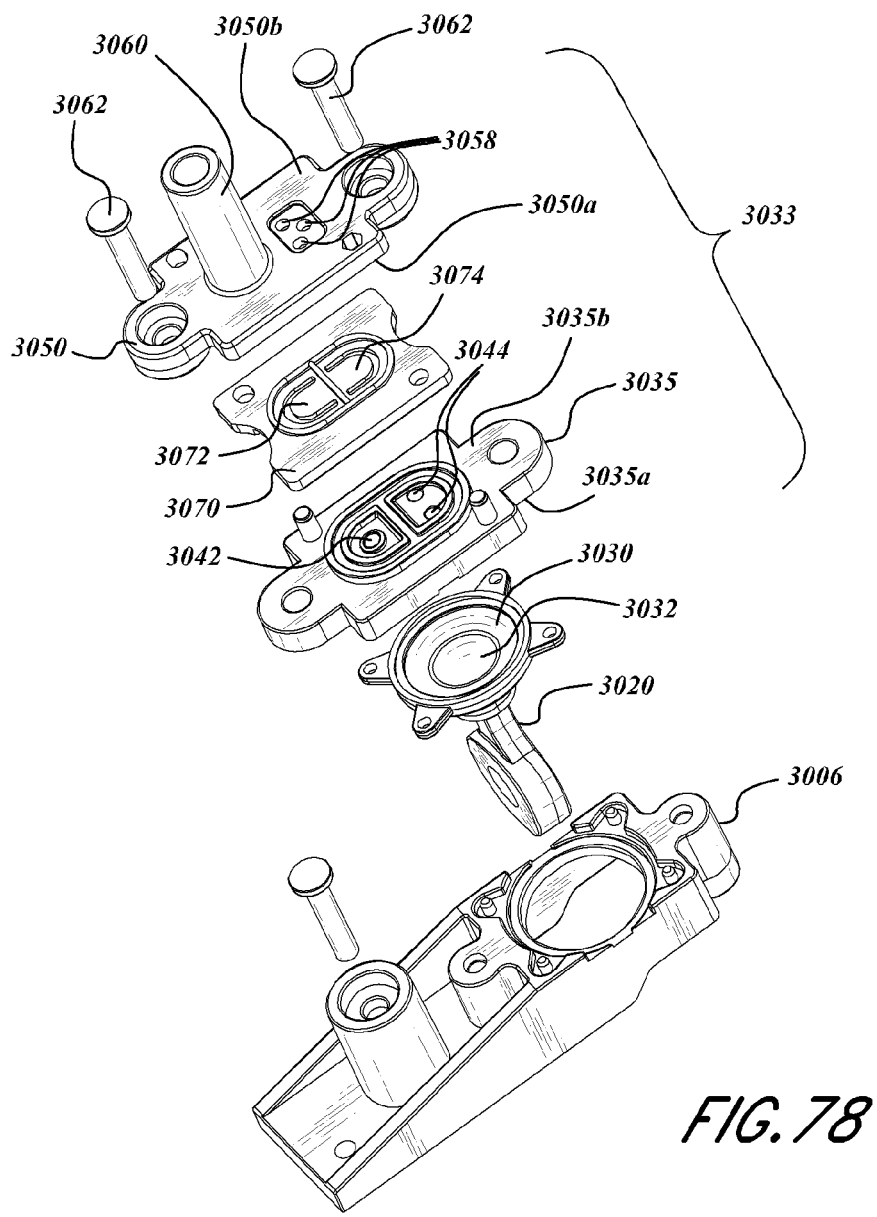
FIG. 78 is an enlarged exploded view of the embodiment of the pump assembly shown in FIG. 72.
Figure 80:
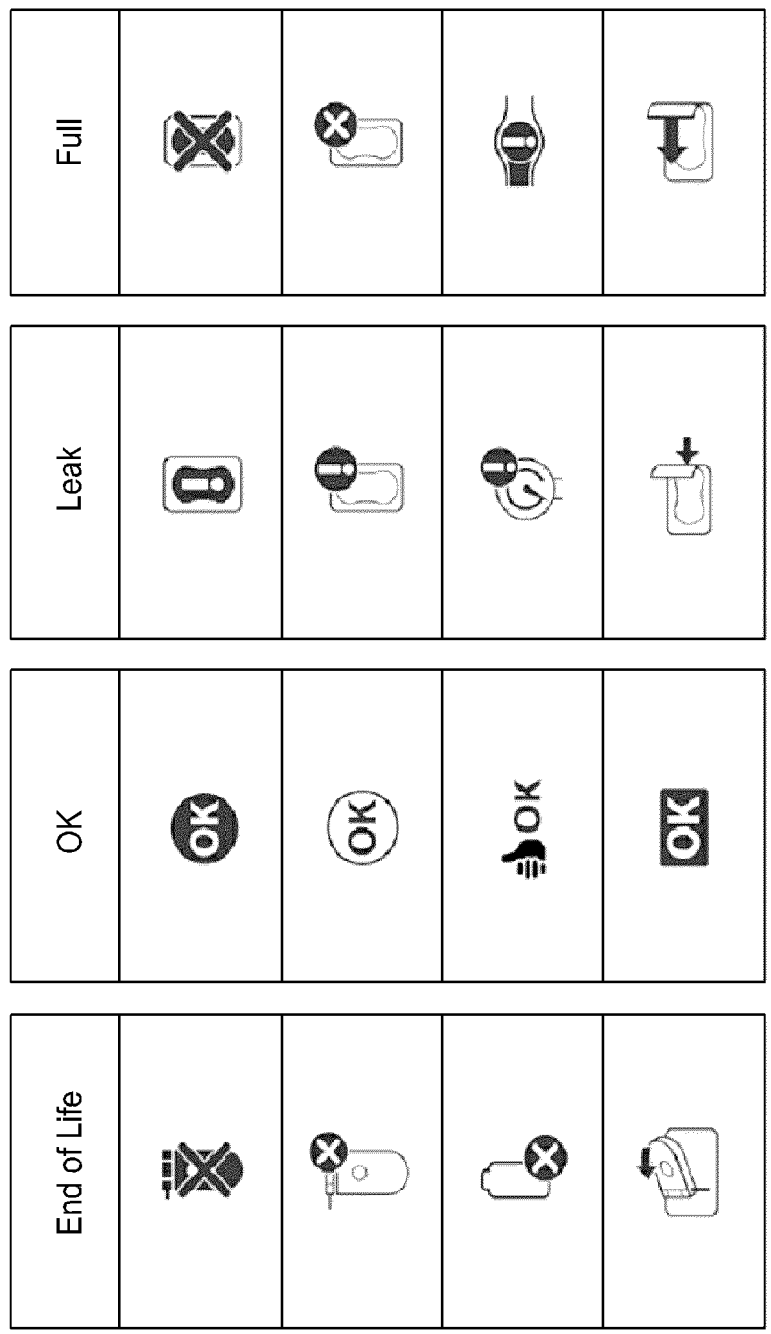
Figure 81:
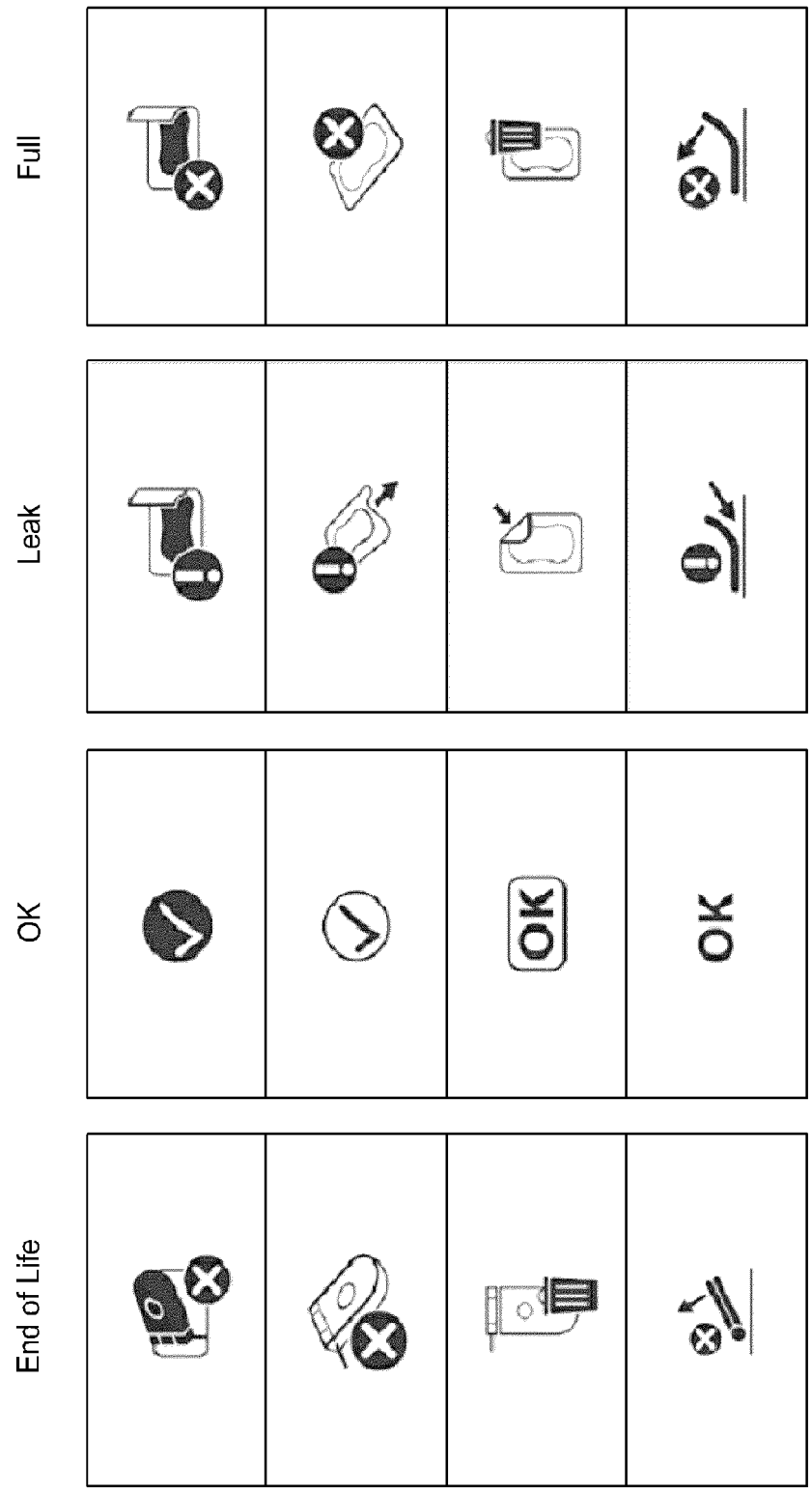
Figure 82:
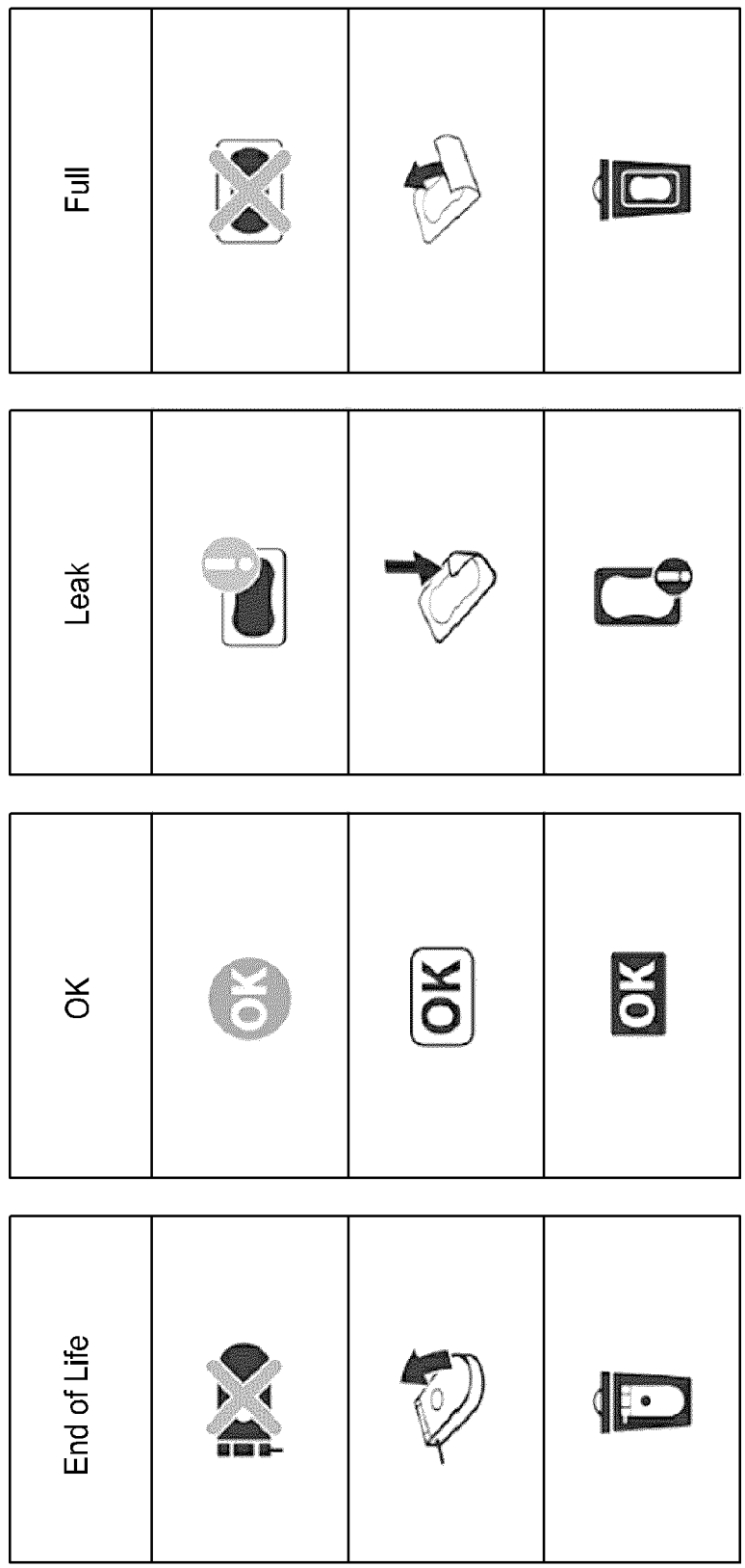
Figure 83:
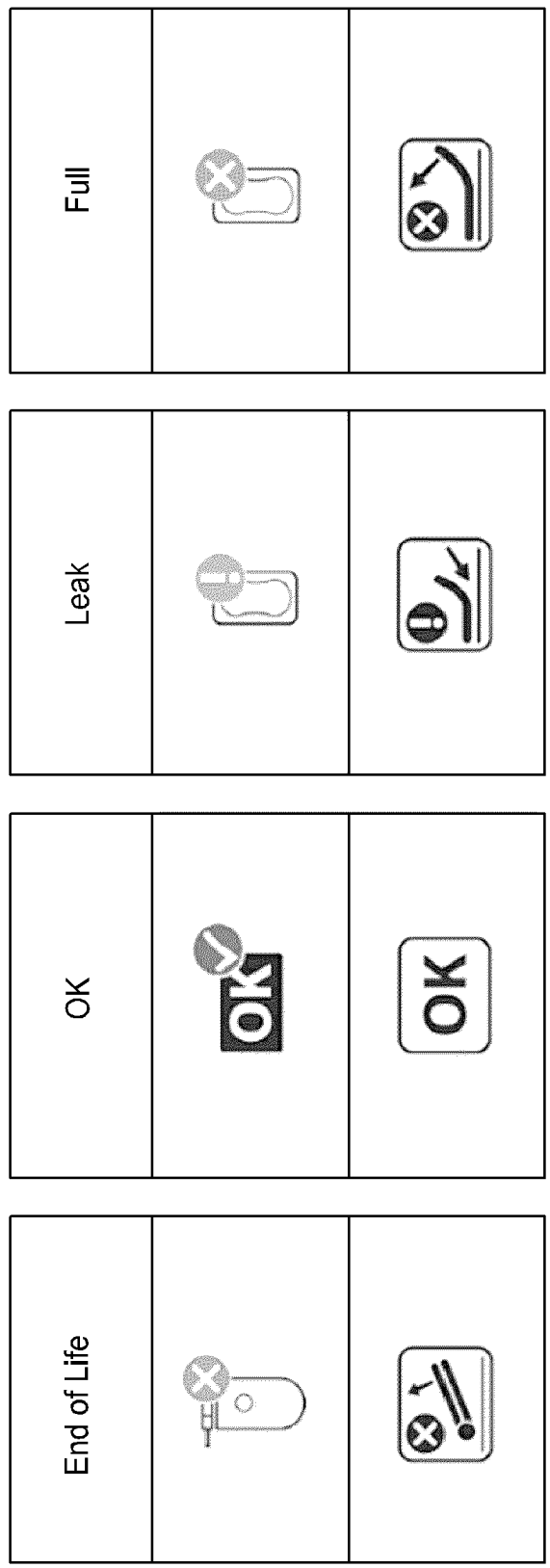
Figure 89:
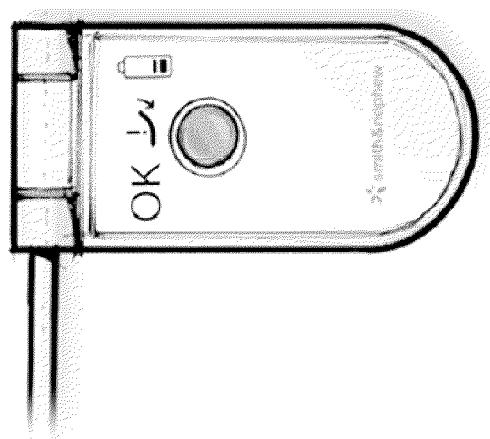
Figure 90:
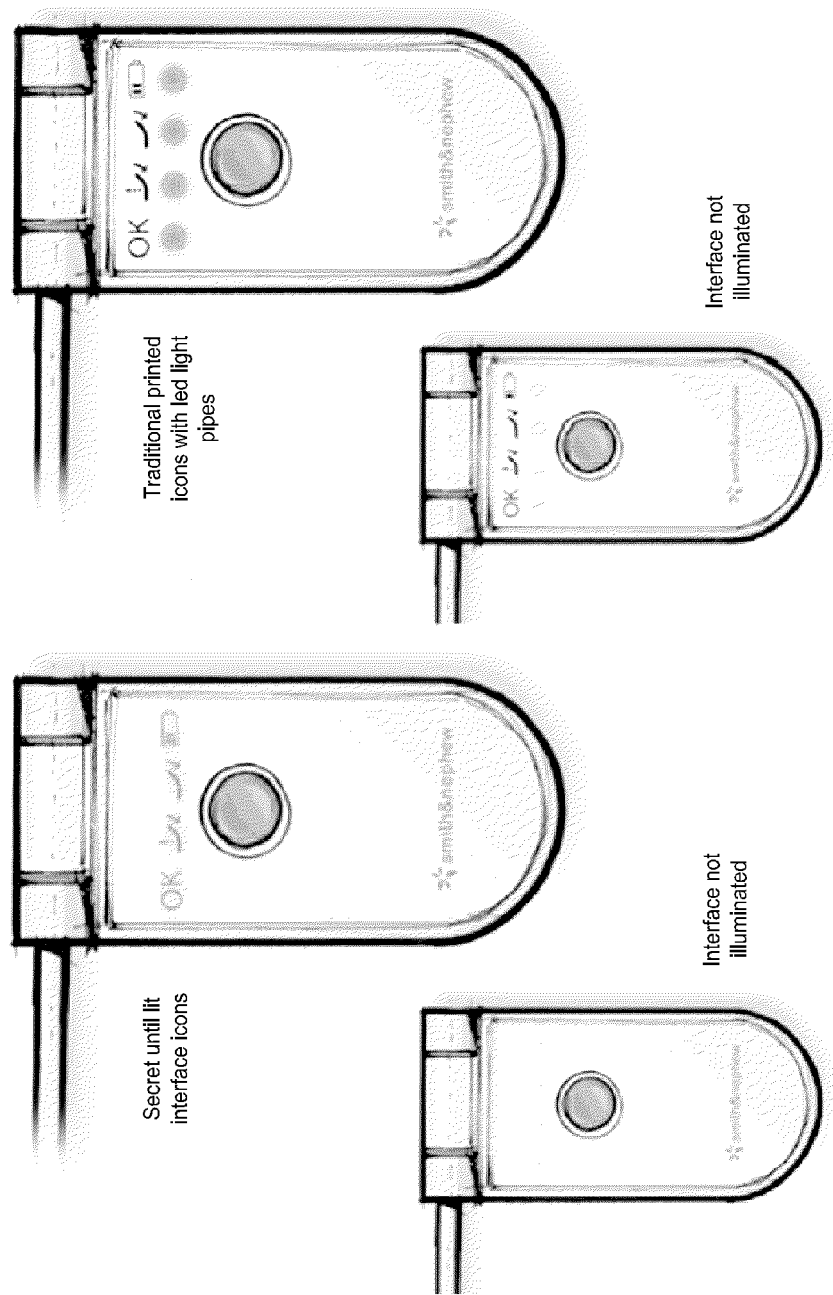
Figure 91:
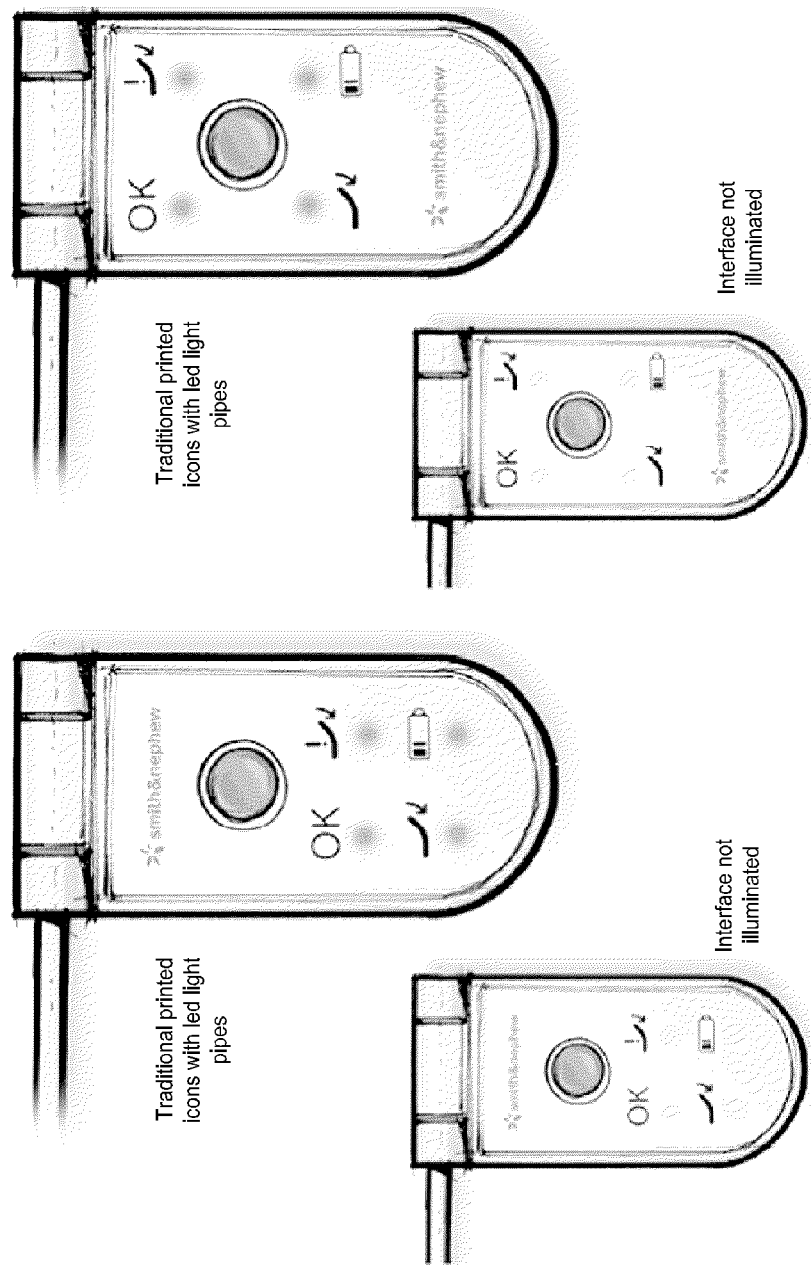
Figure 92:
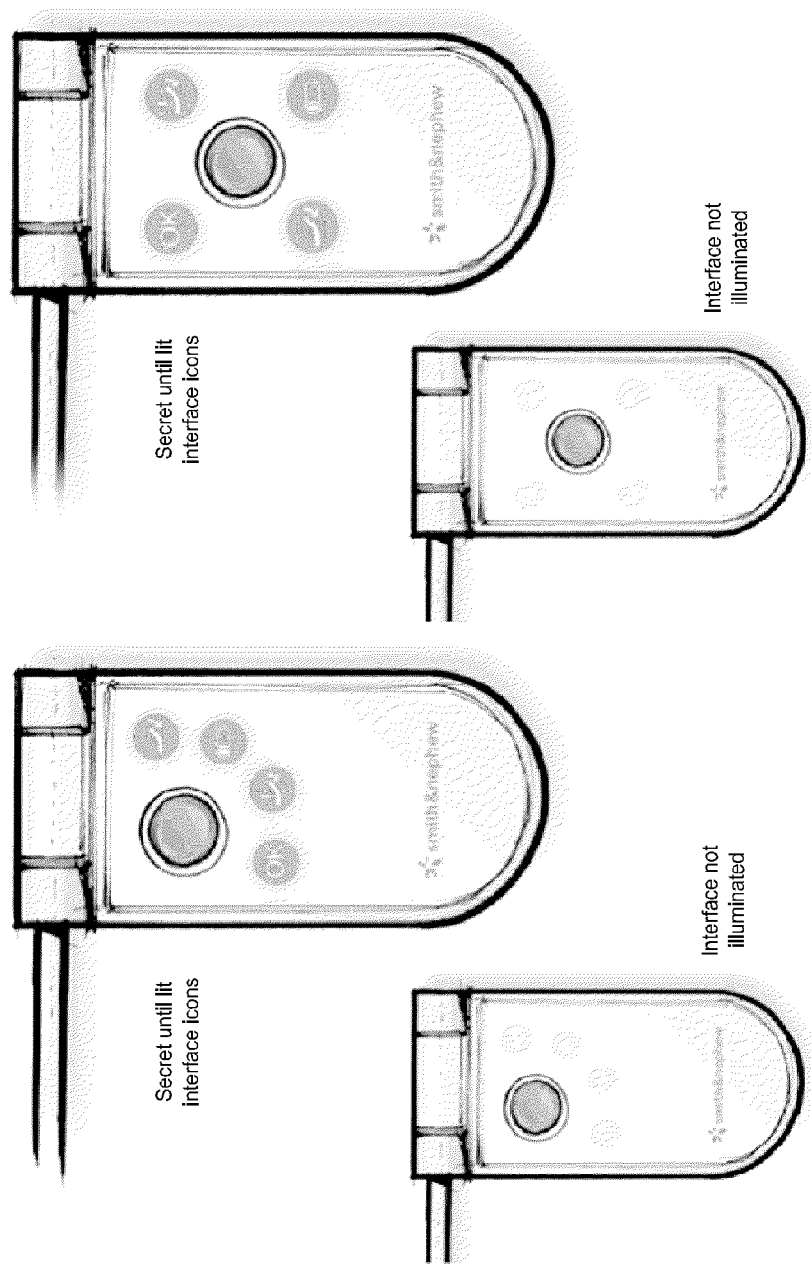
Figure 95:
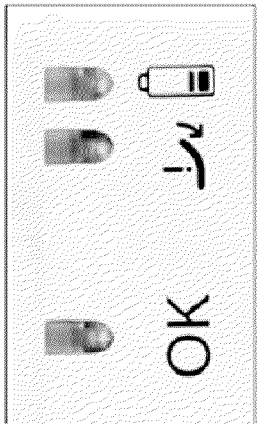

Similarly, the valve assembly 3033 can have a second valve plate 3050 (also referred to herein as a valve nozzle or second valve nozzle) having a first side 3050a, a second side 3050b, and a plurality of apertures or openings therethrough. For example, in the illustrated embodiment, the second valve plate 3050 can have a first inflow opening 3056 and one or more outflow or exhaust openings 3058. The first inflow opening 3056 can be configured to permit the passage of air into the space 3032, while the outflow or exhaust openings 3058 can be configured to permit the passage of air out of the space 3032. Either of the valve nozzles can be machined from aluminium wrought or cast material. In any embodiments disclosed herein, the first valve plate 3035 can be positioned in an opposite orientation relative to how it is illustrated in FIG. 77 such that the openings 3044 can be in fluid communication with the inflow opening 3056 and such that the opening 3042 can be in fluid communication with the openings 3058.

A boss or protrusion 3060 can be used to sealingly receive an end portion of a conduit or tubing used to communicate the reduced pressure produced by the pump 3000 to a negative pressure wound therapy dressing. A lumen or opening 3061 within the protrusion 3060 can form a flow passageway through the first inlet opening 3056, in communication with one or more openings in the flexible valve plate 3070, through the opening 3042 and into the space 3032, when the tab 3072 is not obstructing the flow of fluid through the openings. Similarly, the openings 3044 in the first valve plate 3035 will be in communication with the opening or slit around the flexible tab 3074 of the flexible valve plate 3070 and the openings 3058 of the second valve plate 3050 to permit air within the space 3032 to exit the pump embodiment 3000.

In any embodiments disclosed herein, one or more of the valve plates or the features on the valve plates can be integrated into the housing of the pump assembly. For example, In any embodiments disclosed herein, not illustrated, the second valve plate 3035 or 3050 and/or the protrusion 3060 can be integrated into the housing In use, when the diaphragm 3030 retracts and enlarges the volume of the space 3032, thereby drawing air through the lumen or opening 3061 of the boss 3060 into the space 3032 (and thereby reducing the pressure within a wound dressing in fluid communication with the pump 3000), the tab 3072 of the flexible valve plate 3070 will permit the passage of air into the space 3032 and the outflow tab 3074 of the flexible valve plate 3070 will substantially prevent or restrict the flow of air through the openings 3044 in the first valve plate 3035 and/or the openings 3058 in the second valve plate 3050 into the space 3032. In any embodiments disclosed herein, this can be achieved by sealing the openings 3044 with the flexible tab 3074.

Similarly, when the diaphragm 3030 extends and reduces the volume of the space 3032, thereby increasing the pressure within the space 3032, the valve assembly 3033 can be configured such that air will be substantially prevented from flowing through the openings 3042 of the first valve plate 3035 and the one or more openings 3056 of the second valve plate 3050, thereby preventing air from flowing back into the dressing in fluid communication with the pump. In any embodiments disclosed herein, this can be achieved by configuring the valve tab 3072 to seal the opening 3056 of the second valve plate, so that air is prevented from flowing through the opening 3056.

Additionally, In any embodiments disclosed herein, the pump can be configured such that the openings 3044, 3058 are never sealed by the valve assembly. Rather, a one-way flow valve can be attached external to the valve assembly 3033 which can be configured to only permit the flow of air out of the pump assembly 3000.

In any embodiments disclosed herein, the surface (which can be a raised protrusion around the one or more openings formed in the plates 3035, 3050) against which the flaps or tabs 3072, 3074 contact to seal the opening therethrough can be angled between 2° and 8°, or In any embodiments disclosed herein between 4° and 8°, to improve the surface contact between the tabs 3072, 3074 and the raised portion around the openings in each of the first and second plates 3035, 3050. Additionally, ridges or raised portions around the valve taps 3072, 3074 can be configured to mate with corresponding or complementary groups in the first and second valve plates 3035, 3050 to provide a substantially leak free connection between the components of the valve assembly. The valve assembly 3033 can be coupled with the housing 3002 using one or more screws or other fasteners 3062. Any other suitable attachment method or mechanism, such as with screws, welds, clips, or otherwise, can be used to attach the valve assembly 3033 to the housing or to attach the various portions of the housing together.

Many of the components of the pump embodiment 3000 can be formed from the rigid plastic, metal, alloy, or any other composite or suitable material. For example, In any embodiments disclosed herein, the housing 3002, the connector 3018, bushing 3019, the first valve plate 3035, the second valve plate 3050, the pump shaft 3020 and other portions or components of the pump embodiment 3020 can be made from an injection molded plastic. Where needed or desired, the plastic can be reinforced with a fibrous material, such as glass or graphite. Other components can be formed from of more flexible material, such as a suitable silicone or other rubber. For example, In any embodiments disclosed herein, the diaphragm 3030 and the flap valve plate 3070 can be formed from such a flexible material.

Any of the pump assembly embodiments or pump device embodiments disclosed herein can be configured to work with any of the dressing embodiments disclosed herein. The dressing can be provided as a single article with all wound dressing elements (including a port) pre-attached and integrated into a single unit. The wound dressing can then be connected, via a conduit, to any of the pump assemblies or pump devices disclosed herein. Additionally, In any embodiments disclosed herein, any of the pump assemblies or pump devices disclosed herein can be configured to be supported by any of the dressing embodiments disclosed herein. In any embodiments disclosed herein, though not required, the pump assembly embodiments disclosed herein can be miniaturized and portable.

The wound dressing can be located over a wound site to be treated. The dressing can form a substantially sealed cavity or enclosure over the wound site. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In any embodiments disclosed herein, the components of the TNP system described herein can be particularly suited for incisional wounds that exude a small amount of wound exudate.

As described in U.S. patent application Ser. No. 13/092,042, which disclosure is hereby incorporated by reference as if fully set forth herein, a lower surface of any of the wound dressing embodiments disclosed herein can have an optional wound contact layer. Any of the dressing embodiments disclosed herein can be made without the wound contact layer. The wound contact layer can be a polyurethane layer or polyethylene layer or other flexible layer which can be made porous or perforated, for example via a hot pin process, laser ablation process, ultrasound process or in some other way or otherwise made permeable to liquid and gas. The perforations can enable fluid and/or gas to flow through the layer. The wound contact layer can help prevent tissue ingrowth into the other material of the wound dressing.

The perforations can be sized small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer (not shown). For example, a lower pressure sensitive adhesive can be provided on the underside surface of the wound dressing whilst an upper pressure sensitive adhesive layer can be provided on the upper surface of the wound contact layer. The pressure sensitive adhesive, which can be a silicone, hot melt, hydrocolloid or acrylic based adhesive or other such adhesives, can be formed on both sides or optionally on a selected one or none of the sides of the wound contact layer. When a lower pressure sensitive adhesive layer is utilized this helps adhere the wound dressing to the skin around a wound site.

As mentioned, any dressing embodiments for use in the dressing kits disclosed or incorporated by reference herein can have an adhesive covered bottom (e.g., wound contacting) surface. In any embodiments disclosed herein, as mentioned, the adhesive can be a silicone adhesive including, for example, polysiloxanes or polyorganosiloxanes or other polymeric pressure sensitive silicone adhesives. For example, polydimethylsiloxane or the like can be used. The adhesive formulation may be a mixture of alkyl pendant siloxanes, which can be spread and cast as a two part mix with a catalyst such that a final polymerisation step takes place following casting or spreading. In any embodiments disclosed herein, a dressing layer can have a non-perforated silicone adhesive coating (coat weight 130 gsm nominal) and full spread acrylic adhesive (27 to 37 gsm) coated onto opposite sides of an extruded EU30 polyurethane clear film (27 to 37 gsm). Moisture vapour permeability of some embodiments of such an arrangement can be between approximately 367 $gm^{-2}/24$ hrs to approximately 405 $gm^{-2}/24$ hrs, or a mean moisture vapour permeability of 382 $gm^{-2}/24$ hrs.

Some embodiments or arrangements of a silicone adhesive layer suitable for dressing embodiments disclosed herein can have a moisture vapour transmission rate between approximately 350 $gm^{-2}/24$ hrs and approximately 410 $gm^{-2}/24$ hrs. Aptly, the average moisture vapour permeability of some embodiments or arrangements of a silicone adhesive layer suitable for dressing embodiments disclosed herein can be approximately 380 $gm^{-2}/24$ hrs. Some of the dressing embodiments disclosed herein can have a Wacker silres PSA 45 pressure sensitive adhesive coated thereon.

Additionally, any of the dressing embodiments disclosed herein can have an anti-microbial agent or substance incorporated into the dressing or coated on one or more surfaces of the dressing. For example, without limitation, a wound contact layer of any dressing embodiments disclosed herein can have nanocrystalline silver agents, silver salts, copper salts, or gold salts such as, without limitation, those disclosed in U.S. patent application Ser. No. 11/922,894 (titled ANTIMICROBIAL BIGUANIDE METAL COMPLEXES), filed May 21, 3008, which application is incorporated by reference herein as if made part of this disclosure, PHMB, chlorohexadine, peroxide, hypochloride, or other bleaches therein or thereon. Further, an absorbent layer of any dressing embodiments disclosed herein can have silver sulphur diazine or any of the previously mentioned substances or active agents therein or thereon. These may be used separately or together. These respectively can eliminate micro-organisms in the wound and micro-organisms in the absorption matrix. As a still further option, other active components, for example, pain suppressants such as ibuprofen or healing agents can be incorporated into the dressing. Also agents which enhance cell activity, such as growth factors or that inhibit enzymes, such as matrix metalloproteinase inhibitors, such as tissue inhibitors of metalloproteinase (TIMPS) or zinc chelators, can be incorporated into the dressing. Odor trapping elements such as activated carbon, cyclodextrine, zeolite or the like can also be included in the absorbent layer or other portions or components of the dressing, or above the filter layer.

A layer of porous material can be located above the wound contact layer. This porous layer, or transmission layer, allows transmission of fluid including liquid and gas away from a wound site into upper layers of the wound dressing. In particular, the transmission layer can ensure that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer can be formed of a material having a three dimensional structure. For example, a knitted or woven spacer fabric (for example Baltex 7970 weft knitted polyester) or a non-woven fabric can be used. Other materials can be utilized, and examples of such materials are described in U.S. patent application Ser. No. 13/092,042, which are hereby incorporated by reference and made part of this disclosure.

In any embodiments disclosed herein, the transmission layer can have a 3D polyester spacer fabric layer. This layer can have a top layer (that is to say, a layer distal from the wound-bed in use) which is a 84/144 textured polyester, and a bottom layer (that is to say, a layer which lies proximate to the wound bed in use) which can be a 100 denier flat polyester and a third layer formed sandwiched between these two layers which is a region defined by a knitted polyester viscose, cellulose or the like monofilament fiber. Other suitable materials and other linear mass densities of fiber can be used.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In any embodiments disclosed herein, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Again, as described in greater detail in U.S. patent application Ser. No. 13/092,042, a layer of absorbent material can be provided above the transmission layer. The absorbent material which can be a foam or non-woven natural or synthetic material and which can optionally include or be super-absorbent material forms a reservoir for fluid, particularly liquid, removed from the wound site and draws those fluids towards a cover layer. The material of the absorbent layer can prevent liquid collected in the wound dressing from flowing in a sloshing manner. The absorbent layer can also help distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer can be manufactured from ALLEVYN™ foam, Freudenberg 114-224-4 and/or Chem-Posite™11C-450, or any other suitable material.

In any embodiments disclosed herein, the absorbent layer can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing. The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In any embodiments disclosed herein, the absorbent layer can be an air-laid material. Heat fusible fibers can optionally be used to assist in holding the structure of the pad together. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Optionally, the absorbent layer can include synthetic stable fibers and/or bi-component stable fibers and/or natural stable fibers and/or super-absorbent fibers. Fibers in the absorbent layer can be secured together by latex bonding or thermal bonding or hydrogen bonding or a combination of any bonding technique or other securing mechanism. In any embodiments disclosed herein, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer can comprise a layer of multiple fibers. Preferably, the fibers are strand-like and made from cellulose, polyester, viscose or the like. Preferably, dry absorbent particles are distributed throughout the absorbent layer ready for use. In any embodiments disclosed herein, the absorbent layer comprises a pad of cellulose fibers and a plurality of super absorbent particles. In additional embodiments, the absorbent layer is a non-woven layer of randomly orientated cellulose fibers.

Super-absorber particles/fibers can be, for example, sodium polyacrylate or carbomethoxycellulose materials or the like or any material capable of absorbing many times its own weight in liquid. In any embodiments disclosed herein, the material can absorb more than five times its own weight of 0.9% W/W saline, etc. In any embodiments disclosed herein, the material can absorb more than 15 times its own weight of 0.9% W/W saline, etc. In any embodiments disclosed herein, the material is capable of absorbing more than 30 times its own weight of 0.9% W/W saline, etc. Preferably, the material is capable of absorbing more than 30 times its own weight of 0.9% W/W saline, etc. The absorbent layer can have one or more through holes located so as to underlie the suction port.

The dressing can have a gas impermeable, but moisture vapor permeable, cover layer extending across the width of the wound dressing. The cover layer, which can for example be a polyurethane film (for example, Elastollan SP9109) or any other suitable material having a pressure sensitive adhesive on one side, is substantially gas impermeable, thereby creating a substantially sealed enclosure over the wound. In this way an effective chamber is made between the cover layer and a wound site where a negative pressure can be established. The cover layer can be sealed to the wound contact layer in a border region around the circumference of the dressing, ensuring that no air is drawn in through the border area, for example via adhesive or welding techniques. The cover layer can protect the wound from external bacterial contamination (bacterial barrier) and allows liquid from wound exudates to be transferred through the layer and evaporated from the film outer surface. The cover layer can have a polyurethane film and an adhesive pattern spread onto the film. The polyurethane film is moisture vapor permeable and may be manufactured from a material that has an increased water transmission rate when wet.

An orifice can be provided in the cover film to allow a negative pressure to be applied to the dressing. As mentioned, In any embodiments disclosed herein, a suction port 108 can be sealed to the top of the cover film over the orifice, which can communicate negative pressure through the orifice. The port may be adhered and sealed to the cover film using an adhesive such as an acrylic, cyanoacrylate, epoxy, UV curable or hot melt adhesive. The port 108 can be formed from a soft polymer, for example a polyethylene, a polyvinyl chloride, a silicone or polyurethane having a hardness of 30 to 90 on the Shore A scale.

The dressing can have a filter element that is impermeable to liquids, but permeable to gases. The filter element can act as a liquid barrier, to substantially prevent or inhibit liquids from escaping from the wound dressing, as well as an odor barrier. The filter element may also function as a bacterial barrier. In any embodiments disclosed herein, the pore size of the filter element can be approximately 0.2 µm. Suitable materials for the filter material of the filter element include 0.2 micron Gore™ expanded PTFE from the MMT range, PALL Versapore™ 300R, and Donaldson™ TX6628. The filter element thus enables gas to be exhausted through the orifice. Liquid, particulates and pathogens however are contained in the dressing. Other details regarding the filter are disclosed in U.S. patent application Ser. No. 13/092,042 and incorporated by reference herein.

The wound dressing and its methods of manufacture and use as described herein may also incorporate features, configurations and materials described in the following patents and patent applications, each of which is incorporated by reference in their entireties herein as if made part of this disclosure: U.S. Pat. Nos. 7,524,315, 7,708,724, and 7,909, 805; U.S. Patent Application Publication Nos. 3005/ 0261642, 3007/0167926, 3009/0012483, 3009/0254054, 3010/0160879, 3010/0160880, 3010/0174251, 3010/ 0274207, 3010/0298793, 3011/0009838, 3011/0028918, 3011/0054421, and 3011/0054423; as well as U.S. application Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation, the wound dressing is sealed over a wound site forming a wound cavity. The pump assembly provides a source of a negative pressure to the dressing. Fluid is drawn towards the orifice through the wound dressing from a wound site below the wound contact layer. The fluid moves towards the orifice through the transmission layer. As the fluid is drawn through the transmission layer, wound exudate is absorbed into the absorbent layer.

The general shape of the wound dressing can be square, ovular, rectangular, or otherwise. The dressing can have rounded corner regions. It will be appreciated that wound dressings according to other embodiments of the present invention can be shaped differently such as square, circular or elliptical dressings, or the like.

The desired size of the wound dressing can be selected based on the size and type of wound it will be used in. In any embodiments disclosed herein, the wound dressing can measure between 30 and 40 cm on its long axis, and between 10 to 25 cm on its short axis. For example, dressings can be provided in sizes of approximately 10×30 cm, 10×30 cm, 10×40 cm, 15×30 cm, and 15×30 cm, as described above.

In any embodiments disclosed herein, the wound dressing can be a square-shaped dressing with sides measuring between 15 and 25 cm (e.g., 15×15 cm, 30×30 cm and 25×25 cm). The absorbent layer can have a smaller area than the overall dressing, and In any embodiments disclosed herein may have a length and width that are both about 3 to 10 cm shorter, more preferably about 5 cm shorter, than that of the overall dressing. In some rectangular-shape embodiments, the absorbent layer may measure between approximately 10 and 35 cm on its long axis, and between 5 and 10 cm on its short axis. For example, absorbent layers can be provided in sizes of 5.6×15 cm or 5×10 cm (for 10×30 cm dressings), 5.6×25 cm or 5×30 cm (for 10×30 cm dressings), 5.6×35 cm or 5×30 cm (for 10×40 cm dressings), 10×15 cm (for 15×30 cm dressings), and 10×25 cm (for 15×30 cm dressings). In some square-shape embodiments, the absorbent layer may have sides that are between 10 and 30 cm in length (e.g., 10×10 cm for a 15×15 cm dressing, 15×15 cm for a 30×30 cm dressing, or 30×30 cm for a 25×25 cm dressing). The transmission layer can be of a smaller size than the absorbent layer, and In any embodiments disclosed herein can have a length and width that are both about 0.5 to 2 cm shorter, more preferably about 1 cm shorter, than that of the absorbent layer. In some rectangular-shape embodiments, the transmission layer may measure between 9 and 34 cm on its long axis and between 3 and 5 cm on its short axis. For example, transmission layers may be provided in sizes of 4.6×14 cm or 4×9 cm (for 10×30 cm dressings), 4.6×24 cm or 4×19 cm (for 10×30 cm dressings), 4.6×34 cm or 4×29 cm (for 10×40 cm dressings), 9×14 cm (for 15×30 cm dressings), and 9×24 cm (for 15×30 cm dressings). In some square-shape embodiments, the transmission layer may have sides that are between 9 and 19 cm in length (e.g., 9×9 cm for a 15×15 cm dressing, 14×14 cm for a 30×30 cm dressing, or 19×19 cm for a 25×25 cm dressing).

The dressing can contain anti-microbial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like may be included in the absorbent layer or as a still further layer above the filter layer.

Whilst some embodiments of the present invention have so far been described in which the transmission layer is formed as a 3D knit layer, e.g., two layers spaced apart by a monofilament layer, it will be appreciated that some embodiments of the present invention are not restricted to the use of such a material. In any embodiments disclosed herein, as an alternative to such a 3D knit material, one or more layers of a wide variety of materials could be utilized. In each case, according to embodiments of the present invention, the openings presented by layers of the transmission layer are wider and wider as one moves away from the side of the dressing which, in use will be located proximate to the wound. In any embodiments disclosed herein, the transmission layer may be provided by multiple layers of open celled foam. In any embodiments disclosed herein, the foam is reticulated open cell foam. The foam can be hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In any embodiments disclosed herein, two, three, four or more foam layers may be included. The foam layers may be integrally formed, for example, by selecting a foam having a large pore size and then repeatedly dipping this to a lesser and lesser extent into material which will clog the pores or alternatively, the transmission layer formed by the multiple foam layers may be provided by laminating different types of foam in a layered arrangement or by securing such layers of foam in place in a known manner.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future. Finally, as used herein and unless otherwise stated, the term approximately is meant to represent a range of +/−10% of the stated value.

What is claimed is:

1. A pump assembly apparatus for applying negative pressure to a wound, comprising:
    a magnetic circuit comprising:
        an upper pole;
        a lower pole spaced apart from the upper pole; and
        a magnet positioned between at least a portion of the upper pole and the lower pole;
    an electrically conductive voice coil, at least a portion of which is disposed between the upper pole and the lower pole, the electrically conductive voice coil being configured to move within at least a portion of the magnetic circuit;
    a wound dressing configured to sealingly surround a wound;
    a diaphragm; and
    one or more valves configured to control a flow of fluid through the pump assembly;
    wherein:
        the voice coil is configured to move the diaphragm to pump a fluid through the pump assembly in response to a drive signal applied to the voice coil.

2. The apparatus of claim 1, wherein the drive signal comprises at least one of an offset square wave drive signal or an offset sinusoidal wave drive signal.

3. The apparatus of claim 1, wherein the voice coil is directly or indirectly coupled with the diaphragm and is configured to axially displace at least a middle portion of the diaphragm to pump a fluid through the pump assembly in response to a drive signal applied to the voice coil.

4. The apparatus of claim 1, wherein the upper pole has a first portion and a second portion, the first pole portion extending in a generally planar direction and the second portion extending in a first direction away from the first portion generally transverse to the first portion.

5. The apparatus of claim 4, wherein the second portion of the upper pole extends through an opening in the voice coil so as to shift a magnetic field of the magnet in a direction towards the lower pole.

6. The apparatus of claim 1, further comprising a flat spring member, wherein:
    a periphery of the spring member is supported within the pump assembly so as to be in a fixed position relative to the diaphragm; and
    a middle portion of the spring member is configured to deflect relative to the periphery of the spring member when a middle portion of the diaphragm axially deflects.

7. The apparatus of claim 6, wherein the spring member is configured to directly or indirectly exert a force on a middle portion of the diaphragm so as to displace the middle portion of the diaphragm when the apparatus is in an assembled state but before an electrical current has been applied to the voice coil.

8. The apparatus of claim 6, wherein the spring member is configured to alter a resonant oscillation frequency of the diaphragm member, thereby permitting an adjustment of the resonant frequency of the pump assembly to improve efficiency of the pump assembly.

9. The apparatus of claim 1, wherein the pump assembly comprises a support member configured to provide a radial force to a portion of a diaphragm assembly comprising the diaphragm so as to control a radial position of the diaphragm assembly.

10. The apparatus of claim 1, wherein the one or more valves comprises a first flap valve and a second flap valve, wherein:
    the first flap valve is configured to prevent air from flowing out of a valve chamber defined by the diaphragm during an intake cycle but to permit air to flow out of the valve chamber and through an outlet port during an exhaust cycle; and
    the second flap valve is configured to prevent air from flowing into the valve chamber through an inlet port during the exhaust cycle but to permit air to flow into the valve chamber during the intake cycle.

11. The apparatus of claim 10, wherein the first and second flap valves comprise a base portion and a body portion, the body portion being supported in cantilever and the flap portion being configured to deflect about the base portion, and wherein the base portion has a smaller cross-sectional area than the body portion.

12. The apparatus of claim 1, wherein the pump assembly is supported within a casing having a user interface screen having one or more indicator lights, and at least one operation button.

13. The apparatus of claim 12, wherein the casing comprises one or more tabs configured to clip the pump assembly to at least one of a pocket, pouch, belt, and flap.

14. The apparatus of claim 1, further comprising a controller configured to produce a drive signal for the voice coil and a filter configured to filter the drive signal, wherein the drive signal comprises a first pulse-width modulation drive signal and a second pulse-width modulation drive signal, the first and second pulse-width modulation drive signals having different magnitudes.

15. The apparatus of 28, wherein:
    the filter is further configured to filter the first pulse-width modulation drive signal to produce a first sinusoidal wave and filter the second pulse-width modulation drive signal to produce a second sinusoidal wave; and
    the controller is further configured to combine the first and second sinusoidal waves to produce the sinusoidal drive signal.

16. The apparatus of claim 15, wherein the first and second sinusoidal waves are phase shifted by about 180 degrees.

17. The apparatus of claim 1, wherein the pump assembly comprises a thin film cover covering and sealing a length of an air passageway in a portion of a housing used to support one or more components of the pump assembly.

18. The apparatus of claim 1, wherein the pump assembly is supported on, by, partially within, or fully within a wound dressing.

19. The apparatus of claim 10, wherein at least one of the first flap valve and the second flap valve comprises a flap portion surrounded by a frame portion, the flap portion being configured to deflect away from a relaxed position of the flap portion to block passage of air through an opening adjacent to the flap portion in response to a pressure differential between a first main surface and a second main surface of the flap portion.

20. The apparatus of claim 14, wherein the voice coil comprises the filter.

21. The apparatus of claim 1, wherein at least a portion of the electrically conductive voice coil is disposed radially between the upper pole and the lower pole.

22. An apparatus for applying negative pressure to a wound, comprising:
    a source of negative pressure configured to be coupled to a dressing, the source of negative comprising a voice coil actuator and a diaphragm, wherein the voice coil actuator comprises:
        a magnetic circuit comprising an upper pole, a lower pole spaced apart from the upper pole, and a magnet positioned between at least a portion of the upper pole and the lower pole;
        a voice coil, at least a portion of which is positioned between the upper pole and the lower pole; and
    a controller configured to produce a drive signal for the voice coil actuator.

23. The apparatus of claim 22, wherein the drive signal comprises at least one of an offset square wave drive signal or an offset sinusoidal wave drive signal.

24. The apparatus of claim 22, further comprising a filter configured to filter the drive signal, wherein the drive signal comprises a first pulse-width modulation drive signal and a second pulse-width modulation drive signal, the first and second pulse-width modulation drive signals having different magnitudes.

25. The apparatus of claim 24, wherein:
    the filter is further configured to filter the first pulse-width modulation drive signal to produce a first sinusoidal wave and filter the second pulse-width modulation drive signal to produce a second sinusoidal wave; and
    the controller is further configured to combine the first and second sinusoidal waves to produce the sinusoidal drive signal.

26. The apparatus of claim 24, wherein the voice coil actuator comprises the filter.

27. The apparatus of claim 22, further comprising a dressing configured to sealingly surround a wound.

28. The apparatus of claim 22, further comprising a conduit configured to couple the source of negative pressure and the dressing.

29. The apparatus of claim 22, wherein at least a portion of the voice coil is positioned radially between the upper pole and the lower pole.

30. The apparatus of claim 22, wherein the voice coil is configured to move within at least a portion of the magnetic circuit.

* * * * *